US008034905B2

(12) United States Patent
Kavlie et al.

(10) Patent No.: US 8,034,905 B2
(45) Date of Patent: Oct. 11, 2011

(54) ANTI-VEGF ANTIBODY COMPOSITIONS AND METHODS

(75) Inventors: Anita Kavlie, Oslo (NO); Kyle Schlunegger, Mission Viejo, CA (US)

(73) Assignees: Affitech Research, AS, Oslo (NO); Peregrine Pharmaceuticals, Inc., Tustin, CA (US)

( * ) Notice: Subject to any disclaimer, the term of this patent is extended or adjusted under 35 U.S.C. 154(b) by 222 days.

(21) Appl. No.: 12/267,515

(22) Filed: Nov. 7, 2008

(65) Prior Publication Data
US 2009/0175791 A1 Jul. 9, 2009

Related U.S. Application Data

(60) Provisional application No. 60/987,015, filed on Nov. 9, 2007, provisional application No. 61/106,047, filed on Oct. 16, 2008, provisional application No. 61/108,023, filed on Oct. 24, 2008.

(51) Int. Cl.
*C12P 21/08* (2006.01)
(52) U.S. Cl. ............. 530/387.3; 530/388.23; 530/391.1; 530/391.3; 530/391.7
(58) Field of Classification Search ............... 530/387.3, 530/388.23, 391.1, 391.3, 391.7
See application file for complete search history.

(56) References Cited

U.S. PATENT DOCUMENTS

| 5,942,385 | A * | 8/1999 | Hirth ................................. 435/4 |
| 6,342,219 | B1 | 1/2002 | Thorpe et al. |
| 6,342,221 | B1 | 1/2002 | Thorpe et al. |
| 6,416,758 | B1 | 7/2002 | Thorpe et al. |
| 6,524,583 | B1 | 2/2003 | Thorpe et al. |
| 6,676,941 | B2 | 1/2004 | Thorpe et al. |
| 6,703,020 | B1 | 3/2004 | Thorpe et al. |
| 6,887,468 | B1 | 5/2005 | Thorpe et al. |
| 7,056,509 | B2 | 6/2006 | Thorpe et al. |
| 2005/0123537 | A1 | 6/2005 | Thorpe et al. |
| 2006/0280747 | A1 | 12/2006 | Fuh et al. |

FOREIGN PATENT DOCUMENTS

| WO | 0064946 A2 | 11/2000 |
| WO | 03102157 A2 | 12/2003 |

OTHER PUBLICATIONS

Liang W.C. et al., "Cross-species Vascular Endothelial Growth Factor (VGF)-blocking Antibodies Completely Inhibit the Growth of Human Tumor Xenografts and Measure the Contribution of Stromal VEGF," Journal of Biological Chemistry, American Society for Biochemistry and Molecular Biology, 281(2): 951-961, Jan. 13, 2006.
Klohs W. D. et al., "Antiangiogenic agents," Current Opinion in Biotechnology, vol. 10, No. 6, pp. 544-549, 1999.
Fuh Germaine et al., "Structure-Function Studies fo Two Synthetic Anti-vascular Endothelial Growth Factor Fabs and Comparison with the Avastin Fab," Journal of Biological Chemistry, American Society for Biochemistry and Molecular Biology, Inc., vol. 281, No. 10, pp. 6625-6631, 2006.
Roland C.L. et al., "Cytokine Levels Correlate with Immune Cell Infiltration after Anti-VEGF Therapy in Preclinical Mouse Models of Breast Cancer," PLoS ONE, vol. 4, issue 11, e7699, 13 pp., Nov. 2009.
Sullivan L.A. et al., "r84, a Novel Therapeutic Antibody against Mouse and Human VEGF with Potent Anti-Tumor Activity and Limited Toxicity Induction," PLoS ONE, vol. 5, issue 8, e12031, 13 pages, Aug. 2010.
Roland C.L. et al., "Inhibition of vascular endothelial growth factor reduces angiogenesis and modulates immune cell infiltration of orthotopic breast cancer xenografts," Mol Cancer Ther, 8(7): 1761-1771, 2009.
Sullivan L.A and Brekken R.A.,"The VEGF family in cancer and antibody-based strategies for their inhibition," mAbs 2 (2):2, 165-175, 2010.
Brekken R.A. et al., "Vascular Endothelial Growth Factor as a Marker of Tumor Endothelium," Cancer Research 58: 1952-1959, May 1, 1998.
Brekken R.A. et al., "Selective Inhibition of Vascular Endothelial Growth Factor (VGF) Receptor 2 (KD/Flk-1) Activity by a Monoclonal Anti-VEGF Antibody Blocks Tumor Growth in Mice," Cancer Research 60: 5117-5124, Sep. 15, 2000.
Whitehurst B. et al., "Anti-VEGF-A therapy reduces lymphatic vessel density and expression of VEGFR-3 in an orthotopic breast tumor model," Int. J. Cancer, 121: 2181-2191, 2007.
Dineen S.P. et al., "Vascular Endothelial Growth Factor Receptor 2 Mediates Macrophage Infiltration Into Orthotopic Pancreatic Tumors in Mice," Cancer Res 68(11): 4340-4346, 2008.
Kavlie A., et al., "Human antibodies specific for VEGF that selectively block activation of VEGFR2" (Poster) The 7th International Symposium on Anti-Angiogenic Agents, San Diego, California, Feb. 11-13, 2005.
Carbon et al., (Abstract) 98th Annual Meeting of the American Association for Cancer Research, Los Angeles, CA, USA, Apr. 14-18, 2007, "Blockade of tumor derived VEGF activation of VEGF receptor 2 reduces macrophage infiltration into tumors and decreases metastasis in a pre-clinical orthotopic model of pancreatic cancer", Abstract publication: Proceedings of the American Association for Cancer Research Annual Meeting 48 p. 505-506 Apr. 2007. (Title of this talk was published on line on Feb. 20, 2007 and online publication of the abstract in Mar. 2007).

(Continued)

*Primary Examiner* — Misook Yu
*Assistant Examiner* — Brad Duffy
(74) *Attorney, Agent, or Firm* — Rothwell, Figg, Ernst & Manbeck

(57) ABSTRACT

Disclosed are human antibodies that specifically inhibit VEGF binding to only one (VEGFR2) of the two primary VEGF receptors. The antibodies effectively inhibit angiogenesis and induce tumor regression, and yet have improved safety due to their specificity. The present invention thus provides new human antibody-based compositions, methods and combined protocols for treating cancer and other angiogenic diseases. Advantageous immunoconjugate compositions and methods using the new VEGF-specific human antibodies are also provided.

19 Claims, 27 Drawing Sheets

OTHER PUBLICATIONS

Carbon et al., "Blockade of tumor-derived VEGF activation of VEGF receptor 2 reduces macrophage infiltration into tumors and decreases metastasis in a pre-clinical orthotopic model of pancreatic cancer" (Poster) 98th Annual Meeting of the American Association for Cancer Research, Los Angeles, CA, USA, Apr. 14-18, 2007.

Brekken. (Oral presentation) IBC Life Sciences 5th Annual International Conference: Anti-angiogenesis, Boston, November 12-13, 2007, "Development of 2C3 as a Clinical Candidate for Inhibition of VEGF Activation of VEGF Receptor 2", Nov. 12, 2007.

Kavlie et al., (Abstract) IBC Life Sciences 5th Annual International Conference, Antibody Therapeutics, Advancing Clinical and Preclinical Development of Therapeutic Antibodies and Antibody Conjugates, San Diego, Dec. 4-6, 2007 "Development and characterization of fully human anti-VEGF antibody fragments that selectivity inhibit VEGF Receptor 2 activity".

Kavlie et al., (Poster) IBC Life Sciences 5th Annual International Conference, Antibody Therapeutics, Advancing Clinical and Preclinical Development of Therapeutic Antibodies and Antibody Conjugates, San Diego, Dec. 4-6, 2007 "Identification and characterization of fully human anti-VEGF antibody fragments and IgGs that selectively inhibit VEGF Receptor 2 activity", poster available from Dec. 2-6, 2007.

Freimark, (Oral presentation) IBC Life Sciences 5th Annual International Conference, Antibody Therapeutics, Advancing Clinical and Preclinical Development of Therapeutic Antibodies and Antibody Conjugates, San Diego, Dec. 4-6, 2007, "Development of 2C3 as a Clinical Candidate for Inhibition of VEGF Activation of VEGF Receptor 2", Dec. 5, 2007.

Kavlie et al., "Generating fully human antibodies that are improved with respect to cross reactivity profile and affinity compared to existing murine, chimeric or humanized antibodies" (Abstract) Protein Expression Europe & Antibodies Europe conference, Oct. 20-23, 2008, Lisbon.

Kavlie, (Oral Presentation) Protein Expression Europe & Antibodies Europe conference, Oct. 20-23, 2008, Lisbon, "Generating fully human antibodies that are improved with respect to cross reactivity profile and affinity compared to existing murine, chimeric or humanized antibodies", Oct. 23, 2008.

Kavlie et al., "Generation of fully human anti-cancer antibodies with improved cross-reactivity and affinity profiles in comparison with existing murine, chimeric or humanized antibodies" (Abstract) The 25th International Conference: Advances in the Application of the Monoclonal Antibodies in Clinical Oncology and Symposium on Cancer stem Cells, Island of Rhodes, Greece, Jun. 16-18, 2008.

Kiprijanov, (Oral presentation) The 25th International Conference: Advances in the Application of the Monoclonal Antibodies in Clinical Oncology and Symposium on Cancer stem Cells, Island of Rhodes, Greece, Jun. 16-18, 2008, "Advances in the application of Monoclonal Antibodies in Clinical Oncology", Jun. 16, 2008.

Payton et al., "Selective inhibition of VEGF receptor 2 activity with a fully human monoclonal anti-VEGF antibody blocks tumor growth in mice"(Abstract) 3rd Mayo Clinic Angiogenesis Symposium, Oct. 24-26, 2008.

Dellinger et al., "Novel Anti-VEGF Antibody Affects Stroma in Orthotopic Breast Cancer Xenografts" (Abstracts) 3rd Mayo Clinic Angiogenesis Symposium, Oct. 24-26, 2008.

Brekken, (Oral presentation) 3rd Mayo Clinic Angiogenesis Symposium, Oct. 24-26, 2008, "Selective blockade of VEGFR2 activity with a fully human anti-VEGF monoclonal antibody", Oct. 25, 2008.

Welschof, (Oral presentation) European Life Science CEO Forum Investing & Partnering in Biotech—Medtech—Speciality Pharma & Emerging Markets Conference, Apr. 22-23, 2008, Zurich, Switzerland, Apr. 22, 2008 (one slide).

Brekken, (Oral presentation) 4th Annual Angiogenesis and Vascular Targeting Agents, Drug Discovery and Development World Summit, Boston, MA, Sep. 19-20, 2006, "2C3, an anti-VEGF antibody that selectively inhibits VEGFR2 activity blocks macrophage infiltration and reduces metastasis".

Brekken, (Oral presentation) Anti Cancer Drug Discovery & Development Summit, Boston, MA, Jul. 12-13, 2005, "Pre-clinical Development and Characterization of 2C3, a Monoclonal anti-VEGF Antibody that Selectively Inhibits VEGF Receptor 2 activity".

* cited by examiner

Figure 1

Nucleotide Sequence

<u>CCATGGCC</u>CAGGTGCAGCTGGTGCAATCTGGGGCTGAGGTGAAGAAGCCTGGGG

NcoI       | ----------VH Start (SEQ ID No.20 Start)

CCTCAGTGAAGGTCTCCTGCAAGGCTTCTGGAGGCACCTTCAGCAGCTATGCTATCAG

CTGGGTGCGACAGGCCCCTGGACAAGGGCTTGAGTGGATGGGAGGTTTTGATCCTGAA

GATGGTGAAACAATCTACGCACAGAAGTTCCAGGGCAGAGTCACCATGACCGAGGACA

CATCTACAGACACAGCCTACATGGAGCTGAGCAGCCTGAGATCTGAGGACACGGCCGT

GTATTACTGTGCAACAGGACGTTCTATGGTTCGGGGAGTCATTATACCTTTTAACGGT

ATGGACGTCTGGGGCCAAGGGACCACGGTCACCGTCTCCTCA_AAGCTTTCAGGGAGTG_

VH End---------- || -- HindIII--- Linker Start

_CATCCGCCCCAAAACTTGAAGAAGGTGAATTTTCAGAAGC_<u>_ACGCGT_</u>AGACATCCGGAT

Linker end---------MluI---- || --------VL Start

GACCCAGTCTCCATCCTCCCTGTCTGCATCTGTAGGAGACAGAGTCACCATCACTTGC

CGGGCAAGTCAGAGCATTAGCAGCTATTTAAATTGGTATCAGCAGAAACCAGGGAAAG

CCCCTAAGCTCCTGATCTATGCTGCATCCAGTTTGCAAAGTGGGGTCCCATCAAGGTT

CAGTGGCAGTGGATCTGGGACAGATTTCACTCTCACCATCAGCAGTCTGCAACCTGAA

GATTTTGCAACTTACTACTGTCAACAGAGTTACAGTACCCCGCTCACTTTCGGCGGAG

GGACCAAGGTGGAGATCAAA_GCGGCCGC_   (SEQ ID No. 30)

(SEQ ID No.20 End) VL End----- |    NotI

Amino acid sequence

QVQLVQSGAEVKKPGASVKVSCKASGGTFSSYAISWVRQAPGQGLEWMGGFDPEDGET

| ---------V$_H$ Start (SEQ ID No 21 Start)

IYAQKFQGRVTMTEDTSTDTAYMELSSLRSEDTAVYYCATGRSMVRGVIIPFNGMDVW

GQGTTVTVSS_KLSGSASAPKLEEGEFSEARV_DIRMTQSPSSLSASVGDRVTITCRASQ

V$_H$ End----------- || --------Linker-------------Linker------ || ---- V$_L$ Start

SISSYLNWYQQKPGKAPKLLIYAASSLQSGVPSRFSGSGSGTDFTLTISSLQPEDFAT

YYCQQSYSTPLTFGGGTKVEIK (SEQ ID No 21 End) V$_L$ End-------- |

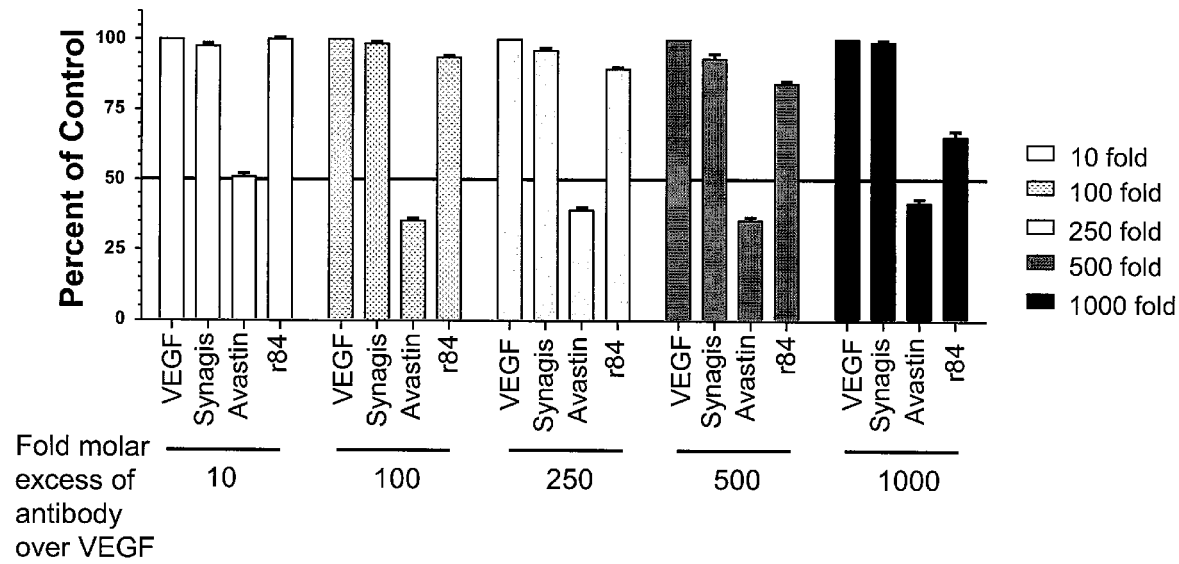

Figure 17A
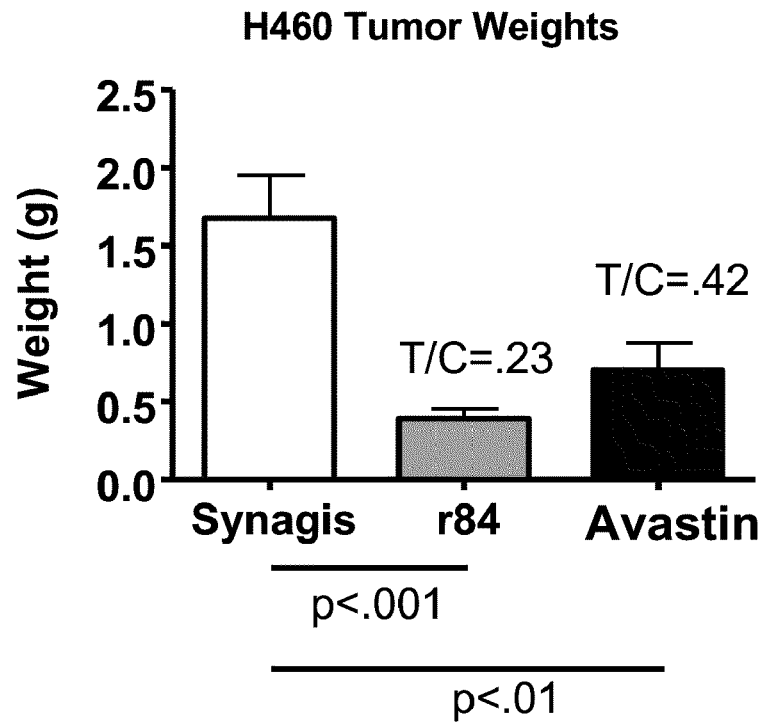
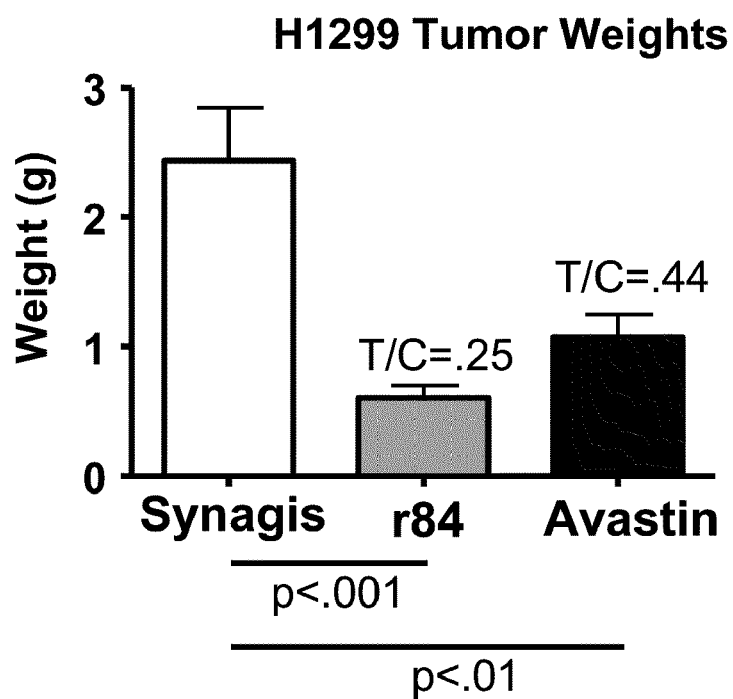
Figure 17B

Figure 20A
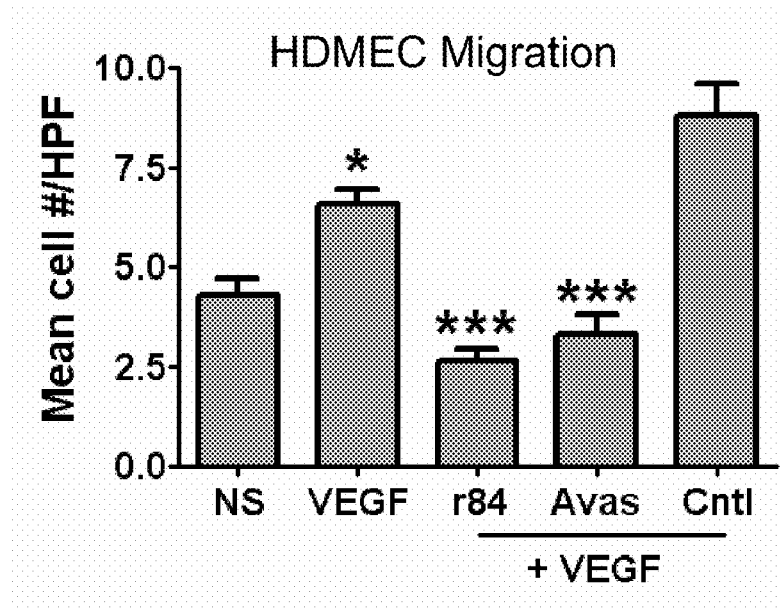
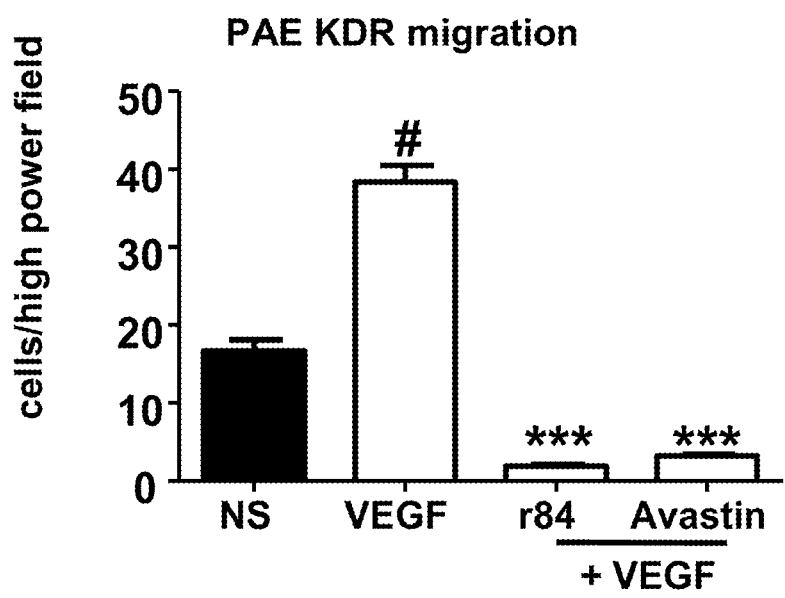
Figure 20B

SEQUENCE LISTING

<160> NUMBER OF SEQ ID NOS: 34

<210> SEQ ID NO 1
<211> LENGTH: 378
<212> TYPE: DNA
<213> ORGANISM: artificial sequence
<220> FEATURE:
<223> OTHER INFORMATION: antibody VH domain

<400> SEQUENCE: 1

```
caggtgcagc tggtgcaatc tggggctgag gtgaagaagc ctggggcctc agtgaaggtc      60
tcctgcaagg cttctggagg caccttcagc agctatgcta tcagctgggt gcgacaggcc     120
cctggacaag gcttgagtg gatgggaggt tttgatcctg aagatggtga acaatctac       180
gcacagaagt tccagggcag agtcaccatg accgaggaca tctacagaca cagcctac      240
atggagctga gcagcctgag atctgaggac acggccgtgt attactgtgc aacaggacgt    300
tctatggttc ggggagtcat taccttttt aacggtatgg acgtctgggg ccaagggacc     360
acggtcaccg tctcctca                                                  378
```

<210> SEQ ID NO 2
<211> LENGTH: 321
<212> TYPE: DNA
<213> ORGANISM: artificial sequence
<220> FEATURE:
<223> OTHER INFORMATION: antibody VL domain

<400> SEQUENCE: 2

```
gacatccgga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321
```

<210> SEQ ID NO 3
<211> LENGTH: 126
<212> TYPE: PRT
<213> ORGANISM: artificial sequence
<220> FEATURE:
<223> OTHER INFORMATION: antibody VH domain

<400> SEQUENCE: 3

```
Gln Val Gln Leu Val Gln Ser Gly Ala Glu Val Lys Lys Pro Gly Ala
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
            100                 105                 110
```

Met Asp Val Trp Gly Gln Gly Thr Thr Val Thr Val Ser Ser
        115                 120                 125

<210> SEQ ID NO 4
<211> LENGTH: 107
<212> TYPE: PRT
<213> ORGANISM: artificial sequence
<220> FEATURE:
<223> OTHER INFORMATION: antibody VL domain

<400> SEQUENCE: 4

Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 5
<211> LENGTH: 5
<212> TYPE: PRT
<213> ORGANISM: artificial sequence
<220> FEATURE:
<223> OTHER INFORMATION: antibody VH CDR1

<400> SEQUENCE: 5

Ser Tyr Ala Ile Ser
1               5

<210> SEQ ID NO 6
<211> LENGTH: 17
<212> TYPE: PRT
<213> ORGANISM: artificial sequence
<220> FEATURE:
<223> OTHER INFORMATION: antibody VH CDR2

<400> SEQUENCE: 6

Gly Phe Asp Pro Glu Asp Gly Glu Thr Ile Tyr Ala Gln Lys Phe Gln
1               5                   10                  15

Gly

<210> SEQ ID NO 7
<211> LENGTH: 17
<212> TYPE: PRT
<213> ORGANISM: artificial sequence
<220> FEATURE:
<223> OTHER INFORMATION: antibody VH CDR3

<400> SEQUENCE: 7

Gly Arg Ser Met Val Arg Gly Val Ile Ile Pro Phe Asn Gly Met Asp
1               5                   10                  15

Val

<210> SEQ ID NO 8

```
<211> LENGTH: 11
<212> TYPE: PRT
<213> ORGANISM: artificial sequence
<220> FEATURE:
<223> OTHER INFORMATION: antibody VL CDR1

<400> SEQUENCE: 8

Arg Ala Ser Gln Ser Ile Ser Ser Tyr Leu Asn
1               5                   10

<210> SEQ ID NO 9
<211> LENGTH: 7
<212> TYPE: PRT
<213> ORGANISM: artificial sequence
<220> FEATURE:
<223> OTHER INFORMATION: antibody VL CDR2

<400> SEQUENCE: 9

Ala Ala Ser Ser Leu Gln Ser
1               5

<210> SEQ ID NO 10
<211> LENGTH: 9
<212> TYPE: PRT
<213> ORGANISM: artificial sequence
<220> FEATURE:
<223> OTHER INFORMATION: antibody VL CDR3

<400> SEQUENCE: 10

Gln Gln Ser Tyr Ser Thr Pro Leu Thr
1               5

<210> SEQ ID NO 11
<211> LENGTH: 30
<212> TYPE: PRT
<213> ORGANISM: artificial sequence
<220> FEATURE:
<223> OTHER INFORMATION: antibody VH FR1

<400> SEQUENCE: 11

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser
            20                  25                  30

<210> SEQ ID NO 12
<211> LENGTH: 14
<212> TYPE: PRT
<213> ORGANISM: artificial sequence
<220> FEATURE:
<223> OTHER INFORMATION: antibody VH FR2

<400> SEQUENCE: 12

Trp Val Arg Gln Ala Pro Gly Gln Gly Leu Glu Trp Met Gly
1               5                   10

<210> SEQ ID NO 13
<211> LENGTH: 32
<212> TYPE: PRT
<213> ORGANISM: artificial sequence
<220> FEATURE:
<223> OTHER INFORMATION: antibody VH FR3

<400> SEQUENCE: 13

Arg Val Thr Met Thr Glu Asp Thr Ser Thr Asp Thr Ala Tyr Met Glu
1               5                   10                  15

Leu Ser Ser Leu Arg Ser Glu Asp Thr Ala Val Tyr Tyr Cys Ala Thr
```

```
            20                  25                  30

<210> SEQ ID NO 14
<211> LENGTH: 11
<212> TYPE: PRT
<213> ORGANISM: artificial sequence
<220> FEATURE:
<223> OTHER INFORMATION: antibody VH FR4

<400> SEQUENCE: 14

Trp Gly Gln Gly Thr Thr Val Thr Val Ser Ser
1               5                   10

<210> SEQ ID NO 15
<211> LENGTH: 23
<212> TYPE: PRT
<213> ORGANISM: artificial sequence
<220> FEATURE:
<223> OTHER INFORMATION: antibody VL FR1

<400> SEQUENCE: 15

Asp Ile Arg Met Thr Gln Ser Pro Ser Ser Leu Ser Ala Ser Val Gly
1               5                   10                  15

Asp Arg Val Thr Ile Thr Cys
            20

<210> SEQ ID NO 16
<211> LENGTH: 15
<212> TYPE: PRT
<213> ORGANISM: artificial sequence
<220> FEATURE:
<223> OTHER INFORMATION: antibody VL FR2

<400> SEQUENCE: 16

Trp Tyr Gln Gln Lys Pro Gly Lys Ala Pro Lys Leu Leu Ile Tyr
1               5                   10                  15

<210> SEQ ID NO 17
<211> LENGTH: 32
<212> TYPE: PRT
<213> ORGANISM: artificial sequence
<220> FEATURE:
<223> OTHER INFORMATION: antibody VL FR3

<400> SEQUENCE: 17

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 18
<211> LENGTH: 10
<212> TYPE: PRT
<213> ORGANISM: artificial sequence
<220> FEATURE:
<223> OTHER INFORMATION: antibody VL FR4

<400> SEQUENCE: 18

Phe Gly Gly Gly Thr Lys Val Glu Ile Lys
1               5                   10

<210> SEQ ID NO 19
<211> LENGTH: 21
<212> TYPE: PRT
<213> ORGANISM: artificial sequence
<220> FEATURE:
<223> OTHER INFORMATION: linker
```

<400> SEQUENCE: 19

Lys Leu Ser Gly Ser Ala Ser Ala Pro Lys Leu Glu Glu Gly Glu Phe
1               5                   10                  15

Ser Glu Ala Arg Val
            20

<210> SEQ ID NO 20
<211> LENGTH: 762
<212> TYPE: DNA
<213> ORGANISM: artificial sequence
<220> FEATURE:
<223> OTHER INFORMATION: Whole scFv clone

<400> SEQUENCE: 20
caggtgcagc tggtgcaatc tggggctgag gtgaagaagc ctggggcctc agtgaaggtc      60
tcctgcaagg cttctggagg caccttcagc agctatgcta tcagctgggt gcgacaggcc     120
cctggacaag gcttgagtg gatgggaggt tttgatcctg aagatggtga acaatctac       180 gcacagaagt tccagggcag agtcaccatg accgaggaca tctacagaca cagcctac       240 atggagctga gcagcctgag atctgaggac acggccgtgt attactgtgc aacaggacgt     300
tctatggttc ggggagtcat tatacctttt aacggtatgg acgtctgggg ccaagggacc     360
acggtcaccg tctcctcaaa gctttcaggg agtgcatccg ccccaaaact tgaagaaggt     420 gaatttcag aagcacgcgt agacatccgg atgacccagt ctccatcctc cctgtctgca      480
tctgtaggag acagagtcac catcacttgc cgggcaagtc agagcattag cagctattta     540
aattggtatc agcagaaacc agggaaagcc cctaagctcc tgatctatgc tgcatccagt     600
ttgcaaagtg ggtcccatc aaggttcagt ggcagtggat ctgggacaga tttcactctc      660
accatcagca gtctgcaacc tgaagatttt gcaacttact actgtcaaca gagttacagt     720
accccgctca ctttcggcgg agggaccaag gtggagatca aa                         762

<210> SEQ ID NO 21
<211> LENGTH: 254
<212> TYPE: PRT
<213> ORGANISM: artificial sequence
<220> FEATURE:
<223> OTHER INFORMATION: whole scFv clone

<400> SEQUENCE: 21

Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
            100                 105                 110

Met Asp Val Trp Gly Gln Gly Thr Thr Val Thr Val Ser Ser Lys Leu
        115                 120                 125

Ser Gly Ser Ala Ser Ala Pro Lys Leu Glu Glu Gly Glu Phe Ser Glu

```
                130             135             140
Ala Arg Val Asp Ile Arg Met Thr Gln Ser Pro Ser Ser Leu Ser Ala
145                 150                 155                 160

Ser Val Gly Asp Arg Val Thr Ile Thr Cys Arg Ala Ser Gln Ser Ile
                165                 170                 175

Ser Ser Tyr Leu Asn Trp Tyr Gln Gln Lys Pro Gly Lys Ala Pro Lys
            180                 185                 190

Leu Leu Ile Tyr Ala Ala Ser Ser Leu Gln Ser Gly Val Pro Ser Arg
        195                 200                 205

Phe Ser Gly Ser Gly Ser Gly Thr Asp Phe Thr Leu Thr Ile Ser Ser
210                 215                 220

Leu Gln Pro Glu Asp Phe Ala Thr Tyr Tyr Cys Gln Gln Ser Tyr Ser
225                 230                 235                 240

Thr Pro Leu Thr Phe Gly Gly Thr Lys Val Glu Ile Lys
                245                 250
```

<210> SEQ ID NO 22
<211> LENGTH: 1977
<212> TYPE: DNA
<213> ORGANISM: artificial sequence
<220> FEATURE:
<223> OTHER INFORMATION: IgG heavy chain

<400> SEQUENCE: 22

```
caggtacagc ttgtgcagtc cggagccgag gtgaagaaac ccggagcatc agtgaaggtt      60
agctgcaagg catctggtgg acatttttcc tcctatgcca tctcctgggt tcggcaggct     120
cccggacagg gcctggagtg gatgggggggg ttcgatcccg aagacggaga gaccatttac    180
gcacagaagt tccagggtcg cgtgaccatg accgaggata cttctaccga cacagcatat    240
atggagctca gtagcttgcg ctccgaggac acggctgtat attactgtgc cactggacgg    300
agcatggtgc gcggggtaat catccctttc aacgggatgg atgtatgggg ccaagggacc    360
accgtgacag tcagctctgc ctccaccaag ggcccatcgg tcttcccccct ggcaccctcc    420
tccaagagca cctctggggg cacagcggcc ctgggctgcc tggtcaagga ctacttcccc    480
gaaccggtga cggtgtcgtg aactcaggc gccctgacca gcggcgtgca ccttcccg       540
gctgtcctac agtcctcagg actctactcc ctcagcagcg tggtgaccgt gccctccagc    600
agcttgggca cccagaccta catctgcaac gtgaatcaca agcccagcaa caccaaggtg    660
gacaagaaag ttggtgagag gccagcacag ggagggaggg tgtctgctgg aagccaggct    720
cagcgctcct gcctggacgc atcccggcta tgcagcccca gtccagggca gcaaggcagg    780
ccccgtctgc ctcttcaccc ggaggcctct gcccgcccca ctcatgctca gggagagggt    840
cttctggctt tttccccagg ctctgggcag gcacaggcta ggtgcccta cccaggccc     900
tgcacacaaa ggggcaggtg ctgggctcag acctgccaag agccatatcc gggaggaccc    960
tgcccctgac ctaagcccac cccaaaggcc aaactctcca ctccctcagc tcggacacct   1020
tctctcctcc cagattccag taactcccaa tcttctctct gcagagccca atcttgtga   1080
caaaactcac acatgcccac cgtgcccagg taagccagcc caggcctcgc cctccagctc   1140
aaggcgggac aggtgcccta gagtagcctc catccaggga caggccccag ccgggtgctg   1200
acacgtccac ctccatctct tcctcagcac ctgaactcct gggggaccg tcagtcttcc    1260
tcttcccccc aaaacccaag gacaccctca tgatctcccg gaccctgag gtcacatgcg    1320
tggtggtgga cgtgagccac gaagaccctg aggtcaagtt caactggtac gtggacggcg   1380
tggaggtgca taatgccaag acaaagccgc gggaggagca gtacaacagc acgtaccgtg   1440
```

```
tggtcagcgt cctcaccgtc ctgcaccagg actggctgaa tggcaaggag tacaagtgca   1500
aggtctccaa caaagccctc ccagccccca tcgagaaaac catctccaaa gccaaaggtg   1560
ggacccgtgg ggtgcgaggg ccacatggac agaggccggc tcggcccacc ctctgccctg   1620
agagtgaccg ctgtaccaac ctctgtccct acagggcagc cccgagaacc acaggtgtac   1680
accctgcccc catcccggga tgagctgacc aagaaccagg tcagcctgac ctgcctggtc   1740
aaaggcttct atcccagcga catcgccgtg gagtgggaga gcaatgggca gccggagaac   1800
aactacaaga ccacgcctcc cgtgctggac tccgacggct ccttcttcct ctacagcaag   1860
ctcaccgtgg acaagagcag gtggcagcag gggaacgtct tctcatgctc cgtgatgcat   1920
gaggctctgc acaaccacta cacgcagaag agcctctccc tgtctccggg taaatag      1977
```

<210> SEQ ID NO 23
<211> LENGTH: 645
<212> TYPE: DNA
<213> ORGANISM: artificial sequence
<220> FEATURE:
<223> OTHER INFORMATION: IgG light chain

<400> SEQUENCE: 23

```
gacattcgga tgactcagtc tccctcctct ttgagcgctt ctgtgggcga tagggttact    60
atcacttgtc gagcctctca atccatcagc tcctacttga actggtacca gcagaaaccc   120
gggaaagcac ccaagctgct tatttacgcc gcctcctccc tgcaatccgg agtgccctcc   180
cggttcagcg gctccggctc tggaacagac tttaccctga ccatttcttc tttgcagcct   240
gaggattttg ctacttacta ctgtcagcag agttactcca ccccctttga cattcgtggt   300
ggaacgaaag tagaaattaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacactgacg   540
ctgagcaaag cagactacga gaaacacaaa gtctacgcct gcgaagtcac ccatcagggc   600
ctgagctcgc ccgtcacaaa gagcttcaac aggggagagt gttag                    645
```

<210> SEQ ID NO 24
<211> LENGTH: 456
<212> TYPE: PRT
<213> ORGANISM: artificial sequence
<220> FEATURE:
<223> OTHER INFORMATION: IgG heavy chain

<400> SEQUENCE: 24

```
Gln Val Gln Leu Val Gln Ser Gly Ala Glu Val Lys Lys Pro Gly Ala
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
```

```
                100              105              110
Met Asp Val Trp Gly Gln Gly Thr Thr Val Thr Val Ser Ser Ala Ser
            115                  120                 125

Thr Lys Gly Pro Ser Val Phe Pro Leu Ala Pro Ser Ser Lys Ser Thr
        130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
            210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455

<210> SEQ ID NO 25
<211> LENGTH: 214
<212> TYPE: PRT
<213> ORGANISM: artificial sequence
<220> FEATURE:
<223> OTHER INFORMATION: IgG light chain

<400> SEQUENCE: 25

Asp Ile Arg Met Thr Gln Ser Pro Ser Ser Leu Ser Ala Ser Val Gly
1               5                   10                  15
```

```
Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 26
<211> LENGTH: 378
<212> TYPE: DNA
<213> ORGANISM: artificial sequence
<220> FEATURE:
<223> OTHER INFORMATION: IgG VH domain

<400> SEQUENCE: 26
caggtacagc ttgtgcagtc cggagccgag gtgaagaaac ccggagcatc agtgaaggtt    60
agctgcaagg catctggtgg acatttttcc tcctatgcca tctcctgggt tcggcaggct   120
cccggacagg gcctggagtg gatggggggg ttcgatcccg aagacggaga gaccatttac   180
gcacagaagt tcagggtcg cgtgaccatg accgaggata cttctaccga cacagcatat   240
atggagctca gtagcttgcg ctccgaggac acggctgtat attactgtgc cactggacgg   300
agcatggtgc gcggggtaat catccctttc aacgggatgg atgtatgggg ccaagggacc   360
accgtgacag tcagctct                                                 378

<210> SEQ ID NO 27
<211> LENGTH: 321
<212> TYPE: DNA
<213> ORGANISM: artificial sequence
<220> FEATURE:
<223> OTHER INFORMATION: IgG VL domain

<400> SEQUENCE: 27
gacattcgga tgactcagtc tcctcctct ttgagcgctt ctgtgggcga tagggttact    60
atcacttgtc gagcctctca atccatcagc tcctacttga actggtacca gcagaaaccc   120
gggaaagcac ccaagctgct tatttacgcc gcctcctccc tgcaatccgg agtgccctcc   180
```

```
cggttcagcg gctccggctc tggaacagac tttaccctga ccatttcttc tttgcagcct    240
gaggattttg ctacttacta ctgtcagcag agttactcca ccccttttgac attcggtggt   300 ggaacgaaag tagaaattaa g                                              321
```

<210> SEQ ID NO 28
<211> LENGTH: 78
<212> TYPE: DNA
<213> ORGANISM: artificial sequence
<220> FEATURE:
<223> OTHER INFORMATION: c-myc and His tag

<400> SEQUENCE: 28

```
gcggccgctg gatccgaaca aaagctgatc tcagaagaag acctaaactc acatcaccat    60
caccatcact aatctaga                                                  78
```

<210> SEQ ID NO 29
<211> LENGTH: 23
<212> TYPE: PRT
<213> ORGANISM: artificial sequence
<220> FEATURE:
<223> OTHER INFORMATION: c-myc and His tag
<220> FEATURE:
<221> NAME/KEY: c-myc epitope tag
<222> LOCATION: (6)..(15)
<220> FEATURE:
<221> NAME/KEY: His epitope tag
<222> LOCATION: (18)..(23)

<400> SEQUENCE: 29

```
Ala Ala Ala Gly Ser Glu Gln Lys Leu Ile Ser Glu Glu Asp Leu Asn
1               5                   10                  15

Ser His His His His His His
            20
```

<210> SEQ ID NO 30
<211> LENGTH: 778
<212> TYPE: DNA
<213> ORGANISM: artificial sequence
<220> FEATURE:
<223> OTHER INFORMATION: whole scFv clone inclusive NcoI and NotI
    restriction sites

<400> SEQUENCE: 30

```
ccatggccca ggtgcagctg gtgcaatctg gggctgaggt gaagaagcct ggggcctcag    60
tgaaggtctc ctgcaaggct tctggaggca ccttcagcag ctatgctatc agctgggtgc   120
gacaggcccc tggacaaggg cttgagtgga tgggaggttt tgatcctgaa gatggtgaaa   180
caatctacgc acagaagttc cagggcagag tcaccatgac cgaggacaca tctacagaca   240
cagcctacat ggagctgagc agcctgagat ctgaggacac ggccgtgtat tactgtgcaa   300
caggacgttc tatggttcgg ggagtcatta ccttttaa cggtatggac gtctggggcc    360
aagggaccac ggtcaccgtc tcctcaaagc tttcagggag tgcatccgcc ccaaaacttg   420
aagaaggtga atttcagaa gcacgcgtag acatccggat gacccagtct ccatcctccc   480
tgtctgcatc tgtaggagac agagtcacca tcacttgccg ggcaagtcag agcattagca   540
gctatttaaa ttggtatcag cagaaaccag ggaaagcccc taagctcctg atctatgctg   600
catccagttt gcaaagtggg gtcccatcaa ggttcagtgg cagtggatct gggacagatt   660
tcactctcac catcagcagt ctgcaacctg aagattttgc aacttactac tgtcaacaga   720
gttacagtac cccgctcact ttcggcggag ggaccaaggt ggagatcaaa gcggccgc    778
```

<210> SEQ ID NO 31
<211> LENGTH: 1368
<212> TYPE: DNA
<213> ORGANISM: artificial sequence
<220> FEATURE:
<223> OTHER INFORMATION: chimeric heavy chain

<400> SEQUENCE: 31

```
caggtgcagc tggtgcaatc tggggctgag gtgaagaagc ctggggcctc agtgaaggtc     60
tcctgcaagg cttctggagg caccttcagc agctatgcta tcagctgggt gcgacaggcc    120
cctggacaag gcttgagtg gatgggaggt tttgatcctg aagatggtga acaatctac      180
gcacagaagt tccagggcag agtcaccatg accgaggaca tctacagaca cagcctac      240
atggagctga gcagcctgag atctgaggac acggccgtgt attactgtgc aacaggacgt    300
tctatggttc ggggagtcat tatccttt aacggtatgg acgtctgggg ccaagggacc      360
acggtcaccg tctcctcacg cgccgatgct gcaccgactg tctatccact ggcccctgtg    420
tgtggagata caactggctc ctcggtgact ctaggatgcc tggtcaaggg ttatttccct    480
gagccagtga ccttgacctg gaactctgga tccctgtcca gtggtgtgca ccttccca      540
gctgtcctgc agtctgacct ctacaccctc agcagctcag tgactgtaac ctcgagcacc    600
tggcccagcc agtccatcac ctgcaatgtg gcccacccgg caagcagcac caaggtggac    660
aagaaagagc ccagagggcc acaatcaag ccctgtcctc catgcaaatg cccagcacct    720
aacctcttgg gtggaccatc cgtcttcatc ttccctccaa agatcaagga tgtactcatg    780
atctccctga gccccatagt cacatgtgtg gtggtggatg tgagcgagga tgacccagat    840
gtccagatca gctggtttgt gaacaacgtg gaagtacaca gctcagac acaaaccat       900
agagaggatt acaacagtac tctccgggtg gtcagtgccc tccccatcca gcaccaggac    960
tggatgagtg gcaaggagtt caaatgcaag gtcaacaaca agacctccc agcgcccatc   1020
gagagaacca tctcaaaacc caagggtca gtaagagctc acaggtata tgtcttgcct    1080
ccaccagaag aagagatgac taagaaacag gtcactctga cctgcatggt cacagacttc   1140
atgcctgaag acatttacgt ggagtggacc aacaacggga aaacagagct aaactacaag   1200
aacactgaac cagtcctgga ctctgatggt tcttacttca tgtacagcaa gctgagagtg   1260
gaaaagaaga actgggtgga agaaatagc tactcctgtt cagtggtcca cgagggtctg    1320
cacaatcacc acacgactaa gagcttctcc cggactccgg gtaaatga               1368
```

<210> SEQ ID NO 32
<211> LENGTH: 455
<212> TYPE: PRT
<213> ORGANISM: artificial sequence
<220> FEATURE:
<223> OTHER INFORMATION: chimeric heavy chain

<400> SEQUENCE: 32

```
Gln Val Gln Leu Val Gln Ser Gly Ala Glu Val Lys Lys Pro Gly Ala
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80
```

```
Met Glu Leu Ser Ser Leu Arg Ser Glu Asp Thr Ala Val Tyr Tyr Cys
                85                  90                  95

Ala Thr Gly Arg Ser Met Val Arg Gly Val Ile Ile Pro Phe Asn Gly
                100                 105                 110

Met Asp Val Trp Gly Gln Gly Thr Thr Val Thr Val Ser Ser Arg Ala
                115                 120                 125

Asp Ala Ala Pro Thr Val Tyr Pro Leu Ala Pro Val Cys Gly Asp Thr
            130                 135                 140

Thr Gly Ser Ser Val Thr Leu Gly Cys Leu Val Lys Gly Tyr Phe Pro
145                 150                 155                 160

Glu Pro Val Thr Leu Thr Trp Asn Ser Gly Ser Leu Ser Ser Gly Val
                165                 170                 175

His Thr Phe Pro Ala Val Leu Gln Ser Asp Leu Tyr Thr Leu Ser Ser
            180                 185                 190

Ser Val Thr Val Thr Ser Ser Thr Trp Pro Ser Gln Ser Ile Thr Cys
        195                 200                 205

Asn Val Ala His Pro Ala Ser Ser Thr Lys Val Asp Lys Lys Glu Pro
        210                 215                 220

Arg Gly Pro Thr Ile Lys Pro Cys Pro Pro Cys Lys Cys Pro Ala Pro
225                 230                 235                 240

Asn Leu Leu Gly Gly Pro Ser Val Phe Ile Phe Pro Pro Lys Ile Lys
                245                 250                 255

Asp Val Leu Met Ile Ser Leu Ser Pro Ile Val Thr Cys Val Val Val
                260                 265                 270

Asp Val Ser Glu Asp Asp Pro Asp Val Gln Ile Ser Trp Phe Val Asn
            275                 280                 285

Asn Val Glu Val His Thr Ala Gln Thr Gln Thr His Arg Glu Asp Tyr
290                 295                 300

Asn Ser Thr Leu Arg Val Val Ser Ala Leu Pro Ile Gln His Gln Asp
305                 310                 315                 320

Trp Met Ser Gly Lys Glu Phe Lys Cys Lys Val Asn Asn Lys Asp Leu
                325                 330                 335

Pro Ala Pro Ile Glu Arg Thr Ile Ser Lys Pro Lys Gly Ser Val Arg
                340                 345                 350

Ala Pro Gln Val Tyr Val Leu Pro Pro Glu Glu Glu Met Thr Lys
            355                 360                 365

Lys Gln Val Thr Leu Thr Cys Met Val Thr Asp Phe Met Pro Glu Asp
            370                 375                 380

Ile Tyr Val Glu Trp Thr Asn Asn Gly Lys Thr Glu Leu Asn Tyr Lys
385                 390                 395                 400

Asn Thr Glu Pro Val Leu Asp Ser Asp Gly Ser Tyr Phe Met Tyr Ser
                405                 410                 415

Lys Leu Arg Val Glu Lys Lys Asn Trp Val Glu Arg Asn Ser Tyr Ser
                420                 425                 430

Cys Ser Val Val His Glu Gly Leu His Asn His His Thr Lys Ser
            435                 440                 445

Phe Ser Arg Thr Pro Gly Lys
            450                 455

<210> SEQ ID NO 33
<211> LENGTH: 642
<212> TYPE: DNA
<213> ORGANISM: artificial sequence
<220> FEATURE:
<223> OTHER INFORMATION: chimeric light chain
```

<400> SEQUENCE: 33

```
gatatcagga tgacgcagag tccaagctct ctgtctgcct ctgtggggga cagggtgact        60
attacttgtc gggcatcaca gagtatctcc agctacctta attggtacca gcaaaagccc       120
ggcaaagccc ccaaattgct gatttacgca gccagctccc ttcagtctgg cgtccctagc       180
cgcttctccg ggagcggatc aggcacagac tttacgttga caatcagttc tctgcagccg       240
gaggattttg ccacttacta ctgtcaacag agctacagta cgcctctcac gtttggcggt       300
gggacaaagg tggaaatcaa acgggctgat gctgcaccga ctgtgtccat cttcccacca       360
tccagtgagc agttaacatc tggaggtgcc tcagtcgtgt gcttcttgaa caacttctac       420
cccaaagaca tcaatgtcaa gtggaagatt gatggcagtg aacgacaaaa tggcgtcctg       480
aacagttgga ctgatcagga cagcaaagac agcacctaca gcatgagcag caccctcacg       540
ttgaccaagg acgagtatga acgacataac agctatacct gtgaggccac tcacaagaca       600
tcaacttcac ccattgtcaa gagcttcaac aggaatgagt gt                          642
```

<210> SEQ ID NO 34
<211> LENGTH: 214
<212> TYPE: PRT
<213> ORGANISM: artificial sequence
<220> FEATURE:
<223> OTHER INFORMATION: chimeric light chain

<400> SEQUENCE: 34

```
Asp Ile Arg Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

ANTI-VEGF ANTIBODY COMPOSITIONS AND METHODS

CROSS-REFERENCE TO RELATED APPLICATIONS

The present application claims priority to first U.S. provisional application Ser. No. 60/987,015, filed Nov. 9, 2007, second U.S. provisional application Ser. No. 61/106,047, filed Oct. 16, 2008, and third U.S. provisional application Ser. No. 61/108,023, filed Oct. 24, 2008, the entire specification, claims, sequences and drawings of which are incorporated herein by reference without disclaimer.

BACKGROUND OF THE INVENTION

1. Field of the Invention

The present invention relates generally to the fields of antibodies, angiogenesis and tumor treatment. More particularly, it provides human anti-VEGF antibodies that specifically inhibit VEGF binding to only one (VEGFR2) of the two VEGF receptors. Such antibodies are designed to inhibit angiogenesis and induce tumor regression, and yet have improved safety due to their specific blocking properties. The antibody-based compositions and methods of the invention also extend to the use of immunoconjugates and other therapeutic combinations, kits and methods.

2. Description of the Related Art

Tumor cell resistance to chemotherapeutic agents represents a significant problem in clinical oncology. In fact, this is one of the main reasons why many of the most prevalent forms of human cancer still resist effective chemotherapeutic intervention, despite certain advances in this field.

Another tumor treatment strategy is the use of an "immunotoxin", in which an anti-tumor cell antibody is used to deliver a toxin to the tumor cells. However, in common with chemotherapeutic approaches, immunotoxin therapy also suffers from significant drawbacks when applied to solid tumors. For example, antigen-negative or antigen-deficient cells can survive and repopulate the tumor or lead to further metastases.

A further reason for solid tumor resistance to antibody-based therapies is that the tumor mass is generally impermeable to macromolecular agents such as antibodies and immunotoxins (Burrows et al., 1992; Dvorak et al., 1991a; Baxter and Jain, 1991). Both the physical diffusion distances and the interstitial pressure within the tumor are significant limitations to this type of therapy. Therefore, solid tumors, which make up over 90% of all human cancers, have thus far proven resistant to antibody and immunotoxin treatment.

A more recent strategy has been to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients (Burrows and Thorpe, 1993; 1994). Exemplary vascular targeting strategies are described in U.S. Pat. Nos. 5,855,866 and 5,965,132, which particularly describe the targeted delivery of anti-cellular agents and toxins to markers of tumor vasculature.

Another effective version of the vascular targeting approach is to target a coagulation factor to a marker expressed or adsorbed within the tumor vasculature (Huang et al., 1997; U.S. Pat. Nos. 5,877,289, 6,004,555, and 6,093,399). The delivery of coagulants, rather than toxins, to tumor vasculature has the further advantages of reduced immunogenicity and even lower risk of toxic side effects. As disclosed in U.S. Pat. No. 5,877,289, a preferred coagulation factor for use in such tumor-specific "coaguligands" is a truncated version of the human coagulation-inducing protein, Tissue Factor (TF), the major initiator of blood coagulation.

Although the specific delivery of toxins and coagulation factors to tumor blood vessels represents a significant advance in tumor treatment, certain peripheral tumor cells can survive the intratumoral destruction caused by such therapies. Anti-angiogenic strategies would therefore be of use in combination with the tumor destruction methods of U.S. Pat. Nos. 5,855,866 and 6,004,555.

Anti-angiogenic tumor treatment strategies are based upon inhibiting the proliferation of budding vessels, generally at the periphery of a solid tumor. These therapies are particularly effective in reducing the risk of micrometastasis and inhibiting growth of a solid tumor after, or in conjunction with, more conventional intervention (such as surgery or chemotherapy).

Angiogenesis is the development of new vasculature from preexisting blood vessels and/or circulating endothelial stem cells (Asahara et al., 1997; Springer et al., 1998; Folkman and Shing, 1992). Angiogenesis plays a vital role in many physiological processes, such as embryogenesis, wound healing and menstruation. Angiogenesis is also important in certain pathological events. In addition to a role in solid tumor growth and metastasis, other notable conditions with an angiogenic component are arthritis, psoriasis and diabetic retinopathy (Hanahan and Folkman, 1996; Fidler and Ellis, 1994).

Angiogenesis is regulated in normal and malignant tissues by the balance of angiogenic stimuli and angiogenic inhibitors that are produced in the target tissue and at distant sites (Fidler et al., 1998; McNamara et al., 1998). Vascular endothelial growth factor-A (VEGF, also known as vascular permeability factor, VPF) is a primary stimulant of angiogenesis. VEGF is a multifunctional cytokine that is induced by hypoxia and oncogenic mutations and can be produced by a wide variety of tissues (Kerbel et al., 1998; Mazure et al., 1996).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (Siemeister et al., 1998). Following the inhibition of tumor growth in mice using a murine antibody, (Kim et al., 1993; Asano et al., 1998; Mesiano et al., 1998; Luo et al., 1998a; 1998b; Borgstrom et al., 1996; 1998), a humanized anti-VEGF antibody termed Avastin (bevacizumab) (Presta et al., 1997) has been approved for clinical use (Hurwitz et al., 2004).

Other murine antibodies that recognize VEGF and inhibit VEGF-induced functions have been reported. These include the murine antibody termed 2C3, which has the advantage of inhibiting VEGF binding to only one of the two primary VEGF receptors (Brekken et al., 2000). By blocking VEGF binding to VEGFR2, but not VEGFR1, the murine 2C3 antibody has an improved safety profile, maintaining beneficial effects mediated via VEGFR1 (Brekken et al., 2000; U.S. Pat. Nos. 6,342,219, 6,524,583, 6,342,221).

The inventors have recognized, however, that the identification of additional agents that recognize VEGF and inhibit VEGF-induced angiogenesis would be of benefit in expanding the number of therapeutic options. For example, the murine 2C3 antibody, although promising, has certain limitations. In particular, the 2C3 antibody does not bind to mouse VEGF, meaning that it cannot be used in preclinical studies using mouse syngeneic tumors. The most effective translation from preclinical studies to clinical use would thus benefit from the development of a new antibody that binds to both mouse and human VEGF.

In addition, the inventors have recognized that the development of therapeutic agents for the treatment of humans that are better tolerated from an immunological perspective would be advantageous. In this regard, human antibodies generally have at least three potential advantages for use in human therapy. First, the human immune system should not recognize the antibody as foreign. Second, the half-life in the human circulation will be similar to naturally occurring human antibodies, allowing smaller and less frequent doses to be given. Third, because the effector portion is human, it will interact better with the other parts of the human immune system, e.g., to destroy target cells more efficiently by complement-dependent cytotoxicity (CDC) or antibody-dependent cellular cytotoxicity (ADCC).

However, although human antibodies are generally recognized to display these advantages, it is known that the development of human antibodies that have high enough affinities and appropriate functional properties to make them candidates for successful human therapy is by no means straightforward. The art therefore still lacks agents that inhibit VEGF-induced angiogenesis for the safe and effective treatment of humans, and poses challenges to the development of such agents.

SUMMARY OF THE INVENTION

The present invention overcomes certain limitations in the prior art by providing new therapeutic compositions and methods for use in anti-angiogenic and anti-tumor treatment. The invention is based on human antibodies that have the functional property of specifically inhibiting VEGF binding to only one (VEGFR2) of the two primary VEGF receptors, and have an affinity for VEGF high enough for effective treatment regimens. Such antibodies inhibit angiogenesis and treat tumors as effectively as other anti-VEGF antibodies, including those already approved for clinical use, and yet have improved safety due to their specific blocking properties. The compositions and methods of the invention also extend to the use of immunoconjugates and combinations, including prodrugs, using the specific category of antibodies provided.

A particular advantage of the present invention is that the human antibodies provided inhibit VEGF binding only to VEGFR2, and not VEGFR1. This contrasts with the leading antibodies in the prior art, including A4.6.1 and the humanized version, Avastin, which inhibit VEGF binding to both VEGFR2 and VEGFR1. As VEGFR1 has important biological roles unconnected to angiogenesis, e.g., in osteoclast and chondroclast function, the present ability to inhibit only VEGFR2-mediated angiogenesis is a distinct advantage. This translates into notable clinical benefits in that bone metabolism, e.g., in the treatment of pediatric cancers, is not adversely affected. The harmful effects of macrophages on tumor progression and metastasis are also inhibited, as this population of macrophages expresses VEGFR2, which is inhibited by the antibodies of the invention.

A further advantage is that, as binding of VEGF to VEGFR1 is maintained in the presence of the antibodies of the invention, they can be used to specifically deliver attached therapeutic agents to tumor vasculature by virtue of binding to VEGF that is bound to VEGFR1, which is upregulated on tumor endothelium. In the context of immunoconjugates, therefore, the present invention provides agents that have both anti-angiogenic and tumor destructive properties within the same molecule.

Yet a further advantage exists in the ability of the compositions provided to neutralize the survival signal of VEGF, which is mediated through VEGFR2. The naked and conjugated antibodies of the invention thus form synergistic combinations with other therapies and/or attached agents, particularly those methods and agents that fail to achieve maximal effectiveness in vivo due to the ability of VEGF to counteract their destructive properties.

Amino acid and/or DNA sequences of antibody molecules of the invention that bind to VEGF, their $V_H$ and $V_L$ domains including complementarity determining regions (CDRs), are set forth in the various SEQ ID NOs. listed herein.

In one embodiment, the present invention provides an antibody that binds to VEGF comprising a heavy chain CDR1 domain comprising the amino acid sequence of SEQ ID NO:5 or a sequence substantially homologous thereto.

Alternatively or in addition, in an embodiment of the invention, the antibody that binds to VEGF comprises a heavy chain CDR2 domain comprising the amino acid sequence of SEQ ID NO:6 or a sequence substantially homologous thereto.

Alternatively or in addition, in an embodiment of the invention, the antibody that binds to VEGF comprises a heavy chain CDR3 domain comprising the amino acid sequence of SEQ ID NO:7 or a sequence substantially homologous thereto.

Alternatively or in addition, in an embodiment of the invention, the antibody that binds to VEGF comprises a light chain CDR1 domain comprising the amino acid sequence of SEQ ID NO:8 or a sequence substantially homologous thereto.

Alternatively or in addition, in an embodiment of the invention, the antibody that binds to VEGF comprises a light chain CDR2 domain comprising the amino acid sequence of SEQ ID NO:9 or a sequence substantially homologous thereto.

Alternatively or in addition, in an embodiment of the invention, the antibody that binds to VEGF comprises a light chain CDR3 domain comprising the amino acid sequence of SEQ ID NO:10 or a sequence substantially homologous thereto.

Thus, in certain embodiments, the invention provides
an antibody that binds to VEGF comprising one or more heavy chain CDR domains,
wherein the heavy chain CDR domain is selected from the group consisting of:
(a) a heavy chain CDR1 domain comprising the amino acid sequence of SEQ ID NO:5 or a sequence substantially homologous thereto;
(b) a heavy chain CDR2 domain comprising the amino acid sequence of SEQ ID NO:6 or a sequence substantially homologous thereto; and
(c) a heavy chain CDR3 domain comprising the amino acid sequence of SEQ ID NO:7 or a sequence substantially homologous thereto.

The invention also provides, in certain embodiments
an antibody that binds to VEGF comprising one or more light chain CDR domains, wherein
the light chain CDR domain is selected from the group consisting of:
(a) a light chain CDR1 domain comprising the amino acid sequence of SEQ ID NO:8 or a sequence substantially homologous thereto;

(b) a light chain CDR2 domain comprising the amino acid sequence of SEQ ID NO:9 or a sequence substantially homologous thereto; and
(c) a light chain CDR3 domain comprising the amino acid sequence of SEQ ID NO:10 or a sequence substantially homologous thereto.

In certain preferred embodiments, the antibody that binds to VEGF comprises both
(a) a heavy chain CDR3 comprising the amino acid sequence of SEQ ID NO:7 or a sequence substantially homologous thereto and
(b) a light chain CDR3 comprising the amino acid sequence of SEQ ID NO:10 or a sequence substantially homologous thereto.

More preferably, a heavy chain CDR1 domain comprising the amino acid sequence of SEQ ID NO:5 or a sequence substantially homologous thereto and/or a light chain CDR1 domain comprising the amino acid sequence of SEQ ID NO:8 or a sequence substantially homologous thereto, and/or a heavy chain CDR2 domain comprising the amino acid sequence of SEQ ID NO:6 or a sequence substantially homologous thereto and/or a light chain CDR2 domain comprising the amino acid sequence of SEQ ID NO:9 or a sequence substantially homologous thereto, are also present.

In one preferred embodiment, the heavy chain CDR1 comprising the amino acid sequence of SEQ ID NO:5 or a sequence substantially homologous thereto, CDR2 comprising the amino acid sequence of SEQ ID NO:6 or a sequence substantially homologous thereto, and CDR3 comprising the amino acid sequence of SEQ ID NO:7, or a sequence substantially homologous thereto, are present individually or in combination.

In yet another preferred embodiment, the light chain CDR1 comprising the amino acid sequence of SEQ ID NO:8 or a sequence substantially homologous thereto, CDR2 comprising the amino acid sequence of SEQ ID NO:9 or a sequence substantially homologous thereto, and CDR3 comprising the amino acid sequence of SEQ ID NO:10 or a sequence substantially homologous thereto, are present individually or in combination.

Viewed alternatively, in certain embodiments, the present invention provides an antibody that binds to VEGF comprising
a heavy chain CDR3 domain comprising the amino acid sequence of SEQ ID NO:7 or a sequence substantially homologous thereto and/or a light chain CDR3 domain comprising the amino acid sequence of SEQ ID NO:10 or a sequence substantially homologous thereto. Said antibody optionally further comprises
a heavy chain CDR2 domain comprising the amino acid sequence of SEQ ID NO:6 or a sequence substantially homologous thereto and/or a light chain CDR2 domain comprising the amino acid sequence of SEQ ID NO:9 or a sequence substantially homologous thereto and/or further comprises
a heavy chain CDR1 domain comprising the amino acid sequence of SEQ ID NO:5 or a sequence substantially homologous thereto and/or
a light chain CDR1 domain comprising the amino acid sequence of SEQ ID NO:8 or a sequence substantially homologous thereto.

Viewed alternatively, in certain embodiments, the present invention provides an antibody that binds to VEGF comprising
a heavy chain CDR2 domain comprising the amino acid sequence of SEQ ID NO:6 or a sequence substantially homologous thereto and/or a light chain CDR2 domain comprising the amino acid sequence of SEQ ID NO:9 or a sequence substantially homologous thereto.
Said antibody optionally further comprises
a heavy chain CDR3 domain comprising the amino acid sequence of SEQ ID NO:7 or a sequence substantially homologous thereto and/or a light chain CDR3 domain comprising the amino acid sequence of SEQ ID NO:10 or a sequence substantially homologous thereto and/or further comprises
a heavy chain CDR1 domain comprising the amino acid sequence of SEQ ID NO:5 or a sequence substantially homologous thereto and/or
a light chain CDR1 domain comprising the amino acid sequence of SEQ ID NO:8 or a sequence substantially homologous thereto.

Viewed alternatively, in certain embodiments, the present invention provides an antibody that binds to VEGF comprising
a heavy chain CDR1 domain comprising the amino acid sequence of SEQ ID NO:5 or a sequence substantially homologous thereto and/or a light chain CDR1 domain comprising the amino acid sequence of SEQ ID NO:8 or a sequence substantially homologous thereto.
Said antibody optionally further comprises
a heavy chain CDR3 domain comprising the amino acid sequence of SEQ ID NO:7 or a sequence substantially homologous thereto and/or a light chain CDR3 domain comprising the amino acid sequence of SEQ ID NO:10 or a sequence substantially homologous thereto and/or further comprises
a heavy chain CDR2 domain comprising the amino acid sequence of SEQ ID NO:6 or a sequence substantially homologous thereto and/or
a light chain CDR2 domain comprising the amino acid sequence of SEQ ID NO:9 or a sequence substantially homologous thereto.

Certain preferred antibodies of the invention comprise one or more of the CDRs selected from the group consisting of SEQ ID NOs:5, 6, 7, 8, 9 and 10 or a sequence substantially homologous to any one of the foregoing SEQ ID NOs.

Certain preferred antibodies comprise two or more of the light chain CDRs of SEQ ID NOs:8, 9 or 10, or sequences substantially homologous to any one of the foregoing SEQ ID NOs. Especially preferred binding molecules comprise 3 of the light chain CDRs of SEQ ID NOs:8, 9 or 10, or sequences substantially homologous to any one of the foregoing SEQ ID NOs (i.e. one of each of the aforementioned light chain CDR1 and CDR2 and CDR3 or sequences substantially homologous thereto).

Other certain preferred antibodies comprise two or more of the heavy chain CDRs of SEQ ID NOs:5, 6 or 7, or sequences substantially homologous to any one of the foregoing SEQ ID NOs. Especially preferred binding molecules comprise 3 of the heavy chain CDRs of SEQ ID NOs:5, 6 and 7, or sequences substantially homologous to any one of the foregoing SEQ ID NOs (i.e., one of each of the aforementioned heavy chain CDR1 and CDR2 and CDR3 or sequences substantially homologous thereto).

Certain more especially preferred antibodies comprise 3 of the light chain CDRs of SEQ ID NOs:8, 9 or 10 or sequences substantially homologous to any one of these sequences (i.e., one of each of the aforementioned light chain CDR1 and CDR2 and CDR3 or sequences substantially homologous thereto), and 3 of the heavy chain CDRs of SEQ ID NOs:5, 6 or 7, or sequences substantially homologous any one of these sequences (i.e., one of each of the aforementioned heavy chain CDR1 and CDR2 and CDR3 or sequences substantially homologous thereto).

Certain especially preferred antibodies comprise
a heavy chain CDR1 domain of SEQ ID NO:5,
a heavy chain CDR2 domain of SEQ ID NO:6, and
a heavy chain CDR3 domain of SEQ ID NO:7,
or sequences substantially homologous to any one of the aforementioned sequences; and/or comprise
a light chain CDR1 domain of SEQ ID NO:8,
a light chain CDR2 domain of SEQ ID NO:9, and
a light chain CDR3 domain of SEQ ID NO:10,
or sequences substantially homologous to any one of the aforementioned sequences.

In a further embodiment, the invention provides an antibody that binds to VEGF and that comprises at least one heavy chain variable region that comprises three CDRs and at least one light chain variable region that comprises three CDRs, wherein said light chain variable region comprises:
(i) a variable light (VL) CDR1 that has the amino acid sequence of SEQ ID NO:8,
(ii) a VL CDR2 that has the amino acid sequence of SEQ ID NO:9, and
(iii) a VL CDR3 that has the amino acid sequence of SEQ ID NO:10.

In a preferred aspect of this embodiment, one or more of said heavy chain variable region CDRs are selected from the group consisting of:
(i) a VH CDR1 that has the amino acid sequence of SEQ ID NO:5,
(ii) a VH CDR2 that has the amino acid sequence of SEQ ID NO:6, and
(iii) a VH CDR3 that has the amino acid sequence of SEQ ID NO:7.

In a further preferred aspect of this embodiment, two of said heavy chain variable region CDRs are selected from the group consisting of: (i) a VH CDR1 that has the amino acid sequence of SEQ ID NO:5,
(ii) a VH CDR2 that has the amino acid sequence of SEQ ID NO:6, and
(iii) a VH CDR3 that has the amino acid sequence of SEQ ID NO:7.

In a yet further preferred aspect of this embodiment, three of said heavy chain variable region CDRs are selected from the group consisting of:
(i) a VH CDR1 that has the amino acid sequence of SEQ ID NO:5,
(ii) a VH CDR2 that has the amino acid sequence of SEQ ID NO:6, and
(iii) a VH CDR3 that has the amino acid sequence of SEQ ID NO:7.

Certain further preferred embodiments of the invention provide an antibody that binds to VEGF and that comprises:
a VH domain that comprises one, two or three of the heavy chain CDRs of SEQ ID NOs:5, 6, or 7, or sequences substantially homologous to one or more of SEQ ID NOs:5, 6, or 7, and/or
a VL domain that comprises one, two or three of the light chain CDRs of SEQ ID NOs:8, 9 or 10, or sequences substantially homologous to one or more of SEQ ID NOs: 8, 9 or 10.

Especially preferred VL domains comprise 3 of the light chain CDRs of SEQ ID NOs:8, 9 and 10, or sequences substantially homologous to one or more of SEQ ID NOs:8, 9 or 10, (i.e., one of each of CDR1, CDR2 and CDR3 or sequences substantially homologous thereto).

Especially preferred VH domains comprise 3 of the heavy chain CDRs of SEQ ID NOs:5, 6, and 7, or sequences substantially homologous to one or more of SEQ ID NOs:5, 6, or 7 (i.e., one of each of CDR1, CDR2 and CDR3 or sequences substantially homologous thereto).

More especially preferred embodiments of the invention provide an antibody that binds to VEGF and that comprises:
a VL domain that comprises 3 light chain CDRs of SEQ ID NOs:8, 9 and 10, and
a VH domain that comprises 3 heavy chain CDRs. In preferred embodiments one, two or three of the heavy chain CDRs are as defined in SEQ ID NOs:5, 6, and 7.

Certain preferred embodiments of the invention provide an antibody that binds VEGF comprising a VH domain that has the amino acid sequence of SEQ ID NO:3 or a sequence substantially homologous thereto and/or a VL domain that has the amino acid sequence of SEQ ID NO:4 or a sequence substantially homologous thereto.

Further preferred embodiments provide an antibody that binds VEGF comprising a VL domain that has the amino acid sequence of SEQ ID NO:4 and a VH domain that comprises 3 heavy chain CDRs. Preferably said VH domain has the amino acid sequence of SEQ ID NO:3.

In a yet further embodiment, the present invention provides an antibody that binds VEGF comprising the amino acid sequence of SEQ ID NO:21 (said antibody also being referred to herein as r84 or PGN311 or EJ173/112-Cl1), or comprising a fragment thereof that binds VEGF, or a sequence substantially homologous thereto.

In a further embodiment, the present invention provides an antibody that binds VEGF comprising the amino acid sequence of SEQ ID NO:21 (said antibody also being referred to herein as r84 or PGN311 or EJ173/112-Cl1), or comprising a fragment thereof that binds VEGF.

The invention is exemplified by monoclonal antibody r84 (also referred to herein as PGN311 and EJ-173-112-Cl1), a single chain form of which is shown in FIG. 1 (SEQ ID NO:21 and SEQ ID NO:20) and a full length IgG form of which is shown in Example 6. The CDR domains, VH and VL domains of the r84 antibody are shown in Table 1 and FIG. 1. Antibodies comprising these CDR domains or VH and VL domains (or sequences substantially homologous thereto) are preferred aspects of the invention.

A preferred embodiment of the invention is a scFv form of the r84 antibody shown in SEQ ID NO:21 (amino acid), which is preferably encoded by SEQ ID NO:20 (nucleic acid).

Another preferred embodiment of the invention is a full length IgG form of the r84 antibody, the heavy chain of which is shown in SEQ ID NO:24 (amino acid), which is preferably encoded by SEQ ID NO:22 (nucleic acid); and the light chain of which is shown in SEQ ID NO:25 (amino acid), which is preferably encoded by SEQ ID NO:23 (nucleic acid).

Certain examples of substantially homologous sequences are sequences that have at least 70% identity to the amino acid sequences disclosed.

In certain embodiments, the antibodies of the invention that bind to VEGF comprise at least one light chain variable region that includes an amino acid sequence region of at least about 75%, more preferably at least about 80%, more preferably at least about 85%, more preferably at least about 90% or 95% and most preferably at least about 97%, 98% or 99% amino acid sequence identity to the amino acid sequence of SEQ ID NO:4; and/or at least one heavy chain variable region that includes an amino acid sequence region of at least about 75%, more preferably at least about 80%, more preferably at least about 85%, more preferably at least about 90% or 95% and most preferably at least about 97%, 98% or 99% amino acid sequence identity to the amino acid sequence of SEQ ID NO:3.

Other preferred examples of substantially homologous sequences are sequences containing conservative amino acid substitutions of the amino acid sequences disclosed.

Other preferred examples of substantially homologous sequences are sequences containing 1, 2 or 3, preferably 1 or 2, altered amino acids in one or more of the CDR regions disclosed. Such alterations might be conserved or non-conserved amino acid substitutions, or a mixture thereof.

In all such embodiments, preferred alterations are conservative amino acid substitutions.

In all embodiments, the antibodies containing substantially homologous sequences retain the ability to bind VEGF.

In embodiments of the invention where alterations in the light chain CDR3 domain are contemplated, it is preferred that the L residue at position 8 in said CDR is retained without variation.

Other embodiments of the present invention provide binding proteins that bind to VEGF and that comprise an antibody of the invention, a VH or VL domain of the invention, or one or more of the CDRs of the invention. In a preferred embodiment, such binding proteins are antibodies.

Preferred antibodies of the invention comprise at least one heavy chain variable region that comprises three CDRs and at least one light chain variable region that comprises three CDRs. Exemplary and preferred sequences for these CDRs are described herein.

As used herein, the succinct term "VEGF", unless otherwise specifically stated or made clear from the scientific terminology, means Vascular Endothelial Growth Factor-A (VEGF-A), also known as vascular permeability factor, VPF.

"VEGF" also means any form of VEGF, particularly as VEGF is conserved across mammalian species. The antibodies or antibody fragments of the invention may thus bind to human, monkey, cow (bovine), mouse, rat, hamster, ferret, guinea pig and/or rabbit VEGF, for example. Preferably, the antibodies or antibody fragments of the invention will bind at least to human VEGF. In certain preferred embodiments, the antibodies or antibody fragments of the invention will bind at least to human and mouse VEGF.

As used herein, the term "that binds VEGF" in the context of antibodies or antibody fragments of the present invention, means human antibodies or antibody fragments that are capable of one or more of the following; preferably, of more than one of the following; and most preferably, of all of the following:

(a) bind to a non-conformationally dependent VEGF epitope, as assessed by binding to VEGF in a Western blot;
(b) bind to free VEGF or to VEGF on a solid support;
(c) bind at least to human VEGF and mouse VEGF;
(d) significantly inhibit or significantly reduce VEGF binding to the VEGF receptor VEGFR2 (KDR/Flk-1);
(e) do not significantly inhibit VEGF or reduce binding to the VEGF receptor VEGFR1 (Flt-1);
(f) inhibit, and preferably, significantly inhibit, VEGF-induced phosphorylation of VEGFR2;
(g) inhibit, and preferably, significantly inhibit, VEGF-induced vascular permeability;
(h) inhibit, and preferably, significantly inhibit, VEGF-mediated endothelial cell proliferation;
(i) inhibit, and preferably, significantly inhibit, angiogenesis;
(j) inhibit, and preferably, significantly inhibit, lymphangiogenesis;
(k) do not significantly inhibit VEGFR1-mediated stimulation or activation of cells, such as VEGFR1-expressing osteoclasts or chondroclasts; and/or
(l) localize to tumor vasculature and/or tumor stroma upon administration to an animal with a vascularized tumor.

Most preferably, the human antibody or antibody fragment of the invention is one that significantly inhibits VEGF binding to the VEGF receptor VEGFR2 (KDR/Flk-1) without significantly inhibiting VEGF binding to the VEGF receptor VEGFR1 (Flt-1).

The present invention therefore provides human antibodies that specifically block VEGF binding to the VEGFR2 receptor, or that block VEGF binding to essentially only the VEGFR2 receptor. Such human antibodies significantly inhibit VEGF binding to the VEGFR2 receptor (KDR/Flk-1) without significantly inhibiting VEGF binding to the VEGFR1 receptor (Flt-1). Such human antibodies thus inhibit VEGF binding to the VEGFR2 receptor (KDR/Flk-1), do not substantially inhibit VEGF binding to the VEGFR1 receptor (Flt-1), exhibit anti-angiogenic and anti-tumor effects in vivo and do not significantly inhibit VEGFR1-mediated events, such as osteoclast or chondroclast functions.

The human antibodies of the invention are thus succinctly termed "VEGFR2-blocking, non-VEGFR1-blocking, human anti-VEGF antibodies". Even more succinctly, they are termed "VEGFR2-blocking, human anti-VEGF antibodies", which is used for simplicity in reference to all compositions, uses and methods of the invention. A "VEGFR2-blocking, human anti-VEGF antibody" is a human antibody against VEGF that blocks VEGF binding to the VEGFR2 receptor. It will be clear that such antibodies are not antibodies against the VEGFR2 receptor itself In light of this invention, therefore, a range of VEGFR2-blocking, human anti-VEGF antibodies can be made and used in a variety of embodiments, including in the inhibition of angiogenesis and the treatment of angiogenic diseases and tumors without inhibiting VEGF signaling via the VEGFR1 receptor and without the notable drawbacks and side effects associated therewith.

In certain embodiments, the present application further describes methodology for generating candidate VEGFR2-blocking, human anti-VEGF antibodies and the routine technical aspects of the assays required to identify actual VEGFR2-blocking specific antibodies from the pool of candidates.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

Human antibodies of the invention that "specifically inhibit VEGF binding to the VEGF receptor VEGFR2 (KDR/Flk-1)" can be identified by competition and/or functional assays. The preferred assays, for simplicity, are competition assays based upon an ELISA. In competition assays, one pre-mixes or admixes VEGF with varying amounts of the test antibodies (e.g., 100-fold to 1000-fold molar excess, e.g., 500-fold or 750-fold molar excess) and determines the ability of the test antibodies to reduce VEGF binding to VEGFR2. VEGF can be pre-labeled and detected directly, or can be detected using a (secondary) anti-VEGF antibody or a secondary and tertiary antibody detection system. An ELISA format of such a competition assay is a preferred format, but any type of immunocompetition assay may be conducted.

VEGF binding to VEGFR2 in the presence of a completely irrelevant antibody (including non-blocking anti-VEGF monoclonal antibodies) is the control high value (100%) in such a competition assay. In a test assay, a significant reduction in VEGF binding to VEGFR2 in the presence of a test antibody is indicative of a test antibody that significantly inhibits VEGF binding to the VEGF receptor VEGFR2 (KDR/Flk-1).

A significant reduction is a "reproducible", i.e., consistently observed, reduction in binding. A "significant reduction" in terms of the present application is defined as a reproducible reduction (in VEGF binding to VEGFR2) of at least about 50%, about 55%, about 60% or about 65% at any amount between about 100 fold and about 1000 fold (e.g., about 500 fold or about 750 fold) molar excess of antibody over VEGF. Viewed alternatively a signal of less than 50% (when compared to a control value of 100%) is considered significant inhibition of binding.

A preferred feature of the invention is that the human antibodies provided do not substantially or significantly inhibit, reduce or block VEGF binding to VEGFR1. Human antibodies that exhibit a moderately significant reduction of VEGF binding to VEGFR2 will still be useful, so long as they do not substantially inhibit VEGF binding to VEGFR1. Nonetheless, more preferred antibodies will be those that have a more significant ability to inhibit VEGF binding to VEGFR2. These antibodies are those that exhibit a reproducible ability to reduce VEGF binding to VEGFR2 by at least about 70%, about 75% or about 80% at any amount between about 100 fold and about 1000 fold (e.g., about 500 fold or about 750 fold) molar excess of antibody over VEGF. Although not required to practice the invention, antibodies that reduce VEGF binding to VEGFR2 by at least about 85%, about 90%, about 95% or even higher are by no means excluded.

Human anti-VEGF antibodies, or antigen-binding fragments thereof, that inhibit VEGF binding to the VEGF receptor VEGFR2 (KDR/Flk-1) without significantly inhibiting VEGF binding to the VEGF receptor VEGFR1 (Flt-1) are readily confirmed by simple competition assays such as those described above, but using VEGFR1.

Absence of a significant inhibition or reduction is a "reproducible", i.e., consistently observed, "substantial maintenance of binding". A "substantial maintenance of binding" in terms of the present application is defined as a reproducible maintenance (in VEGF binding to VEGFR1) of at least about 60%, about 75%, about 80% or about 85% at any amount between about 100 fold and about 1000 fold molar excess of antibody over VEGF.

The intention of using human antibodies that do not substantially inhibit VEGF binding to VEGFR1 is to maintain the biological functions mediated by VEGFR1. Therefore, an antibody need only maintain sufficient VEGF binding to VEGFR1 so that a biological response is induced by VEGF. Nonetheless, more preferred antibodies will be those that have a more significant ability to maintain VEGF binding to VEGFR1. These antibodies are those that exhibit a reproducible ability to maintain VEGF binding to VEGFR1 at levels of at least about 88%, about 90%, about 92%, about 95% or of about 98-99% at any amount between about 100 fold and about 1000 fold molar excess of antibody over VEGF.

It will be understood that human antibodies that more substantially inhibit VEGF binding to VEGFR2 can likely tolerate more reduction in binding VEGFR1. Equally, where an antibody has a moderate reduction in VEGF binding to VEGFR2, the maintenance of binding to VEGFR1 should be more stringently pursued.

Another preferred binding assay to identify and/or confirm that an antibody inhibits VEGF binding to the VEGF receptor VEGFR2 (KDR/Flk-1) is a co-precipitation assay. A co-precipitation assay tests the ability of an antibody to block the binding of VEGF to one or more receptors in solution. In such an assay, VEGF or detectably-labeled VEGF is incubated with a suitable form of the receptor.

There are many formats for conducting immunoprecipitation or co-precipitation assays. In the present case, a "suitable form of the receptor" may be the VEGFR2 receptor at issue or the extracellular domain of the receptor. Immunoprecipitation will then require, as well as the standard reagents, the presence of an antibody against the VEGFR2 receptor or an epitope on the extracellular domain of the receptor distinct from the site to which VEGF binds. The present invention provides other "suitable" forms of the VEGF receptors, namely the extracellular domains of the receptors linked to an Fc antibody portion. Such receptor/Fc constructs can be precipitated by incubation with an effective immunoprecipitating composition, such as a Protein A-based composition.

Irrespective of the suitable receptor, the immunoprecipitation or co-precipitation assays are preferably conducted with controls. The ability of VEGF alone to bind to the chosen receptor should be confirmed by precipitation in the absence of an anti-VEGF antibody. Preferably, parallel incubations are conducted in the presence or absence of an antibody with known binding properties to act as a control. Most preferably, assays using both a blocking control and non-blocking control antibody are run in parallel.

Any bound immunological species are then immunoprecipitated, e.g., by incubation with an effective immunoprecipitating composition, such as a Protein A composition or Protein A sepharose beads. The precipitate is then tested for the presence of VEGF. Where the VEGF in the initial incubation was detectably-labeled VEGF, such as radio-labeled VEGF, any VEGF in the immunoprecipitates can be detected directly. Any non-labeled VEGF in the immunoprecipitates may be detected by other suitable means, e.g., by gel separation and immunodetection with an anti-VEGF antibody.

The ability of a human antibody to block VEGF binding to a VEGF receptor, such as VEGFR2, in such a co-precipitation assay can be readily quantitated, although qualitative results are also valuable. Quantification can be achieved by direct measurement of labeled VEGF or e.g., by densitometric analyses of immunodetected VEGF. Antibodies that exhibit a reproducible, i.e., consistently observed, ability to inhibit VEGF binding to VEGFR2 can thus be detected, and useful antibodies can be chosen according to the quantitative criteria outlined above.

Human anti-VEGF antibodies that do not significantly inhibit VEGF binding to the VEGF receptor VEGFR1 (Flt-1) can also be readily identified by conducting co-precipitation assays as described above, but using VEGFR1 rather than VEGFR2. Therefore, anti-VEGF antibodies that inhibit VEGF binding to the VEGF receptor VEGFR2 (KDR/Flk-1) without significantly inhibiting VEGF binding to the VEGF receptor VEGFR1 (Flt-1) can also be readily identified using such methods.

The present application also provides various functional assays to identify and/or confirm that a human antibody significantly inhibits VEGF binding to the VEGF receptor VEGFR2 (KDR/Flk-1). These are generally related to the identification of VEGFR2 as the receptor responsible for certain defined biological responses. Although the foregoing competition-type assays, which are conducted in cell-free systems, are most reproducible, reliable, labor-saving and cost-effective, the following assays are also useful in the context of the present invention.

For example, a VEGFR2-blocking, human anti-VEGF antibody may be identified by testing for the ability to inhibit VEGF-mediated endothelial cell growth (inhibiting the mitogenic activity of VEGF). Any suitable assay may be employed using any of a variety of endothelial cells in the presence of VEGF with or without test antibodies. Preferably, duplicate assays are run in parallel, such as those without VEGF and those with control antibodies of defined properties (both blocking and non-blocking). Endothelial cell growth may be determined and preferably accurately quantified by any acceptable means of determining cell number, including colorimetric assays.

A human antibody with an ability to inhibit VEGF-mediated endothelial cell growth will generally exhibit a consistently observed inhibition of VEGF-mediated endothelial cell growth of about 25%, 30%, 35%, 40% 45% or 50% or so. Inhibition in such ranges will indicate an antibody with properties sufficient to inhibit angiogenesis in vivo. Antibodies with more significant inhibitory activity are not excluded from the invention.

Further functional assays to identify human antibodies in accordance with the present invention are assays to test blocking of VEGF-induced phosphorylation. Any suitable assay may be employed using any of a variety of endothelial cells that express any form of native or recombinant phosphorylatable VEGFR2. Cells are incubated with VEGF in the presence or absence of the antibody to be tested for a suitable time period. Preferably, duplicate assays are run in parallel, such as those without VEGF and those with control antibodies of defined properties (both blocking and non-blocking).

VEGF-induced phosphorylation of VEGFR2 may be determined and preferably accurately quantified by any acceptable means. Generally, VEGFR2 is immunoprecipitated for further analyses. The degree of phosphorylation of VEGFR2 may be determined directly, for example, the cells may have been incubated with $^{32}$P-labelled ATP, allowing direct quantification of the $^{32}$P within the immunoprecipitated VEGFR2. Preferably, the immunoprecipitated VEGFR2 are analyzed by other means, e.g., by gel separation and immunodetection with an antibody that binds to phosphotyrosine residues. A human antibody with an ability to inhibit VEGF-induced phosphorylation of VEGFR2 will generally exhibit a consistently observed reduction in the levels of phosphorylated VEGFR2.

Yet further functional assays to identify VEGFR2-blocking, human anti-VEGF antibodies in accordance with the present invention are assays to test inhibition of VEGF-induced vascular permeability. Although any such assay may be used, a particularly suitable assay is the Miles permeability assay, wherein animals such as guinea pigs are injected with a dye, such as Evan's blue dye, and the appearance of the dye in the animal skin is determined after the provision of VEGF in the presence or absence of test antibodies. Preferably, duplicate studies are conducted in parallel, such as those without VEGF and those with control antibodies of defined properties (both blocking and non-blocking). The appearance of dye in the animal skin is typically as spots, such as blue spots, in the back of the animal, which can be photographed and measured.

VEGFR2-blocking, human anti-VEGF antibodies will inhibit VEGF-induced-vascular permeability as a consistently observed inhibition at low concentrations, such as when provided at a 100-fold, or 1000-fold molar excess over VEGF. Antibodies that do not block VEGF binding to VEGFR2 will not show any significant inhibition of VEGF induced-vascular permeability. Generally, antibodies that block VEGF-induced permeability only at high concentrations, such as at a 10-fold molar excess over VEGF, will not be antibodies with properties in accordance with the present invention.

Widely accepted functional assays of angiogenesis and, hence, anti-angiogenic agents are the corneal micropocket assay of neovascularization and the chick chorio-allantoic membrane assay (CAM) assay. U.S. Pat. No. 5,712,291 is specifically incorporated herein by reference to show that the corneal micropocket and CAM assays are sufficiently predictive to identify agents for use in the treatment of an extremely wide range of angiogenic diseases.

U.S. Pat. No. 5,001,116 is also specifically incorporated herein by reference for purposes of describing the CAM assay. Essentially, fertilized chick embryos are removed from their shell on day 3 or 4, and a methylcellulose disc containing the test compound is implanted on the chorioallantoic membrane. The embryos are examined approximately 48 hours later and, if a clear avascular zone appears around the methylcellulose disc, the diameter of that zone is measured. As disclosed in U.S. Pat. No. 5,712,291, specifically incorporated herein by reference for this purpose, in the context of the present invention, the appearance of any avascular zone is sufficient to evidence an anti-angiogenic antibody. The larger the zone, the more effective the antibody.

The corneal micropocket assay of neovascularization may be practiced using rat or rabbit corneas. This in vivo model is widely accepted as being predictive of clinical usefulness, as evidenced by U.S. Pat. Nos. 5,712,291 and 5,871,723, each specifically incorporated herein by reference for evidence purposes. Although not believed to be particularly relevant the present invention, the corneal assays are preferable over the CAM assay because they will generally recognize compounds that are inactive per se but are metabolized to yield active compounds.

In the present invention, the corneal micropocket assay is used to identify an anti-angiogenic agent. This is evidenced by a significant reduction in angiogenesis, as represented by a consistently observed and preferably marked reduction in the number of blood vessels within the cornea. Such responses are preferably defined as those corneas showing only an occasional sprout and/or hairpin loop that displayed no evidence of sustained growth when contacted with the test substance.

The invention as claimed is enabled in accordance with the present specification and readily available technological references, know-how and starting materials.

Certain preferred embodiments of the invention are therefore compositions comprising at least a first human anti-VEGF antibody of the invention, or antigen binding fragment thereof.

Human anti-VEGF antibodies, or antigen-binding fragments thereof, that specifically inhibit VEGF binding to the VEGF receptor VEGFR2 (KDR/Flk-1); and anti-VEGF antibodies, or antigen-binding fragments thereof, that inhibit VEGF binding to the VEGF receptor VEGFR2 (KDR/Flk-1) without significantly inhibiting VEGF binding to the VEGF receptor VEGFR1 (Flt-1) form other aspects of the invention.

Human antibodies with the desired combinations of properties can be readily identified by one or more or a combination of the receptor competition, ELISA, co-precipitation, and/or functional assays described above. The guidance concerning the quantitative assessment of antibodies that consistently significantly reduce VEGF binding to VEGFR2 and that consistently do not significantly inhibit VEGF binding to VEGFR1 is as described above.

r84 is herein shown to reduce the amount of VEGF that bound to VEGFR2-coated ELISA wells to about 11% and 2%, respectively, at 100 fold and 500 fold molar excesses over VEGF. These figures equate to reductions in VEGF binding to VEGFR2 of about 89% and about 98%, respectively. r84 is herein shown to maintain the amount of VEGF that bound to VEGFR1-coated ELISA wells at about 94% and 84%, respectively, at 100 fold and 500 fold molar excesses over VEGF. Even at 1000 fold molar excesses over VEGF, r84 still maintains VEGF binding to VEGFR1 at about 65%. It will again be understood that antibodies that more substantially inhibit VEGF binding to VEGFR2 can likely tolerate more reduction in binding VEGFR1. Equally, where an antibody has a moderate reduction in VEGF binding to VEGFR2, the maintenance of binding to VEGFR1 should be more stringently pursued. It will thus be appreciated that a "comparative" difference between the two values is important.

Nucleic acid molecules comprising nucleotide sequences that encode the human antibodies of the present invention as defined herein or parts or fragments thereof, or nucleic acid molecules substantially homologous thereto, form yet further aspects of the invention. Preferred nucleic acid molecules comprise sequences which encode the amino acid sequence set out in SEQ ID NO:21 (which is preferably encoded by SEQ ID NO:20). Other preferred nucleic acid molecules comprise sequences which encode a heavy chain that has the amino acid sequence of SEQ ID NO:24 (which is preferably encoded by SEQ ID NO:22) and encode a light chain which has the amino acid sequence of SEQ ID NO:25 (which is preferably encoded by SEQ ID NO:23).

Other preferred nucleic acid molecules comprise sequences that encode IgG forms of the antibodies of the invention or murine chimeric forms, for example those as described in Example 6.

As indicated above, other nucleic acid molecules encompassed by the present invention are those encoding parts or fragments of the human antibodies of the present invention, e.g., those encoding a heavy chain of an antibody (e.g., those encoding SEQ ID NO:24, such as SEQ ID NO:22) or those encoding a light chain of an antibody (e.g., those encoding SEQ ID NO:25, such as SEQ ID NO:23). Other preferred nucleic acid molecules are those encoding a VH region of an antibody of the present invention (e.g., those encoding SEQ ID NO:3, such as SEQ ID NO:1 or SEQ ID NO:26). Other preferred nucleic acid molecules are those encoding a VL region of an antibody of the present invention (e.g., those encoding SEQ ID NO:4, such as SEQ ID NO:2 or SEQ ID NO:27).

Thus, fragments of the antibodies of the invention as defined herein, or sequences substantially homologous thereto, or nucleic acid molecules comprising sequences encoding such fragments form a yet further aspect of the invention.

Advantageously, the antibodies of the present invention, when in IgG format, have a high binding affinity for VEGF, i.e., have a Kd in the range of $1\times10^{-8}$ M or less. Importantly, antibodies with such an affinity are in the established range that has been shown to be useful for therapy. Preferably, the antibodies of the invention, when in IgG format, have a binding affinity for VEGF (preferably human VEGF) that corresponds to a Kd of less than 20 nM, 15 nM or 10 nM, more preferably of less than 10, 9.5, 9, 8.5, 8, 7.5, 7, 6.5, 6, 5.5, 5, 4.5, 4, 3.5, 3, 2.5, 2, 1.5 or 1 nM. For example, the binding affinity of the antibodies of the invention, when in IgG format, may be $6.7\times10^{-9}$ M or less, such as being about $7\times10^{-9}$ M or about $6\times10^{-9}$ M or as being $6.7\times10^{-9}$ M. Any appropriate method of determining Kd may be used. However, preferably the Kd is determined by testing various concentrations of the test antibody against various concentrations of antigen (VEGF) in vitro to establish a saturation curve, for example using the Lineweaver-Burk method, or preferably by using commercially available binding model software, such as the 1:1 binding model in the Biacore 3000 Evaluation software. A suitable assay is described in Example 5 for illustrative purposes. Preferably the Kd is determined by immobilizing antigen (VEGF) on a solid support, e.g. a Biacore chip, and assessing the binding of the antibody to the antigen. Preferably the binding affinity is assessed at room temperature, e.g. a temperature of 25° C., although it may also be assessed at other temperatures, e.g. 37° C. (e.g. body temperature).

As discussed elsewhere herein, preferred antibodies of the invention bind to both human VEGF and murine VEGF. This is an important advantage to allow the most effective translation from preclinical studies to clinical use. For example, the ability of an antibody of the invention to bind to both human VEGF and murine VEGF means that such antibodies can be tested in preclinical studies using both syngeneic and xenograft tumor models. Antibodies which do not bind to mouse VEGF cannot be used in syngeneic mouse models.

In addition, the ability to bind both mouse and human VEGF means that the results shown by such antibodies of the invention in xenograft mouse models are more likely to be representative of the activity of the antibodies in human subjects. The reason for this is that antibodies which can bind to human VEGF but not mouse VEGF (e.g. Avastin and 2C3) will bind to VEGF produced by the human tumor cells in the mouse model but will not be able to bind to endogenous murine VEGF. This is of course unlike the situation in a human patient, in which VEGF produced by the tumor and endogenous VEGF would be present.

The potential disadvantage with such a situation is that an antibody which binds to human VEGF but not mouse VEGF might perform well in a mouse xenograft model but this might not be reflected by a similar performance in a human system where much more VEGF was present. In other words, the anti-tumor effect seen in a mouse xenograft system with an antibody which can bind to human VEGF but not mouse VEGF might look better than the clinical reality. In contrast, if you are working with an antibody that can bind to both human and mouse VEGF then this will bind to all forms of VEGF present in the mouse model system and is likely to be more representative of the situation when the antibody is put into humans.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of VEGFR2-blocking, human anti-VEGF antibodies as well as to the specific r84 antibodies.

The terms "antibody" and "immunoglobulin", as used herein, refer broadly to any immunological binding agent or molecule that comprises a human antigen binding domain, including polyclonal and monoclonal antibodies. Depending on the type of constant domain in the heavy chains, whole antibodies are assigned to one of five major classes: IgA, IgD, IgE, IgG, and IgM. Several of these are further divided into subclasses or isotypes, such as IgG1, IgG2, IgG3, IgG4, and the like. The heavy-chain constant domains that correspond to the difference classes of immunoglobulins are termed α, δ, ε, γ and μ, respectively. The subunit structures and three-dimensional configurations of different classes of immunoglobulins are well known.

Generally, where whole antibodies rather than antigen binding regions are used in the invention, IgG and/or IgM are preferred because they are the most common antibodies in the physiological situation and because they are most easily made in a laboratory setting.

The "light chains" of mammalian antibodies are assigned to one of two clearly distinct types: kappa (κ) and lambda (λ), based on the amino acid sequences of their constant domains and some amino acids in the framework regions of their variable domains. There is essentially no preference to the use of κ or λ light chain constant regions in the antibodies of the present invention.

As will be understood by those in the art, the immunological binding reagents encompassed by the term "antibody" extend to all human antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any human antibody-like molecule that has an antigen binding region, and this term includes antibody fragments that comprise an antigen binding domain such as Fab', Fab, F(ab')$_2$, single domain antibodies (DABs), T and Abs dimer, Fv, scFv (single chain Fv), dsFv, ds-scFv, Fd, linear antibodies, minibodies, diabodies, bispecific antibody fragments and the like.

The techniques for preparing and using various antibody-based constructs and fragments are well known in the art (see Kabat et al., 1991, specifically incorporated herein by reference). Diabodies, in particular, are further described in EP 404, 097 and WO 93/11161; whereas linear antibodies are further described in Zapata et al. (1995).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The human antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the human antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not necessary for antigen binding. Thus, constructs smaller than the above classical antibody fragment are known to be effective.

For example, camelid antibodies (Hamers-Casterman et al., 1993; Arbabi Ghahroudi et al., 1997) have an extensive antigen binding repertoire but are devoid of light chains. Also, results with single domain antibodies comprising VH domains alone (Ward et al., 1989; Davies and Riechmann, 1995) or VL domains alone (van den Beucken et al., 2001) show that these domains can bind to antigen with acceptably high affinities. Thus, three CDRs can effectively bind antigen.

It is also known that a single CDR, or two CDRs, can effectively bind antigen. As a first example, a single CDR can be inserted into a heterologous protein and confer antigen binding ability on the heterologous protein, as exemplified by showing that a VH CDR3 region inserted into a heterologous protein, such as GFP, confers antigen binding ability on the heterologous protein (Kiss et al., 2006; Nicaise et al., 2004).

It is further known that two CDRs can effectively bind antigen, and even confer superior properties than possessed by the parent antibody. For example, it has been shown (Qiu et al., 2007) that two CDRs from a parent antibody (a VH CDR1 and a VL CDR3 region) retain the antigen recognition properties of the parent molecule but have a superior capacity to penetrate tumors. Joining these CDR domains with an appropriate linker sequence (e.g., from VH FR2) to orientate the CDRs in a manner resembling the native parent antibody produced even better antigen recognition. Therefore, it is known in the art that it is possible to construct antigen binding antibody mimetics comprising two CDR domains (preferably one from a VH domain and one from a VL domain, more preferably, with one of the two CDR domains being a CDR3 domain) orientated by means of an appropriate framework region to maintain the conformation found in the parent antibody.

Thus, although preferred antibodies of the invention might comprise six CDR regions (three from a light chain and three from a heavy chain), antibodies with fewer than six CDR regions and as few as one or two CDR regions are encompassed by the invention. In addition, antibodies with CDRs from only the heavy chain or light chain are also contemplated.

Preferred antibodies of the invention that bind to VEGF comprise at least one heavy chain variable region that comprises three CDRs and at least one light chain variable region that comprises three CDRs, wherein said light chain variable region comprises:

(a) a variable light (VL) CDR1 that has the amino acid sequence of SEQ ID NO:8 or a sequence substantially homologous thereto, (b) a VL CDR2 that has the amino acid sequence of SEQ ID NO:9 or a sequence substantially homologous thereto, and (c) a VL CDR3 that has the amino acid sequence of SEQ ID NO:10 or a sequence substantially homologous thereto.

Preferred heavy chain CDR regions for use in conjunction with the specified light chain CDR regions are described elsewhere herein. However, other heavy chain variable regions that comprise three CDRs for use in conjunction with the light chain variable regions of the invention are also contemplated. Appropriate heavy chain variable regions which can be used in combination with the light chain variable regions of the invention and which give rise to an antibody which binds VEGF can be readily identified by a person skilled in the art.

For example, a light chain variable region of the invention can be combined with a single heavy chain variable region or a repertoire of heavy chain variable regions and the resulting antibodies tested for binding to VEGF. It would be expected that a reasonable number of such combinations of light chain variable regions of the invention with different heavy chain variable regions would retain the ability to bind VEGF. Indeed, this has been demonstrated with the preferred antibody of the invention (r84/PGN311) where it has been shown that the VL domain of this antibody can be combined with several different VH domains and still retain the ability to bind VEGF. In these experiments 3 out of 7 VH domains which were tested in combination with the VL domain of the r84 antibody showed significant binding to VEGF, which is a very reasonable proportion and is evidence that the light chain variable region of the antibodies of the invention is particularly important in determining VEGF binding specificity and also that other heavy chain variable regions which can be combined with the light chain variable regions of the invention and give rise to antibodies which bind VEGF can readily be identified. Preferred heavy chain variable regions for use in combination with the light chain variable regions of the antibodies of the invention are those obtained or derived from antibodies or antibody fragments which are known to bind to VEGF.

Similar methods could be used to identify alternative light chain variable regions for use in combination with preferred heavy chain variable regions of the invention. In certain embodiments, the antibody or antibody fragment comprises all or a portion of a heavy chain constant region, such as an IgG1, IgG2, IgG3, IgG4, IgA1, IgA2, IgE, IgM or IgD constant region. Preferably, the heavy chain constant region is an IgG1 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies Antibodies containing an Fc region are preferred for certain uses, particularly therapeutic uses in vivo, where the Fc region mediates effector functions such as ADCC and CDC.

The term "substantially homologous" as used herein in connection with an amino acid or nucleic acid sequence includes sequences having at least 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain only 1, 2, 3, 4 or 5, preferably 1, 2 or 3, more preferably 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

The substantially homologous nucleic acid sequences also include nucleotide sequences that hybridize to the nucleic acid sequences disclosed (or their complementary sequences), e.g., hybridize to nucleotide sequences encoding one or more of the light chain or heavy chain CDRs of the invention, the light or heavy chain variable regions of the invention, or the antibodies of the invention (or hybridize to their complementary sequences), under at least moderately stringent hybridization conditions.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody (or the substantially homologous nucleic acid encoding it) should retain the ability to bind to VEGF as described above. Preferably, any substantially homologous binding protein should retain the ability to specifically bind to the same epitope of VEGF as recognized by the binding protein in question, for example, the same epitope recognized by the CDR domains of the invention or the VH and VL domains of the invention as described herein. Binding to the same epitope/antigen can be readily tested by methods well known and described in the art, e.g., using binding assays, e.g., a competition assay.

Thus, a person skilled in the art will appreciate that binding assays can be used to test whether "substantially homologous" antibodies have the same binding specificities as the antibodies and antibody fragments of the invention, for example, binding assays such as ELISA assays or Biacore assays can readily be used to establish whether such "substantially homologous" antibodies can bind to VEGF. As outlined below, a competition binding assay can be used to test whether "substantially homologous" antibodies retain the ability to specifically bind to substantially the same epitope of VEGF as recognized by the antibodies of the invention. The method described below is only one example of a suitable competition assay. The skilled person will be aware of other suitable methods and variations.

An exemplary competition assay involves assessing the binding of various effective concentrations of an antibody of the invention to VEGF in the presence of varying concentrations of a test antibody (e.g., a substantially homologous antibody). The amount of inhibition of binding induced by the test antibody can then be assessed. A test antibody that shows increased competition with an antibody of the invention at increasing concentrations (i.e., increasing concentrations of the test antibody result in a corresponding reduction in the amount of antibody of the invention binding to VEGF) is evidence of binding to substantially the same epitope. Preferably, the test antibody significantly reduces the amount of antibody of the invention that binds to VEGF. Preferably, the test antibody reduces the amount of antibody of the invention that binds to VEGF by at least about 80%. ELISA assays are appropriate for assessing inhibition of binding in such a competition assay but other suitable techniques would be well known to a person skilled in the art.

Substantially homologous sequences of proteins of the invention include, without limitation, conservative amino acid substitutions, or for example alterations that do not effect the VH, VL or CDR domains of the antibodies, e.g., include scFv antibodies where a different linker sequence is used or antibodies where tag sequences or other components are added that do not contribute to the binding of antigen, or alterations to convert one type or format of antibody molecule or fragment to another type or format of antibody molecule or fragment (e.g., conversion from Fab to scFv or vice versa), or the conversion of an antibody molecule to a particular class or subclass of antibody molecule (e.g., the conversion of an antibody molecule to IgG or a subclass thereof, e.g., IgG1 or IgG3).

A "conservative amino acid substitution", as used herein, is one in which the amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., glycine, cysteine, alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Homology may be assessed by any convenient method. However, for determining the degree of homology between sequences, computer programs that make multiple alignments of sequences are useful, for instance Clustal W (Thompson et al., 1994). If desired, the Clustal W algorithm can be used together with BLOSUM 62 scoring matrix (Henikoff and Henikoff, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (1970), as revised by Smith and Waterman (1981) so that the highest order match is obtained between the two sequences and the number of identical amino acids is determined between the two sequences. Other methods to calculate the percentage identity between two amino acid sequences are generally art recognized and include, for example, those described by Carillo and Lipton (1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, 1988), FASTA (Pearson and Lipman, 1988; Pearson, 1990) and gapped BLAST (Altschul et al., 1997), BLASTP, BLASTN, or GCG (Devereux et al., 1984) are also useful for this purpose. Furthermore, the Dali server at the European Bioinformatics institute offers structure-based alignments of protein sequences (Holm, 1993; 1995; 1998).

By way of providing a reference point, sequences according to the present invention having 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

By "at least moderately stringent hybridization conditions" it is meant that conditions are selected that promote selective hybridization between two complementary nucleic acid molecules in solution. Hybridization may occur to all or a portion of a nucleic acid sequence molecule. The hybridizing portion is typically at least 15 (e.g., 20, 25, 30, 40 or 50) nucleotides in length. Those skilled in the art will recognize that the stability of a nucleic acid duplex, or hybrids, is determined by the Tm, which in sodium containing buffers is a function of the sodium ion concentration and temperature (Tm=81.5° C.−16.6 (Log 10[Na+])+0.41(% (G+C)−600/1), or similar equation). Accordingly, the parameters in the wash conditions that determine hybrid stability are sodium ion concentration and temperature. In order to identify molecules that are similar, but not identical, to a known nucleic acid molecule, a 1% mismatch may be assumed to result in about a 1° C. decrease in Tm. For example, if nucleic acid molecules are sought that have a >95% identity, the final wash temperature will be reduced by about 5° C. Based on these considerations those skilled in the art will be able to readily select appropriate hybridization conditions. In preferred embodiments, stringent hybridization conditions are selected. By way of example the following conditions may be employed to achieve stringent hybridization: hybridization at 5× sodium chloride/sodium citrate (SSC)/5×Denhardt's solution/1.0% SDS at Tm −5° C. based on the above equation, followed by a wash of 0.2×SSC/0.1% SDS at 60° C. Moderately stringent hybridization conditions include a washing step in 3×SSC at 42° C. By way of further example, sequences that "hybridize" are those sequences binding (hybridizing) under non-stringent conditions (e.g., 6×SSC, 50% formamide at room temperature) and washed under conditions of low stringency (e.g., 2×SSC, room temperature, more preferably 2×SSC, 42° C.) or conditions of higher stringency (e.g., 2×SSC, 65° C.) (where SSC=0.15M NaCl, 0.015M sodium citrate, pH 7.2).

It is understood, however, that equivalent stringencies may be achieved using alternative buffers, salts and temperatures. Additional guidance regarding hybridization conditions may be found in: Current Protocols in Molecular Biology, John Wiley & Sons, N.Y., 1989, 6.3.1-6.3.6 and in: Sambrook et al., Molecular Cloning, a Laboratory Manual, Cold Spring Harbor Laboratory Press, 1989, Vol. 3.

Generally speaking, sequences that hybridize under conditions of high stringency are preferred, as are sequences which, but for the degeneracy of the code, would hybridize under high stringency conditions.

In other preferred embodiments, second generation antibodies are provided that have enhanced or superior properties in comparison to an original VEGFR2-blocking, human anti-VEGF antibody, such as r84. For example, the second generation antibodies may have a stronger binding affinity, more effective blocking of VEGF binding to VEGFR2, more specific blocking of VEGF binding to VEGFR2, even less blocking of VEGF binding to VEGFR1, enhanced ability to inhibit VEGF-induced proliferation and/or migration of endothelial cells, superior ability to inhibit VEGF-induced vascular permeability, and preferably, an increased ability to inhibit VEGF-induced angiogenesis in vivo, and to treat angiogenic diseases, including vascularized tumors.

Comparisons to identify effective second generation antibodies are readily conducted and quantified, e.g., using one or more of the various assays described in detail herein. Second generation antibodies that have an enhanced biological property or activity of at least about 2-fold, 5-fold, 10-fold, 20-fold, and preferably, at least about 50-fold, in comparison to the VEGFR2-blocking, human anti-VEGF antibodies of the present invention, as exemplified by the r84 antibody, are encompassed by the present invention.

The antibody, binding protein and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins or polypeptides, e.g., antibodies, refers to such molecules when isolated from, purified from, or substantially free of their natural environment, e.g., isolated from or purified from the human or animal body (if indeed they occur naturally), or refers to such molecules when produced by a technical process, i.e., includes recombinant and synthetically produced molecules.

Thus, when used in connection with a nucleic acid molecule, such terms may refer to a nucleic acid substantially free of material with which it is naturally associated such as other nucleic acids/genes or polypeptides. These terms may also refer to a nucleic acid substantially free of cellular material or culture medium when produced by recombinant DNA techniques, or substantially free of chemical precursors, or other chemicals when chemically synthesized. An isolated or purified nucleic acid may also be substantially free of sequences that naturally flank the nucleic acid (i.e., sequences located at the 5' and 3' ends of the nucleic acid) from which the nucleic acid is derived or sequences that have been made to flank the nucleic acid (e.g., tag sequences or other sequence that have no therapeutic value) by, for example, genetic engineering.

Thus, when used in connection with a protein or polypeptide molecule such as light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized. Such isolated or purified proteins may also be free of flanking sequences such as those described above for the isolated nucleic acid molecules.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans, e.g., in the human germline or somatic cells. The r84 antibody is an example of such a human antibody molecule wherein the variable regions have been isolated from a human repertoire.

The "human" antibodies and binding proteins of the invention further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in 5, 4, 3, 2 or 1 of the residues of the antibody or binding protein, preferably e.g., in 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, the "human" antibodies of the invention include sequences derived from and related to sequences found in humans, but which may not naturally exist within the human antibody germline repertoire in vivo. In addition, the human antibodies and binding proteins of the present invention include proteins comprising human consensus sequences identified from human sequences, or sequences substantially homologous to human sequences.

In addition, the human antibodies and binding proteins of the present invention are not limited to combinations of $V_H$, $V_L$, CDR or FR regions that are themselves found in combination in human antibody molecules. Thus, the human antibodies and binding proteins of the invention can include or correspond to combinations of such regions that do not necessarily exist naturally in humans.

In preferred embodiments, the human antibodies will be fully human antibodies. "Fully human" antibodies, as used herein, are antibodies comprising "human" variable region domains and/or CDRs, as defined above, without substantial non-human antibody sequences or without any non-human antibody sequences. For example, antibodies comprising human variable region domains and/or CDRs "without substantial non-human antibody sequences" are antibodies, domains and/or CDRs in which only about 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

The term "fragment" as used herein refers to fragments of biological relevance, e.g., fragments that contribute to antigen binding, e.g., form part of the antigen binding site, and/or contribute to the inhibition or reduction in function of the VEGF antigen and/or contribute to the prevention of the VEGF antigen interacting with the natural ligand, VEGFR2. Certain preferred fragments comprise a heavy chain variable region ($V_H$ domain) and/or a light chain variable region ($V_L$ domain) of the antibodies of the invention. Other preferred fragments comprise one or more of the heavy chain CDRs of the antibodies of the invention (or of the $V_H$ domains of the invention), or one or more of the light chain CDRs of the antibodies of the invention (or of the $V_L$ domains of the invention). Certain preferred fragments are at least 5 amino acids in length and comprise at least one CDR region, preferably a CDR3 region, more preferably a heavy chain CDR3 region.

In embodiments where the antibodies of the invention comprise a fragment of any of the defined sequences (for example comprise a fragment of SEQ ID NO:21, e.g., are antibodies comprising $V_H$ and/or $V_L$ domains of the invention, or are antibodies or binding proteins comprising one or more CDRs of the invention, then these regions/domains are generally separated within the antibody or binding protein so that each region/domain can perform its biological function and so that the contribution to antigen binding is retained. Thus, the $V_H$ and $V_L$ domains are preferably separated by appropriate scaffold sequences/linker sequences and the CDRs are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g., T cell receptor frameworks can be used.

Appropriate sequences that can be used for framework regions are well known and documented in the art and any of these may be used. Preferred sequences for framework regions are one or more of the framework regions making up the $V_H$ and/or $V_L$ domains of the invention, i.e., one or more of the framework regions disclosed in SEQ ID NO:21 or in Table 1, or framework regions substantially homologous thereto, and in particular framework regions that allow the maintenance of antigen specificity, for example framework regions that result in substantially the same or the same 3D structure of the antibody. In certain preferred embodiments, all four of the variable light chain (SEQ ID NOs:15, 16, 17 and 18) and/or variable heavy chain (SEQ ID NOs:11, 12, 13 and 14), as appropriate, FR regions of SEQ ID NO:21 (also shown in Table 1), or FR regions substantially homologous thereto, are found in the antibodies of the invention.

In addition, although preferred antibodies of the invention are made up of $V_H$, $V_L$ or CDRs of the invention, it should be noted that the antibodies of the invention also encompass one or more $V_H$, $V_L$ or CDRs of the invention in combination with other $V_H$, $V_L$ or CDRs not of the invention, provided that the VEGF binding properties of the antibodies or binding proteins of the invention as outlined above are still present.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

It should be noted that the Kabat nomenclature is followed herein, where necessary, in order to define the positioning of the CDRs (Kabat et al., 1991, specifically incorporated herein by reference).

A person skilled in the art will appreciate that the proteins and polypeptides of the invention, such as the light and heavy CDRs, the light and heavy chain variable regions, antibodies, antibody fragments, and immunoconjugates, may be prepared in any of several ways well known and described in the art, but are most preferably prepared using recombinant methods.

Nucleic acid fragments encoding the light and heavy chain variable regions of the antibodies of the invention can be derived or produced by any appropriate method, e.g., by cloning or synthesis. Such sequences could, for example, be prepared by cloning appropriate sequences from e.g., human germ line genes and then making any necessary modifications to the germ line sequences to obtain the sequences of the invention using methods well known and described in the art. An alternative and more efficient method would be to synthesize the appropriate light or heavy chain variable region sequence as overlapping primers, and use primer extension to obtain the full sequence. This full sequence could then be amplified via PCR with primers containing appropriate restriction sites for further cloning and manipulation, e.g., for cloning into an appropriate expression vector. Five to seven overlapping primers per variable region are normally be sufficient, thereby making this technique very efficient and precise.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g., Fab fragments, scFv fragments, etc. Typically, or as part of this further manipulation procedure, the nucleic acid fragments encoding the antibody molecules of the invention are generally incorporated into an appropriate expression vector in order to facilitate production of the antibodies of the invention.

Possible expression vectors include but are not limited to cosmids, plasmids, or modified viruses (e.g., replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes (For example, see the regulatory sequences described in Goeddel, 1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention. Examples of selectable marker genes are genes encoding a protein such as neomycin and hygromycin that confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags). For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMa1 (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. The term "transformed host cell" as used herein is intended to also include cells capable of glycosylation that have been transformed with a recombinant expression vector of the invention. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al., 1989, and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, 1990. In addition, the proteins of the invention may be expressed in prokaryotic cells, such as *Escherichia coli* (Zhang et al., 2004).

Yeast and fungi host cells suitable for carrying out the present invention include, but are not limited to *Saccharomyces cerevisiae*, the genera *Pichia* or *Kluyveromyces* and various species of the genus *Aspergillus*. Examples of vectors for expression in yeast *S. cerevisiae* include pYepSec1 (Baldari. et al., 1987), pMFa (Kurjan and Herskowitz, 1982), pJRY88 (Schultz et al., 1987), and pYES2 (Invitrogen Corporation, San Diego, Calif.). Protocols for the transformation of yeast and fungi are well known to those of ordinary skill in the art (see Hinnen et al., 1978; Ito et al., 1983, and Cullen et al. 1987).

Mammalian cells suitable for carrying out the present invention include, among others: COS (e.g., ATCC No. CRL 1650 or 1651), BHK (e.g., ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., 1987) and pMT2PC (Kaufman et al., 1987).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., 1987, which reviews the use of *Agrobacterium rhizogenes* vectors; see also Zambryski et al., 1984, which describes the use of expression vectors for plant cells, including, among others, PAPS2022, PAPS2023, and PAPS2034).

Insect cells suitable for carrying out the present invention include cells and cell lines from *Bombyx*, *Trichoplusia* or *Spodotera* species. Baculovirus vectors available for expression of proteins in cultured insect cells (SF 9 cells) include the pAc series (Smith et al., 1983) and the pVL series (Luckow and Summers 1989). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. 1985; Palmiter et al. 1983; Brinster et al. 1985; Palmiter and Brinster 1985, and U.S. Pat. No. 4,736,866).

The proteins of the invention may also be prepared by chemical synthesis using techniques well known in the chemistry of proteins such as solid phase synthesis (Merrifield (1964); Frische et al., 1996) or synthesis in homogenous solution (Houbenweyl, 1987).

N-terminal or C-terminal fusion proteins comprising the antibodies and proteins of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins that may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

Irrespective of the manner of preparation of a first VEGFR2-blocking, anti-VEGF antibody nucleic acid segment, further suitable antibody nucleic acid segments may be readily prepared by standard molecular biological techniques. In order to confirm that any variant, mutant or second generation VEGFR2-blocking, anti-VEGF antibody nucleic acid segment is suitable for use in the present invention, the nucleic acid segment will be tested to confirm expression of a VEGFR2-blocking, anti-VEGF antibody in accordance with the present invention. Preferably, the variant, mutant or second generation nucleic acid segment will also be tested to confirm hybridization under standard, more preferably, standard stringent hybridization conditions. Exemplary suitable hybridization conditions include hybridization in about 7% sodium dodecyl sulfate (SDS), about 0.5 M $NaPO_4$, about 1 mM EDTA at about 50° C.; and washing with about 1% SDS at about 42° C.

As a variety of human antibodies may be readily prepared, the treatment methods of the invention may be executed by providing to the animal or patient at least a first nucleic acid segment or molecule that expresses a biologically effective amount of at least a first VEGFR2-blocking, human anti-VEGF antibody of the invention in the patient. The "nucleic acid segment or molecule that expresses a VEGFR2-blocking, human anti-VEGF antibody" will generally be in the form of at least an expression construct or vector, and may be in the form of an expression construct or vector comprised within a virus or within a recombinant host cell. Preferred gene therapy vectors of the present invention will generally be viral vectors, such as comprised within a recombinant retrovirus, herpes simplex virus (HSV), adenovirus, adeno-associated virus (AAV), cytomegalovirus (CMV), and the like.

Thus, this invention further provides nucleic acid segments or molecules comprising nucleotide sequences that encode the antibodies of the present invention. Nucleic acid molecules substantially homologous to such sequences are also included. Preferred nucleic acid molecules encode the amino acid sequence set out in SEQ ID NO:21. More preferred nucleic acid molecules comprise the nucleic acid sequence as defined in SEQ ID NO:20 or a sequence substantially homologous thereto.

A yet further aspect provides an expression construct or expression vector comprising one or more of the nucleic acid segments or molecules of the invention. Preferably the expression constructs or vectors are recombinant. Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell or virus expressing an antibody of the invention forms a yet further aspect.

A yet further aspect of the invention provides a method of producing an antibody of the present invention comprising a step of culturing the host cells of the invention. Preferred methods comprise the steps of (i) culturing a host cell comprising one or more of the recombinant expression vectors or one or more of the nucleic acid sequences of the invention under conditions suitable for the expression of the encoded antibody or protein; and optionally (ii) isolating the antibody or protein from the host cell or from the growth medium/supernatant. Such methods of production may also comprise a step of purification of the antibody or protein product and/or formulating the antibody or product into a composition including at least one additional component, such as a pharmaceutically acceptable carrier or excipient.

In embodiments when the antibody or protein of the invention is made up of more than one polypeptide chain (e.g., certain fragments such as Fab fragments), then all the polypeptides are preferably expressed in the host cell, either from the same or a different expression vector, so that the complete proteins, e.g., binding proteins of the invention, can assemble in the host cell and be isolated or purified therefrom.

The antibodies of the invention may also be used to produce further antibodies that bind to VEGF. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies specific for VEGF. Such methods can be used to form multiple new antibodies that can all be tested for their ability to bind VEGF. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding (Davies and Cohen, 1996). Subsequently, those residues can be mutated to enhance the interaction. Alternatively, one or more amino acid residues can simply be targeted for directed mutagenesis and the effect on binding to tumor cells assessed.

Random mutagenesis can be carried out in any appropriate way, e.g., by error-prone PCR, chain shuffling or mutator *E. coli* strains.

Thus, one or more of the $V_H$ domains of the invention can be combined with a single $V_L$ domain or a repertoire of $V_L$ domains from any appropriate source and the resulting new antibodies tested to identify antibodies specific for VEGF.

Conversely, one or more of the $V_L$ domains of the invention can be combined with a single $V_H$ domain or repertoire of $V_H$ domains from any appropriate source and the resulting new antibodies tested to identify antibodies specific for VEGF. For example, as discussed above, it has been shown that the $V_L$ domain of the preferred antibody of the invention (r84/PGN311) can be combined with several different $V_H$ domains and still retain the ability to bind VEGF.

Similarly, one or more, or preferably all three CDRs of the $V_H$ and/or $V_L$ domains of the invention can be grafted into a single $V_H$ and/or $V_L$ domain or a repertoire of $V_H$ and/or $V_L$ domains, as appropriate, and the resulting new antibodies tested to identify antibodies specific for VEGF.

The targeted mutations of the CDRs, especially CDR3 of the light and/or heavy chains, have been shown to be an effective technique for increasing antibody affinity and are preferred. Preferably, blocks of 3 to 4 amino acids of the CDR3 or specific regions called "hot-spots" are targeted for mutagenesis.

"Hot spots" are the sequences where somatic hypermutation takes place in vivo (Neuberger and Milstein, 1995). The hotspot sequences can be defined as consensus nucleotide sequences in certain codons. The consensus sequence is the tetranucleotide, RGYW, in which R can be either A or G, Y can be C or T and W can be either A or T (Neuberger and Milstein, 1995). In addition, the serine residues encoded by the nucleotides AGY are predominantly present in the CDRs regions of the variable domain over those encoded by TCN corresponding to a potential hot-spot sequences (Wagner et al., 1995).

Thus, the nucleotide sequence of the CDRs of the heavy and light chains of each antibody of the invention can be scanned for the presence of the hot-spot sequences and AGY codons. The identified hot-spots of the CDR regions of the light and heavy chain can then optionally be compared to the germinal sequences of the heavy and light chains using the International ImMunoGen Tics database (IMGT, http://imgt-.cines.fr/textes/vquest/) (Davies et al., 1990). A sequence, identical to the germ line, suggest that somatic mutation has not occurred; therefore random mutations can be introduced mimicking the somatic events occurring in vivo or alternatively, site directed mutagenesis can be carried out, e.g., at the hot spots and/or AGY codons. In contrast, a different sequence shows that some somatic mutations have already occurred. It will remain to be determined if the in vivo somatic mutation was optimal.

Preferred hot-spots for mutation are those that code for exposed amino acids and preferably those that encode amino acids that form part of the antigen binding sites. Other preferred hot-spots for mutation are those that code for non-conserved amino acids. The hot-spots that code for buried or conserved amino acids within the CDRs are preferably not mutagenized. These residues are usually critical for the overall structure and are unlikely to interact with the antigen since they are buried.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

Testing the ability of one or more new antibodies to specifically bind to VEGF can be carried out by any appropriate method, which are well known and described in the art. VEGF samples are widely available (see the Examples) and these can readily be used to assay binding, for example by conventional methods such as ELISA, affinity chromatography, etc.

The new antibodies produced by these methods will preferably have a higher or enhanced affinity (or at least an equivalent affinity) for VEGF as the parent antibodies and can be treated and used in the same way as the antibodies of the invention as described elsewhere herein (e.g., for therapy, diagnosis, in compositions etc).

New antibodies produced, obtained or obtainable by these methods form a yet further aspect of the invention.

This invention further provides compositions comprising at least one human antibody or antibody fragment of the invention, optionally including a diluent. Such compositions may be pharmaceutically acceptable compositions or compositions for use in laboratory studies. In terms of the pharmaceutical compositions, they may preferably be formulated for parenteral administration, such as for intravenous administration, or for ocular administration.

The present invention provides a number of methods and uses of the human antibodies and antibody fragments of the invention. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections, may be used, up to and including multiple injections. Combined therapeutics may be used, administered before, after or during administration of the anti-VEGF therapeutic antibody.

Various useful in vitro methods and uses of the antibodies of the invention are provided that have important biological implications. First provided are methods of, and uses in, binding VEGF, which generally comprise effectively contacting a composition comprising VEGF, preferably free (non-receptor bound) VEGF with at least a first VEGFR2-blocking, anti-VEGF antibody of the invention, or antigen-binding fragment thereof.

Methods of, and uses in, detecting VEGF are provided, which generally comprise contacting a composition suspected of containing VEGF with at least a first human antibody of the invention, or antigen-binding fragment thereof, under conditions effective to allow the formation of VEGF/antibody complexes and detecting the complexes so formed. The detection methods and uses may be used in connection with biological samples, e.g., in diagnostics for angiogenesis and tumors, and diagnostic kits based thereon are also provided.

The present invention provides methods of, and uses in, preferentially or specifically inhibiting VEGF binding to the VEGF receptor VEGFR2, which generally comprise contacting, in the presence of VEGF, a population of cells or tissues that includes endothelial cells that express VEGFR2 (KDR/Flk-1) with a composition comprising a biologically effective amount of at least a first VEGFR2-blocking, human anti-VEGF antibody of the invention, or an antigen-binding fragment thereof, under conditions effective to inhibit VEGF binding to the VEGF receptor VEGFR2.

Methods of, and uses in, significantly inhibiting VEGF binding to the VEGF receptor VEGFR2, without significantly inhibiting VEGF binding to the VEGF receptor VEGFR1 are provided. These methods comprise contacting, in the presence of VEGF, a population of cells or tissues that includes a population of endothelial cells that express VEGFR2 (KDR/Flk-1) and VEGFR1 (Flt-1) with a composition comprising a biologically effective amount of at least a first VEGFR2-blocking, human anti-VEGF antibody of the invention, or an antigen-binding fragment thereof, under conditions effective to inhibit VEGF binding to the VEGF receptor VEGFR2, without significantly inhibiting VEGF binding to the VEGF receptor VEGFR1.

Further methods and uses of the invention are in analyzing the biological roles of the VEGF receptors termed VEGFR2 and VEGFR1, comprising the steps of:
  (a) contacting a biological composition or tissue that comprises VEGF and a population of cells that express VEGFR2 (KDR/Flk-1) and VEGFR1 (Flt-1). receptors with a composition comprising a biologically effective amount of at least a first VEGFR2-blocking, human anti-VEGF antibody of the invention, or an antigen-binding fragment thereof; and
  (b) determining the effect of the VEGFR2-blocking, anti-VEGF antibody of the invention on at least a first biological response to VEGF; wherein:
    (i) an alteration in a biological response in the presence of the VEGFR2-blocking, anti-VEGF antibody of the invention is indicative of a response mediated by the VEGFR2 receptor; and
    (ii) the maintenance of a biological response in the presence of the VEGFR2-blocking, anti-VEGF antibody of the invention is indicative of a response mediated by the VEGFR1 receptor.

Proliferation inhibition methods and uses are provided, including those to specifically inhibit VEGF-induced endothelial cell proliferation and/or migration, which generally comprise contacting a population of cells or tissues that includes a population of endothelial cells and VEGF with a composition comprising a biologically effective amount of at least a first VEGFR2-blocking, human anti-VEGF antibody of the invention, or an antigen-binding fragment of the VEGFR2-blocking, anti-VEGF antibody of the invention, under conditions effective to inhibit VEGF-induced endothelial cell proliferation and/or migration.

Methods of, and uses in, inhibiting VEGFR2-induced macrophage function are also provided, which generally comprise contacting a population of cells or tissues that contains macrophages and VEGF with a composition comprising a biologically effective amount of at least a first VEGFR2-blocking, human anti-VEGF antibody of the invention, or an antigen-binding fragment of the anti-VEGF antibody, under conditions effective to inhibit VEGFR2-induced macrophage function.

The foregoing methods are preferably applied in the treatment of tumors, wherein the methods inhibit VEGFR2-induced macrophage function, thereby reducing the ability of tumor-infiltrating macrophages, which express VEGFR2, to promote tumor progression and/or metastasis.

Methods of, and uses in, inhibiting VEGF-induced endothelial cell proliferation and/or migration and, optionally, angiogenesis, without significantly inhibiting VEGFR1-mediated stimulation of osteoclasts or chondroclasts are further provided. The methods generally comprise contacting a population of cells or tissues that contain endothelial cells and at least one of osteoclasts or chondroclasts, with a composition comprising a biologically effective amount of at least a first VEGFR2-blocking, human anti-VEGF antibody of the invention, or an antigen-binding fragment of the antibody, under conditions effective to inhibit VEGF-induced endothelial cell proliferation and/or migration or angiogenesis, without significantly inhibiting VEGFR1-mediated stimulation of osteoclasts or chondroclasts.

The foregoing methods and uses can be performed in vitro and in vivo, in the latter case,
wherein the tissues or cells are located within an animal and the human anti-VEGF antibody is administered to the animal. In both cases, the methods and uses become methods and uses for inhibiting angiogenesis, comprising contacting a tissue comprising, or a population of, angiogenic or potentially angiogenic blood vessels, i.e., those exposed to or potentially exposed to VEGF, with an anti-angiogenic composition comprising a biologically effective amount of at least a first VEGFR2-blocking, anti-VEGF antibody of the invention, or an antigen-binding fragment thereof, under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promoter angiogenesis, as well as in the delineation of further information on the angiogenic process. Where the population of potentially angiogenic blood vessels is located within an animal or patient, the anti-angiogenic composition is administered to the animal as a form of therapy.

"Biologically effective amounts", in terms of each of the foregoing inhibitory methods are therefore amounts of VEGFR2-blocking, human anti-VEGF antibodies of the invention, effective to inhibit VEGF-induced endothelial cell proliferation and/or migration; to inhibit VEGF-induced endothelial cell proliferation and/or migration, without significantly inhibiting VEGFR1-induced cellular events; to inhibit VEGF-induced endothelial cell proliferation and/or migration or angiogenesis, without significantly inhibiting VEGFR1 stimulation of osteoclasts or chondroclasts; and, overall, to reduce vascular endothelial cell proliferation and/or migration in a manner effective to inhibit blood vessels growth or angiogenesis.

The invention thus provides methods of, and uses in, inhibiting VEGF-induced angiogenesis and, preferably, treating an angiogenic disease, without significantly inhibiting VEGF stimulation of osteoclasts or chondroclasts. The methods generally comprise contacting a population of cells or tissues that contain endothelial cells and at least one of osteoclasts or chondroclasts, with a composition comprising a biologically effective amount of at least a first VEGFR2-blocking, human anti-VEGF antibody of the invention, or an antigen-binding fragment of the antibody, under conditions effective to inhibit VEGF-induced angiogenesis and to treat an angiogenic disease without significantly inhibiting VEGF stimulation of osteoclasts or chondroclasts.

Methods of, and uses in, inhibiting VEGF-induced angiogenesis and, preferably, treating an angiogenic disease, without causing significant side effects on bone metabolism are further provided. The methods generally comprise contacting a tissue or a population of angiogenic vessels that contain vascular endothelial cells and at least one of osteoclasts or chondroclasts, with a composition comprising a biologically effective amount of at least a first VEGFR2-blocking, human anti-VEGF antibody of the invention, or an antigen-binding fragment of the antibody, under conditions effective to inhibit VEGF-induced angiogenesis and to treat an angiogenic disease without causing significant side effects on bone metabolism by not significantly impairing the activities of osteoclasts or chondroclasts.

Anti-angiogenic drug screening (in vitro) and therapy (in vivo) are provided in terms of animals and patients that have, or are at risk for developing, any disease or disorder characterized by undesired, inappropriate, aberrant, excessive and/ or pathological vascularization. It is well known to those of ordinary skill in the art that as aberrant angiogenesis occurs in a wide range of diseases and disorders, a given anti-angiogenic therapy, once shown to be effective in any acceptable model system, can be used to treat the entire range of diseases and disorders connected with angiogenesis.

The methods and uses of the present invention are particularly intended for use in animals and patients that have, or are at risk for developing, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; and psoriasis.

The methods and uses of the invention are further intended for the treatment of animals and patients that have, or are at risk for developing, arteriovenous malformations (AVM), meningioma, and vascular restenosis, including restenosis following angioplasty. Other intended targets of the therapeutic methods and uses are animals and patients that have, or are at risk for developing, angiofibroma, dermatitis, endometriosis, hemophilic joints, hypertrophic scars, inflammatory diseases and disorders, pyogenic granuloma, scleroderma, synovitis, trachoma and vascular adhesions.

As disclosed in U.S. Pat. Nos. 5,712,291 and 6,524,583, each specifically incorporated herein by reference, each of the foregoing somewhat preferred treatment groups are by no means exhaustive of the types of conditions that are to be treated by the present invention. U.S. Pat. Nos. 5,712,291 and 6,524,583 are each incorporated herein by reference for certain specific purposes, including the purpose of identifying a number of other conditions that may be effectively treated by an anti-angiogenic therapeutic; the purpose of showing that the treatment of all angiogenic diseases represents a unified concept, once a defined category of angiogenesis-inhibiting compounds have been disclosed and claimed (in the present case, VEGFR2-blocking, human anti-VEGF antibodies of the invention, and the purpose of showing that the treatment of all angiogenic diseases is enabled by data from only a single model system.

In yet further aspects, and as disclosed in U.S. Pat. Nos. 5,712,291 and 6,524,583, each incorporated herein by reference, the methods and uses of the present invention are intended for the treatment of animals and patients that have, or are at risk for developing, abnormal proliferation of fibrovascular tissue, acne rosacea, acquired immune deficiency syndrome, artery occlusion, atopic keratitis, bacterial ulcers, Bechets disease, blood borne tumors, carotid obstructive disease, chemical burns, choroidal neovascularization, chronic inflammation, chronic retinal detachment, chronic uveitis, chronic vitritis, contact lens overwear, corneal graft rejection, corneal neovascularization, corneal graft neovascularization, Crohn's disease, Eales disease, epidemic keratoconjunctivitis, fungal ulcers, Herpes simplex infections, Herpes zoster infections, hyperviscosity syndromes, Kaposi's sarcoma, leukemia, lipid degeneration, Lyme's disease, marginal keratolysis, Mooren ulcer, *Mycobacteria* infections other than leprosy, myopia, ocular neovascular disease, optic pits, Osler-Weber syndrome (Osler-Weber-Rendu, osteoarthritis, Pagets disease, pars planitis, pemphigoid, phylectenulosis, polyarteritis, post-laser complications, protozoan infections, pseudoxanthoma elasticum, pterygium keratitis sicca, radial keratotomy, retinal neovascularization, retinopathy of prematurity, retrolental fibroplasias, sarcoid, scleritis, sickle cell anemia, Sogrens syndrome, solid tumors, Stargarts disease, Steven's Johnson disease, superior limbic keratitis, syphilis, systemic lupus, Terrien's marginal degeneration, toxoplasmosis, trauma, tumors of Ewing sarcoma, tumors of neuroblastoma, tumors of osteosarcoma, tumors of retinoblastoma, tumors of rhabdomyosarcoma, ulceritive colitis, vein occlusion, Vitamin A deficiency and Wegeners sarcoidosis.

The present invention further provides methods and uses for the treatment of animals and patients that have, or are at risk for developing, arthritis, in common with the treatment of arthritis using immunological agents described in U.S. Pat. No. 5,753,230, specifically incorporated herein by reference. U.S. Pat. No. 5,972,922 is also specifically incorporated herein by reference to even further exemplify the application of anti-angiogenic strategies to the treatment of undesired angiogenesis associated with diabetes, parasitic diseases, abnormal wound healing, hypertrophy following surgery, burns, injury or trauma, inhibition of hair growth, inhibition of ovulation and corpus luteum formation, inhibition of implantation and inhibition of embryo development in the uterus. All of the foregoing conditions are therefore contemplated for treatment by the methods and uses of the present invention.

U.S. Pat. No. 5,639,757 is further specifically incorporated herein by reference to exemplify the use of anti-angiogenic strategies to the general treatment of graft rejection. The treatment of lung inflammation, nephrotic syndrome, preeclampsia, pericardial effusion, such as that associated with pericarditis, and pleural effusion using anti-angiogenic strategies based upon VEGF inhibition is described in WO 98/45331, specifically incorporated herein by reference. Animals and patients that have, or are at risk for developing, any of the foregoing conditions are therefore contemplated for treatment by the methods and uses of the present invention.

As disclosed in WO 98/16551, specifically incorporated herein by reference, biological molecules that antagonize VEGF function are also suitable for use in treating diseases and disorders characterized by undesirable vascular permeability. Accordingly, the VEGF antagonizing antibodies, methods and uses of the present invention are applicable to the treatment of animals and patients that have, or are at risk for developing, diseases and disorders characterized by undesirable vascular permeability, e.g., edema associated with brain tumors, ascites associated with malignancies, Meigs' syndrome, lung inflammation, nephrotic syndrome, pericardial effusion and pleural effusion and the like.

Although the treatment of all the foregoing diseases is enabled within the present, unified invention, a particularly preferred aspect of the methods and uses of the present invention is application of anti-angiogenic therapy to animals and patients that have, or are at risk for developing, a vascularized solid tumor, a metastatic tumor or metastases from a primary tumor.

Methods of, and uses in, inhibiting VEGF-induced angiogenesis, and, preferably, exerting an anti-tumor or improved anti-tumor effect without significantly inhibiting VEGF stimulation of osteoclasts or chondroclasts are further provided. The methods generally comprise contacting a tissue, tumor environment or population of angiogenic vessels that contain vascular endothelial cells and at least one of macrophages, osteoclasts or chondroclasts, with a composition comprising a biologically effective amount of at least a first VEGFR2-blocking, human anti-VEGF antibody of the invention, or an antigen-binding fragment of the antibody, under conditions effective to inhibit VEGF-induced angiogenesis and to exert an anti-tumor or improved anti-tumor effect without significantly inhibiting VEGF stimulation of osteoclasts or chondroclasts.

The present invention thus further provides methods of, and uses in, treating a disease associated with angiogenesis, including all forms of cancer associated with angiogenesis, comprising administering to an animal or patient with such a disease or cancer a therapeutically effective amount of at least a first pharmaceutical composition that comprises a VEGFR2-blocking, human anti-VEGF antibody of the invention, or an antigen-binding fragment or immunoconjugate of such an anti-VEGF antibody.

In addition, the methods and uses of the invention include methods and uses for inhibiting lymphangiogenesis, which comprise contacting a tissue comprising, or a population of, lymphatic vessels ("lymphatics"), particularly, lymphatics exposed to or potentially exposed to VEGF, with an anti-angiogenic composition comprising a biologically effective amount of at least a first VEGFR2-blocking, anti-VEGF antibody of the invention, or an antigen-binding fragment thereof, under conditions effective to inhibit lymphangiogenesis.

Where populations of lymphatics are maintained ex vivo, the present invention has utility in drug discovery programs. Where the population of lymphatics is located within an animal or patient, the composition of the invention is administered to the animal as a form of therapy.

In terms of inhibiting lymphangiogenesis, "biologically effective amounts" are amounts of VEGFR2-blocking, human anti-VEGF antibodies of the invention effective to inhibit VEGF-induced lymphangiogenesis, i.e., VEGF-A stimulated lymphangiogenesis induced by VEGFR2. Preferably, VEGF-induced lymphangiogenesis will be induced without significantly inhibiting VEGFR1-stimulated events, such as osteoclast or chondroclast stimulation.

The invention thus includes methods of, and uses in, treating a disease associated with lymphangiogenesis, including all forms of cancer associated with lymphangiogenesis, comprising administering to an animal or patient with such a disease or cancer a therapeutically effective amount of at least a first pharmaceutical composition that comprises a VEGFR2-blocking, human anti-VEGF antibody of the invention, or an antigen-binding fragment or immunoconjugate of such an anti-VEGF antibody.

A yet further aspect of the invention provides the use of the human antibodies of the invention or an antigen-binding fragment or immunoconjugate of such an antibody in the manufacture of a composition or medicament for use in therapy, imaging or diagnosis.

A yet further aspect provides the human antibodies of the invention or an antigen-binding fragment or immunoconjugate of such an antibody for use in therapy, diagnosis or imaging.

In addition, the invention provides compositions comprising the human antibodies of the invention or an antigen-binding fragment or immunoconjugate of such an antibody with one or more pharmaceutically acceptable excipient, carrier, diluent, buffer or stabilizer.

The in vivo methods as described herein are generally carried out in a mammal. Any mammal may be treated, for example humans and any livestock, domestic or laboratory animal. Specific examples include mice, rats, pigs, cats, dogs, sheep, rabbits, cows and monkey. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkey. Preferably, however, the animal or patient is a human subject.

This invention links both anti-angiogenic methods using unconjugated or naked antibodies and fragments thereof, and vascular targeting methods using immunoconjugates in which a human antibody of the invention or antigen-binding fragment thereof, is operatively attached to a therapeutic agent. Unless otherwise specifically stated or made clear in scientific terms, the terms "antibody and fragment thereof", as used herein, therefore mean an "unconjugated or naked" human antibody or fragment, which is not attached to another agent, particularly a therapeutic or diagnostic agent. These definitions do not exclude modifications of the antibody, such as, by way of example only, modifications to improve the biological half life, affinity, avidity or other properties of the antibody, or combinations of the antibody with other effectors.

The anti-angiogenic treatment methods and uses of the invention also encompass the use of both unconjugated or naked antibodies and immunoconjugates. In the immunoconjugate-based anti-angiogenic treatment methods, the human antibody of the invention, or antigen-binding fragment thereof, is preferably operatively attached to a second anti-angiogenic agent (the anti-VEGF antibody itself, being the first anti-angiogenic agent). The attached anti-angiogenic agents may be those that have a direct or indirect anti-angiogenic effect.

The anti-angiogenic treatment methods and uses comprise administering to an animal or patient with a disease associated with angiogenesis, including all forms of cancer associated with angiogenesis, a therapeutically effective amount of at least a first pharmaceutical composition that comprises at least a first unconjugated or naked VEGFR2-blocking, human anti-VEGF antibody of the invention, or antigen-binding fragment thereof. Equally, the administered antibody may be operatively associated with a second anti-angiogenic agent.

Methods for, and uses in, treating metastatic cancer comprise administering to an animal or patient with metastatic cancer a therapeutically effective amount of at least a first pharmaceutical composition that comprises at least a first unconjugated or naked VEGFR2-blocking, human anti-VEGF antibody of the invention, or antigen-binding fragment thereof. Further methods are those wherein the administered antibody may be operatively associated with a second anti-angiogenic agent.

Methods for, and uses in, reducing metastases from a primary cancer comprise administering a therapeutically effective amount of at least a first unconjugated or naked VEGFR2-blocking, human anti-VEGF antibody of the invention, or antigen-binding fragment thereof, to an animal or patient that has, or was treated for, a primary cancer. Similarly, the administered antibody may be operatively associated with a second anti-angiogenic agent.

Methods for, and uses in, treating a disease associated with angiogenesis, including all forms of cancer associated with angiogenesis, further comprise administering to an animal or patient with such a disease, e.g., a vascularized tumor, at least a first unconjugated or naked VEGFR2-blocking, human anti-VEGF antibody of the invention, or an antigen-binding fragment thereof, in an amount effective to inhibit angiogenesis within the disease site or vascularized tumor. Equally, the administered antibody may be operatively associated with a second anti-angiogenic agent.

The methods for, and uses in, treating a disease associated with angiogenesis, including all forms of cancer associated with angiogenesis, further comprise administering to an animal or patient with such a disease or cancer at least a first unconjugated or naked VEGFR2-blocking, human anti- VEGF antibody of the invention, or an antigen-binding fragment thereof, in an amount effective to inhibit VEGF binding to the VEGF receptor VEGFR2 (KDR/Flk-1), thereby inhibiting angiogenesis within the disease or cancerous site. The administered antibody may alternatively be operatively associated with a second anti-angiogenic agent.

Methods for, and uses in, treating a disease associated with angiogenesis, including all forms of cancer associated with angiogenesis, also comprise administering to an animal or patient with a vascularized tumor a therapeutically effective amount of at least a first unconjugated or naked VEGFR2-blocking, human anti-VEGF antibody of the invention, or antigen-binding fragment thereof, wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1). Equally, the administered antibody may be operatively associated with a second anti-angiogenic agent.

Yet further methods for, and uses in, treating a disease associated with angiogenesis, including all forms of cancer associated with angiogenesis, comprise administering to an animal or patient with such a disease, cancer or vascularized tumor a therapeutically effective amount of at least a first unconjugated or naked VEGFR2-blocking, human anti-VEGF antibody of the invention, or an antigen-binding fragment thereof, wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1), thereby inhibiting angiogenesis within the disease site, cancer or vascularized tumor without significantly impairing VEGFR1-mediated events in the animal. The administered antibody may also be operatively associated with a second anti-angiogenic agent.

Additional methods for, and uses in, treating a disease associated with angiogenesis, including all forms of cancer associated with angiogenesis, comprise administering to an animal or patient with such a disease, cancer or vascularized tumor a therapeutically effective amount of at least a first unconjugated or naked VEGFR2-blocking, human anti-VEGF antibody of the invention, or an antigen-binding fragment thereof, wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1), thereby inhibiting angiogenesis within the disease site, cancer or vascularized tumor, including inhibiting VEGFR2-expressing macrophages in the disease site, particularly VEGFR2-expressing tumor-infiltrating macrophages. The administered antibody may also be operatively associated with a second anti-angiogenic agent.

Still further methods for, and uses in, treating a disease associated with angiogenesis, including all forms of cancer associated with angiogenesis, comprise administering to an animal or patient with such a disease, cancer or vascularized tumor a therapeutically effective amount of at least a first unconjugated or naked VEGFR2-blocking, human anti-VEGF antibody of the invention, or an antigen-binding fragment thereof; wherein the anti-VEGF antibody substantially inhibits VEGF binding to the VEGF receptor VEGFR2 (KDR/Flk-1) without significantly inhibiting VEGF binding to the VEGF receptor VEGFR1 (Flt-1), thereby inhibiting angiogenesis within the disease site, cancer or vascularized tumor without significantly impairing osteoclast and/or chondroclast activity in the animal. Equally, the administered antibody may be operatively associated with a second anti-angiogenic agent.

Methods for, and uses in, treating a disease associated with angiogenesis, including all forms of cancer associated with angiogenesis, further comprise administering to an animal or patient with such a disease, e.g., a vascularized tumor, at least a first unconjugated or naked VEGFR2-blocking, human anti-VEGF antibody of the invention, or an antigen-binding fragment thereof, in an amount effective to inhibit angiogenesis within the disease site or vascularized tumor without exerting a significant adverse effect on bone metabolism.

The foregoing anti-angiogenic treatment methods and uses will generally involve the administration of the pharmaceutically effective composition to the animal or patient systemically, such as by transdermal, intramuscular, intravenous injection and the like. However, any route of administration that allows the therapeutic agent to localize to the angiogenic site or sites, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder.

For uses and methods for the treatment of arthritis, e.g., intrasynovial administration may be employed, as described for other immunological agents in U.S. Pat. No. 5,753,230, specifically incorporated herein by reference. For conditions associated with the eye, ophthalmic formulations and administration are contemplated.

"Administration", as used herein, means provision or delivery of VEGFR2-blocking, human anti-VEGF antibody therapeutics in an amount(s) and for a period of time(s) effective to exert anti-angiogenic and/or anti-tumor effects. The passive administration of proteinaceous therapeutics is generally preferred, in part, for its simplicity and reproducibility.

However, the term "administration" is herein used to refer to any and all means by which VEGFR2-blocking, anti-VEGF antibodies of the invention are delivered or otherwise provided to the tumor vasculature. "Administration" therefore includes the provision of cells that produce the VEGFR2-blocking, human anti-VEGF antibody of the invention in a manner effective to result in delivery to the tumor. In such embodiments, it may be desirable to formulate or package the cells in a selectively permeable membrane, structure or implantable device, generally one that can be removed to cease therapy. Exogenous VEGFR2-blocking, human anti-VEGF antibody of the invention will still generally be preferred, as this represents a non-invasive method that allows the dose to be closely monitored and controlled.

The therapeutic methods and uses of the invention also extend to the provision of nucleic acids that encode a VEGFR2-blocking, human anti-VEGF antibody of the invention in a manner effective to result in their expression in the vicinity of the tumor or their localization to the tumor. Any gene therapy technique may be employed, such as naked DNA delivery, recombinant genes and vectors, cell-based delivery, including ex vivo manipulation of patients' cells, and the like.

In yet further embodiments, the invention provides methods for, and uses in, delivering selected therapeutic or diagnostic agents to angiogenic blood vessels associated with disease. Such embodiments are preferably used for delivering selected therapeutic or diagnostic agents to tumor or intratumoral vasculature or stroma, and comprise administering to an animal or patient having a vascularized tumor a biologically effective amount of a composition comprising at least a first immunoconjugate in which a diagnostic or therapeutic agent is operatively attached to a VEGFR2-blocking, human anti-VEGF antibody of the invention, or antigen-binding fragment thereof.

Although understanding the mechanism of action underlying the targeting aspects of the invention is not required in order to practice such embodiments, it is believed that the antibodies of the invention deliver attached agents to angiogenic and tumor vasculature by virtue of binding to VEGF bound to the VEGFR1 expressed thereon. These methods and uses of the invention thus concern delivering selected therapeutic or diagnostic agents to angiogenic blood vessels, tumor or intratumoral vasculature, and comprise administering to an animal or patient in need of treatment a biologically effective amount of a composition comprising an immunoconjugate in which a diagnostic or therapeutic agent is operatively attached to at least a first VEGFR2-blocking, human anti-VEGF antibody of the invention, or antigen-binding fragment thereof, in a manner effective to allow binding of the antibody to VEGF bound to VEGFR1 expressed, overexpressed or upregulated on the angiogenic blood vessels, tumor or intratumoral vasculature, thus delivering the diagnostic or therapeutic agent to the VEGF-VEGFR1 on the angiogenic blood vessels, tumor or intratumoral vasculature.

The delivery of selected therapeutic agents to tumor or intratumoral vasculature or stroma acts to arrest blood flow, or specifically arrest blood flow, in tumor vasculature; to destroy, or specifically destroy, tumor vasculature; and to induce necrosis, or specific necrosis in a tumor. These methods and uses may thus be summarized as methods for treating an animal or patient having a vascularized tumor, comprising administering to the animal or patient a therapeutically effective amount of at least a first pharmaceutical composition comprising at least a first immunoconjugate that comprises a VEGFR2-blocking, human anti-VEGF antibody of the invention, or antigen-binding fragment thereof, operatively attached to a therapeutic agent.

The "therapeutically effective amounts" for use in the invention are amounts of VEGFR2-blocking, human anti-VEGF antibody of the invention, or immunoconjugates thereof, effective to specifically kill at least a portion of tumor or intratumoral vascular endothelial cells; to specifically induce apoptosis in at least a portion of tumor or intratumoral vascular endothelial cells; to specifically promote coagulation in at least a portion of tumor or intratumoral blood vessels; to specifically occlude or destroy at least a portion of blood transporting vessels of the tumor; to specifically induce necrosis in at least a portion of a tumor; and/or to induce tumor regression or remission upon administration to selected animals or patients. Such effects are achieved while exhibiting little or no binding to, or little or no killing of, vascular endothelial cells in normal, healthy tissues; little or no coagulation in, occlusion or destruction of blood vessels in healthy, normal tissues; and exerting negligible or manageable adverse side effects on normal, healthy tissues of the animal or patient.

The terms "preferentially" and "specifically", as used herein in the context of promoting coagulation in, or destroying, tumor vasculature, and/or in the context of binding to tumor stroma and/or causing tumor necrosis, thus mean that the VEGFR2-blocking, human anti-VEGF antibody of the invention or immunoconjugates thereof function to achieve stromal binding, coagulation, destruction and/or tumor necrosis that is substantially confined to the tumor stroma, vasculature and tumor site, and does not substantially extend to causing coagulation, destruction and/or tissue necrosis in normal, healthy tissues of the animal or subject. The structure and function of healthy cells and tissues is therefore maintained substantially unimpaired by the practice of the invention.

Although the antibodies of the invention effectively deliver agents to angiogenic and tumor vasculature by binding to VEGF in association with VEGFR1, other methods and uses operate on the basis of delivering a therapeutic agent to tumor stroma, wherein it exerts a therapeutic effect on the nearby vessels. These methods and uses comprise administering to an animal or patient with a vascularized tumor an immunoconjugate that comprises a therapeutic agent operatively attached to at least a first VEGFR2-blocking, human anti-VEGF antibody of the invention, or antigen-binding fragment thereof, in an amount effective to bind the immunoconjugate to non-receptor bound VEGF within the tumor stroma.

These methods and uses comprise administering to an animal or patient with a vascularized tumor an immunoconjugate that comprises a therapeutic agent operatively attached to at least a first VEGFR2-blocking, human anti-VEGF antibody of the invention, or antigen-binding fragment thereof, in an amount effective to localize the immunoconjugate within the tumor stroma such that the attached therapeutic agent exerts an anti-tumor effect on the surrounding tumor vasculature and/or tumor cells.

The antibodies and compositions, as well as the methods and uses, of the invention thus extend to compositions comprising VEGFR2-blocking, anti-VEGF antibodies comprising at least a first VEGFR2-blocking, human anti-VEGF antibody of the invention, or antigen-binding fragment thereof, operatively attached to at least a first therapeutic or diagnostic agent, more particularly, a first "distinct or exogenous" therapeutic agent. In this regard, the "VEGFR2-blocking, human anti-VEGF antibody" may itself be termed a "first therapeutic agent". Accordingly, any attached therapeutic agent may be termed a first "distinct or exogenous therapeutic agent", meaning that it is also a therapeutic agent, but distinct from and attached to the VEGFR2-blocking, human anti-VEGF antibody. Equivalent terminology for such conjugates is to describe the at least a first VEGFR2-blocking, human anti-VEGF antibody of the invention, or antigen-binding fragment thereof, as being operatively attached to at least a "second, distinct" therapeutic or diagnostic agent.

VEGFR2-blocking, human anti-VEGF antibodies of the invention or therapeutic conjugates are preferably linked to one or more radiotherapeutic agents, anti-angiogenic agents, apoptosis-inducing agents, anti-tubulin drugs, anti-cellular or cytotoxic agents, or coagulants (coagulation factors).

The invention thus provides a range of conjugated antibodies and fragments thereof in which the human antibody is operatively attached to at least a first therapeutic or diagnostic agent. The term "immunoconjugate" is broadly used to define the operative association of the antibody with another effective agent and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

Attachment of agents via the carbohydrate moieties on antibodies is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr) into the primary sequence of the antibody.

Currently preferred agents for use in VEGFR2-blocking, human anti-VEGF antibody or therapeutic conjugates of the invention and related methods and uses are those that complement or enhance the effects of the antibody and/or those selected for a particular tumor type or patient. "Therapeutic agents that complement or enhance the effects of the antibody" include radiotherapeutic agents, anti-angiogenic agents, apoptosis-inducing agents and anti-tubulin drugs, any one or more of which are preferred for use herewith.

The attachment or association of the preferred agents with VEGFR2-blocking, human anti-VEGF antibodies of the invention gives "immunoconjugates", wherein such immunoconjugates often have enhanced and even synergistic anti-tumor properties. Currently preferred anti-angiogenic agents for use in this manner are angiostatin, endostatin, any one of the angiopoietins, vasculostatin, canstatin and maspin. Currently preferred anti-tubulin drugs include colchicine, taxol, vinblastine, vincristine, vindescine and one or more of the combretastatins.

The use of anti-cellular and cytotoxic agents results in VEGFR2-blocking, human anti-VEGF antibody "immunotoxins" of the invention, whereas the use of coagulation factors results in VEGFR2-blocking, human anti-VEGF antibody or "coaguligands" of the invention. The use of at least two therapeutic agents is also contemplated, such as combinations of one or more radiotherapeutic agents, anti-angiogenic agents, apoptosis-inducing agents, anti-tubulin drugs, anti-cellular and cytotoxic agents and coagulation factors.

In certain applications, the VEGFR2-blocking, human anti-VEGF antibody therapeutics of the invention will be operatively attached to cytotoxic, cytostatic or otherwise anti-cellular agents that have the ability to kill or suppress the growth or cell division of endothelial cells. Suitable anti-cellular agents include chemotherapeutic agents, as well as cytotoxins and cytostatic agents. Cytostatic agents are generally those that disturb the natural cell cycle of a target cell, preferably so that the cell is taken out of the cell cycle.

Exemplary chemotherapeutic agents include: steroids; cytokines; anti-metabolites, such as cytosine arabinoside, fluorouracil, methotrexate or aminopterin; anthracyclines; mitomycin C; vinca alkaloids; antibiotics; demecolcine; etoposide; mithramycin; and anti-tumor alkylating agents, such as chlorambucil or melphalan. Indeed, any of the agents disclosed herein in Table C could be used. Certain preferred anti-cellular agents are DNA synthesis inhibitors, such as daunorubicin, doxorubicin/adriamycin, and the like. Overall, taxol/paclitaxel, docetaxel, cisplatin, gemcitabine, a combretastatin and doxorubicin/adriamycin are currently preferred anti-cancer agents.

Of the cytokines and chemokines, currently preferred agents are IL-2, IL-12, TNF-α, interferon-α (IFN-α), IFN-β, IFN-γ, and LEC (liver-expressed chemokine). V-type ATPase inhibitors are also currently preferred, such as salicylihalamide, concanamycin or bafilomycin, as are protein synthesis inhibitors, such as psymberin, pederin, irciniastatin A.

In certain therapeutic applications, toxin moieties will be preferred, due to the much greater ability of most toxins to deliver a cell killing effect, as compared to other potential agents. Therefore, certain preferred anti-cellular agents for VEGFR2-blocking, human anti-VEGF antibody constructs of the invention are plant-, fungus- or bacteria-derived toxins. Exemplary toxins include epipodophyllotoxins; bacterial endotoxin or the lipid A moiety of bacterial endotoxin; ribosome inactivating proteins, such as saporin or gelonin; a-sarcin; aspergillin; restrictocin; ribonucleases, such as placental ribonuclease; diphtheria toxin and pseudomonas exotoxin. Currently preferred examples are ricin, gelonin, abrin, diphtheria, pseudomonas and pertussis toxins.

Certain preferred toxins are the A chain toxins, such as ricin A chain. The most preferred toxin moiety is often ricin A chain that has been treated to modify or remove carbohydrate residues, so called "deglycosylated A chain" (dgA). Deglycosylated ricin A chain is preferred because of its extreme potency, longer half-life, and because it is economically feasible to manufacture it a clinical grade and scale. Recombinant and/or truncated ricin A chain may also be used.

For tumor targeting and treatment with immunotoxins, the following patents are specifically incorporated herein by reference for the purposes of even further supplementing the present teachings regarding anti-cellular and cytotoxic agents: U.S. Pat. Nos. 6,004,554; 5,855,866; 5,965,132; 5,776,427; 5,863,538; 5,660,827 and 6,051,230.

The VEGFR2-blocking, human anti-VEGF antibody of the present invention may be linked to an anti-tubulin drug. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Currently preferred anti-tubulin drugs for use herewith are colchicine; taxanes, such as taxol, docetaxel and paclitaxel; vinca alkaloids, such as vinblastine, vincristine and vindescine; and combretastatins. Exemplary combretastatins are combretastatin A, B and/or D, including A-1, A-2, A-3, A-4, A-5, A-6, B-1, B-2, B-3, B-4, D-1 and D-2 and prodrug forms thereof.

The VEGFR2-blocking, human anti-VEGF antibody therapeutics of the invention may comprise a component that is capable of promoting coagulation, i.e., a coagulant. Here, the targeting antibody may be directly or indirectly, e.g., via another antibody, linked to a factor that directly or indirectly stimulates coagulation.

Preferred coagulation factors for such uses are Tissue Factor (TF) and TF derivatives, such as truncated TF (tTF), dimeric, trimeric, polymeric/multimeric TF, and mutant TF deficient in the ability to activate Factor VII. Other suitable coagulation factors include vitamin K-dependent coagulants, such as Factor II/IIa, Factor VII/VIIa, Factor IX/IXa and Factor X/Xa; vitamin K-dependent coagulation factors that lack the Gla modification; Russell's viper venom Factor X activator; platelet-activating compounds, such as thromboxane $A_2$ and thromboxane $A_2$ synthase; and inhibitors of fibrinolysis, such as $\alpha$2-antiplasmin. Overall, truncated Tissue Factor (tTF) is currently preferred.

Tumor targeting and treatment with coaguligands is described in the following patents, each of which are specifically incorporated herein by reference for the purposes of even further supplementing the present teachings regarding coaguligands and coagulation factors: U.S. Pat. Nos. 5,855,866; 5,965,132; 6,093,399; 6,004,555; 5,877,289; and 6,036,955.

The preparation of immunoconjugates and immunotoxins is generally well known in the art (see, e.g., U.S. Pat. No. 4,340,535). Each of the following patents are further incorporated herein by reference for the purposes of even further supplementing the present teachings regarding immunotoxin generation, purification and use: U.S. Pat. Nos. 6,004,554; 5,855,866; 5,965,132; 5,776,427; 5,863,538; 5,660,827 and 6,051,230.

In the preparation of immunoconjugates and immunotoxins, advantages may be achieved through the use of certain linkers. For example, linkers that contain a disulfide bond that is sterically "hindered" are often preferred, due to their greater stability in vivo, thus preventing release of the toxin moiety prior to binding at the site of action. It is generally desired to have a conjugate that will remain intact under conditions found everywhere in the body except the intended site of action, at which point it is desirable that the conjugate have good "release" characteristics.

Depending on the specific toxin compound used, it may be necessary to provide a peptide spacer operatively attaching the VEGFR2-blocking, human anti-VEGF antibody of the invention and the toxin compound, wherein the peptide spacer is capable of folding into a disulfide-bonded loop structure. Proteolytic cleavage within the loop would then yield a heterodimeric polypeptide wherein the antibody and the toxin compound are linked by only a single disulfide bond.

When certain other toxin compounds are utilized, a non-cleavable peptide spacer may be provided to operatively attach the VEGFR2-blocking, human anti-VEGF antibody of the invention and the toxin compound. Toxins that may be used in conjunction with non-cleavable peptide spacers are those that may, themselves, be converted by proteolytic cleavage, into a cytotoxic disulfide-bonded form. An example of such a toxin compound is a *Pseudomonas* exotoxin compound.

A variety of chemotherapeutic and other pharmacological agents can also be successfully conjugated to VEGFR2-blocking, human anti-VEGF antibody therapeutics of the invention. Exemplary antineoplastic agents that have been conjugated to antibodies include doxorubicin, daunomycin, methotrexate and vinblastine. Moreover, the attachment of other agents such as neocarzinostatin, macromycin, trenimon and α-amanitin has been described (see U.S. Pat. Nos. 5,660,827; 5,855,866; and 5,965,132; each incorporated herein.)

The preparation of coaguligands is also easily practiced. The operable association of one or more coagulation factors with a VEGFR2-blocking, human anti-VEGF antibody of the invention may be a direct linkage, such as those described above for the immunotoxins. Alternatively, the operative association may be an indirect attachment, such as where the antibody is operatively attached to a second binding region, preferably an antibody or antigen binding region of an antibody, which binds to the coagulation factor. The coagulation factor should be attached to the VEGFR2-blocking, human anti-VEGF antibody of the invention at a site distinct from its functional coagulating site, particularly where a covalent linkage is used to join the molecules.

Indirectly linked coaguligands are often based upon bispecific antibodies. The preparation of bispecific antibodies is also well known in the art. One preparative method involves the separate preparation of antibodies having specificity for the targeted tumor component, on the one hand, and the coagulating agent on the other. Peptic F(ab'γ)$_2$ fragments from the two chosen antibodies are then generated, followed by reduction of each to provide separate Fab'γ$_{SH}$ fragments. The SH groups on one of the two partners to be coupled are then alkylated with a cross-linking reagent, such as o-phenylenedimaleimide, to provide free maleimide groups on one partner. This partner may then be conjugated to the other by means of a thioether linkage, to give the desired F(ab'γ)$_2$ heteroconjugate (Glennie et al., 1987). Other approaches, such as cross-linking with SPDP or protein A may also be carried out.

In the preparation of immunoconjugates, immunotoxins and coaguligands, recombinant expression may be employed. The nucleic acid sequences encoding the chosen VEGFR2-blocking, human anti-VEGF antibody of the invention, and therapeutic agent, toxin or coagulant, are attached in-frame in an expression vector. Recombinant expression thus results in translation of the nucleic acid to yield the desired immunoconjugate. Chemical cross-linkers and avidin:biotin bridges may also join the therapeutic agents to the VEGFR2-blocking, human anti-VEGF antibody of the invention.

The following patents are each incorporated herein by reference for the purposes of even further supplementing the present teachings regarding coaguligand preparation, purification and use, including bispecific antibody coaguligands: U.S. Pat. Nos. 5,855,866; 5,965,132; 6,093,399; 6,004,555; 5,877,289; and 6,036,955.

Immunoconjugates with radiotherapeutic agents, anti-angiogenic agents, apoptosis-inducing agents, anti-tubulin drugs, toxins and coagulants, whether prepared by chemical conjugation or recombinant expression, may employ a biologically-releasable bond and/or a selectively cleavable spacer or linker. Such compositions are preferably reasonably stable during circulation and are preferentially or specifically released upon delivery to the disease or tumor site.

Certain preferred examples are acid sensitive spacers, wherein VEGFR2-blocking, human anti-VEGF antibodies of the invention linked to colchicine or doxorubicin are particularly contemplated. Other preferred examples are peptide linkers that include a cleavage site for peptidases and/or proteinases that are specifically or preferentially present or active within a disease site, such as a tumor environment. The delivery of the immunoconjugate to the disease or tumor site results in cleavage and the relatively specific release of the coagulation factor.

Peptide linkers that include a cleavage site for urokinase, pro-urokinase, plasmin, plasminogen, TGFβ, staphylokinase, Thrombin, Factor IXa, Factor Xa or a metalloproteinase (MMP), such as an interstitial collagenase, a gelatinase or a stromelysin, are particularly preferred, as described and enabled by U.S. Pat. Nos. 5,877,289 and 6,342,221, each incorporated herein by reference for such purposes.

The VEGFR2-blocking, human anti-VEGF antibody of the invention may also be derivatized to introduce functional groups permitting the attachment of the therapeutic agent(s) through a biologically releasable bond. The targeting antibody may thus be derivatized to introduce side chains terminating in hydrazide, hydrazine, primary amine or secondary amine groups. Therapeutic agents may be conjugated through a Schiff's base linkage, a hydrazone or acyl hydrazone bond or a hydrazide linker (U.S. Pat. Nos. 5,474,765 and 5,762,918).

Whether primarily anti-angiogenic or vascular-targeting based, the compositions and methods of the present invention may be used in combination with other therapeutics and diagnostics. In terms of biological agents, preferably diagnostic or therapeutic agents, for use "in combination" with a VEGFR2-blocking, human anti-VEGF antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where the VEGFR2-blocking, human anti-VEGF of the invention is a naked antibody and is used in combination with an agent or therapeutic agent that is not operatively attached thereto. In such cases, the agent or therapeutic agent may be used in a non-targeted or targeted form. In "non-targeted form", the agent, particularly therapeutic agents, will generally be used according to their standard use in the art. In "targeted form", the agent will generally be operatively attached to a distinct antibody or targeting region that delivers the agent or therapeutic agent to the angiogenic disease site or tumor. The use of such targeted forms of biological agents, both diagnostics and therapeutics, is also quite standard in the art.

In other "combined" embodiments of the invention, the VEGFR2-blocking, human anti-VEGF antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of VEGFR2-blocking, human anti-VEGF antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the VEGFR2-blocking, human anti-VEGF antibodies of the present invention.

In certain preferred embodiments, the therapeutic compositions, combinations, pharmaceuticals, cocktails, kits, methods, and first and second medical uses will be "prodrug combinations". As will be understood by those of ordinary skill in the art, the term "prodrug combination", unless otherwise stated, means that the antibody of the invention is operatively attached to a component capable of converting the prodrug to the active drug, not that the antibody is attached to the prodrug itself. However, there is no requirement that the prodrug embodiments of the invention need to be used as prodrug combinations. Accordingly, prodrugs may be used in any manner that they are used in the art, including in ADEPT and other forms.

Thus, where combined compositions, pharmaceuticals, cocktails, kits, methods, and first and second medical uses are described, preferably in terms of diagnostic agents, and more preferably therapeutic agents, the combinations include VEGFR2-blocking, human anti-VEGF antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

Particularly preferred combined compositions, methods and uses of the invention are those including VEGFR2-blocking, human anti-VEGF antibodies of the invention and endostatin (U.S. Pat. No. 5,854,205). These include where the VEGFR2-blocking, human anti-VEGF antibody of the invention is a naked antibody or immunoconjugate; and when an immunoconjugate, wherein the VEGFR2-blocking, human anti-VEGF antibody of the invention is linked to endostatin, optionally with angiostatin; wherein the combined therapeutic method or use involves the prior, simultaneous, or subsequent administration of endostatin, optionally with angiostatin; so long as, in some conjugated or unconjugated form, the overall provision of the antibody, endostatin and optionally angiostatin is achieved. VEGFR2-blocking, human anti-VEGF antibodies of the invention operatively associated with collagenase are also provided, as the collagenase, when specifically delivered to the tumor, will produce endostatin in situ, achieving similar benefits.

The foregoing and other explanations of the effects of the present invention on tumors are made for simplicity to explain the combined mode of operation, type of attached agent(s) and such like. This descriptive approach should not be interpreted as either an understatement or an oversimplification of the beneficial properties of the VEGFR2-blocking, human anti-VEGF antibodies of the invention. It will therefore be understood that such antibodies themselves have anti-angiogenic properties and VEGF neutralization properties (such as neutralizing the survival function of VEGF), that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first VEGFR2-blocking, human anti-VEGF antibody of the invention, or an antigen-binding fragment or immunoconjugate of such an anti-VEGF antibody; and a biologically effective amount of at least a second biological agent, component or system.

The "at least a second biological agent, component or system" will often be a therapeutic or diagnostic agent, component or system, but it not be. For example, the at least a second biological agent, component or system may comprise components for modification of the antibody and/or for attaching other agents to the antibody. Certain preferred second biological agents, components or systems are prodrugs or components for making and using prodrugs, including components for making the prodrug itself and components for adapting the antibodies of the invention to function in such prodrug or ADEPT embodiments.

Where therapeutic or diagnostic agents are included as the at least a second biological agent, component or system, such therapeutics and/or diagnostics will typically be those for use in connection with angiogenic diseases. Such agents are those suitable for use in treating or diagnosing a disease or disorder as disclosed in any one of U.S. Pat. Nos. 5,712,291, 5,753,230, 5,972,922, 5,639,757, WO 98/45331 and WO 98/16551, each specifically incorporated herein by reference.

Where the disease to be treated is cancer, "at least a second anti-cancer agent" will be included in the therapeutic kit or cocktail. The term "at least a second anti-cancer agent" is chosen in reference to the VEGFR2-blocking, human anti-VEGF antibody of the invention being the first anti-cancer agent. The antibodies of the invention may thus be combined with chemotherapeutic agents, radiotherapeutic agents, cytokines, anti-angiogenic agents, apoptosis-inducing agents or anti-cancer immunotoxins or coaguligands.

"Chemotherapeutic agents", as used herein, refer to classical chemotherapeutic agents or drugs used in the treatment of malignancies. This term is used for simplicity notwithstanding the fact that other compounds may be technically described as chemotherapeutic agents in that they exert an anti-cancer effect. However, "chemotherapeutic" has come to have a distinct meaning in the art and is being used according to this standard meaning. A number of exemplary chemotherapeutic agents are described herein. Those of ordinary skill in the art will readily understand the uses and appropriate doses of chemotherapeutic agents, although the doses may well be reduced when used in combination with the present invention.

A new class of drugs that may also be termed "chemotherapeutic agents" are agents that induce apoptosis. Any one or more of such drugs, including genes, vectors, antisense constructs and ribozymes, as appropriate, may also be used in conjunction with the present invention. Currently preferred second agents are anti-angiogenic agents, such as angiostatin, endostatin, vasculostatin, canstatin and maspin.

Other exemplary anti-cancer agent include, e.g., neomycin, podophyllotoxin(s), TNF-α, $\alpha_v\beta_3$ antagonists, calcium ionophores, calcium-flux inducing agents, and any derivative or prodrug thereof. Currently preferred anti-tubulin drugs include colchicine, taxol, vinblastine, vincristine, vindescine, a combretastatin or a derivative or prodrug thereof.

Anti-cancer immunotoxins or coaguligands are further appropriate anti-cancer agents.

"Anti-cancer immunotoxins or coaguligands", or targeting-agent/therapeutic agent constructs, are based upon targeting agents, including antibodies or antigen binding fragments thereof, that bind to a targetable or accessible component of a tumor cell, tumor vasculature or tumor stroma, and that are operatively attached to a therapeutic agent, including cytotoxic agents (immunotoxins) and coagulation factors (coaguligands). A "targetable or accessible component" of a tumor cell, tumor vasculature or tumor stroma, is preferably a surface-expressed, surface-accessible or surface-localized component, although components released from necrotic or otherwise damaged tumor cells or vascular endothelial cells may also be targeted, including cytosolic and/or nuclear tumor cell antigens.

Both antibody and non-antibody targeting agents may be used, including growth factors, such as VEGF and FGF; peptides containing the tripeptide R-G-D, that bind specifically to the tumor vasculature; and other targeting components such as annexins and related ligands.

Anti-tumor cell immunotoxins or coaguligands may comprise antibodies exemplified by the group consisting of antibodies termed B3 (ATCC HB 10573), 260F9 (ATCC HB 8488), D612 (ATCC HB 9796) and KS1/4, said KS1/4 antibody obtained from a cell comprising the vector pGKC2310 (NRRL B-18356) or the vector pG2A52 (NRRL B-18357).

Anti-tumor cell targeting agents that comprise an antibody, or an antigen-binding region thereof, that binds to an intracellular component that is released from a necrotic tumor cell are also contemplated. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal.

U.S. Pat. Nos. 5,019,368, 4,861,581 and 5,882,626, each issued to Alan Epstein and colleagues, are each specifically incorporated herein by reference for purposes of even further describing and teaching how to make and use antibodies specific for intracellular antigens that become accessible from malignant cells in vivo. The antibodies described are sufficiently specific to internal cellular components of mammalian malignant cells, but not to external cellular components. Exemplary targets include histones, but all intracellular components specifically released from necrotic tumor cells are encompassed.

Upon administration to an animal or patient with a vascularized tumor, such antibodies localize to the malignant cells by virtue of the fact that vascularized tumors naturally contain necrotic tumor cells, due to the process(es) of tumor remodeling that occur in vivo and cause at least a proportion of malignant cells to become necrotic. In addition, the use of such antibodies in combination with other therapies that enhance tumor necrosis serves to enhance the effectiveness of targeting and subsequent therapy.

These types of antibodies may thus be used to directly or indirectly associate with angiopoietins and to administer the angiopoietins to necrotic malignant cells within vascularized tumors, as generically disclosed herein.

As also disclosed in U.S. Pat. Nos. 5,019,368, 4,861,581 and 5,882,626, each incorporated herein by reference, these antibodies may be used in combined diagnostic methods (see below) and in methods for measuring the effectiveness of anti-tumor therapies. Such methods generally involve the preparation and administration of a labeled version of the antibodies and measuring the binding of the labeled antibody to the internal cellular component target preferentially bound within necrotic tissue. The methods thereby image the necrotic tissue, wherein a localized concentration of the antibody is indicative of the presence of a tumor and indicate ghosts of cells that have been killed by the anti-tumor therapy.

Anti-tumor stroma immunotoxins or coaguligands will generally comprise antibodies that bind to a connective tissue component, a basement membrane component or an activated platelet component; as exemplified by binding to fibrin, RIBS or LIBS.

Anti-tumor vasculature immunotoxins or coaguligands may comprise ligands, antibodies, or fragments thereof, which bind to a surface-expressed, surface-accessible or surface-localized component of the blood transporting vessels, preferably the intratumoral blood vessels, of a vascularized tumor. Such antibodies include those that bind to surface-expressed components of intratumoral blood vessels of a vascularized tumor, including intratumoral vasculature cell surface receptors, such as endoglin (TEC-4 and TEC-11 antibodies), a TGFβ receptor, E-selectin, P-selectin, VCAM-1, ICAM-1, PSMA, a VEGF/VPF receptor, an FGF receptor, a TIE, $\alpha_v\beta_3$ integrin, pleiotropin, endosialin and MHC Class II proteins. The antibodies may also bind to cytokine-inducible or coagulant-inducible components of intratumoral blood vessels. Certain preferred agents will bind to aminophospholipids, such as phosphatidylserine or phosphatidylethanolamine.

Other anti-tumor vasculature immunotoxins or coaguligands may comprise antibodies, or fragments thereof, that bind to a ligand or growth factor that binds to an intratumoral vasculature cell surface receptor. Such antibodies include those that bind to VEGF/VPF (GV39 and GV97 antibodies), FGF, TGFβ, a ligand that binds to a TIE, a tumor-associated fibronectin isoform, scatter factor/hepatocyte growth factor (HGF), platelet factor 4 (PF4), PDGF and TIMP. The antibodies, or fragments thereof, may also bind to a ligand:receptor complex or a growth factor:receptor complex, but not to the ligand or growth factor, or to the receptor, when the ligand or growth factor or the receptor is not in the ligand:receptor or growth factor:receptor complex.

Anti-tumor cell, anti-tumor stroma or anti-tumor vasculature antibody-therapeutic agent constructs may comprise anti-angiogenic agents, apoptosis-inducing agents, anti-tubulin drugs, cytotoxic agents such as plant-, fungus- or bacteria-derived toxins. Ricin A chain and deglycosylated ricin A chain will often be preferred. Anti-tumor cell, anti-tumor stroma or anti-tumor vasculature antibody-therapeutic agent constructs may comprise coagulants (direct and indirect acting coagulation factors) or second antibody binding regions that bind to coagulation factors. The operative association with Tissue Factor or Tissue Factor derivatives, such as truncated Tissue Factor, will often be preferred.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second anti-cancer agent may be administered to the animal or patient substantially simultaneously with the VEGFR2-blocking, human anti-VEGF antibody of the invention; such as from a single pharmaceutical composition or from two pharmaceutical compositions administered closely together.

Alternatively, the at least a second anti-cancer agent may be administered to the animal or patient at a time sequential to the administration of the VEGFR2-blocking, human anti-VEGF antibody of the invention. "At a time sequential", as used herein, means "staggered", such that the at least a second anti-cancer agent is administered to the animal or patient at a time distinct to the administration of the VEGFR2-blocking, human anti-VEGF antibody of the invention. Generally, the two agents are administered at times effectively spaced apart to allow the two agents to exert their respective therapeutic effects, i.e., they are administered at "biologically effective time intervals". The at least a second anti-cancer agent may be administered to the animal or patient at a biologically effective time prior to the VEGFR2-blocking, human anti-VEGF antibody of the invention, or at a biologically effective time subsequent to that therapeutic.

Accordingly, the present invention provides methods for treating an animal or patient with a vascularized tumor, comprising:
(a) subjecting the animal or patient to a first treatment that substantially reduces the tumor burden; and
(b) subsequently administering at least a first anti-angiogenic agent to the animal or patient in an amount effective to inhibit metastasis from any surviving tumor cells; wherein the first anti-angiogenic agent is at least a first VEGFR2-blocking, human anti-VEGF antibody of the invention, or antigen-binding fragment thereof; optionally wherein the antibody or fragment is operatively associated with a second anti-angiogenic agent.

Preferred first treatments include surgical resection and chemotherapeutic intervention. Combined anti-angiogenics can also be used.

Other treatment methods for animals or patients with vascularized tumors, comprise:
(a) administering a first antibody-therapeutic agent construct to the animal or patient in an amount effective to induce substantial tumor necrosis; wherein the first antibody-therapeutic agent construct comprises a therapeutic agent operatively linked to a first antibody, or antigen binding fragment thereof, that binds to a surface-expressed, surface-accessible or surface-localized component of a tumor cell, tumor vasculature or tumor stroma; and
(b) subsequently administering a second antibody to the animal or patient in an amount effective to inhibit metastasis from any surviving tumor cells; wherein the second antibody is at least a first VEGFR2-blocking, human anti-VEGF antibody of the invention, or antigen-binding fragment thereof, and further optionally wherein the antibody or fragment is operatively associated with a second anti-angiogenic agent.

In particularly preferred embodiments, human VEGFR2-blocking, anti-VEGF antibodies of the invention are provided for use in combination with prodrugs and ADEPT. In such compositions, combination, pharmaceuticals, kits, methods and uses, the VEGFR2-blocking, human anti-VEGF antibody of the invention or fragment thereof will be modified to provide a converting or enzymatic capacity, or operatively associated with, preferably covalently linked or conjugated to, at least a first converting agent or enzyme capable of converting at least one prodrug to the active form of the drug.

The enzymatic or enzyme-conjugated antibody or fragment will combined with an initially separate formulation of the "prodrug". The prodrug will be an inactive or weakly active form of a drug that is that is converted to the active form of the drug on contact with the enzymatic capacity, converting function or enzyme associated with the VEGFR2-blocking, human anti-VEGF of the invention.

Accordingly, kits are provided that comprise, preferably in separate compositions and/or containers:
(a) a biologically effective amount of at least a first VEGFR2-blocking, human anti-VEGF antibody of the invention or fragment thereof, that has an enzymatic function, preferably where the antibody or fragment is operatively associated with, covalently linked or conjugated to, at least a first enzyme; and
(b) a biologically effective amount of at least a first substantially inactive prodrug that is converted to a substantially active drug by the enzymatic function of, or enzyme associated with, linked to or conjugated to the VEGFR2-blocking, human anti-VEGF antibody or fragment.

The present invention further provides advantageous methods and uses that comprise:
(a) administering to an animal or patient with a vascularized tumor a biologically effective amount of at least a first pharmaceutical composition comprising at least a first VEGFR2-blocking, human anti-VEGF antibody of the invention, or antigen binding fragment thereof, wherein the antibody or fragment has an enzymatic function, preferably wherein the antibody or fragment is operatively associated with, covalently linked to, or conjugated to, at least a first enzyme; wherein said antibody or fragment localizes to the vasculature, intratumoral vasculature or stroma of the vascularized tumor after administration; and
(b) subsequently administering to the animal or patient, after an effective time period, a biologically effective amount of at least a second pharmaceutical composition comprising a biologically effective amount of at least one substantially inactive prodrug; wherein the prodrug is converted to a substantially active drug by the enzymatic function of, or enzyme associated with, linked to, or conjugated to the VEGFR2-blocking, human anti-VEGF antibody or fragment of the invention localized within the vasculature, intratumoral vasculature or stroma of said vascularized tumor.

In certain other embodiments, the antibodies and immunoconjugates of the invention may be combined with one or more diagnostic agents, typically diagnostic agents for use in connection with angiogenic diseases. A range of diagnostic compositions, kits and methods are thus included within the invention.

Yet further aspects are methods of diagnosis or imaging of a subject comprising the administration of an appropriate amount of a human antibody or other protein of the invention as defined herein to the subject and detecting the presence and/or amount and/or the location of the antibody or other protein of the invention in the subject.

Appropriate diseases to be imaged or diagnosed in accordance with the above described uses and methods include any disease associated with angiogenesis as described elsewhere herein.

In one embodiment, the invention provides a method of diagnosing a disease associated with angiogenesis in a mammal comprising the step of:
(a) contacting a test sample taken from said mammal with any one or more of the antibodies of the invention.

In a further embodiment, the invention provides a method of diagnosing disease associated with angiogenesis in a mammal comprising the steps of:
(a) contacting a test sample taken from said mammal with one or more of the antibodies of the invention;
(b) measuring the presence and/or amount and/or location of antibody-antigen complex in the test sample; and, optionally
(c) comparing the presence and/or amount of antibody-antigen complex in the test sample to a control.

In the above methods, said contacting step is carried out under conditions that permit the formation of an antibody-antigen complex. Appropriate conditions can readily be determined by a person skilled in the art.

In the above methods any appropriate test sample may be used, for example biopsy cells, tissues or organs suspected of being affected by disease or histological sections:

In certain of the above methods, the presence of any amount of antibody-antigen complex in the test sample would be indicative of the presence of disease. Preferably, for a positive diagnosis to be made, the amount of antibody-antigen complex in the test sample is greater than, preferably significantly greater than, the amount found in an appropriate control sample. More preferably, the significantly greater levels are statistically significant, preferably with a probability value of <0.05. Appropriate methods of determining statistical significance are well known and documented in the art and any of these may be used.

Appropriate control samples could be readily chosen by a person skilled in the art, for example, in the case of diagnosis of a particular disease, an appropriate control would be a sample from a subject that did not have that disease. Appropriate control "values" could also be readily determined without running a control "sample" in every test, e.g., by reference to the range for normal subjects known in the art.

For use in the diagnostic or imaging applications, the antibodies of the invention may be labeled with a detectable marker such as a radio-opaque or radioisotope, such as $^3$H, $^{14}$C, $^{32}$P, $^{35}$S, $^{123}$I, $^{125}$I, $^{131}$I; a radioactive emitter (e.g., α, β or γ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g., labelled avidin/streptavidin. Methods of attaching a label to a binding protein, such as an antibody or antibody fragment, are known in the art. Such detectable markers allow the presence, amount or location of binding protein-antigen complexes in the test sample to be examined.

Preferred detectable markers for in vivo use include an X-ray detectable compound, such as bismuth (III), gold (III), lanthanum (III) or lead (II); a radioactive ion, such as copper gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

The invention also includes diagnostic or imaging agents comprising the antibodies of the invention attached to a label that produces a detectable signal, directly or indirectly. Appropriate labels are described elsewhere herein.

The invention further includes kits comprising one or more of the human antibodies or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g., the therapeutic, diagnostic or imaging methods as described herein, or are for use in the in vitro assays or methods as described herein. The antibody in such kits may preferably be an antibody conjugate as described elsewhere herein, e.g., may be conjugated to a detectable moiety or may be an immunoconjugate. Preferably said kits comprise instructions for use of the kit components, for example in diagnosis. Preferably said kits are for diagnosing diseases associated with angiogenesis and optionally comprise instructions for use of the kit components to diagnose such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

In terms of cancer diagnosis and treatment, the diagnostic and imaging compositions, kits and methods of the present invention include in vivo and in vitro diagnostics. For example, a vascularized tumor may be imaged using a diagnostically effective amount of a tumor diagnostic component that comprises at least a first binding region that binds to an accessible component of a tumor cell, tumor vasculature or tumor stroma, operatively attached to an in vivo diagnostic imaging agent.

The tumor imaging is preferably conducted to provide an image of the stroma and/or vasculature of a vascularized tumor using a diagnostic component that comprises at least a first binding region that binds to an accessible component of tumor vasculature or tumor stroma. Any suitable binding region or antibody may be employed, such as those described above in terms of the therapeutic constructs. Certain advantages will be provided by using a detectably-labeled VEGFR2-blocking, human anti-VEGF antibody of the invention construct, wherein the image formed will be predictive of the binding sites of the therapeutic to be used.

Detectably-labeled in vivo tumor diagnostics, preferably a VEGFR2-blocking, human anti-VEGF antibody of the invention, may comprise an X-ray detectable compound, such as bismuth (III), gold (III), lanthanum (III) or lead (II); a radioactive ion, such as copper gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Pre-imaging before tumor treatment may be carried out by:
(a) administering to the animal or patient a diagnostically effective amount of a pharmaceutical composition comprising a diagnostic agent operatively attached to at least a first binding region that binds to an accessible component of a tumor cell, tumor vasculature (preferably) or tumor stroma (preferably), including diagnostic agents operatively attached to a VEGFR2-blocking, human anti-VEGF antibody construct of the invention; and
(b) subsequently detecting the detectably-labeled first binding region (or VEGFR2-blocking, human anti-VEGF antibody of the invention) bound to the tumor cells, tumor blood vessels (preferably) or tumor stroma (preferably); thereby obtaining an image of the tumor, tumor vasculature and/or tumor stroma.

Cancer treatment may also be carried out by:
(a) forming an image of a vascularized tumor by administering to an animal or patient having a vascularized tumor a diagnostically minimal amount of at least a first detectably-labeled tumor binding agent, preferably a VEGFR2-blocking, human anti-VEGF antibody construct of the invention, comprising a diagnostic agent operatively attached to the tumor binding agent or VEGFR2-blocking, anti-VEGF antibody of the invention, thereby forming a detectable image of the tumor, tumor vasculature (preferably), or tumor stroma (preferably); and
(b) subsequently administering to the same animal or patient a therapeutically optimized amount of at least a first naked VEGFR2-blocking, human anti-VEGF antibody of the invention or therapeutic agent-antibody construct using such an antibody, thereby causing an anti-tumor effect.

Imaging and treatment formulations or medicaments are thus provided, which generally comprise:
(a) a first pharmaceutical composition comprising a diagnostically effective amount of a detectably-labeled tumor binding agent, preferably a VEGFR2-blocking, human anti-VEGF antibody construct of the invention, that comprises a detectable agent operatively attached to the tumor binding agent or VEGFR2-blocking, human anti-VEGF antibody of the invention; and
(b) a second pharmaceutical composition comprising a therapeutically effective amount of at least one naked VEGFR2-blocking, human anti-VEGF antibody of the invention or therapeutic agent-antibody construct using such an antibody.

The invention also provides in vitro diagnostic kits comprising at least a first composition or pharmaceutical composition comprising a biologically effective amount of at least one diagnostic agent that is operatively associated with at least a first VEGFR2-blocking, human anti-VEGF antibody of the invention, or an antigen-binding fragment thereof.

The invention still further provides combined kits in which the diagnostic agent is intended for use outside the body, preferably in connection with a test conducted on a biological sample obtained from an animal or patient. As such, the invention provides kits comprising, generally in at least two distinct containers, at least a first composition, pharmaceutical composition or medicinal cocktail comprising a biologically effective amount of at least a first VEGFR2-blocking, human anti-VEGF antibody of the invention, or an antigen-binding fragment or immunoconjugate of such an anti-VEGF antibody; and a biologically effective amount of at least one diagnostic agent, component or system for in vitro use.

The "diagnostic agent, component or system for in vitro use" will be any diagnostic agent or combination of agents that allow the diagnosis of one or more diseases that have an angiogenic component. The in vitro diagnostics thus include those suitable for use in generating diagnostic or prognostic information in relation to a disease or disorder as disclosed in any one of U.S. Pat. Nos. 5,712,291, 5,753,230, 5,972,922, 5,639,757, WO 98/45331 and WO 98/16551, each specifically incorporated herein by reference. In terms of cancer diagnosis and treatment, the in vitro diagnostics will preferably include a diagnostic component that comprises at least a first binding region that binds to an accessible component of a tumor cell, tumor vasculature (preferably) or tumor stroma (preferably) operatively attached to a "detectable or reporter agent" directly or indirectly detectable by an in vitro diagnostic test. "Detectable or reporter agents" directly detectable in vitro include those such as radiolabels and reporter agents detectable by immunofluorescence.

"Detectable or reporter agents" indirectly detectable in vitro include those that function in conjunction with further exogenous agent(s), such as detectable enzymes that yield a colored product on contact with a chromogenic substrate. Indirect detection in vitro also extends to detectable or reporter components or systems that comprise the first binding region that binds to an accessible component of a tumor cell, tumor vasculature (preferably) or tumor stroma (preferably) in combination with at least one detecting antibody that has immunospecificity for the first binding region. The "detecting antibody" is preferably a "secondary antibody" that is attached to a direct or indirect detectable agent, such a radiolabel or enzyme. Alternatively, a "secondary and tertiary antibody detection system" may be used, including a first detecting antibody that has immunospecificity for the first binding region in combination with a second detecting antibody that has immunospecificity for the first detecting antibody, the second detecting antibody being attached to a direct or indirect detectable agent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the nucleotide and amino acid sequences of the heavy (VH) and light (VL) chain variable region of a scFv form of clone EJ 173/112-Cl1 (r84/PGN311). ScFv were cloned via Nco/NotI site into pHOG21 (3.7 Kb). The restriction sites used for initial cloning (NcoI, HindIII, MluI and NotI) are italicized and underlined. The linker sequence between VH and VL is in italic.

FIG. 2 shows the results of an ELISA assay to assess the binding of clone EJ173/112-Cl1 (r84), its mother clone and a positive control antibody (murine B9) to plated VEGF-A. Clone EJ173/112-Cl1 (r84) showed the highest binding signal and hence the highest affinity.

FIG. 8A and FIG. 8B together show that r84/PGN311 substantially blocks the interaction of VEGF with VEGFR2 but does not substantially block the interaction of VEGF with VEGFR1. VEGF-biotin in the presence or absence of the indicated antibodies was incubated in wells of an ELISA plate that were coated with soluble VEGFR1 (FIG. 8A) or VEGFR2 (FIG. 8B). The signal of VEGF alone (VEGF) or VEGF in the presence of the indicated antibody was normalized to VEGF alone (100%). The mean+/−SEM is shown. N=12 (4 identical plates with each treatment performed in triplicate). A signal of less than 50% is considered significant and substantial inhibition of binding. Synagis is a human anti-RSV antibody used as a negative control. For comparison, results with the Avastin (bevacizumab) (Presta et al., 1997) antibody are also presented, which show that Avastin substantially blocks the interaction of VEGF with both VEGFR2 and VEGFR1.

FIG. 9A shows the scFv expression vector pHOG21. ApR, Ampicillin resistance gene; ColE1, origin of DNA replication; fllG, intergenic region of phage fl; c-myc, epitope recognized by the monoclonal antibody 9E10; His6, six histidine residues; pelB, signal peptide of bacterial pectate lyase; P/O, wild type lac promoter operator. FIG. 9B shows the nucleotide (SEQ ID NO:28) and amino acid (SEQ ID NO:29) sequences of the C-terminal coding region.

FIG. 10A shows co-localization of T014 (VEGFR2 antibody) and F4/80 (macrophage marker) staining on tumor sections from control treated or 2C3 treated animals. FIG. 10A shows that 2C3 decreases macrophage infiltration. However, both the control and 2C3 groups demonstrate co-localization of VEGFR2 and macrophage markers. FIG. 10B shows the number of cells double positive for one of three different macrophage markers and VEGFR2. FIG. 10C uses two different antibodies to VEGFR2 to show that peritoneal macrophages from tumor bearing animals express VEGFR2.

FIG. 11 shows results from a study using an in vivo (mouse) MDA-MB-231 breast cancer tumor model and the effect of r84, Avastin or saline (control) on tumor volume. Mean tumor volume+/−SEM is shown. Avastin and r84 treated mice have tumor volumes that are significantly smaller than control treated animals.

FIG. 13 shows results from a study using an in vivo (mouse) A673 tumor model and the effect of r84, 2C3 or a control antibody (Synagis-human anti-RSV) on tumor volume. Mean tumor volume +/−SEM is shown. 2C3 and r84 treated mice have tumor volumes that are significantly smaller than control treated animals. 2C3 and r84 are thus effective at controlling the growth of A673 tumors.

FIG. 14 shows that tumors from r84 and 2C3 treated animals showed significantly reduced expression of the macrophage marker Mac-3, and that r84 has a more pronounced effect than 2C3 (p<0.01 for r84).

FIG. 15 shows that tumors from r84 and 2C3 treated animals showed a significantly reduced number of blood vessels/high power field (MECA-32, p<0.0001).

FIG. 16A shows that r84/PGN311 inhibits the VEGF stimulated (+VEGF) phosphorylation of Erk1/2 (pERK1/2) and PLC-γ (pPLC-γ) on VEGFR2 expressing cells (HDMEC). The positive control Avastin also inhibits the VEGF stimulated phosphorylation of Erk1/2 and PLC-γ. FIG. 16B shows that r84/PGN311 does not inhibit the VEGF stimulated phosphorylation of VEGFR1 on VEGFR1 expressing cells (PAE Flt) whereas the positive control, Avastin, does inhibit phosphorylation of VEGFR1.

FIG. 17A, FIG. 17B, FIG. 17C and FIG. 17D show that r84/PGN311 leads to a significant reduction in growth of tumors produced by non-small cell lung cancer cell lines. FIG. 17A, FIG. 17B, FIG. 17C and FIG. 17D show results from studies using an in vivo mouse model and four different non-small cell lung cancer cell lines, H460 (FIG. 17A), H1299 (FIG. 17B), H358 (FIG. 17C) and A549 (FIG. 17D). The effect of r84/PGN311, Avastin or a control antibody (Synagis or XTL) on tumor weight is shown (mean weight of tumors+/−SEM is shown). r84/PGN311- and Avastin-treated mice have mean tumor weights that are significantly lower than control treated animals. r84/PGN311 and Avastin are thus effective at controlling the growth of non-small cell lung cancer cell lines. r84/PGN311 performs better than Avastin at least in the H460 (FIG. 17A), H11299 (FIG. 17B) and the A549 (FIG. 17D) models. r84 is significantly better than Avastin in the A549 model (FIG. 17D).

FIG. 18A (six panels) is immunofluorescence staining of frozen MDA-MB-231 tumor sections showing the lymphatic markers, podoplanin (green), Prox1 (red) and the merged images, in control (top panels) and r84-treated tumors (bottom panels). FIG. 18B (two panels) shows MDA-MB-231 tumor sections stained for LYVE-1 in control (top panel) and r84-treated tumors (bottom panel). The pattern of LYVE-1 staining (FIG. 18B) is similar to that for podoplanin and Prox1 (FIG. 18A). The entire area of each LYVE-1 stained tumor section was examined at low magnification and the percent of LYVE-1 positive area was determined for each field using NIS-Elements imaging software (FIG. 18C). The ten fields with the highest LYVE-1 positive percent area were averaged together to yield a final score for each tumor and group means were tested for significance by an unpaired student's t-test. The percent of LYVE-1 positive area of control tumors (7.03±1.013; n=6) was significantly greater than r84 treated tumors (2.23±0.986; n=5), with P=0.0042.

FIG. 20A and FIG. 20B show that r84/PGN311 potently inhibits VEGF-induced migration of VEGFR2-expressing endothelial cells. HDMEC (FIG. 20A) and PAE KDR-expressing cells (FIG. 20B) were used in transwell assays. The cells were either not stimulated (NS), or exposed to VEGF at 100 ng/ml to stimulate migration (VEGF), and the ability of a 500-fold molar excess of r84, Avastin (Avas) or control (Cntl) antibodies (IgG format) to inhibit VEGF-induced migration was tested. VEGF induces migration in comparison to not stimulated cells (p<0.01). r84 and Avastin inhibit VEGF-induced migration (***, p<0.0001 vs. VEGF alone).

FIG. 21 shows that r84/PGN311 does not inhibit VEGF-induced migration of VEGFR1-expressing endothelial cells. PAE Flt1, endothelial cells that express VEGFR1 exclusively, were serum-starved for 24 hours and then plated in serum-free media in transwell inserts (8 µM pores, 5,000 cells/insert). Migration to the underside of the membrane was stimulated by adding the following to the well below the insert: serum-free media (NS); VEGF (100 ng/ml); VEGF+a control IgG (Cntl); VEGF+Avastin (Avastin); VEGF+r84 (r84). The cells were allowed to migrate for 24 hours at which time the membranes were removed, cells removed from the upper surface of the membrane, fixed, and stained with DAPI. DAPI stained nuclei on the underside of the member were then counted by fluorescence microscopy and quantified using software (Elements, Nikon). *, p<0.05 r84 vs Avastin; **, p<0.01 Avastin vs control. FIG. 22 shows that r84/PGN311 reduces the growth of subcutaneous human pancreatic tumor xenografts. Panc1 tumor cells were injected subcutaneously into SCID mice ($2 \times 10^6$ cells/animal) on day 0. Mice were treated starting on Day 12x/week with 500 µg of a control IgG (Synagis) or r84. Tumor volume was monitored over time using calipers. Mean (SEM) tumor volume (n=5/group) versus day post tumor cell injection (TCI) is shown.

DESCRIPTION OF ILLUSTRATIVE EMBODIMENTS

Figure 2:
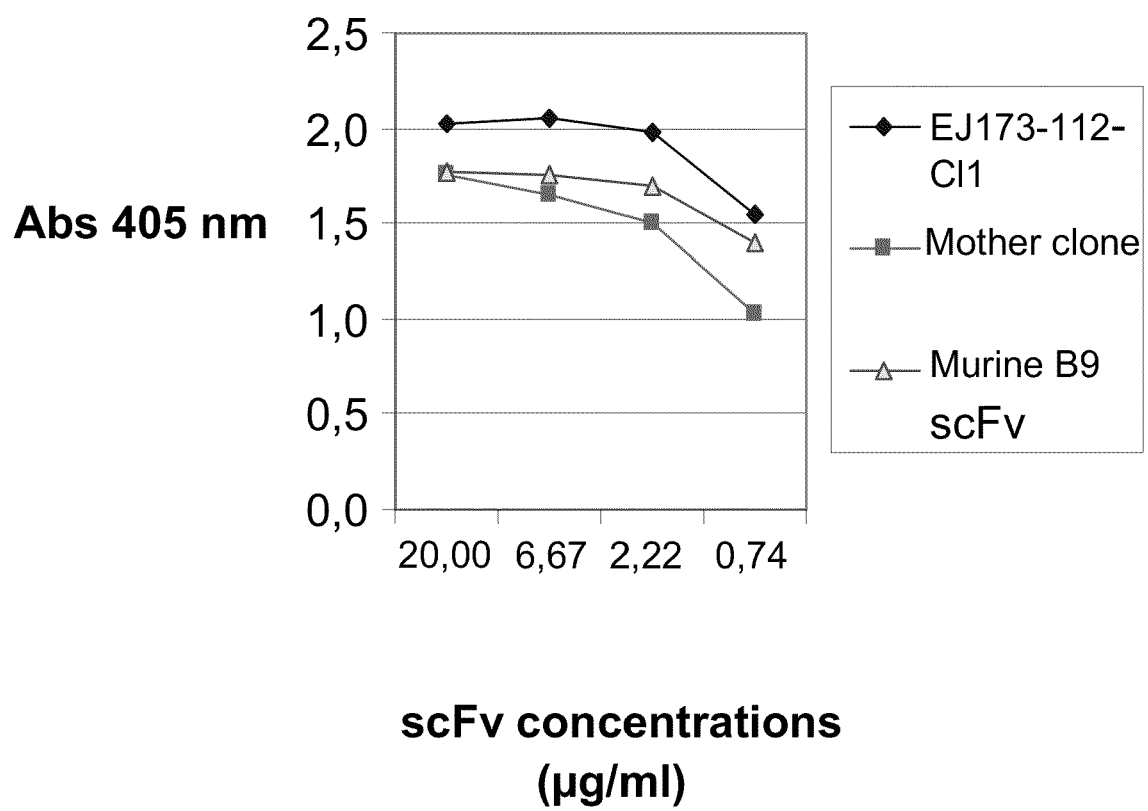
FIG. 2 shows that clone EJ173/112-Cl1 (r84/PGN311) scFv binds VEGF.

Solid tumors and carcinomas account for more than 90% of all cancers in man. Although the use of monoclonal antibodies and immunotoxins has been investigated in the therapy of lymphomas and leukemias, these agents have been disappointingly ineffective in clinical trials against carcinomas and other solid tumors (Abrams and Oldham, 1985). A principal reason for the ineffectiveness of antibody-based treatments is that macromolecules are not readily transported into solid tumors. Even once within a tumor mass, these molecules fail to distribute evenly due to the presence of tight junctions between tumor cells, fibrous stroma, interstitial pressure gradients and binding site barriers (Dvorak et al., 1991a).

In developing new strategies for treating solid tumors, the methods that involve targeting the vasculature of the tumor, rather than the tumor cells, offer distinct advantages. An effective destruction or blockade of the tumor vessels arrests blood flow through the tumor and results in an avalanche of tumor cell death. Antibody-toxin and antibody-coagulant constructs have already been effectively used in the specific targeting and destruction of tumor vessels, resulting in tumor necrosis (Burrows et al., 1992; Burrows and Thorpe, 1993; WO 93/17715; WO 96/01653; U.S. Pat. Nos. 5,855,866; 5,877,289; 5,965,132; 6,051,230; 6,004,555; 6,093,399.

Where antibodies, growth factors or other binding ligands are used to specifically deliver a coagulant to the tumor vasculature, such agents are termed "coaguligands". A currently preferred coagulant for use in coaguligands is truncated Tissue Factor (tTF) (Huang et al., 1997; WO 96/01653; U.S. Pat. No. 5,877,289). TF is the major initiator of blood coagulation. At sites of injury, Factor VII/VIIa in the blood comes into contact with, and binds to, TF on cells in the perivascular tissues. The TF:VIIa complex, in the presence of the phospholipid surface, activates factors IX and X. This, in turn, leads to the formation of thrombin and fibrin and, ultimately, a blood clot.

A range of suitable target molecules that are available on tumor endothelium, but largely absent from normal endothelium, have been described. For example, expressed targets may be utilized, such as endoglin, E-selectin, P-selectin, VCAM-1, ICAM-1, PSMA, a TIE, a ligand reactive with LAM-1, a VEGF/VPF receptor, an FGF receptor, $\alpha_v\beta_3$ integrin, pleiotropin or endosialin (U.S. Pat. Nos. 5,855,866; 5,877,289 and 6,004,555; Burrows et al., 1992; Burrows and Thorpe, 1993; Huang et al., 1997; each incorporated herein by reference).

Other targets inducible by the natural tumor environment or following intervention by man are also targetable entities, as described in U.S. Pat. Nos. 5,776,427 and 6,036,955; each incorporated herein by reference). When used in conjunction with prior suppression in normal tissues and tumor vascular induction, MHC Class II antigens may also be employed as targets (U.S. Pat. Nos. 5,776,427; 6,004,554 and 6,036,955; each incorporated herein by reference).

Adsorbed targets are another suitable group, such as VEGF, FGF, TGFβ, HGF, PF4, PDGF, TIMP, a ligand that binds to a TIE or a tumor-associated fibronectin isoform (U.S. Pat. Nos. 5,877,289 and 5,965,132; each incorporated herein by reference). Fibronectin isoforms are ligands that bind to the integrin family of receptors. Tumor-associated fibronectin isoforms are targetable components of both tumor vasculature and tumor stroma.

One currently preferred marker for such clinical targeting applications is receptor-associated VEGF. In fact, assemblies of VEGF:receptor complexes are one of the most specific markers of tumor vasculature observed to date (U.S. Pat. Nos. 5,877,289; 5,965,132 and 6,051,230; Lin-Ke et al., 1996; Dvorak et al., 1991b).

The VEGF:receptor complex presents an attractive target for the specific delivery of drugs or other effectors to tumor endothelium - - as tumors are rich in cytokines and growth factors and as VEGF receptors are upregulated under the hypoxic conditions that are found in most solid tumors (Mazure et al., 1996; Forsythe et al., 1996; Waltenberger et al., 1996; Gerber et al., 1997; Kremer et al., 1997). Upregulation of both the ligand and its receptor specifically in the tumor microenvironment leads to a high concentration of occupied receptor on tumor vascular endothelium, as compared with the endothelium in normal tissue (U.S. Pat. Nos. 5,877,289 and 5,965,132). Dvorak and colleagues also showed that rabbit polyclonal antibodies directed against the N-terminus of VEGF selectively stain tumor blood vessels after injection into mice bearing syngeneic tumors (Lin-Ke et al., 1996).

The role of VEGF as a target for clinical intervention is not limited to immunotoxin or coaguligand therapies. Indeed, VEGF is one of the key factors involved in angiogenesis of solid tumors (Ferrara, 1995; Potgens et al., 1995), being both a potent permeability agent (Senger et al., 1983; Senger et al., 1990; Senger et al., 1986) and endothelial cell mitogen (Keck et al., 1989; Connolly et al., 1989; Thomas, 1996). The link between VEGF and angiogenesis has led to proposals of various therapeutic strategies aimed at VEGF intervention (Siemeister et al., 1998).

A. VEGF and VEGF Receptors

Vascular endothelial growth factor isoform A (VEGF-A, succinctly termed "VEGF" in the present application) is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and endothelial cell proliferation factor (Thomas, 1996; Neufeld et al., 1999). Its activity is required for normal embryonic development (Fong et al., 1995; Shalaby et al., 1995), as targeted disruption of one or both alleles of VEGF results in embryonic lethality (Carmeliet et al., 1996; Ferrara et al., 1996).

VEGF is an important factor driving angiogenesis or vasculogenesis in numerous physiological and pathological processes, including wound healing (Frank et al., 1995; Burke et al., 1995), diabetic retinopathy (Alon et al., 1995; Malecaze et al., 1994), psoriasis (Detmar et al., 1994), atherosclerosis (Inoue et al., 1998), rheumatoid arthritis (Harada et al., 1998; Nagashima et al., 1999), solid tumor growth (Plate et al., 1994; Claffey et al., 1996).

A wide variety of cells and tissues produce VEGF, which exists in at least five isoforms (121, 145, 165, 189, and 206 amino acids) that are splice variants encoded by the same gene (Houck et al., 1991; Ferrara et al., 1991; Tischer et al., 1991). The two smaller isoforms, 121 and 165, are secreted from cells (Houck et al., 1991; Anthony et al., 1994). Secreted VEGF is an obligate dimer of between 38-46 kDa in which the monomers are linked by two disulfide bonds.

VEGF dimers bind with high affinity to two well-characterized receptors, VEGFR1 (FLT-1) and VEGFR2 (KDR/Flk-1), which are selectively expressed on endothelial cells (Flt-1 and Flk-1 are the mouse homologues). The $K_d$ of VEGF binding to VEGFR1 and VEGFR2 is 15-100 pM and 400-800 pM, respectively (Terman et al., 1994). A recently identified third cell surface protein, neuropilin-1, also binds VEGF with high affinity (Olander et al., 1991; De Vries et al., 1992; Terman et al., 1992; Soker et al., 1998).

VEGFR1 and VEGFR2 are members of the Type III receptor tyrosine kinase (RTK III) family that is characterized by seven extracellular IgG-like repeats, a single spanning transmembrane domain, and an intracellular split tyrosine kinase domain (Mustonen and Alitalo, 1995). Until very recently, VEGFR1 and VEGFR2 were thought to be almost exclusively expressed on endothelial cells (Mustonen and Alitalo, 1995). Although VEGFR1 and VEGFR2 have been reported to have different functions with respect to stimulating endothelial cell proliferation, migration, and differentiation (Waltenberger et al., 1994; Guo et al., 1995), the precise role that each receptor plays in VEGF biology and endothelial cell homeostasis was not clearly defined prior to the present invention.

Recent studies using knockout mice have shown each of VEGF, VEGFR1 and VEGFR2 to be essential for vasculogenesis, angiogenesis and embryo development (Fong et al., 1995; Shalaby et al., 1995; Hiratsuka et al., 1998). In studies of lethal knockouts, the phenotypes associated with the lack of each receptor were different. Targeted disruption of VEGFR2 resulted in an embryo that lacked endothelial cell differentiation and failed to form yolk sac blood islands or go through vasculogenesis (Shalaby et al., 1995). VEGFR1 null mutants showed impaired vasculogenesis, disorganized assembly of endothelial cells, and dilated blood vessels (Fong et al., 1995; Hiratsuka et al., 1998). VEGFR1 evidently has a vital biological role.

VEGFR1 has a higher affinity for VEGF than VEGFR2, although it has a lower tyrosine kinase activity. This suggests that the extracellular domain of VEGFR1 is particularly important. This hypothesis was strongly supported by results from studies in knockout mice in which the tyrosine kinase domain of VEGFR1 was deleted whilst leaving the VEGF binding domain intact (Hiratsuka et al., 1998). The VEGFR1-tyrosine kinase deficient embryos developed normal blood vessels and survived to term (Hiratsuka et al., 1998).

In addition to the earlier knockouts (Fong et al., 1995; Shalaby et al., 1995), the Hiratsuka et al. (1998) studies indicate that VEGFR1 has a vital biological role. However, tyrosine kinase signaling does not seem to be the critical factor. It is interesting to note that macrophages from the VEGFR1 knockout mice did not exhibit VEGF-induced chemotaxis (Hiratsuka et al., 1998; incorporated herein by reference), thereby implicating VEGFR1 as the receptor responsible for mediating this important biological response to VEGF.

Certain groups have reported VEGFR2 to be the dominant signaling receptor in VEGF-induced mitogenesis, and permeability (Waltenberger et al., 1994; Zachary, 1998; Korpelainen and Alitalo, 1998). The role of VEGFR1 in endothelial cell function is much less clear, although functions in macrophage migration and chemotaxis were documented in the Hiratsuka et al. (1998) studies discussed above.

Clauss et al. (1996; incorporated herein by reference) also reported that VEGFR1 has important roles in monocyte activation and chemotaxis. In fact, cells of the macrophage/monocyte lineage express only VEGFR1, which is the receptor responsible for mediating monocyte recruitment and procoagulant activity (Clauss et al., 1996). VEGF binding to VEGFR1 on monocytes and macrophages also acts by raising intracellular calcium and inducing tyrosine phosphorylation (Clauss et al., 1996).

Binding of the VEGF dimer to the VEGF receptor is believed to induce receptor dimerization. Dimerization of the receptor then causes autotransphosphorylation of specific tyrosine residues, Y801 and Y1175, and Y1213 and Y1333 on the intracellular side of VEGFR2 and VEGFR1, respectively. This leads to a signal transduction cascade, which includes activation of phospholipase Cγ (PLCγ) and phosphatidylinositol 3-kinase (PI3K) and an increase in intracellular calcium ions (Hood and Meininger, 1998; Hood et al., 1998; Kroll and Waltenberger, 1998).

The intracellular events further downstream in VEGF-induced signaling are less clear, although a number of groups have shown that nitric oxide (NO) is produced after VEGF activation of VEGFR2 (Hood and Meininger, 1998; Hood et al., 1998; Kroll and Waltenberger, 1998). Activation of VEGFR2, but not VEGFR1, by VEGF has also been shown to activate Src and the Ras-MAP kinase cascade, including the MAP kinases, ERK1 and ERK2 (Waltenberger et al., 1994, 1996; Kroll and Waltenberger, 1997).

The role of VEGFR1 in endothelial cell function is much less clear, particularly as Flt-1 tyrosine kinase-deficient mice are viable and develop normal vessels (Hiratsuka et al., 1998). It has been suggested that the main biological role of VEGFR1 on endothelial is as a non-signaling ligand-binding molecule, or "decoy" receptor that might be required to present VEGF to VEGFR2.

The connection between VEGF and pathological angiogenic conditions has prompted various attempts to block VEGF activity. These include the development of certain neutralizing antibodies against VEGF (Kim et al., 1992; Presta et al., 1997; Sioussat et al., 1993; Kondo et al., 1993; Asano et al., 1995). Antibodies against VEGF receptors have also been described, such as described in U.S. Pat. Nos. 5,840,301 and 5,874,542 and, subsequent to the present invention, in WO 99/40118. U.S. Pat. Nos. 5,840,301 and 5,874,542 indeed suggest that blocking VEGF receptors rather than VEGF itself is advantageous for various reasons.

Soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors have also been reported (Saleh et al., 1996; Cheng et al., 1996; each incorporated herein by reference).

B. Anti-VEGF Antibodies

B1. Antibody Properties

The application of various inhibitory methods has been shown to be at least somewhat effective in either blocking angiogenesis and/or suppressing tumor growth by interfering with VEGF signaling. In fact, monoclonal antibodies against VEGF have been shown to inhibit human tumor xenograft growth and ascites formation in mice (Kim et al., 1993; Asano et al., 1995; 1998; Mesiano et al., 1998; Luo et al., 1998a; 1998b; Borgstrom et al., 1996; 1998).

The antibody A4.6.1 is a high affinity anti-VEGF antibody capable of blocking VEGF binding to both VEGFR1 and VEGFR2 (Kim et al., 1992; Wiesmann et al., 1997; Muller et al., 1998). Alanine scanning mutagenesis and X-ray crystallography of VEGF bound by the Fab fragment of A4.6.1 showed that the epitope on VEGF that A4.6.1 binds is centered around amino acids 89-94. This structural data demonstrates that A4.6.1 competitively inhibits VEGF from binding to VEGFR2, but inhibits VEGF from binding to VEGFR1 most likely by steric hindrance (Muller et al., 1998; Keyt et al., 1996; each incorporated herein by reference)

A4.6.1 is the most extensively utilized neutralizing anti-VEGF antibody in the literature to date. It has been shown to inhibit the growth and VEGF-induced vascular permeability of a variety of human tumors in mice (Brem, 1998; Baca et al., 1997; Presta et al., 1997; Mordenti et al., 1999; Borgstrom et al., 1999; Ryan et al., 1999; Lin et al., 1999; each specifically incorporated herein by reference). A4.6.1 also inhibits ascites formation in a well-characterized human ovarian carcinoma mouse model and tumor dissemination in a metastasis mouse model. A4.6.1 has been humanized by monovalent phage display techniques (Brem, 1998; Baca et al., 1997; Presta et al., 1997; each incorporated herein by reference). The resulting humanized antibody, termed Avastin (bevacizumab), has been approved for clinical use (Hurwitz et al., 2004).

Despite success in the art with neutralizing antibodies against VEGF, the present inventors realized that new antibodies, particularly human antibodies with a more precisely defined mode of interaction with VEGFR1 (FLT-1) and/or VEGFR2 (KDR/Flk-1) would of benefit for a variety of reasons. For example, the development of anti-VEGF antibodies that selectively block the interaction of VEGF with only one of the two VEGF receptors would allow for a more precise dissection of the pathways activated by VEGF in cells that express both VEGFR1 and VEGFR2.

The present inventors believed that human antibodies of defined epitope-specificity that blocked VEGF binding to only one receptor (VEGFR2s) will have clinical benefits. The knockout mice studies of Hiratsuka et al. (1998) show that both VEGFR1 and VEGFR2 have important biological roles. Prior to the present invention, realistic opportunities for therapeutic intervention aimed at inhibiting VEGF-mediated effects through only one of the two receptors were hampered by the lack of effective, tailored inhibitory agents optimized for human administration.

Given the need for therapeutic specific human antibodies that block angiogenesis, human antibodies have been identified that are reactive against an epitope on VEGF that specifically and substantially blocks its interaction with VEGF receptor 2 (VEGFR2, KDR/Flk-1), but does not substantially blocks its interaction with VEGF receptor 1 (VEGFR 1, Flt-1).

The present inventors first developed a range of fully human anti-VEGF antibodies that competed with the murine antibody 2C3 for binding to VEGF. A number of antibody clones displaying high affinity for VEGF and showing selective disruption for the interaction between VEGF and VEGFR2 and not between VEGF and VEGFR1 were selected for further analysis. Eventually one of these clones, termed a "mother clone", was subjected to maturation, after which a new clone was selected that displayed further important and significant improvements, for example, a better binding affinity to both mouse VEGF and human VEGF, a higher stability in serum and a reduced tendency to form aggregates in scFv format. This antibody is called r84 (and PGN311) and displays excellent binding affinity to VEGF, with a Kd in IgG format in the order of 7 nM or less, which is well within the range shown to be effective in human therapy.

Furthermore, the r84 antibody is shown herein to significantly reduce tumor volume/tumor growth in several art-accepted in vivo tumor models (specifically, the A673 rhabdomyosarcoma tumor model, the MDA-MB 231 breast cancer cell tumor model, various human non-small cell lung cancer models, Panc 1 pancreatic cancer cell tumor model and 4T1 mammary tumor model). Notably, the results with r84 are at least as good as the humanized anti-VEGF antibody termed Avastin, which has been approved for clinical use. A fully human antibody such as r84 will provide advantages over the available humanized antibody. In addition, r84 has the advantageous property of binding to mouse VEGF and human VEGF. The ability to bind mouse VEGF is an important advantage that the r84 antibody displays over 2C3 and Avastin. Furthermore, results from the MDA-MB 231 tumor model also show that r84 significantly reduces infiltration of tumor associated macrophages, which are now known to play a positive role in cancer development and metastasis and thus to be detrimental to patients In this regard, it has been shown that r84 significantly reduces expression of the macrophage marker Mac-3 ($p<0.01$). In addition, results from the MDA-MB 231 tumor model show that r84 significantly ($p<0.0001$) reduces the number of blood vessels in tumors and hence significantly reduces microvessel density (MVD) in tumors.

r84 has also been shown to significantly inhibit VEGF induced migration of VEGFR2 expressing cells and to significantly reduce lymphatic vessel density in MDAMB231 tumors. The effect on lymphatic vessel density supports the use of the human antibodies of the invention to inhibit lymphangiogenesis.

Figure 25:
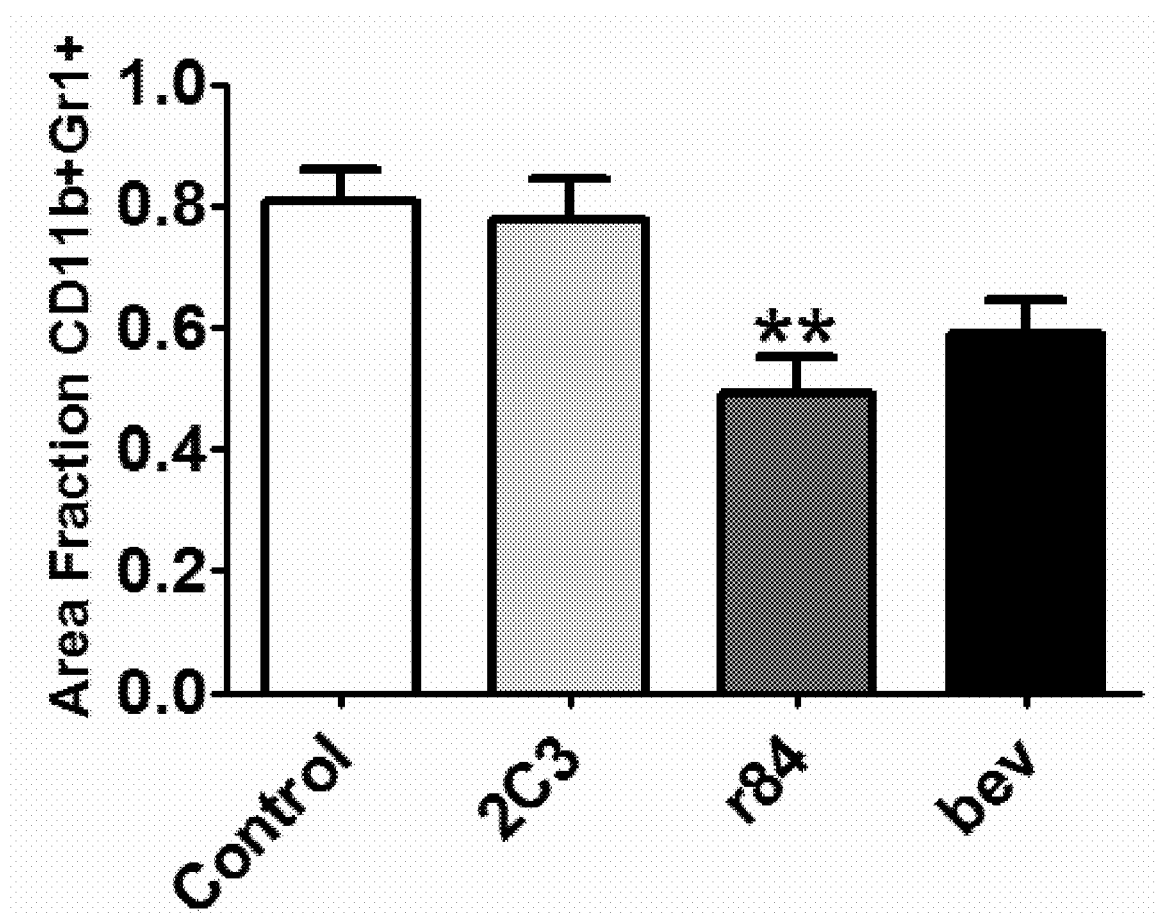
FIG. 25 shows that r84, and to a lesser extent Avastin (bev), decreases the infiltration of CD11b+/Gr1+ cells into MDA-MB-231 tumors in vivo, while 2C3 does not. The reduction for r84 is 39%. One-way ANOVA indicates that the decreased infiltration observed with r84 treated animals, but not the 2C3 or Avastin (bev) treated animals, is statistically different from the control treated animals (designated **, p<0.01)

A further advantageous property shown by r84 is the ability to significantly reduce infiltration of myeloid-derived suppressor cells, in particular CD11b+/Gr1+ cells, into tumors. Furthermore, this property is not shown by the 2C3 antibody and only at a more reduced level by Avastin. Thus, further studies in MDA-MB-231 tumor-bearing mice have shown that significantly less CD11b/Gr1 double positive cells infiltrate tumors in r84-treated animals as opposed to control. In comparative studies, neither the 2C3 antibody nor Avastin showed a statistically significant decrease in CD11b+/Gr1+ infiltration, although some reduction was measurable in Avastin-treated animals. The reduction in the number of double positive cells observed in r84/PGN311 treated animals is 39% (FIG. 25).

The reduced infiltration of myeloid derived suppressor cells CD11b+/Gr1+ is of special interest, as cells expressing both markers have recently been associated with mediation of tumor refractoriness to anti-VEGF therapy (Shojaei et al., 2007). Myeloid-derived suppressor cells (CD11b+Gr1+) are also an important contributor to tumor progression. In the tumor microenvironment these cells secrete immunosuppressive mediators and induce T-lymphocyte dysfunction (Gabrilovich et al., 2001; Serafini et al., 2004).

As CD11b+/Gr1+ cells are associated with tumor refractoriness to anti-VEGF therapy and contribute to tumor progression, the effect of r84/PGN311 to reduce infiltration or recruitment of these cells into tumors clearly has a potential importance for therapeutic applications of r84, in particular therapeutic applications related to the treatment of angiogenic diseases, including cancer.

Indeed, as the results herein show that the tumor infiltration of CD11b+/Gr1+ cells is least pronounced/significantly lower in the animals treated with r84/PGN311, it suggests that treatment with r84 is likely to be less prone to the development of drug resistance or refractoriness to anti-VEGF therapy than treatment with other drugs targeting VEGF, e.g. other anti-VEGF antibodies. In addition, given the proposed role of CD11b+/Gr1+ cells in tumor progression, the ability of r84/PGN311 to reduce infiltration or recruitment of such cells into tumors might well form part of the mechanism involved in the anti-tumor activity, e.g. the inhibition of tumor growth shown by r84/PGN311.

It has also been shown that chronic administration of r84/PGN311 does not induce toxicity in mice.

These are further positive indications of the therapeutic potential of the r84 antibody.

B2. VEGFR2-Blocking, Human Anti-VEGF Antibodies

An important part of this invention, confirmed using ELISA, receptor binding assays and receptor activation assays, is that the antibodies of the invention selectively block the interaction of VEGF with VEGFR2 (KDR/Flk-1), but not VEGFR1 (FLT-1). The antibodies inhibit VEGF-induced phosphorylation of VEGFR2 and inhibits signalling via the VEGFR2. The antibodies also have potent anti-tumor activity, arresting the growth of established human solid tumors in art-accepted animal models of human cancer. In addition, the human antibodies of the invention have anti-angiogenic properties and reduce microvessel density in tumors.

These properties demonstrate the usefulness of the antibodies in dissecting the pathways that are activated by VEGF in cells that express both VEGFR1 and VEGFR2, as well as highlighting the importance of VEGFR2 activity in the process of tumor growth and survival. More importantly, they provide a unique mode of therapeutic intervention for a human antibody, allowing specific inhibition of VEGFR2-induced angiogenesis, without concomitant inhibition of VEGFR1-mediated events, such as osteoclast and chondroclast function.

The antibodies of the present invention, succinctly termed "VEGFR2-blocking, human anti-VEGF antibodies", represent an advance in the field and provide numerous advantages, both in terms of uses in unconjugated or "naked" form and when conjugated to or associated with other therapeutic agents.

The in vitro binding studies of the present invention demonstrate that the human antibodies block the binding of VEGF to VEGFR2, but do not inhibit the binding of VEGF to VEGFR1.

The human antibodies of the present invention are thus significantly improved over other blocking antibodies to VEGF, including the murine A4.6.1 antibody and its humanized counterpart, Avastin (bevacizumab). The A4.6.1 and Avastin anti-VEGF antibodies block the binding of VEGF to both VEGF receptors. Crystallographic and mutagenesis studies have shown that the binding epitopes for VEGFR2 and VEGFR1 are concentrated towards the two symmetrical poles of the VEGF dimer (Wiesmann et al., 1997; Muller et al., 1997). The binding determinants on VEGF that interact with the two receptors overlap partially and are distributed over four different segments that span across the dimer surface (Muller et al., 1998). Antibody 4.6.1 binds to a region of VEGF within the receptor binding region of both receptors (Muller et al., 1998).

Studies on the effect of the human antibodies of the invention on VEGF-induced phosphorylation of the receptors showed that the antibodies do block VEGF-induced phosphorylation of VEGFR2. Studies have also shown that the human antibodies of the invention inhibit cell signalling via VEGFR2, for example, the antibodies have been shown to inhibit phosphorylation of Erk 1/2 and PLC-γ in in vitro assays.

The human antibodies of the invention inhibit the growth of human tumor types in vivo. The magnitude of tumor growth suppression by the human antibodies of the invention is similar to that using different neutralizing anti-VEGF antibodies, including Avastin. The effectiveness of these human antibodies, being similar to what other investigators have found using different anti-VEGF antibodies, further demonstrates the role of VEGF in tumor angiogenesis and tumor growth. However, the human antibodies of the invention should provide a safer therapeutic, based on the specific inhibitory properties discussed herein and in light of being fully human antibodies.

The fact that regressions, rather than tumor stasis, can be achieved suggests that VEGF is providing more than just an angiogenic signal for tumor endothelium. Benjamin et al. (1999) recently reported that tumors contain a large fraction of immature blood vessels that have yet to establish contact with periendothelial cells and that these blood vessels are dependent upon VEGF for survival. It is possible that neutralization of VEGF causes these immature blood vessels to undergo apoptosis, thereby reducing the existing vascular network in the tumor. It is also possible that a dynamic process of vascular remodeling occurs in tumors, involving both vessel formation and vessel regression, and that neutralization of VEGF prevents vessel formation leading to a net shift towards vessel regression.

The finding that the human antibodies of the invention suppress tumor growth as completely as Avastin (if not more so) indicates a dominant role for VEGFR2 in tumor angiogenesis. The multistep process of angiogenesis requires endothelial cell chemotaxis, metalloproteinase production, invasion, proliferation and differentiation. VEGFR1 may have no role in these processes, or may assist in the processes by binding VEGF and presenting it to the signaling receptor, VEGFR2.

The comparable figures for the human antibodies of the invention and Avastin in tumor treatment are highly relevant: the human antibodies of the invention are at least as effective as Avastin, although they only inhibit VEGF binding to VEGFR2 and not VEGFR1. The present studies therefore indicate that VEGFR1 does not play a notable role in VEGF-mediated tumor angiogenesis, and further suggest that VEGFR1 specific inhibitors may not influence tumor angiogenesis. These results also signify that the human antibodies of the invention can be equally or more effective than Avastin, whilst causing less side-effects.

The ability to specifically block VEGF binding to and activation of VEGFR2, but not VEGFR1 (Flt-1), has clinical importance. The human antibodies of the present invention thus block VEGF angiogenic activity, but do not inhibit other beneficial actions of VEGF, mediated through VEGFR1, such as those on certain immune and bone cells. One area of clinical importance thus concerns the ability of the human antibodies of this invention to function in vivo without inhibiting the beneficial effects of osteoclasts and chondroclasts. This means that use of the present VEGFR2-blocking, human anti-VEGF antibody therapeutics will not be associated with side effects on bone and/or cartilage.

In vivo studies have shown that VEGF couples hypertrophic cartilage remodeling, ossification and angiogenesis during endochondral bone formation and that VEGF is essential for cartilage remodeling (Gerber et al., 1999; specifically incorporated herein by reference). Inactivation of VEGF signaling through VEGFR1, by administration of the soluble VEGFR1 receptor chimeric protein (Flt-(1-3)-IgG), was shown to impair trabecular bone formation and the expansion of the hypertrophic chondrocyte zone by decreasing the recruitment and/or differentiation of chondroclasts (Gerber et al., 1999).

It has further been shown that VEGF can substitute for macrophage colony-stimulating factor (M-CSF) in the support of osteoclast function in vivo (Niida et al., 1999; specifically incorporated herein by reference). In studies using osteopetrotic (op/op) mice with a deficiency in osteoclasts resulting from a mutation in the M-CSF gene, injection of recombinant human M-CSF (rhM-CSF) allows osteoclast recruitment and survival. In recent studies, it was shown that a single injection of recombinant human VEGF can similarly induce osteoclast recruitment in op/op mice (Niida et al., 1999).

Niida et al. (1999) reported that as osteoclasts predominantly express VEGFR1, and the activity of recombinant human placenta growth factor 1 on osteoclast recruitment was comparable to that of rhVEGF, the beneficial effects of VEGF signaling in osteopetrotic (op/op) mice are mediated via the VEGF receptor 1 (VEGFR-1). These authors further showed that rhM-CSF-induced osteoclasts died after VEGF was inhibited (using a VEGFR1 receptor chimeric protein, VEGFR1/Fc), but that such effects were abrogated by concomitant injections of rhM-CSF. Osteoclasts supported by rhM-CSF or endogenous VEGF showed no significant difference in in vivo activity (Niida et al., 1999).

Mutant op/op mice undergo an age-related resolution of osteopetrosis accompanied by an increase in osteoclast number. In the Niida et al. (1999) studies, most of the osteoclasts disappeared after injections of anti-VEGF antibody, demonstrating that endogenously produced VEGF is responsible for the appearance of osteoclasts in the mutant mice. In addition, rhVEGF replaced rhM-CSF in the support of in vitro osteoclast differentiation. These results demonstrate that M-CSF and VEGF have overlapping functions in the support of osteoclast function and that VEGF acts through the VEGFR-1 receptor (Niida et al., 1999).

It can thus be concluded that the VEGFR2-blocking, human anti-VEGF antibodies of the invention do not block VEGF from binding and activating VEGFR1, but do block VEGF from binding and activating VEGFR2. The anti-tumor effects of such VEGFR2 inhibition are clearly demonstrated. These results show VEGFR2 to be the VEGF receptor that mediates permeability and highlight its role in tumor angiogenesis.

This invention therefore further validates VEGF inhibition as therapy for the treatment of solid tumors. More importantly, the invention provides a range of new VEGFR2-blocking, human anti-VEGF antibodies for therapeutic intervention and, in particular, for use as safe and effective drugs for inhibiting angiogenesis in tumors and other diseases.

The benefits of the present invention are not limited to the lack of side effects. Although these are important features that will have notable benefits, particularly in the treatment of children and patients with bone disorders, the antibodies of the invention have numerous other advantages.

For example, the VEGFR2-blocking, human anti-VEGF antibodies of the present invention have important advantages in inhibiting the detrimental actions of tumor-associated macrophages. It is now known that tumor-associated macrophages play important roles in cancer, both in the initial development stages and in tumor progression and metastasis. As detailed below, the human antibodies of this invention are ideally suited to counteracting the adverse effects of these macrophages.

The formation of a tumor vasculature and/or access to the host vasculature is a crucial step in the development of malignant tumors. Indeed, the formation of a high-density vessel network, termed "the angiogenic switch", is closely associated with the transition to malignancy (Hanahan and Folkman, 1996). It is now known that macrophages associated with the primary tumor play a key role in both the angiogenic switch and the progression to malignancy (Lin et al., 2006). Furthermore, it has been shown that inhibiting macrophage infiltration into tumors delays the angiogenic switch and malignant transition (Lin et al., 2006).

In many patients with cancer, metastasis is the ultimate cause of death. Invasion of tumor cells from the primary tumor into the surrounding connective tissue and blood vessels is a key step in the metastatic process. Macrophages were earlier reported to be associated with tumor progression and metastasis (Lin et al., 2001). Subsequent studies have shown that the interaction between tumor cells and macrophages facilitates the migration of carcinoma cells in the primary tumor, and that this process involves a paracrine loop (Wyckoff et al., 2004; Goswami et al., 2005).

Moreover, tumor-infiltrating or tumor-associated macrophages are now known to be prominent in various tumor microenvironments, including areas of invasion, stromal and perivascular areas and avascular and perinecrotic areas. The actions of macrophages in each of these tumor microenvironments stimulate tumor progression and metastasis by promoting cancer cell motility, metastasis and angiogenesis, respectively (Lewis and Pollard, 2006). Therefore, macrophages have recently become an important target in the battle against cancer (Condeelis and Pollard, 2006).

In this regard, the human antibodies of the present invention have important advantages as they block activation of VEGFR2 and thus reduce macrophage infiltration into tumors, and can therefore reduce the transition to malignancy, tumor progression and/or metastasis. This is validated by results from animal studies presented herein showing that tumor-associated macrophages express VEGFR2, and that VEGFR2 mediates the VEGF-induced chemotaxis of these cells. It is also shown herein that the selective blockade of VEGFR2 caused by the human antibodies of this invention exerts a potent anti-cancer effect. This anti-cancer effect is accompanied by a reduction in macrophage infiltration into the tumor, indicating that selectively blocking the VEGF-VEGFR2 interaction in host macrophages contributes to the observed therapeutic effects.

The VEGFR2-blocking, human anti-VEGF antibodies of this invention also have advantages in connection with reducing lymphatic vessel density in tumors. In addition to egress of tumor cells into tumor blood vessels, metastasis is facilitated by lymphangiogenesis, i.e., the growth of new intratumoral or peritumoral lymphatic vessels from pre-existing vessels. Indeed, in several types of cancer, including breast cancer, escape of tumor cells via the lymphatic system is believed to be the predominant means by which malignant cells from the primary tumor are seeded to distant sites.

For several years, it was thought that lymphangiogenesis was primarily induced by VEGF-C and/or VEGF-D. However, a body of evidence has now accumulated implicating VEGF-A in lymphangiogenesis. Moreover, recent studies have shown that murine antibodies against VEGF-A are effective in inhibiting tumor lymphangiogenesis and metastases in vivo (Whitehurst et al., 2007).

Figure 18B:
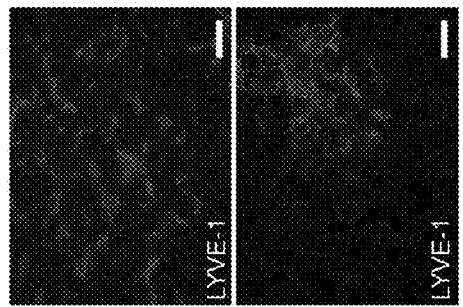
FIG. 18A, FIG. 18B and FIG. 18C show that the lymphatic vessel density in r84-treated tumors is significantly lower than in control tumors.
Figure 18A:
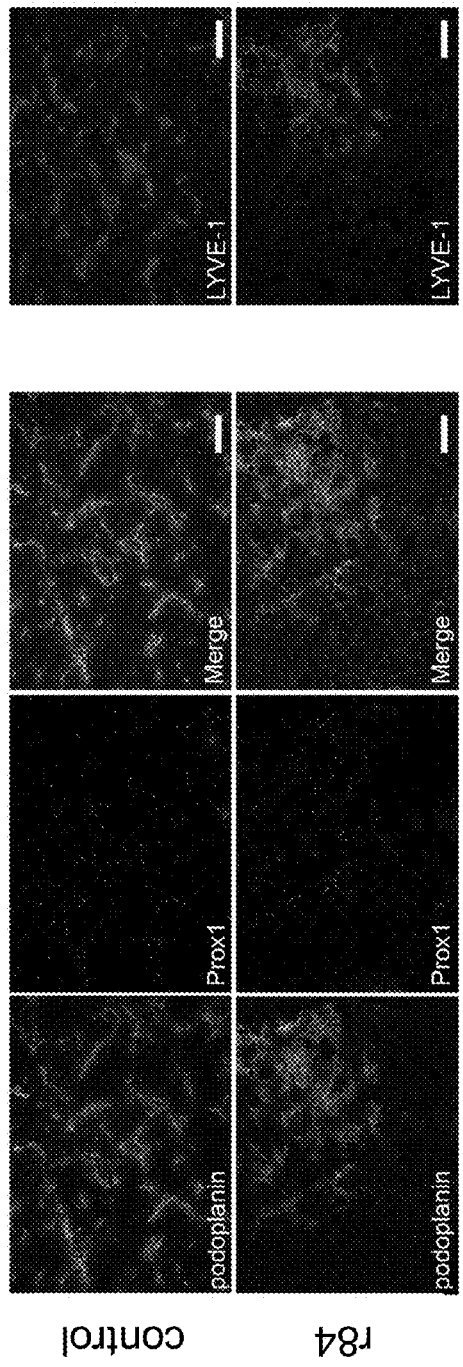
Figure 18C:
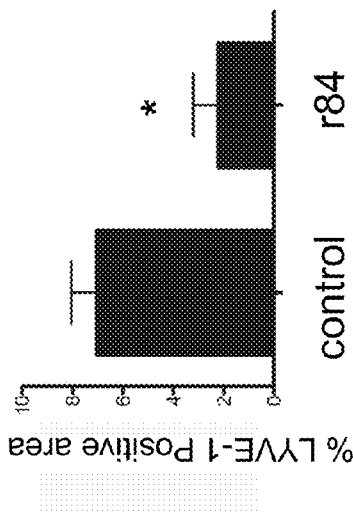

Results are presented herein to show that the VEGFR2-blocking, human anti-VEGF antibodies of this invention do, indeed, reduce tumor lymphatic vessel density (FIG. 18A, FIG. 18B and FIG. 18C). The human antibodies of the present invention will therefore inhibit tumor lymphangiogenesis and provide the additional benefit of reducing metastases via the lymphatic route, as well as inhibiting angiogenesis and metastatic escape via tumor blood vessels. It can be seen, therefore, that the human antibodies of the present invention have the ability to reduce metastasis or metastatic events via several points of intervention.

Moreover, the data in FIG. 18A show that the antibodies of the present invention reduce tumor lymphatic vessel density as measured by a reduction in podoplanin and in PROX1. As podoplanin is a marker for soft tissue cancers, such as chondrosarcoma, and for lymphatic tumors, such as follicular dendritic cell sarcoma) (Xie et al., 2008), and as PROX1 has been implicated in predicting the invasiveness of colon cancer (Petrova et al., 2008), this emphasizes the use of the VEGFR2-blocking, human anti-VEGF antibodies of the invention to treat those particular disease indications.

A further advantageous property shown by the VEGFR2-blocking, human anti-VEGF antibodies of this invention is the ability to significantly reduce infiltration or recruitment of myeloid-derived suppressor cells, in particular CD11b+/Gr1+ cells, into tumors. Furthermore, this property is not shown by the 2C3 antibody and only at a more reduced level by Avastin. Preferred antibodies of the invention can decrease the infiltration or recruitment of CD11b+/Gr1+ cells into tumors (e.g. decrease the number of double-positive cells present in tumors) by 30% or more, preferably by 32%, 34%, 36%, 38% or more, compared to a control level (e.g. an untreated tumor or a tumor treated with a control antibody).

Thus, further studies in MDA-MB-231 tumor-bearing mice have shown that significantly less CD11b/Gr1 double positive cells infiltrate tumors in r84-treated animals as opposed to control. In comparative studies, neither the 2C3 antibody nor Avastin showed a statistically significant decrease in CD11b+/Gr1+ infiltration, although some reduction was measurable in Avastin-treated animals. The reduction in the number of double positive cells observed is 39% (FIG. 25).

The reduced infiltration of myeloid derived suppressor cells CD11b+/Gr1+ is of special interest, as cells expressing both markers have recently been associated with mediation of tumor refractoriness to anti-VEGF therapy (Shojaei et al., 2007). Myeloid-derived suppressor cells (CD11b+Gr1+) are also an important contributor to tumor progression. In the tumor microenvironment these cells secrete immunosuppressive mediators and induce T-lymphocyte dysfunction (Gabrilovich et al., 2001; Serafini et al., 2004).

As CD11b+/Gr1+ cells are associated with tumor refractoriness to anti-VEGF therapy and contribute to tumor progression, the effect of the antibodies of the invention to reduce infiltration of these cells into tumors clearly has a potential importance for therapeutic applications of the antibodies of the invention, in particular therapeutic applications related to the treatment of angiogenic diseases, including cancer.

Indeed, as the results herein show that the tumor infiltration of CD11b+/Gr1+ cells is least pronounced/significantly lower in the animals treated with antibodies of the invention, it suggests that treatment with antibodies of the invention is likely to be less prone to the development of drug resistance or refractoriness to anti-VEGF therapy than treatment with other drugs targeting VEGF, e.g. other anti-VEGF antibodies. In addition, given the proposed role of CD11b+/Gr1+ cells in tumor progression, the ability of the antibodies of the invention to reduce infiltration or recruitment of such cells into tumors might well form part of the mechanism involved in the anti-tumor activity, e.g. the inhibition of tumor growth shown by the antibodies of the invention.

The VEGFR2-blocking, human anti-VEGF antibodies of this invention have also been shown to not induce toxicity when administered chronically in in vivo mouse models.

The VEGFR2-blocking, human anti-VEGF antibodies of this invention preferably have the advantageous property of binding to mouse VEGF and human VEGF. The ability to bind mouse VEGF is an important advantage over the antibodies 2C3 and Avastin. In addition, antibody conjugates based upon the VEGFR2-blocking; human anti-VEGF antibodies of the present invention can be used to deliver therapeutic agents to the tumor environment, whereas many other anti-VEGF antibodies cannot. The human antibodies of the invention bind to both tumor vasculature and tumor stroma upon administration in vivo, but do not bind to vasculature or connective tissue in normal organs or tissues. Therapeutic constructs based upon the present human antibodies therefore have the advantage of combining two functions within one molecule: the anti-angiogenic properties of the antibody or fragment thereof and the properties of the therapeutic agent selected for attachment. In summary, a human antibody of the present invention may be used both as an anti-angiogenic agent and a vascular targeting agent, whereas many anti-VEGF antibodies of the prior art cannot be used in a vascular targeting capacity.

As VEGFR2 is the key receptor on endothelium, blocking VEGF binding to VEGFR2 is critical for an anti-angiogenic effect. Although VEGFR1 is expressed on endothelium, it is non-signal transducing, or passive, in this context. Therefore, the inability of the human antibodies of the present invention to block VEGF binding to VEGFR1 is without consequence to their effectiveness as anti-angiogenic and anti-tumor agents. In fact, rather than inhibiting VEGF binding to VEGFR1, which occurs with the blocking antibodies of the prior art, the ability of the present human antibodies to bind to VEGF and yet to not substantially disturb VEGF-VEGFR1 interactions enhances the drug delivery properties of these new antibodies.

The present inventors realized that blocking antibodies would still be expected to function to deliver therapeutic agents to the tumor environment by binding to tumor-localized VEGF that is not bound to a receptor. Specifically, they understood that such human antibodies will bind to VEGF in the tumor stroma and deliver therapeutic agents thereto. This provides a reservoir of drug around the endothelium, causing cytotoxic or other destructive effects on the vascular endothelial cells and exerting an anti-tumor effect.

The VEGF associated with the stroma or connective tissue is not bound to a VEGF receptor in a classic sense, i.e., a cell surface receptor. Rather, VEGF is bound to one or more connective tissue components, including proteoglycans, such as heparan sulfate proteoglycan, through a basic region of VEGF. These sequences (and the exons encoding them) are missing in VEGF121 protein (and underlying DNA), so this isoform should not be present in stroma in significant amounts. VEGF in the tumor stroma is often termed "free", although it is still localized within the tumor, so "free" essentially means non-receptor-bound.

The inventors further deduced that a human antibody that blocks VEGF binding to one, but not both receptors, would still be able to deliver therapeutic agents to the tumor environment by binding to receptor bound VEGF on the vasculature. This is one of the advantageous features of the present invention. Namely, the provision of human antibodies that block VEGF binding to VEGFR2, and hence inhibit the angiogenic signal from VEGF, but that do not block VEGF binding to VEGFR1. In addition to reducing systemic side effects by maintaining VEGF signaling via VEGFR1 in other cell types and tissues, these human antibodies are able to localize to VEGF-VEGFR1 complex on tumor vasculature and to deliver therapeutic agents directly thereto.

Both VEGFR1 and VEGFR2 are upregulated on tumor endothelial cells, as opposed to endothelial cells in normal tissues. VEGFR1 is highly expressed on tumor vascular endothelium, which makes the targeting aspects of the present invention particularly effective. In fact, VEGFR1, although "non-signaling" in endothelium, is expressed at least at the same levels as VEGFR2, if not at higher levels. A factor underlying this phenomenon is that VEGFR1 is upregulated in response to both hypoxia and VEGF, whereas VEGFR2 is only upregulated in response to VEGF and is not influenced by hypoxia.

Although the role of VEGFR1 on endothelium remains uncertain, VEGFR1 may act as a decoy receptor to "capture" VEGF and pass the ligand onto the signaling receptor, VEGFR2. For this to be true, one would expect the decoy receptor to have a higher affinity for VEGF than the signaling receptor, which is indeed the case. In light of this, and perhaps also due to enhanced expression levels, the VEGFR2-blocking, non-VEGFR1-blocking human antibodies of this invention are ideal delivery agents for tumor treatment. Therapeutic conjugates of these antibodies are able to simultaneously inhibit angiogenesis through VEGFR2 and destroy the existing vasculature by delivering a therapeutic agent to VEGF-VEGFR1 receptor complex.

The inventors are by no means limited to the foregoing scientific reasoning as an explanation for the beneficial anti-angiogenic and tumor-localizing properties of the present human antibodies. Although the utility of the invention is self-evident and needs no underlying theory to be put into practice, the inventors have considered alternative mechanisms by which VEGFR2-blocking, non-VEGFR1-blocking human antibodies may effectively and specifically localize to tumor vasculature.

Such human antibodies could bind to VEGF that is associated with another known or, as yet, uncharacterized VEGF binding protein on the cell surface or could bind VEGF that is bound to heparan sulfate proteoglycans on the surface of endothelial cells. Antibody localization could also be enhanced by binding to another member of the VEGF family of proteins, i.e., VEGF-B, VEGF-C, VEGF-D, which are associated with the blood vessels, although this is less likely.

Another advantageous property of the VEGFR2-blocking, human anti-VEGF antibodies of the invention is that these antibodies neutralize the survival signal or "protective effect" of VEGF, which is mediated through VEGFR2. In addition to making the human antibodies more effective themselves, this property makes them particularly useful in combination with other agents that are hampered by VEGF's survival function.

For example, VEGF protects the endothelium from radiotherapy. Therefore, both the naked antibodies and immunoconjugates of the present invention are ideal for use in combination with radiotherapy. Even more benefits are provided by the use of such a human antibody attached to a radiotherapeutic agent. This type of construct would have the triple advantages of: (1) exerting an anti-angiogenic effect through the antibody portion; (2) exerting a tumor vasculature destructive effect through delivery of the radiotherapeutic agent; and (3) preventing VEGF's typical survival signal from counteracting the effects of the radiotherapeutic agent.

Other constructs with similarly synergistic effects are VEGFR2-blocking, human anti-VEGF antibodies in association with anti-tubulin drugs or prodrugs, anti-apoptopic agents and other anti-angiogenic agents. The actions of agents or drugs that cause apoptosis are antagonized by VEGF. The present invention therefore improves the effectiveness of such agents by neutralizing VEGF. VEGF survival signals also oppose endostatin, limiting this therapy. Therefore, in combined use with endostatin, the VEGFR2-blocking, human anti-VEGF antibodies of the invention will neutralize VEGF and amplify the anti-tumor effects of endostatin. The VEGFR2-blocking, human anti-VEGF antibodies may also be used to specifically delivery collagenase to the tumor, where the collagenase will produce endostatin in situ, achieving similar benefits.

In all such enhanced or synergistic combinations, the human antibodies and other agents may be administered separately, or the second agents may be linked to the human antibodies for specific delivery (i.e., targeted delivery to VEGFR1). In combinations with endostatin, chemical conjugates or recombinant fusion proteins will be preferred, as these will counteract the short half life of endostatin, which is currently a limitation of potential endostatin therapy. Combinations with, or targeted forms of, tissue plasminogen activator (tPA) may also be employed.

Further advantages of the human therapeutics of the present invention include the ability to lower the interstitial pressure. As VEGF-mediated increased permeability contributes to the interstitial pressure, reduced signaling via VEGFR2 will reduce both permeability and interstitial pressure. This, in turn, will reduce the barrier to drugs traversing the entirety of the tumor tissue, so that tumor cells distant from the vasculature can be killed. Prolonged therapy can also be achieved as the present compositions with have no, negligible or low immunogenicity.

B3. Antibody CDR Sequences

The term "variable", as used herein in reference to antibodies, means that certain portions of the variable domains differ extensively in sequence among antibodies, and are used in the binding and specificity of each particular antibody to its particular antigen. However, the variability is not evenly distributed throughout the variable domains of antibodies. It is concentrated in three segments termed "hypervariable regions", both in the light chain and the heavy chain variable domains.

The more highly conserved portions of variable domains are called the framework region (FR). The variable domains of native heavy and light chains each comprise four FRs (FR1, FR2, FR3 and FR4, respectively), largely adopting a β-sheet configuration, connected by three hypervariable regions, which form loops connecting, and in some cases, forming part of, the β-sheet structure.

The hypervariable regions in each chain are held together in close proximity by the FRs and, with the hypervariable regions from the other chain, contribute to the formation of the antigen-binding site of antibodies (Kabat et al., 1991, specifically incorporated herein by reference). The constant domains are not involved directly in binding an antibody to an antigen, but exhibit various effector functions, such as participation of the antibody in antibody-dependent cellular toxicity.

The term "hypervariable region", as used herein, refers to the amino acid residues of an antibody that are responsible for antigen-binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-56 (H2) and 95-102 (H3) in the heavy chain variable domain; Kabat et al., 1991, specifically incorporated herein by reference) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain). "Framework" or "FR" residues are those variable domain residues other than the hypervariable region residues as herein defined.

The DNA and deduced amino acid sequences of the VH and VL chains of the r84 ScFv fragment are provided herein as SEQ ID NO:1 (VH, nucleic acid), SEQ ID NO:2 (VL, nucleic acid) SEQ ID NO:3 (VH, amino acid) and SEQ ID NO:4 (VL, amino acid). The DNA sequences of the VH and VL chains of the r84 full length IgG are provided herein as SEQ ID NO:26 (VH, nucleic acid) and SEQ ID NO:27 (VL, nucleic acid). These sequences encompass CDR1-3 of the variable regions of the heavy and light chains of the antibody.

As described herein (Section C7), with the provision of structural and functional information for a biological molecule, a range of equivalent, or even improved molecules can be generated. This applies to the VEGFR2-blocking, human anti-VEGF antibodies of the present invention, as exemplified by the r84 antibody. Although antigen-binding and other functional properties of an antibody must be conserved, there is an extremely high degree of skill in the art in making equivalent and even improved antibodies once a reference antibody has been provided. Such technical skill can, in light of the sequences and information provided herein, be applied to the production of further antibodies that have like, improved or otherwise desirable characteristics.

For equivalent antibodies, certain amino acids may substituted for other amino acids in the antibody constant or variable domain framework regions without appreciable loss of interactive binding capacity. It is preferable that such changes be made in the DNA sequences encoding the antibody portions and that the changes be conservative in nature (see Section C7, the codon information in Table A, and the supporting technical details on site-specific mutagenesis). Naturally, there is a limit to the number of changes that should be made, but this will be known those of ordinary skill in the art.

Other types of variants are antibodies with improved biological properties relative to the parent antibody from which they are generated. Such variants, or second generation compounds, are typically substitutional variants involving one or more substituted hypervariable region residues of a parent antibody. A convenient way for generating such substitutional variants is affinity maturation using phage display.

In affinity maturation using phage display, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Alternatively, or in addition, it is contemplated that the crystal structure of the antigen-antibody complex be delineated and analyzed to identify contact points between the antibody and VEGF. Such contact residues and neighboring residues are candidates for substitution. Once such variants are generated, the panel of variants is subjected to screening, as described herein, and antibodies with analogues but different or even superior properties in one or more relevant assays are selected for further development.

Further aspects of the invention therefore concern isolated or purified DNA segments and recombinant vectors encoding CDR regions of VEGFR2-blocking, human anti-VEGF antibody heavy and light chains of the invention, such as r84 heavy and light chains, and the creation and use of recombinant host cells through the application of DNA technology, that express such CDR regions.

The present invention thus concerns human or synthetic DNA segments, which are free from total genomic DNA and are capable of expressing CDR regions of VEGFR2-blocking, human anti-VEGF antibody heavy and/or light chains of the invention, such as r84 heavy and/or light chains. As used herein, the term "DNA segment" refers to a DNA molecule that has been isolated or purified free of total genomic DNA of a particular species. Included within the term "DNA segment", are DNA segments and smaller fragments of such segments, and also recombinant vectors, including, for example, plasmids, cosmids, phage, viruses, and the like.

Similarly, a DNA segment comprising a coding segment or isolated or purified gene portion encoding purified CDR regions of VEGFR2-blocking, human anti-VEGF antibody heavy and/or light chains of the invention, such as r84 heavy and/or light chains, refers to a DNA segment including such coding sequences and, in certain aspects, regulatory sequences, isolated or purified substantially away from other naturally occurring genes or protein encoding sequences. In this respect, the term "gene" is used for simplicity to refer to a functional protein, polypeptide or peptide encoding unit. As will be understood by those in the art, this functional term includes the native antibody-encoding sequences and smaller engineered segments that express, or may be adapted to express, suitable antigen binding proteins, polypeptides or peptides.

"Isolated or purified substantially away from other coding sequences" means that the coding segment or isolated gene portion of interest forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated or purified coding segments or isolated or purified gene portions and recombinant vectors incorporating DNA sequences that encode CDR regions of VEGFR2-blocking, human anti-VEGF antibody heavy and/or light chains of the invention, such as r84 heavy and/or light chains, that comprise at least a first sequence region that includes an amino acid sequence region of at least about 75%, more preferably, at least about 80%, more preferably, at least about 85%, more preferably, at least about 90% and most preferably, at least about 95% or so amino acid sequence identity to the amino acid sequence of SEQ ID NO:3 or SEQ ID NO:4; wherein said CDR regions at least substantially maintain the biological properties of the CDR regions of amino acid sequences SEQ ID NO:3 or SEQ ID NO:4.

As disclosed herein, the sequences may comprise certain biologically functional equivalent amino acids or "conservative substitutions". Other sequences may comprise functionally non-equivalent amino acids or "non-conservative substitutions" deliberately engineered to improve the properties of the CDR or antibody containing the CDR, as is known those of ordinary skill in the art and further described herein.

It will also be understood that amino acid and nucleic acid sequences may include additional residues, such as additional N- or C-terminal amino acids or 5' or 3' sequences, and yet still correspond to a sequence of the invention, so long as the sequence meets the criteria set forth above, preferably including the maintenance or improvement of biological protein activity where protein expression is concerned. The addition of terminal sequences includes various non-coding sequences flanking either of the 5' or 3' portions of the coding region, and also control regions.

The nucleic acid segments of the present invention may thus be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

Recombinant vectors therefore form further aspects of the present invention. Particularly useful vectors are contemplated to be those vectors in which the coding portion of the DNA segment is positioned under the control of a promoter. Generally, although not exclusively, a recombinant or heterologous promoter will be employed, i.e., a promoter not normally associated with coding sequences in their natural environment. Such promoters may include bacterial, viral, eukaryotic and mammalian promoters, so long as the promoter effectively directs the expression of the DNA segment in the cell type, organism, or even animal, chosen for expression.

The use of promoter and cell type combinations for protein expression is known to those of skill in the art of molecular biology. The promoters employed may be constitutive, or inducible, and can be used under the appropriate conditions to direct high level expression of the introduced DNA segment, such as is advantageous in the large-scale production of recombinant proteins or peptides.

The expression of the nucleic acid sequences of the invention may be conveniently achieved by any one or more standard techniques known those of ordinary skill in the art and further described herein. For example, the later description of the recombinant expression of fusion proteins applies equally well to antibodies and antibody fragments that are not operatively associated with another coding sequence at the nucleic acid level.

B4. Antibodies from Phagemid Libraries

Recombinant technology now allows the preparation of antibodies having the desired specificity from recombinant genes encoding a range of antibodies (Van Dijk et al., 1989; incorporated herein by reference). Certain recombinant techniques involve the isolation of the antibody genes by immunological screening of combinatorial immunoglobulin phage expression libraries prepared from RNA isolated from the spleen of an immunized animal (Morrison et al., 1986; Winter and Milstein, 1991; each incorporated herein by reference).

For such methods, combinatorial immunoglobulin phagemid libraries are prepared from RNA isolated from the spleen of the immunized animal, and phagemids expressing appropriate antibodies are selected by panning using cells expressing the antigen and control cells. The advantages of this approach over conventional hybridoma techniques are that approximately $10^4$ times as many antibodies can be produced and screened in a single round, and that new specificities are generated by H and L chain combination, which further increases the percentage of appropriate antibodies generated.

One method for the generation of a large repertoire of diverse antibody molecules in bacteria utilizes the bacteriophage lambda as the vector (Huse et al., 1989; incorporated herein by reference). Production of antibodies using the lambda vector involves the cloning of heavy and light chain populations of DNA sequences into separate starting vectors. The vectors are subsequently combined randomly to form a single vector that directs the co-expression of heavy and light chains to form antibody fragments. The heavy and light chain DNA sequences are obtained by amplification, preferably by PCR™ or a related amplification technique, of mRNA isolated from spleen cells (or hybridomas thereof) from an animal that has been immunized with a selected antigen. The heavy and light chain sequences are typically amplified using primers that incorporate restriction sites into the ends of the amplified DNA segment to facilitate cloning of the heavy and light chain segments into the starting vectors.

Another method for the generation and screening of large libraries of wholly or partially synthetic antibody combining sites, or paratopes, utilizes display vectors derived from filamentous phage such as M13, fl or fd. These filamentous phage display vectors, referred to as "phagemids", yield large libraries of monoclonal antibodies having diverse and novel immunospecificities. The technology uses a filamentous phage coat protein membrane anchor domain as a means for linking gene-product and gene during the assembly stage of filamentous phage replication, and has been used for the cloning and expression of antibodies from combinatorial libraries (Kang et al., 1991; Barbas et al., 1991; each incorporated herein by reference).

This general technique for filamentous phage display is described in U.S. Pat. No. 5,658,727, incorporated herein by reference. In a most general sense, the method provides a system for the simultaneous cloning and screening of preselected ligand-binding specificities from antibody gene repertoires using a single vector system. Screening of isolated members of the library for a pre-selected ligand-binding capacity allows the correlation of the binding capacity of an expressed antibody molecule with a convenient means to isolate the gene that encodes the member from the library.

Linkage of expression and screening is accomplished by the combination of targeting of a fusion polypeptide into the periplasm of a bacterial cell to allow assembly of a functional antibody, and the targeting of a fusion polypeptide onto the coat of a filamentous phage particle during phage assembly to allow for convenient screening of the library member of interest. Periplasmic targeting is provided by the presence of a secretion signal domain in a fusion polypeptide. Targeting to a phage particle is provided by the presence of a filamentous phage coat protein membrane anchor domain (i.e., a cpIII- or cpVIII-derived membrane anchor domain) in a fusion polypeptide.

The diversity of a filamentous phage-based combinatorial antibody library can be increased by shuffling of the heavy and light chain genes, by altering one or more of the complementarity determining regions of the cloned heavy chain genes of the library, or by introducing random mutations into the library by error-prone polymerase chain reactions. Additional methods for screening phagemid libraries are described in U.S. Pat. Nos. 5,580,717; 5,427,908; 5,403,484; and 5,223,409, each incorporated herein by reference.

Another method for the screening of large combinatorial antibody libraries has been developed, utilizing expression of populations of diverse heavy and light chain sequences on the surface of a filamentous bacteriophage, such as M13, fl or fd (U.S. Pat. No. 5,698,426; incorporated herein by reference). Two populations of diverse heavy (Hc) and light (Lc) chain sequences are synthesized by polymerase chain reaction (PCR™). These populations are cloned into separate M13-based vector containing elements necessary for expression. The heavy chain vector contains a gene VIII (gVIII) coat protein sequence so that translation of the heavy chain sequences produces gVIII-Hc fusion proteins. The populations of two vectors are randomly combined such that only the vector portions containing the Hc and Lc sequences are joined into a single circular vector.

The combined vector directs the co-expression of both Hc and Lc sequences for assembly of the two polypeptides and surface expression on M113 (U.S. Pat. No. 5,698,426; incorporated herein by reference). The combining step randomly brings together different Hc and Lc encoding sequences within two diverse populations into a single vector. The vector sequences donated from each independent vector are necessary for production of viable phage. In addition, since the pseudo gVIII sequences are contained in only one of the two starting vectors, co-expression of functional antibody fragments as Lc associated gVIII-Hc fusion proteins cannot be accomplished on the phage surface until the vector sequences are linked in the single vector.

Surface expression of the antibody library is performed in an amber suppressor strain. An amber stop codon between the Hc sequence and the gVIII sequence unlinks the two components in a non-suppressor strain. Isolating the phage produced from the non-suppressor strain and infecting a suppressor strain will link the Hc sequences to the gVIII sequence during expression. Culturing the suppressor strain after infection allows the coexpression on the surface of M13 of all antibody species within the library as gVIII fusion proteins (gVIII-Fab fusion proteins). Alternatively, the DNA can be isolated from the non-suppressor strain and then introduced into a suppressor strain to accomplish the same effect.

The surface expression library is screened for specific Fab fragments that bind preselected molecules by standard affinity isolation procedures. Such methods include, for example, panning (Parmley and Smith, 1988; incorporated herein by reference), affinity chromatography and solid phase blotting procedures. Panning is preferred, because high titers of phage can be screened easily, quickly and in small volumes. Furthermore, this procedure can select minor Fab fragments species within the population, which otherwise would have been undetectable, and amplified to substantially homogenous populations. The selected Fab fragments can be characterized by sequencing the nucleic acids encoding the polypeptides after amplification of the phage population.

Another method for producing diverse libraries of antibodies and screening for desirable binding specificities is described in U.S. Pat. Nos. 5,667,988 and 5,759,817, each incorporated herein by reference. The method involves the preparation of libraries of heterodimeric immunoglobulin molecules in the form of phagemid libraries using degenerate oligonucleotides and primer extension reactions to incorporate the degeneracies into the CDR regions of the immunoglobulin variable heavy and light chain variable domains, and display of the mutagenized polypeptides on the surface of the phagemid. Thereafter, the display protein is screened for the ability to bind to a preselected antigen.

The method for producing a heterodimeric immunoglobulin molecule generally involves (1) introducing a heavy or light chain V region-coding gene of interest into the phagemid display vector; (2) introducing a randomized binding site into the phagemid display protein vector by primer extension with an oligonucleotide containing regions of homology to a CDR of the antibody V region gene and containing regions of degeneracy for producing randomized coding sequences to form a large population of display vectors each capable of expressing different putative binding sites displayed on a phagemid surface display protein; (3) expressing the display protein and binding site on the surface of a filamentous phage particle; and (4) isolating (screening) the surface-expressed phage particle using affinity techniques such as panning of phage particles against a preselected antigen, thereby isolating one or more species of phagemid containing a display protein containing a binding site that binds a preselected antigen.

A further variation of this method for producing diverse libraries of antibodies and screening for desirable binding specificities is described in U.S. Pat. No. 5,702,892, incorporated herein by reference. In this method, only heavy chain sequences are employed, the heavy chain sequences are randomized at all nucleotide positions that encode either the CDRI or CDRIII hypervariable region, and the genetic variability in the CDRs is generated independent of any biological process.

In the method, two libraries are engineered to genetically shuffle oligonucleotide motifs within the framework of the heavy chain gene structure. Through random mutation of either CDR1 or CDRIII, the hypervariable regions of the heavy chain gene were reconstructed to result in a collection of highly diverse sequences. The heavy chain proteins encoded by the collection of mutated gene sequences possessed the potential to have all of the binding characteristics of an immunoglobulin while requiring only one of the two immunoglobulin chains.

Specifically, the method is practiced in the absence of the immunoglobulin light chain protein. A library of phage displaying modified heavy chain proteins is incubated with an immobilized ligand to select clones encoding recombinant proteins that specifically bind the immobilized ligand. The bound phage are then dissociated from the immobilized ligand and amplified by growth in bacterial host cells. Individual viral plaques, each expressing a different recombinant protein, are expanded, and individual clones can then be assayed for binding activity.

B5. Transgenic Mice Containing Human Antibody Libraries

Recombinant technology is now available for the preparation of antibodies. In addition to the combinatorial immunoglobulin phage expression libraries disclosed above, another molecular cloning approach is to prepare antibodies from transgenic mice containing human antibody libraries. Such techniques are described in U.S. Pat. No. 5,545,807, incorporated herein by reference.

In a most general sense, these methods involve the production of a transgenic animal that has inserted into its germline genetic material that encodes for at least part of an immunoglobulin of human origin or that can rearrange to encode a repertoire of immunoglobulins. The inserted genetic material may be produced from a human source, or may be produced synthetically. The material may code for at least part of a known immunoglobulin or may be modified to code for at least part of an altered immunoglobulin.

The inserted genetic material is expressed in the transgenic animal, resulting in production of an immunoglobulin derived at least in part from the inserted human immunoglobulin genetic material. It is found the genetic material is rearranged in the transgenic animal, so that a repertoire of immunoglobulins with part or parts derived from inserted genetic material may be produced, even if the inserted genetic material is incorporated in the germline in the wrong position or with the wrong geometry.

The inserted genetic material may be in the form of DNA cloned into prokaryotic vectors such as plasmids and/or cosmids. Larger DNA fragments are inserted using yeast artificial chromosome vectors (Burke et al., 1987; incorporated herein by reference), or by introduction of chromosome fragments (Richer and Lo, 1989; incorporated herein by reference). The inserted genetic material may be introduced to the host in conventional manner, for example by injection or other procedures into fertilized eggs or embryonic stem cells.

In preferred aspects, a host animal that initially does not carry genetic material encoding immunoglobulin constant regions is utilized, so that the resulting transgenic animal will use only the inserted human genetic material when producing immunoglobulins. This can be achieved either by using a naturally occurring mutant host lacking the relevant genetic material, or by artificially making mutants e.g., in cell lines ultimately to create a host from which the relevant genetic material has been removed.

Where the host animal carries genetic material encoding immunoglobulin constant regions, the transgenic animal will carry the naturally occurring genetic material and the inserted genetic material and will produce immunoglobulins derived from the naturally occurring genetic material, the inserted genetic material, and mixtures of both types of genetic material. In this case the desired immunoglobulin can be obtained by screening hybridomas derived from the transgenic animal, e.g., by exploiting the phenomenon of allelic exclusion of antibody gene expression or differential chromosome loss.

Once a suitable transgenic animal has been prepared, the animal is simply immunized with the desired immunogen. Depending on the nature of the inserted material, the animal may produce a chimeric immunoglobulin, e.g. of mixed mouse/human origin, where the genetic material of foreign origin encodes only part of the immunoglobulin; or the animal may produce an entirely foreign immunoglobulin, e.g. of wholly human origin, where the genetic material of foreign origin encodes an entire immunoglobulin.

Polyclonal antisera may be produced from the transgenic animal following immunization. Immunoglobulin-producing cells may be removed from the animal to produce the immunoglobulin of interest. Preferably, monoclonal antibodies are produced from the transgenic animal, e.g., by fusing spleen cells from the animal with myeloma cells and screening the resulting hybridomas to select those producing the desired antibody. Suitable techniques for such processes are described herein.

In an alternative approach, the genetic material may be incorporated in the animal in such a way that the desired antibody is produced in body fluids such as serum or external secretions of the animal, such as milk, colostrum or saliva. For example, by inserting in vitro genetic material encoding for at least part of a human immunoglobulin into a gene of a mammal coding for a milk protein and then introducing the gene to a fertilized egg of the mammal, e.g., by injection, the egg may develop into an adult female mammal producing milk containing immunoglobulin derived at least in part from the inserted human immunoglobulin genetic material. The desired antibody can then be harvested from the milk. Suitable techniques for carrying out such processes are known to those skilled in the art.

The foregoing transgenic animals are usually employed to produce human antibodies of a single isotype, more specifically an isotype that is essential for B cell maturation, such as IgM and possibly IgD. Another preferred method for producing human anti-VEGF antibodies is to use the technology described in U.S. Pat. Nos. 5,545,806; 5,569,825; 5,625,126; 5,633,425; 5,661,016; and 5,770,429; each incorporated by reference, wherein transgenic animals are described that are capable of switching from an isotype needed for B cell development to other isotypes.

In the development of a B lymphocyte, the cell initially produces IgM with a binding specificity determined by the productively rearranged $V_H$ and $V_L$ regions. Subsequently, each B cell and its progeny cells synthesize antibodies with the same L and H chain V regions, but they may switch the isotype of the H chain. The use of mu or delta constant regions is largely determined by alternate splicing, permitting IgM and IgD to be coexpressed in a single cell. The other heavy chain isotypes (gamma, alpha, and epsilon) are only expressed natively after a gene rearrangement event deletes the C mu and C delta exons. This gene rearrangement process, termed isotype switching, typically occurs by recombination between so called switch segments located immediately upstream of each heavy chain gene (except delta). The individual switch segments are between 2 and 10 kb in length, and consist primarily of short repeated sequences.

For these reasons, it is preferable that transgenes incorporate transcriptional regulatory sequences within about 1-2 kb upstream of each switch region that is to be utilized for isotype switching. These transcriptional regulatory sequences preferably include a promoter and an enhancer element, and more preferably include the 5' flanking (i.e., upstream) region that is naturally associated (i.e., occurs in germline configuration) with a switch region. Although a 5' flanking sequence from one switch region can be operably linked to a different switch region for transgene construction, in some embodiments it is preferred that each switch region incorporated in the transgene construct have the 5' flanking region that occurs immediately upstream in the naturally occurring germline configuration. Sequence information relating to immunoglobulin switch region sequences is known (Mills et al., 1990; Sideras et al., 1989; each incorporated herein by reference).

In the method described in U.S. Pat. Nos. 5,545,806; 5,569,825; 5,625,126; 5,633,425; 5,661,016; and 5,770,429, the human immunoglobulin transgenes contained within the transgenic animal function correctly throughout the pathway of B-cell development, leading to isotype switching. Accordingly, in this method, these transgenes are constructed so as to produce isotype switching and one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus consists of approximately 200 V gene segments spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14. Heavy chain transgene fragments containing members of all six of the known $V_H$ families, the D and J gene segments, as well as the mu, delta, gamma 3, gamma 1 and alpha 1 constant regions are known (Berman et al., 1988; incorporated herein by reference). Genomic fragments containing all of the necessary gene segments and regulatory sequences from a human light chain locus is similarly constructed.

The expression of successfully rearranged immunoglobulin heavy and light transgenes usually has a dominant effect by suppressing the rearrangement of the endogenous immunoglobulin genes in the transgenic nonhuman animal. However, in certain embodiments, it is desirable to effect complete inactivation of the endogenous Ig loci so that hybrid immunoglobulin chains comprising a human variable region and a non-human (e.g., murine) constant region cannot be formed, for example by trans-switching between the transgene and endogenous Ig sequences. Using embryonic stem cell technology and homologous recombination, the endogenous immunoglobulin repertoire can be readily eliminated. In addition, suppression of endogenous Ig genes may be accomplished using a variety of techniques, such as antisense technology.

In other aspects of the invention, it may be desirable to produce a trans-switched immunoglobulin. Antibodies comprising such chimeric trans-switched immunoglobulins can be used for a variety of applications where it is desirable to have a non-human (e.g., murine) constant region, e.g., for retention of effector functions in the host. The presence of a murine constant region can afford advantages over a human constant region, for example, to provide murine effector functions (e.g., ADCC, murine complement fixation) so that such a chimeric antibody may be tested in a mouse disease model. Subsequent to the animal testing, the human variable region encoding sequence may be isolated, e.g., by PCR™ amplification or cDNA cloning from the source (hybridoma clone), and spliced to a sequence encoding a desired human constant region to encode a human sequence antibody more suitable for human therapeutic use.

B6. Mutagenesis by PCR™

Site-specific mutagenesis is a technique useful in the preparation of individual antibodies through specific mutagenesis of the underlying DNA. The technique further provides a ready ability to prepare and test sequence variants, incorporating one or more of the foregoing considerations, whether humanizing or not, by introducing one or more nucleotide sequence changes into the DNA.

Although many methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence.

Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of MgCl$_2$ in the amplification buffer will generally be about 15 mM. Generally about 20-25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subclone the fragments and to check the point mutation, one would subclone the two amplified fragments into an appropriately digested vector by blunt-end ligation. This would be used to transform E. coli, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

When performing site-specific mutagenesis, Table A can be employed as a reference.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAGC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

B7. Antibody Fragments and Derivatives

Irrespective of the source of the original VEGFR2-blocking, human anti-VEGF antibody of the invention, either the intact antibody, antibody multimers, or any one of a variety of functional, antigen-binding regions of the antibody may be used in the present invention. Exemplary functional regions include antibody fragments that comprise an antigen binding domain such as Fab', Fab, F(ab')$_2$, single domain antibodies (DABs), T and Abs dimer, Fv, scFv (single chain Fv), dsFv, ds-scFv, Fd, linear antibodies, minibodies, diabodies, bispecific antibody fragments and the like. Techniques for preparing such constructs are well known to those in the art and are further described herein.

The choice of antibody construct may be influenced by various factors. For example, prolonged half-life can result from the active readsorption of intact antibodies within the kidney, a property of the Fc piece of immunoglobulin. IgG based antibodies, therefore, are expected to exhibit slower blood clearance than their Fab' counterparts. However, Fab' fragment-based compositions will generally exhibit better tissue penetrating capability.

If desired, particular Fc regions could be selected to provide longevity. For example, see WO 99/43713, which concerns constant domains with enhanced circulating half-lives achieved by substantially reduced binding to the Fcγ receptors, FcγRI, FcγRII and FcγRIII (Fridman, 1991). Additionally, U.S. Pat. No. 7,083,784 concerns modified constant domains with increased in vivo half-lives resulting from modifications that increase their affinity for the FcRn (neonatal Fc receptor). The techniques of U.S. Pat. No. 7,083,784 may be applied to create antibodies with better longevity, either with or without substantial effector functions.

Antibody fragments can be obtained by proteolysis of the whole human immunoglobulin by the non-specific thiol protease, papain. Papain digestion yields two identical antigen-binding fragments, termed "Fab fragments", each with a single antigen-binding site, and a residual "Fc fragment".

Papain must first be activated by reducing the sulfhydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

The usual procedure for preparation of F(ab')$_2$ fragments from IgG of human origin is limited proteolysis by the enzyme pepsin. The conditions, 100× antibody excess w/w in acetate buffer at pH 4.5, 37° C., suggest that antibody is cleaved at the C-terminal side of the inter-heavy-chain disulfide bond. Rates of digestion of mouse IgG may vary with subclass and conditions should be chosen to avoid significant amounts of completely degraded IgG. In particular, IgG$_{2b}$ is susceptible to complete degradation. The other subclasses require different incubation conditions to produce optimal results, all of which is known in the art.

Pepsin treatment of intact antibodies yields an F(ab')$_2$ fragment that has two antigen-combining sites and is still capable of cross-linking antigen. Exemplary conditions for digestion of IgG by pepsin requires conditions including dialysis in 0.1 M acetate buffer, pH 4.5, and then incubation for four hours with 1% w/w pepsin; IgG$_1$ and IgG$_{2a}$ digestion is improved if first dialyzed against 0.1 M formate buffer, pH 2.8, at 4° C., for 16 hours followed by acetate buffer. IgG$_{2b}$ gives more consistent results with incubation in staphylococcal V8 protease (3% w/w) in 0.1 M sodium phosphate buffer, pH 7.8, for four hours at 37° C.

An Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. F(ab')$_2$ antibody fragments were originally produced as pairs of Fab' fragments that have hinge cysteines between them. Other chemical couplings of antibody fragments are also known.

An "Fv" fragment is the minimum antibody fragment that contains a complete antigen-recognition and binding site. This region consists of a dimer of one heavy chain and one light chain variable domain in tight, non-covalent association. It is in this configuration that the three hypervariable regions (CDRs) of each variable domain interact to define an antigen-binding site on the surface of the V$_H$-V$_L$ dimer. Collectively, the six hypervariable regions (CDRs) confer antigen-binding specificity to the antibody. However, even a single variable domain (or half of an Fv comprising only three hypervariable regions (CDRs) specific for an antigen) has the ability to recognize and bind antigen.

"Single-chain Fv" or "sFv" or "scFv" antibody fragments comprise the V$_H$ and V$_L$ domains of antibody, wherein these domains are present in a single polypeptide chain. Generally, the Fv polypeptide further comprises a polypeptide linker between the V$_H$ and V$_L$ domains that enables the sFv to form the desired structure for antigen binding.

The following patents are specifically incorporated herein by reference for the purposes of even further supplementing the present teachings regarding the preparation and use of functional, antigen-binding regions of antibodies, including scFv, Fv, Fab', Fab and F(ab')$_2$ fragments of the anti-VEGF antibodies: U.S. Pat. Nos. 5,855,866; 5,965,132; 6,051,230; 6,004,555; 5,877,289; and 6,093,399. WO 98/45331 is also incorporated herein by reference for purposes including even further describing and teaching the preparation of variable, hypervariable and complementarity determining (CDR) regions of antibodies.

"Diabodies" are small antibody fragments with two antigen-binding sites, which fragments comprise a heavy chain variable domain (V$_H$) connected to a light chain variable domain (V$_L$) in the same polypeptide chain (V$_H$-V$_L$). By using a linker that is too short to allow pairing between the two domains on the same chain, the domains are forced to pair with the complementary domains of another chain and create two antigen-binding sites. Diabodies are described in EP 404,097 and WO 93/11161. "Linear antibodies", which can be bispecific or monospecific, comprise a pair of tandem Fd segments (V$_H$-C$_H$1-V$_H$-C$_H$1) that form a pair of antigen binding regions, as described in Zapata et al. (1995).

In using a Fab' or antigen binding fragment of an antibody, with the attendant benefits on tissue penetration, one may derive additional advantages from modifying the fragment to increase its half-life. A variety of techniques may be employed, such as manipulation or modification of the antibody molecule itself, and also conjugation to inert carriers. Any conjugation for the sole purpose of increasing half-life, rather than to deliver an agent to a target, should be approached carefully in that Fab' and other fragments are chosen to penetrate tissues. Nonetheless, conjugation to non-protein polymers, such PEG and the like, is contemplated.

Modifications other than conjugation are therefore based upon modifying the structure of the antibody fragment to render it more stable, and/or to reduce the rate of catabolism in the body. One mechanism for such modifications is the use of D-amino acids in place of L-amino acids. Those of ordinary skill in the art will understand that the introduction of such modifications needs to be followed by rigorous testing of the resultant molecule to ensure that it still retains the desired biological properties. Further stabilizing modifications include the use of the addition of stabilizing moieties to either the N-terminal or the C-terminal, or both, which is generally used to prolong the half-life of biological molecules. By way of example only, one may wish to modify the termini by acylation or amination.

Moderate conjugation-type modifications for use with the present invention include incorporating a salvage receptor binding epitope into the antibody fragment. Techniques for achieving this include mutation of the appropriate region of the antibody fragment or incorporating the epitope as a peptide tag that is attached to the antibody fragment. WO 96/32478 is specifically incorporated herein by reference for the purposes of further exemplifying such technology. Salvage receptor binding epitopes are typically regions of three or more amino acids from one or two loops of the Fc domain that are transferred to the analogous position on the antibody fragment. The salvage receptor binding epitopes of WO 98/45331 are incorporated herein by reference for use with the present invention.

B8. Binding and Functional Assays

Although the present invention has significant utility in animal and human treatment regimens, it also has many other practical uses, including many in vitro uses. Certain of these uses are related to the specific binding properties of the human antibodies or immunoconjugates. In that all the compounds of the invention include at least one VEGF binding component, they may be used in virtually all of the binding embodiments in which any anti-VEGF antibody may be used.

The presence of an attached agent, where relevant, although providing advantageous properties, does not negate the utility of the human antibody regions in any binding assay. Suitably useful binding assays thus include those commonly employed in the art, such as in immunoblots, Western blots, dot blots, RIAs, ELISAs, immunohistochemistry, fluorescent activated cell sorting (FACS), immunoprecipitation, affinity chromatography, and the like, as further described herein.

Certain standard binding assays are those in which an antigen is immobilized onto a solid support matrix, e.g., nitrocellulose, nylon or a combination thereof, such as in immunoblots, Western blots and related assays. Other important assays are ELISAs. All such assays may be readily adapted for use in the detection of VEGF, as may be applied in the diagnosis of an angiogenic disease. The agents of the invention may also be used in conjunction with both fresh-frozen and formalin-fixed, paraffin-embedded tissue blocks in immunohistochemistry; in fluorescent activated cell sorting, flow cytometry or flow microfluorometry; in immunoprecipitation; in antigen purification embodiments, such as affinity chromatography, even including, in cases of bispecific antibodies, the one-step rapid purification of one or more antigens at the same time; and in many other binding assays that will be known to those of skill in the art given the information presented herein.

Further practical uses of the present human antibodies are as controls in functional assays. These include many in vitro and ex vivo assays and systems, as well as animal model studies. As the binding and functional properties of the human antibodies of the invention are particularly specific, i.e., they inhibit VEGF binding to and signaling via VEGFR2, but not VEGFR1, such "control" uses are actually extremely valuable. The assays that benefit from such a practical application of the present invention include, for example, assays concerning VEGF-mediated endothelial cell growth, VEGF-induced phosphorylation and VEGF-induced vascular permeability, as well as the corneal micropocket assay of neovascularization and the chick chorio-allantoic membrane assay (CAM) assay. These assays systems can also be developed into in vitro or ex vivo drug screening assays, wherein the present provision of biological materials with well defined properties is particularly important.

C. Immunoconjugates

Although the present invention provides surprisingly effective naked or unconjugated human antibodies for use in anti-angiogenic methods, VEGFR2-blocking, human anti-VEGF antibody immunoconjugates, immunotoxins and coaguligands are also provided hereby. Currently preferred agents for use in VEGFR2-blocking, human anti-VEGF antibody therapeutic conjugates are radiotherapeutic agents (as exemplified by the radiodiagnostics disclosed herein), chemotherapeutic agents, anti-angiogenic agents, apoptosis-inducing agents, anti-tubulin drugs, anti-cellular or cytotoxic agents, cytokines, chemokine, V-type ATPase inhibitors and coagulants (coagulation factors).

To generate immunoconjugates, immunotoxins and coaguligands, recombinant expression may be employed to create a fusion protein, as is known to those of skill in the art and further disclosed herein. Equally, immunoconjugates, immunotoxins and coaguligands may be generated using avidin:biotin bridges or any of the chemical conjugation and cross-linker technologies developed in reference to antibody conjugates.

C1. Toxic and Anti-Cellular Agents

For certain applications, the therapeutic agents will be cytotoxic or pharmacological agents, particularly cytotoxic, cytostatic or otherwise anti-cellular agents having the ability to kill or suppress the growth or cell division of endothelial cells. In general, these aspects of the invention contemplate the use of any pharmacological agent that can be conjugated to a VEGFR2-blocking, human anti-VEGF antibody of the invention, and delivered in active form to the targeted endothelium.

Exemplary anti-cellular agents include chemotherapeutic agents, as well as cytotoxins. Chemotherapeutic agents that may be used include: hormones, such as steroids; anti-metabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments may include agents such as cytokines. Basically, any anti-cellular agent may be used, so long as it can be successfully conjugated to, or associated with, an antibody in a manner that will allow its targeting, internalization, release and/or presentation to blood components at the site of the targeted endothelial cells.

There may be circumstances, such as when the target antigen does not internalize by a route consistent with efficient intoxication by the toxic compound, where one will desire to target chemotherapeutic agents, such as anti-tumor drugs, cytokines, antimetabolites, alkylating agents, hormones, and the like. A variety of chemotherapeutic and other pharmacological agents have now been successfully conjugated to antibodies and shown to function pharmacologically, including doxorubicin, daunomycin, methotrexate, vinblastine, neocarzinostatin, macromycin, trenimon and α-amanitin.

In other circumstances, any potential side-effects from cytotoxin-based therapy may be eliminated by the use of DNA synthesis inhibitors, such as daunorubicin, doxorubicin, adriamycin, and the like. These agents are therefore preferred examples of anti-cellular agents for use in the present invention. In terms of cytostatic agents, such compounds generally disturb the natural cell cycle of a target cell, preferably so that the cell is taken out of the cell cycle.

A wide variety of cytotoxic agents are known that may be conjugated to VEGFR2-blocking, human anti-VEGF antibodies. Examples include numerous useful plant-, fungus- or bacteria-derived toxins, which, by way of example, include various A chain toxins, particularly ricin A chain; ribosome inactivating proteins, such as saporin or gelonin; α-sarcin; aspergillin; restrictocin; ribonucleases, such as placental ribonuclease; diphtheria toxin; and pseudomonas exotoxin, to name just a few.

The well-known 1992 toxin book, "Genetically Engineered Toxins", edited by Arthur E. Frankel, including the appendix, which includes the primary amino acid sequences of a large number of toxins, is specifically incorporated herein by reference, for purposes of further describing and enabling the use of toxins in targeted constructs.

Of the toxins, gelonin and ricin A chains are preferred. The most preferred toxin moiety for use herewith is toxin A chain that has been treated to modify or remove carbohydrate residues, so-called deglycosylated A chain (dgA). Deglycosylated ricin A chain is preferred because of its extreme potency, longer half-life, and because it is economically feasible to manufacture it in a clinical grade and scale.

It may be desirable from a pharmacological standpoint to employ the smallest molecule possible that nevertheless provides an appropriate biological response. One may thus desire to employ smaller A chain peptides that will provide an adequate anti-cellular response. To this end, it has been discovered that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional benefits in accordance the invention. In that the cloning and expression of biologically active ricin A chain has been achieved, it is now possible to identify and prepare smaller, or otherwise variant peptides, which nevertheless exhibit an appropriate toxin activity. Moreover, the fact that ricin A chain has now been cloned allows the application of site-directed mutagenesis, through which one can readily prepare and screen for A chain-derived peptides and obtain additional useful moieties for use in connection with the present invention.

C2. Coagulation Factors

The VEGFR2-blocking, human anti-VEGF antibody of the invention may be linked to a component that is capable of directly or indirectly stimulating coagulation, to form a coaguligand. Here, the antibodies may be directly linked to the coagulant or coagulation factor, or may be linked to a second binding region that binds and then releases the coagulant or coagulation factor. As used herein, the terms "coagulant" and "coagulation factor" are each used to refer to a component that is capable of directly or indirectly stimulating coagulation under appropriate conditions, preferably when provided to a specific in vivo environment, such as the tumor vasculature.

Preferred coagulation factors are Tissue Factor compositions, such as truncated TF (tTF), dimeric, multimeric and mutant TF molecules. "Truncated TF" (tTF) refers to TF constructs that are rendered membrane-binding deficient by removal of sufficient amino acid sequences to effect this change in property. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes. Truncated TF thus substantially fails to convert Factor VII to Factor VIIa in a standard TF assay, and yet retains so-called catalytic activity including activating Factor X in the presence of Factor VIIa.

U.S. Pat. No. 5,504,067 is specifically incorporated herein by reference for the purposes of further describing such truncated Tissue Factor proteins. Preferably, the Tissue Factors for use in these aspects of the present invention will generally lack the transmembrane and cytosolic regions (amino acids 220-263) of the protein. However, there is no need for the truncated TF molecules to be limited to molecules of the exact length of 219 amino acids.

Tissue Factor compositions may also be useful as dimers. Any of the truncated, mutated or other Tissue Factor constructs may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety.

Such membrane insertion sequences may be located either at the N-terminus or the C-terminus of the TF molecule, or generally appended at any other point of the molecule so long as their attachment thereto does not hinder the functional properties of the TF construct. The intent of the hindered insertion moiety is that it remains non-functional until the TF construct localizes within the tumor environment, and allows the hydrophobic appendage to become accessible and even further promote physical association with the membrane. Again, it is contemplated that biologically-releasable bonds and selectively-cleavable sequences will be particularly useful in this regard, with the bond or sequence only being cleaved or otherwise modified upon localization within the tumor environment and exposure to particular enzymes or other bioactive molecules.

In other embodiments, the tTF constructs may be multimeric or polymeric. In this context a "polymeric construct" contains 3 or more Tissue Factor constructs. A "multimeric or polymeric TF construct" is a construct that comprises a first TF molecule or derivative operatively attached to at least a second and a third TF molecule or derivative. The multimers may comprise between about 3 and about 20 such TF molecules. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

Even further TF constructs useful in context of the present invention are those mutants deficient in the ability to activate Factor VII. Such "Factor VII activation mutants" are generally defined herein as TF mutants that bind functional Factor VII/VIIa, proteolytically activate Factor X, but are substantially free from the ability to proteolytically activate Factor VII. Accordingly, such constructs are TF mutants that lack Factor VII activation activity.

The ability of such Factor VII activation mutants to function in promoting tumor-specific coagulation is based upon their specific delivery to the tumor vasculature, and the presence of Factor VIIa at low levels in plasma. Upon administration of such a Factor VII activation mutant conjugate, the mutant will be localized within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis. Exogenous Factor VIIa could also be administered to the patient.

Any one or more of a variety of Factor VII activation mutants may be prepared and used in connection with the present invention. There is a significant amount of scientific knowledge concerning the recognition sites on the TF molecule for Factor VII/VIIa. It will thus be understood that the Factor VII activation region generally lies between about amino acid 157 and about amino acid 167 of the TF molecule. However, it is contemplated that residues outside this region may also prove to be relevant to the Factor VII activating activity, and one may therefore consider introducing mutations into any one or more of the residues generally located between about amino acid 106 and about amino acid 209 of the TF sequence (WO 94/07515; WO 94/28017; each incorporated herein by reference).

A variety of other coagulation factors may be used in connection with the present invention, as exemplified by the agents set forth below. Thrombin, Factor V/Va and derivatives, Factor VIII/VIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

Russell's viper venom Factor X activator is contemplated for use in this invention. Monoclonal antibodies specific for the Factor X activator present in Russell's viper venom have also been produced, and could be used to specifically deliver the agent as part of a bispecific binding ligand.

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation. Both thromboxane $A_2$ and active analogues thereof are contemplated for use in the present invention.

Thromboxane synthase, and other enzymes that synthesize platelet-activating prostaglandins, may also be used as "coagulants" in the present context. Monoclonal antibodies to, and immunoaffinity purification of, thromboxane synthase are known; as is the cDNA for human thromboxane synthase.

α2-antiplasmin, or α2-plasmin inhibitor, is a proteinase inhibitor naturally present in human plasma that functions to efficiently inhibit the lysis of fibrin clots induced by plasminogen activator. α2-antiplasmin is a particularly potent inhibitor, and is contemplated for use in the present invention.

As the cDNA sequence for α2-antiplasmin is available, recombinant expression and/or fusion proteins are preferred. Monoclonal antibodies against α2-antiplasmin are also available that may be used in the bispecific binding ligand embodiments of the invention. These antibodies could both be used to deliver exogenous α2-antiplasmin to the target site or to garner endogenous α2-antiplasmin and concentrate it within the targeted region.

C3. Anti-Tubulin Drugs

A range of drugs exert their effects via interfering with tubulin activity. As tubulin functions are essential to mitosis and cell viability, certain "anti-tubulin drugs" are powerful chemotherapeutic agents. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Some of the more well known and currently preferred anti-tubulin drugs for use with the present invention are colchicine; taxanes, such as taxol (paclitaxel) and docetaxel; vinca alkaloids, such as vinblastine, vincristine and vindescine; and combretastatins. Other suitable anti-tubulin drugs are cytochalasins (including B, J, E), dolastatin, auristatin PE, paclitaxel, ustiloxin D, rhizoxin, 1069C85, colcemid, albendazole, azatoxin and nocodazole.

As described in U.S. Pat. Nos. 5,892,069, 5,504,074 and 5,661,143, combretastatins are estradiol derivatives that generally inhibit cell mitosis. Exemplary combretastatins that may be used in conjunction with the invention include those based upon combretastatin A, B and/or D and those described in U.S. Pat. Nos. 5,892,069, 5,504,074 and 5,661,143. Combretastatins A-1, A-2, A-3, A4, A-5, A-6, B-1, B-2, B-3 and B-4 are exemplary of the foregoing types.

U.S. Pat. Nos. 5,569,786 and 5,409,953 describe the isolation, structural characterization and synthesis of each of combretastatin A-1, A2, A-3, B-1, B-2, B-3 and B-4 and formulations and methods of using such combretastatins to treat neoplastic growth. Any one or more of such combretastatins may be used in conjunction with the present invention. Combretastatin A-4, as described in U.S. Pat. Nos. 5,892,069, 5,504,074, 5,661,143 and 4,996,237, may also be used herewith. U.S. Pat. No. 5,561,122 further describes suitable combretastatin A-4 prodrugs, which are contemplated for combined use with the present invention.

U.S. Pat. No. 4,940,726 particularly describes macrocyclic lactones denominated combretastatin D-1 and 'Combretastatin D-2', each of which may be used in combination with the compositions and methods of the present invention. U.S. Pat. No. 5,430,062 concerns stilbene derivatives and combretastatin analogues with anti-cancer activity that may be used in combination with the present invention.

C4. Anti-Angiogenic Agents

The present invention particularly provides combined anti-angiogenics. The human antibodies of the invention may be attached to an angiopoietin (Davis and Yancopoulos, 1999; Holash et al., 1999; incorporated herein by reference), such as angiopoietin-1 (Ang-1), angiopoietin-2 (Ang-2), angiopoietin-3 (mouse) or angiopoietin-4 (human) (Valenzuela et al., 1999; Kim et al., 1999).

Exemplary anti-angiogenics for use herewith include angiostatin and endostatin. Angiostatin is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type IV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro. The mechanism of action for angiostatin is currently unclear, it is hypothesized that it binds to an unidentified cell surface receptor on endothelial cells inducing endothelial cell to undergo programmed cell death or mitotic arrest.

Endostatin appears to be an even more powerful anti-angiogenesis and anti-tumor agent and is particularly preferred for linking to VEGFR2-blocking, human anti-VEGF antibodies. Endostatin is effective at causing regressions in a number of tumor models in mice. Tumors do not develop resistance to endostatin and, after multiple cycles of treatment, tumors enter a dormant state during which they do not increase in volume. In this dormant state, the percentage of tumor cells undergoing apoptosis was increased, yielding a population that essentially stays the same size.

U.S. Pat. No. 5,854,205, to Folkman and O'Reilly, specifically incorporated herein by reference, concerns endostatin and its use as an inhibitor of endothelial cell proliferation and angiogenesis. The endostatin protein corresponds to a C-terminal fragment of collagen type XVIII, and the protein can be isolated from a variety of sources. U.S. Pat. No. 5,854,205 also teaches that endostatin can have an amino acid sequence of a fragment of collagen type XVIII, a collagen type XV, or BOVMPE 1 pregastric esterase. Combinations of endostatin with other anti-angiogenic proteins, particularly angiostatin, are also described by U.S. Pat. No. 5,854,205, such that the combined compositions are capable of effectively regressing the mass of an angiogenesis-dependent tumor.

Endostatin and angiostatin, particularly endostatin, are preferred agents for tumor delivery according to the present invention. Vasculostatin, canstatin and maspin are also preferred agents. Endostatin fusion proteins may be prepared, as described in U.S. Pat. No. 6,342,221, incorporated herein by reference. Various forms of chemically linked endostatin constructs may also be prepared, again as exemplified in U.S. Pat. No. 6,342,221.

C5. Apoptosis-Inducing Agents

The present invention may also be used to deliver agents that induce apoptosis in any cells within the tumor, including tumor cells and tumor vascular endothelial cells. Although many anti-cancer agents may have, as part of their mechanism of action, an apoptosis-inducing effect, certain agents have been discovered, designed or selected with this as a primary mechanism, as described below.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other compositions that may be delivered by VEGFR2-blocking, human anti-VEGF antibodies include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to the agents of the present invention that target the cell surface receptor, VEGFR1 (as supported by U.S. Pat. No. 5,587,459; incorporated herein by reference).

"Second mitochondrial-derived activator of caspase" (SMAC), also known as DIABLO, is a protein that is released from the mitochondria during apoptosis and binds to a family of proteins termed "inhibitor of apoptosis proteins" (IAPs). IAP expression levels are increased in a number of human tumors. Therefore, IAP antagonists or SMAC mimetics have been developed as anti-cancer agents. These may be used in conjunction with the present invention, both as conjugates and in combination therapies.

Exemplary IAP inhibitors include those developed on the basis of the crystal structure of the interaction of SMAC with the B1R3 domain of X-linked IAP (XIAP, also known as BIRC4) and monovalent and bivalent IAP antagonists designed using a structure-based approach (Vince et al., 2007; Varfolomeev et al., 2007). SMAC mimetics designed to resemble the N-terminal amino acids of SMAC, which interact with the BIR3 domain of XIAP (Petersen et al., 2007), may also be used. It has been shown that SMAC mimetics can induce regression of sensitive human lung cancer xenografts even as single agents, with 40% of treated animals remaining free of tumors (Petersen et al., 2007).

C6. Cytokines

Cytokines and chemokines are particular examples of agents for linking to a VEGFR2-blocking, human anti-VEGF antibody of the present invention. A range of cytokines may be used, including IL-3, IL-4, IL-5, IL-7, IL-8, IL-9, IL-11, IL-13, TGF-β, M-CSF, G-CSF, TNFβ, LAF, TCGF, BCGF, TRF, BAF, BDG, MP, LIF, OSM, TMF, IFN-α, IFN-β. More preferred cytokines include IL-1α, IL-1β, IL-2, IL-6, IL-10, GM-CSF, IFN-γ, monocyte chemoattractant protein-1 (MCP-1), platelet-derived growth factor-BB (PDGF-BB) and C-reactive protein (CRP) and the like. Particularly preferred examples are TNFα, TNFα inducers, L-2, IL-12, IFN-α, IFN-β, IFN-γ and LEC.

IL-12, for example, may be attached to a VEGFR2-blocking, human anti-VEGF antibody and used to redirect host defenses to attack the tumor vessels. The chemokine LEC (liver-expressed chemokine, also known as NCC-4, HCC-4, or LMC) is another preferred component (Giovarelli et al., 2000). LEC is chemotactic for dendritic cells, monocytes, T cells, NK cells and neutrophils and can therefore improve host-mediated anti-tumor responses.

C7. Biologically Functional Equivalents

Equivalents, or even improvements, of the VEGFR2-blocking, human anti-VEGF antibodies of the invention can now be made. Modifications and changes may be made in the structure of such an antibody and still obtain a molecule having like or otherwise desirable characteristics. For example, certain amino acids may substituted for other amino acids in a protein structure without appreciable loss of interactive binding capacity. These considerations also apply to toxins, anti-angiogenic agents, apoptosis-inducing agents, coagulants and the like.

Since it is the interactive capacity and nature of a protein that defines that protein's biological functional activity, certain amino acid sequence substitutions can be made in a protein sequence (or of course, the underlying DNA sequence) and nevertheless obtain a protein with like (agonistic) properties. It is thus contemplated that various changes may be made in the sequence of the antibodies or therapeutic agents (or underlying DNA sequences) without appreciable loss of their biological utility or activity. Biological functional equivalents made from mutating an underlying DNA sequence can be made using the codon information provided herein in Table A, and the supporting technical details on site-specific mutagenesis.

It also is well understood by the skilled artisan that, inherent in the definition of a "biologically functional equivalent" protein or peptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention. Such "biologically functional equivalent" peptides may be regarded as further examples of "substantially homologous" sequences as described herein.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is thus understood that an amino acid can be substituted for another having a similar hydrophilicity value and still obtain a biologically equivalent protein. As detailed in U.S. Pat. No. 4,554,101 (incorporated herein by reference), the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon hydrophilicity values, the substitution of amino acids whose hydrophilicity values are within ±2 is preferred, those which are within ±1 are particularly preferred, and those within ±0.5 are even more particularly preferred.

C8. Fusion Proteins and Recombinant Expression

The VEGFR2-blocking, human anti-VEGF antibody or immunoconjugates of the present invention may be readily prepared as fusion proteins using molecular biological techniques. Any fusion protein may be designed and made using any of the therapeutic agents disclosed herein and those known in the art. The fusion protein technology is readily adapted to prepare fusion proteins in which the two portions are joined by a selectively cleavable peptide sequence. Any therapeutic agent may be attached to the terminus of the antibody or to any point distinct from the CDRs. Therapeutic agents may also be prepared "integrally", wherein they are preferably associated with a selectively cleavable peptide to allow release of the agent after targeting.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989; incorporated herein by reference).

The preparation of such a fusion protein generally entails the preparation of a first and second DNA coding region and the functional ligation or joining of such regions, in frame, to prepare a single coding region that encodes the desired fusion protein. In the present context, the VEGFR2-blocking, human anti-VEGF antibody DNA sequence will be joined in frame with a DNA sequence encoding a therapeutic agent. It is not generally believed to be particularly relevant which portion of the construct is prepared as the N-terminal region or as the C-terminal region.

Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

To obtain a so-called "recombinant" version of the VEGFR2-blocking, human anti-VEGF antibody of the invention or immunoconjugate thereof, it is expressed in a recombinant cell. The engineering of DNA segment(s) for expression in a prokaryotic or eukaryotic system may be performed by techniques generally known to those of skill in recombinant expression. It is believed that virtually any expression system may be employed in the expression of a VEGFR2-blocking, human anti-VEGF antibody or immunoconjugate constructs.

Such proteins may be successfully expressed in eukaryotic expression systems, e.g., CHO cells, however, it is envisioned that bacterial expression systems, such as E. coli pQE-60 will be particularly useful for the large-scale preparation and subsequent purification of the VEGFR2-blocking, human anti-VEGF antibody or immunoconjugates. cDNAs may also be expressed in bacterial systems, with the encoded proteins being expressed as fusions with α-galactosidase, ubiquitin, Schistosoma japonicum glutathione S-transferase, and the like. It is believed that bacterial expression will have advantages over eukaryotic expression in terms of ease of use and quantity of materials obtained thereby.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

Recombinantly produced VEGFR2-blocking, human anti-VEGF antibodies immunoconjugates may be purified and formulated for human administration. Alternatively, nucleic acids encoding the immunoconjugates may be delivered via gene therapy. Although naked recombinant DNA or plasmids may be employed, the use of liposomes or vectors is preferred. The ability of certain viruses to enter cells via receptor-mediated endocytosis and to integrate into the host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

C9. Antibody Conjugates

VEGFR2-blocking, human anti-VEGF antibodies may be conjugated to anti-cellular or cytotoxic agents, to prepare "immunotoxins"; or operatively associated with components that are capable of directly or indirectly stimulating coagulation, thus forming a "coaguligand". In coaguligands, the antibody may be directly linked to a direct or indirect coagulation factor, or may be linked to a second binding region that binds and then releases a direct or indirect coagulation factor. The 'second binding region' approach generally uses a coagulant-binding antibody as a second binding region, thus resulting in a bispecific antibody construct. The preparation and use of bispecific antibodies in general is well known in the art, and is further disclosed herein.

In the preparation of immunotoxins, coaguligands and bispecific antibodies, recombinant expression may be employed. The nucleic acid sequences encoding the chosen antibody are attached, in-frame, to nucleic acid sequences encoding the chosen toxin, coagulant, or second binding region to create an expression unit or vector. Recombinant expression results in translation of the new nucleic acid, to yield the desired protein product. Although antibody-encoding nucleic acids are employed, rather than protein binding ligands, the recombinant approach is essentially the same as those described hereinabove.

Returning to conjugate technology, the preparation of immunotoxins is generally well known in the art. However, certain advantages may be achieved through the application of certain preferred technology, both in the preparation of the immunotoxins and in their purification for subsequent clinical administration. For example, while IgG based immunotoxins will typically exhibit better binding capability and slower blood clearance than their Fab' counterparts, Fab' fragment-based immunotoxins will generally exhibit better tissue penetrating capability as compared to IgG based immunotoxins.

Additionally, while numerous types of disulfide-bond containing linkers are known that can be successfully employed to conjugate the toxin moiety to the VEGFR2-blocking, human anti-VEGF antibody, certain linkers will generally be preferred over other linkers, based on differing pharmacological characteristics and capabilities. For example, linkers that contain a disulfide bond that is sterically "hindered" are to be preferred, due to their greater stability in vivo, thus preventing release of the toxin moiety prior to binding at the site of action.

A wide variety of cytotoxic agents are known that may be conjugated to VEGFR2-blocking, human anti-VEGF antibody, including plant-, fungus- and bacteria-derived toxins, such as ricin A chain or deglycosylated A chain. The cross-linking of a toxin A chain to an antibody, in certain cases, requires a cross-linker that presents disulfide functions. The reason for this is unclear, but is likely due to a need for certain toxin moieties to be readily releasable from the antibody once the agent has "delivered" the toxin to the targeted cells.

Each type of cross-linker, as well as how the cross-linking is performed, will tend to vary the pharmacodynamics of the resultant conjugate. Ultimately, in cases where a releasable toxin is contemplated, one desires to have a conjugate that will remain intact under conditions found everywhere in the body except the intended site of action, at which point it is desirable that the conjugate have good "release" characteristics. Therefore, the particular cross-linking scheme, including in particular the particular cross-linking reagent used and the structures that are cross-linked, will be of some significance.

Depending on the specific toxin compound used as part of the fusion protein, it may be necessary to provide a peptide spacer operatively attaching the antibody and the toxin compound that is capable of folding into a disulfide-bonded loop structure. Proteolytic cleavage within the loop would then yield a heterodimeric polypeptide wherein the antibody and the toxin compound are linked by only a single disulfide bond. An example of such a toxin is a Ricin A-chain toxin.

When certain other toxin compounds are utilized, a non-cleavable peptide spacer may be provided to operatively attach the VEGFR2-blocking, human anti-VEGF antibody and the toxin compound of the fusion protein. Toxins that may be used in conjunction with non-cleavable peptide spacers are those which may, themselves, be converted by proteolytic cleavage, into a cytotoxic disulfide-bonded form. An example of such a toxin compound is a *Pseudomonas* exotoxin compound.

There may be circumstances, such as when the target antigen does not internalize by a route consistent with efficient intoxication by immunotoxins, where one will desire to target chemotherapeutic agents such as anti-tumor drugs, other cytokines, antimetabolites, alkylating agents, hormones, and the like. A variety of chemotherapeutic and other pharmacological agents have now been successfully conjugated to antibodies and shown to function pharmacologically. Exemplary antineoplastic agents that have been investigated include doxorubicin, daunomycin, methotrexate, vinblastine, and various others. Moreover, the attachment of other agents such as neocarzinostatin, macromycin, trenimon and α-amanitin has been described.

Where coagulation factors are used in connection with the present invention, any covalent linkage to the antibody should be made at a site distinct from its functional coagulating site. The compositions are thus "linked" in any operative manner that allows each region to perform its intended function without significant impairment. Thus, the antibody binds to VEGF, and the coagulation factor promotes blood clotting.

C10. Biochemical Cross-linkers

In additional to the general information provided above, VEGFR2-blocking, human anti-VEGF antibodies may be conjugated to one or more therapeutic agents using certain preferred biochemical cross-linkers. Cross-linking reagents are used to form molecular bridges that tie together functional groups of two different molecules. To link two different proteins in a step-wise manner, hetero-bifunctional cross-linkers can be used that eliminate unwanted homopolymer formation. Exemplary hetero-bifunctional cross-linkers are referenced in Table B.

TABLE B

HETERO-BIFUNCTIONAL CROSS-LINKERS

| Linker | Reactive Toward | Advantages and Applications | Spacer Arm Length after cross-linking |
|---|---|---|---|
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulfhydryls | Extended spacer arm Water-soluble | 15.6 A |
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulfhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulfhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulfhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

Hetero-bifunctional cross-linkers contain two reactive groups: one generally reacting with primary amine group (e.g., N-hydroxy succinimide) and the other generally reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the coagulant).

Compositions therefore generally have, or are derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, or alkylating groups may be used for binding or cross-linking.

The spacer arm between the two reactive groups of a cross-linker may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed to conjugate antibodies and toxic or coagulating agents. Linkers that contain a disulfide bond that is sterically hindered may prove to give greater stability in vivo, preventing release of the agent prior to binding at the site of action. These linkers are thus one preferred group of linking agents.

One of the most preferred cross-linking reagents for use in immunotoxins is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the bispecific ligands of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers can also be employed in accord-ance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated targeting and therapeutic agents and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

C11. Biologically Releasable Linkers

Although it is preferred that any linking moiety will have reasonable stability in blood, to prevent substantial release of the attached agent before targeting to the disease or tumor site, in certain aspects, the use of biologically-releasable bonds and/or selectively cleavable spacers or linkers is contemplated. "Biologically-releasable bonds" and "selectively cleavable spacers or linkers" still have reasonable stability in the circulation.

The VEGFR2-blocking, human anti-VEGF antibodies of the present invention may thus be linked to one or more therapeutic agents via a biologically-releasable bond. Any form of VEGFR2-blocking, human anti-VEGF antibody may be employed, including intact antibodies, although ScFv fragments will be preferred in certain embodiments.

"Biologically-releasable bonds" or "selectively hydrolyzable bonds" include all linkages that are releasable, cleavable or hydrolyzable only or preferentially under certain conditions. This includes disulfide and trisulfide bonds and acid-labile bonds, as described in U.S. Pat. Nos. 5,474,765 and 5,762,918, each specifically incorporated herein by reference.

The use of an acid sensitive spacer for attachment of a therapeutic agent or drug to an antibody of the invention is particularly contemplated. In such embodiments, the therapeutic agents or drugs are released within the acidic compartments inside a cell. It is contemplated that acid-sensitive release may occur extracellularly, but still after specific targeting, preferably to the tumor site. Certain currently preferred examples include human antibodies linked to colchicine or doxorubicin via an acid sensitive spacer. Attachment via the carbohydrate moieties of the antibodies is also contemplated. In such embodiments, the therapeutic agents or drugs are released within the acidic compartments inside a cell.

The human anti-VEGF antibody may also be derivatized to introduce functional groups permitting the attachment of the therapeutic agent(s) through a biologically releasable bond. The human antibody may thus be derivatized to introduce side chains terminating in hydrazide, hydrazine, primary amine or secondary amine groups. Therapeutic agents may be conjugated through a Schiffs base linkage, a hydrazone or acyl hydrazone bond or a hydrazide linker (U.S. Pat. Nos. 5,474,765 and 5,762,918, each specifically incorporated herein by reference).

Also as described in U.S. Pat. Nos. 5,474,765 and 5,762,918, each specifically incorporated herein by reference, the human anti-VEGF antibody may be operatively attached to the therapeutic agent(s) through one or more biologically releasable bonds that are enzyme-sensitive bonds, including peptide bonds, esters, amides, phosphodiesters and glycosides.

Preferred aspects of the invention concern the use of peptide linkers that include at least a first cleavage site for a peptidase and/or proteinase that is preferentially located within a disease site, particularly within the tumor environment. The antibody-mediated delivery of the attached therapeutic agent thus results in cleavage specifically within the disease site or tumor environment, resulting in the specific release of the active agent. Certain peptide linkers will include a cleavage site that is recognized by one or more enzymes involved in remodeling.

Peptide linkers that include a cleavage site for urokinase, pro-urokinase, plasmin, plasminogen, TGFβ, staphylokinase, Thrombin, Factor IXa, Factor Xa or a metalloproteinase, such as an interstitial collagenase, a gelatinase or a stromelysin, are particularly preferred. U.S. Pat. Nos. 6,004,555, 5,877,289, and 6,093,399, are specifically incorporated herein by reference for the purpose of further describing and enabling how to make and use targeting agent-therapeutic agent constructs comprising biologically-releasable bonds and selectively-cleavable linkers and peptides. U.S. Pat. Nos. 5,877,289 and 6,342,221, in particular, are specifically incorporated herein by reference for the purpose of further describing and enabling how to make and use antibody constructs that comprise a selectively-cleavable peptide linker that is cleaved by urokinase, plasmin, Thrombin, Factor IXa, Factor Xa or a metalloproteinase, such as an interstitial collagenase, a gelatinase or a stromelysin, within a tumor environment.

Currently preferred selectively-cleavable peptide linkers are those that include a cleavage site for plasmin or a metalloproteinase (also known as "matrix metalloproteases" or "MMPs"), such as an interstitial collagenase, a gelatinase or a stromelysin. Additional peptide linkers that may be advantageously used in connection with the present invention include, for example, the cleavable sequences from pro-urokinase, TGFβ, plasminogen, staphylokinase, Gelatinase A, various collagens, $\alpha_2 M$, PZP, $\alpha_1 M$, $\alpha_1 I_3 (2J)$ and $\alpha_1 I_3$ (27J), including those particular sequences disclosed and claimed in U.S. Pat. No. 6,342,221, specifically incorporated herein by reference.

C12. Bispecific Antibodies

Bispecific antibodies are particularly useful in the coaguligand and combined anti-angiogenic aspects of the present invention. However, bispecific antibodies in general may be employed, so long as one arm binds to VEGF, and the bispecific antibody is attached to a therapeutic agent, generally at a site distinct from the antigen binding site.

In general, the preparation of bispecific antibodies is also well known in the art. One method involves the separate preparation of antibodies having specificity for the targeted antigen, on the one hand, and (as herein) a coagulating agent on the other. Peptic $F(ab'\gamma)_2$ fragments are prepared from the two chosen antibodies, followed by reduction of each to provide separate $Fab'\gamma_{SH}$ fragments. The SH groups on one of the two partners to be coupled are then alkylated with a cross-linking reagent such as o-phenylenedimaleimide to provide free maleimide groups on one partner. This partner may then be conjugated to the other by means of a thioether linkage, to give the desired $F(ab'\gamma)_2$ heteroconjugate. Other techniques are known wherein cross-linking with SPDP or protein A is carried out, or a trispecific construct is prepared.

D. Pharmaceutical Compositions

The pharmaceutical compositions of the present invention will generally comprise an effective amount of at least a first VEGFR2-blocking, human anti-VEGF antibody or immunoconjugate, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

D1. Injectable Formulations

The VEGFR2-blocking, human anti-VEGF antibody antibodies or immunoconjugates of the present invention will most often be formulated for parenteral administration, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains such an antibody or immunoconjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The VEGFR2-blocking, human anti-VEGF antibody or immunoconjugate compositions can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the VEGFR2-blocking, human anti-VEGF antibody or immunoconjugate should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the VEGFR2-blocking, human anti-VEGF antibody or immunoconjugate admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards. Upon formulation, the antibody or immunoconjugate solutions will be administered in a manner compatible with the dosage formulation and in such amount as is therapeutically effective.

D2. Sustained Release Formulations

Formulations of VEGFR2-blocking, human anti-VEGF antibodies or immunoconjugate solutions are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver a VEGFR2-blocking, human anti-VEGF antibody or immunoconjugate in accordance with the present invention. The slow release formulations are typically implanted in the vicinity of the disease site, for example, at the site of a tumor.

Suitable examples of sustained-release preparations include semipermeable matrices of solid hydrophobic polymers containing the antibody or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and γ ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(-)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thiodisulfide interchange, stabilization is achieved by modifying sulfhydryl residues, lyophilizing from acidic solutions, controlling moisture content, using appropriate additives, developing specific polymer matrix compositions, and the like.

D3. Liposomes and Nanoparticles

In certain embodiments, liposomes and/or nanoparticles may also be employed with the VEGFR2-blocking, human anti-VEGF antibodies or immunoconjugates. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition that markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

D4. Ophthalmic Formulations

Many diseases with an angiogenic component are associated with the eye. For example, diseases associated with corneal neovascularization that can be treated according to the present invention include, but are not limited to, diabetic retinopathy, retinopathy of prematurity, corneal graft rejection, neovascular glaucoma and retrolental fibroplasia, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, trauma, rheumatoid arthritis, systemic lupus, polyarteritis, Wegeners sarcoidosis, Scleritis, Steven's Johnson disease, periphigoid radial keratotomy, and corneal graft rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases that can be treated according to the present invention include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

The VEGFR2-blocking, human anti-VEGF antibodies and immunoconjugates of the present invention may thus be advantageously employed in the preparation of pharmaceutical compositions suitable for use as ophthalmic solutions, including those for intravitreal and/or intracameral administration, either as a single agent or in combination with other ocular drugs or agents. For the treatment of any of the foregoing or other disorders a VEGFR2-blocking, human anti-VEGF antibody composition of the invention would be administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation will contain at least a VEGFR2-blocking, human anti-VEGF antibody in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

D5. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of VEGFR2-blocking, human anti-VEGF antibodies for topical use, such as in creams, ointments and gels, includes the preparation of oleaginous or water-soluble ointment bases, as is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

D6. Nasal Formulations

Local delivery via the nasal and respiratory routes is contemplated for treating various conditions. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 µm. Fine mists are produced by pressurized aerosols and hence their use in considered advantageous.

E. Therapeutic Kits

This invention also provides therapeutic kits comprising a VEGFR2-blocking, human anti-VEGF antibody or immunoconjugate for use in the present treatment methods. Such kits will generally contain, in suitable container means, a pharmaceutically acceptable formulation of at least one VEGFR2-blocking, human anti-VEGF antibody or immunoconjugate. The kits may also contain other pharmaceutically acceptable formulations, either for diagnosis/imaging or combined therapy. For example, such kits may contain any one or more of a range of chemotherapeutic or radiotherapeutic drugs; anti-angiogenic agents; anti-tumor cell antibodies; and/or anti-tumor vasculature or anti-tumor stroma immunotoxins or coaguligands.

The kits may have a single container (container means) that contains the VEGFR2-blocking, human anti-VEGF antibody or immunoconjugate, with or without any additional components, or they may have distinct containers for each desired agent. Where combined therapeutics are provided, a single solution may be pre-mixed, either in a molar equivalent combination, or with one component in excess of the other. Alternatively, each of the VEGFR2-blocking, human anti-VEGF antibody or immunoconjugate and other anti-cancer agent components of the kit may be maintained separately within distinct containers prior to administration to a patient.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

The containers of the kit will generally include at least one vial, test tube, flask, bottle, syringe or other container means, into which the VEGFR2-blocking, human anti-VEGF antibody or immunoconjugate, and any other desired agent, may be placed and, preferably, suitably aliquoted. Where separate components are included, the kit will also generally contain a second vial or other container into which these are placed, enabling the administration of separated designed doses. The kits may also comprise a second/third container means for containing a sterile, pharmaceutically acceptable buffer or other diluent.

The kits may also contain a means by which to administer the VEGFR2-blocking, human anti-VEGF antibody or immunoconjugate to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

F. Anti-Angiogenic Therapy

The present invention may be used to treat animals and patients with aberrant angiogenesis, such as that contributing to a variety of diseases and disorders, either alone or in combination therapies. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypettrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Harada et al. (1998, specifically incorporated herein by reference) showed that VEGF is involved in the pathogenesis of rheumatoid arthritis and, furthermore, that measurement of serum concentration of VEGF is a noninvasive, useful method for monitoring the disease activity of rheumatoid arthritis. This supports the therapeutic and diagnostic uses of the present invention in connection with rheumatoid arthritis.

Nagashima et al. (1999, specifically incorporated herein by reference) described the inhibitory effects of anti-rheumatic drugs on VEGF in cultured rheumatoid synovial cells. VEGF is constitutively expressed in the synovium of rheumatoid arthritis. The known anti-rheumatic drug, bucillamine (BUC), was shown to include within its mechanism of action the inhibition of VEGF production by synovial cells. Thus, the anti-rheumatic effects of BUC are mediated by suppression of angiogenesis and synovial proliferation in the arthritic synovium through the inhibition of VEGF production by synovial cells. The use of the present invention as an antiarthritic therapy is supported by the VEGF inhibitory actions of this existing therapeutic.

Another example of a disease mediated by angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, *Mycobacteria* infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, including age-related macular degeneration (AMD), sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

As to choroidal neovascularization, such as that associated with macular degeneration, AMD and other ocular diseases, the VEGFR2-blocking, human anti-VEGF antibodies of the present invention are particularly well suited for use in treatment. This is, in part, because they substantially block VEGF binding to VEGFR2 without substantially blocking VEGF binding to VEGFR1 and the resultant benefits in the eye (Nozaki et al., 2006), which highlights another advantage of the present invention over existing anti-VEGF treatments, such as, e.g., Avastin and the related product, Lucentis®.

Other diseases include, but are not limited to, diseases associated with rubeosis (neovascularization of the angle) and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stimulatory activity. VEGF expression in human coronary atherosclerotic lesions was demonstrated by Inoue et al. (1998, specifically incorporated herein by reference). This evidences the pathophysiological significance of VEGF in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the present invention in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases. Moreover, U.S. Pat. No. 6,524,583 is specifically incorporated herein by reference for purposes including further describing and enabling the treatment of a wide-range of diseases and disorders using an anti-VEGF antibody.

The human antibodies and/or immunoconjugates of the invention are most preferably utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen.

Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs (see below).

The VEGFR2-blocking, human anti-VEGF antibody or immunoconjugate methods provided by this invention are thus broadly applicable to the treatment of any malignant tumor having a vascular component. In using the antibodies and/or immunoconjugates of the invention in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an anti-VEGF antibody.

Knowledge of the role of angiogenesis in the maintenance and metastasis of tumors has led to a prognostic indicator for cancers such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies of the present invention will reduce or negate the recurrence of such tumors.

The present invention is contemplated for use in the treatment of any patient that presents with a solid tumor. In light of the specific properties of the VEGFR2-blocking, human anti-VEGF antibody compositions, the therapeutics of the present invention will have reduced side effects. Particular advantages will result in the maintenance or enhancement of host immune responses against the tumor, and in the lack of adverse effects on bone tissue. The invention will thus be the anti-angiogenic therapy of choice for the treatment of pediatric cancers and patients having, or at risk for developing, osteoporosis and other bone deficiencies.

Although all malignancies and solid tumors may be treated by the invention, the unconjugated VEGFR2-blocking, human anti-VEGF antibodies of this invention are particularly contemplated for use in treating patients with more angiogenic tumors, or patients at risk for metastasis.

The present invention is also intended as a preventative or prophylactic treatment. These aspects of the invention include the ability of the invention to treat patients presenting with a primary tumor who may have metastatic tumors, or tumor cells in the earlier stages of metastatic tumor seeding. As an anti-angiogenic strategy, the present invention may also be used to prevent tumor development in subjects at moderate or high risk for developing a tumor, as based upon prognostic tests and/or close relatives suffering from a hereditary cancer.

The conjugated or immunotoxin forms of the VEGFR2-blocking, human anti-VEGF antibodies of the invention are particularly contemplated for use in destroying or de-bulking solid tumors. These aspects of the invention may be used in conjunction with the unconjugated anti-angiogenic antibodies of the invention, or with other anti-angiogenic approaches.

It will be readily appreciated by those of skill in the art that the immunoconjugate and prodrug forms of the present treatment methods have the distinct advantage of providing a single therapeutic agent with two properties: the inherent anti-angiogenic property of the antibody and the therapeutic property of the attached agent (e.g., cytotoxic, coagulative, apoptopic, etc). The conjugated and prodrug treatment forms of the present antibodies thus have an incredibly wide utility throughout the field of cancer treatment.

The guidance provided herein regarding the more suitable patients for use in connection with the different aspects of the present invention is intended as teaching that certain patient's profiles may assist with the selection of patients for treatment by the present invention. The pre-selection of certain patients, or categories of patients, does not in any way negate the usefulness of the present invention in connection with the treatment of all patients having a vascularized tumor, or other angiogenic disease as described above. A further consideration is the fact that the assault on the tumor provided by the invention may predispose the tumor to further therapeutic treatment, such that the subsequent treatment results in an overall synergistic effect or even leads to total remission or cure.

It is not believed that any particular type of tumor should be excluded from treatment using the present invention. However, the type of tumor cells may be relevant to the use of the invention in combination with other therapeutic agents, particularly chemotherapeutics and anti-tumor cell immunotoxins. Both the unconjugated and conjugated aspects of the present therapies will include an anti-angiogenic effect that will inhibit tumor vasculature proliferation. The conjugated and prodrug treatment aspects will further destroy or occlude the tumor vasculature. As the vasculature is substantially or entirely the same in all solid tumors, the present methodology will be understood to be widely or entirely applicable to the treatment of all solid tumors, irrespective of the particular phenotype or genotype of the tumor cells themselves.

Therapeutically effective doses of VEGFR2-blocking, human anti-VEGF antibodies or immunoconjugate constructs are readily determinable using data from an animal model, e.g., as shown in the studies detailed herein. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of therapeutic agents that give beneficial anti-tumor effects with minimal toxicity.

In using unconjugated VEGFR2-blocking, human anti-VEGF antibodies in anti-angiogenic therapies, one can also draw on other published data in order to assist in the formulation of doses for clinical treatment. For instance, although the antibodies of the present invention have distinct advantages over those in the art, the information in the literature concerning treatment with other anti-VEGF antibodies can still be used in combination with the data and teaching in the present application to design and/or optimize treatment protocols and doses.

For example, Borgstrom et al. (1999), specifically incorporated herein by reference, described the importance of VEGF in breast cancer angiogenesis in vivo using MAb A4.6.1. The humanized form of the A4.6.1 antibody (Avastin, bevacizumab) has been approved for clinical use (Hurwitz et al., 2004). As the human antibodies of this invention exhibited equivalent or even improved anti-tumor responses in comparative studies with A4.6.1/Avastin, these antibodies will also have significant utility in the treatment of cancer in humans, including breast cancer. The inventors further realized, as will be appreciated by those of ordinary skill in the art, that patients with breast cancer are typically women in the middle or later age groups, where concerns regarding osteoporosis are also apparent. The VEGFR2-blocking, human anti-VEGF antibodies of the present invention will thus have the added advantage of not causing an adverse effect on bone metabolism, and so will be preferred for use in breast cancer patients having or at risk for developing osteoporosis.

The same type of benefits make VEGFR2-blocking, human anti-VEGF antibody therapeutics the preferred drugs for the treatment of pediatric cancers. In children with cancer, the need to continue healthy and substantial bone growth is evident. As VEGFR2-blocking, human anti-VEGF antibodies will not substantially impair the activities of osteoclasts and chondroclasts; which are important in developing bone, these antibodies will have important advantages over other antibodies, such as Avastin.

Borgstrom et al. (1999), specifically incorporated herein by reference, also reported that MAb A4.6.1 resulted in significant tumors regression when used in combination with doxorubicin. This further supports the combined use of VEGFR2-blocking, human anti-VEGF antibodies and conventional cytotoxic or chemotherapeutic agents to achieve significant clinical results in treating a variety of cancers. Both unconjugated doxorubicin and doxorubicin prodrug combinations are contemplated.

Ferrara and colleagues also reported on the efficacy and concentration-response of a murine anti-VEGF monoclonal antibody in tumor-bearing mice and the extrapolation to human treatment (Mordenti et al., 1999, specifically incorporated herein by reference). The studies were designed to evaluate the concentration-response relationship of the murine anti-VEGF monoclonal antibody so that an efficacious plasma concentration of the recombinant humanized form of the antibody could be estimated in cancer patients. Mordenti et al. (1999) concluded that satisfactory tumor suppression in nude mice was achieved using doses of the murine antibody that could be readily applied to the human system in order to define clinical dosing regimens effective to maintain a therapeutic antibody for human use in the required efficacious range. Accordingly, the data from the present art-accepted mouse models can also be translated into appropriate human doses using the type of analyses reported in Mordenti et al. (1999), in addition to the techniques known to the skilled artisan as described herein.

Results from preclinical safety evaluations of a recombinant, humanized form of Genentech's anti-VEGF antibody in monkeys (Ryan et al., 1999, specifically incorporated herein by reference) serve to exemplify the drawbacks with that particular candidate therapeutic. Although the antibody has pharmacological activity in this animal, the monkeys in these studies exhibited physeal dysplasia characterized by a dose-related increase in hypertrophied chondrocytes, subchondral bony plate formation, and inhibition of vascular invasion of the growth plate. No such drawbacks will be evident in the use of the VEGFR2-blocking, human anti-VEGF antibodies, which do not inhibit VEGF binding and signaling in chondroclasts and chondrocytes, which is mediated by VEGFR1.

Data from a further study on the preclinical pharmacokinetics, interspecies scaling and tissue distribution of Genentech's humanized monoclonal anti-VEGF antibody was reported by Lin et al. (1999, specifically incorporated herein by reference). These studies were conducted in mice, rats, monkeys and rabbits, the latter using $^{125}$I-labelled antibody. The pharmacokinetic data from mice, rats and monkeys were used to predict the pharmacokinetics of the humanized counterpart antibody using allometric scaling in humans. Accordingly, appropriate dosage information can be developed for the treatment of human pathological conditions, such as rheumatoid arthritis, ocular neovascularization and cancer.

The humanized version of the anti-VEGF antibody A4.6.1 (Avastin, bevacizumab) is now approved for clinical use (Hurwitz et al., 2004, incorporated herein by reference). Therefore, such clinical data can also be considered as a reference source when designing therapeutic doses for the present VEGFR2-blocking, human anti-VEGF antibody treatment. The present invention shows the new human antibodies to be as effective as A4.6.1/Avastin in studies in tumor-bearing mice, although the specificity for inhibiting only VEGFR2-mediated actions of VEGF is an advantage. WO 98/45331 is also incorporated herein by reference to further exemplify the doses of humanized anti-VEGF antibodies that may be used in treatment.

In terms of using conjugated VEGFR2-blocking, human anti-VEGF antibodies in tumor therapy, one may refer to the scientific and patent literature on the success of delivering a wide range of therapeutics to tumor vasculature to achieve a beneficial effect. By way of example, each of U.S. Pat. Nos. 5,855,866; 5,877,289; 5,965,132; 6,051,230; 6,004,555; 5,776,427; 6,004,554; 6,036,955; and 6,093,399 are incorporated herein by reference for the purpose of further describing the use of such therapeutic agent-targeting agent constructs. In the present case, the therapeutic agent-targeting agent constructs include targeting agent portions that exert an anti-angiogenic effect, which will magnify or otherwise enhance the anti-tumor activity of the attached therapeutic agent.

As is known in the art, there are realistic objectives that may be used as a guideline in connection with pre-clinical testing before proceeding to clinical treatment. However, in light of the progress of other anti-VEGF antibodies in the clinic, the demonstrated anti-tumor effects in accepted models shown herein, and the enhanced safety of the present strategies, the current invention provides a therapeutic with a fast track to clinical treatment. Thus, pre-clinical testing may be employed to select the most advantageous antibodies, doses or combinations.

Any VEGFR2-blocking, human anti-VEGF antibody or immunoconjugate dose, or combined medicament, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the VEGFR2-blocking, human anti-VEGF antibody or immunoconjugate dose, or combined therapy, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of VEGFR2-blocking, human anti-VEGF antibody or immunoconjugate constructs, or combined therapeutics, for the treatment of vascularized tumors, one may readily extrapolate from the animal studies described herein and the knowledge in the literature in order to arrive at appropriate doses for clinical administration. To achieve a conversion from animal to human doses, one would account for the mass of the agents administered per unit mass of the experimental animal and, preferably, account for the differences in the body surface area ($m^2$) between the experimental animal and the human patient. All such calculations are well known and routine to those of ordinary skill in the art.

For example, taking the successful doses in the mouse studies, and by applying standard calculations based upon mass and surface area, effective doses for use in human patients would be between about 1 $mg/m^2$ and about 1000 $mg/m^2$, preferably, between about 50 $mg/m^2$ and 500 $mg/m^2$ 10, and most preferably, between about 10 $mg/m^2$ and about 100 $mg/m^2$. These doses are appropriate for VEGFR2-blocking, human anti-VEGF naked antibodies and VEGFR2-blocking, human anti-VEGF immunoconjugates, although the doses are preferred for use in connection with naked or unconjugated antibodies for use as anti-angiogenics.

Accordingly, using this information, the inventors contemplate that useful low doses of VEGFR2-blocking, human anti-VEGF antibodies or immunoconjugates for human administration will be about 1, 2, 3, 4, 5, 6, 7, 8, 9, 10, 12, 15, 20, 25, 30, 35, 40, 45 or about 50 $mg/m^2$; and that useful high doses of such antibodies or immunoconjugates for human administration will be about 600, 650, 700, 750, 800, 850, 900, 925, 950, 975 or about 1000 $mg/m^2$. Useful intermediate doses of VEGFR2-blocking, human anti-VEGF antibodies or immunoconjugates for human administration are contemplated to be any dose between the low and high ranges, such as about 55, 60, 70, 80, 90, 100, 125, 150, 175, 200, 250, 300, 350, 400, 450, 500, 525, 550 or about 575 $mg/m^2$ or so.

Any particular range using any of the foregoing recited exemplary doses or any value intermediate between the particular stated ranges is contemplated. Where VEGFR2-blocking, human anti-VEGF immunoconjugates are used, it will also be understood that coagulant immunoconjugates can generally be used at higher doses than toxin immunoconjugates.

In general, dosage ranges of between about 10-100 $mg/m^2$, about 10-90 $mg/m^2$, about 10-80 $mg/m^2$, about 20-100 $mg/m^2$, about 20-90 $mg/m^2$, about 20-80 $mg/m^2$, about 30-100 $mg/m^2$, about 30-90 $mg/m^2$, about 30-80 $mg/m^2$, about 15-100 $mg/m^2$, about 25-100 $mg/m^2$, about 35-100 $mg/m^2$, about 15-90 $mg/m^2$, about 25-90 $mg/m^2$, about 35-90 $mg/m^2$, or so of VEGFR2-blocking, human anti-VEGF antibodies or immunoconjugates will be preferred. Notwithstanding these stated ranges, it will be understood that, given the parameters and detailed guidance presented herein, further variations in the active or optimal ranges will be encompassed within the present invention.

Therefore, it will be understood that lower doses may be more appropriate in combination with other agents, and that high doses can still be tolerated, particularly given the enhanced safety of the VEGFR2-blocking, human anti-VEGF antibodies and immunoconjugates. The use of human antibodies (and optionally, human coagulant or anti-angiogenic proteins) renders the present invention even safer for clinical use, further reducing the chances of significant toxicity or side effects in healthy tissues.

The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. One treatment protocol is to administer between about 1 $mg/m^2$ and about 1000 $mg/m^2$, preferably, between about 50 $mg/m^2$ and 500 $mg/m^2$ 10, and most preferably, between about 10 $mg/m^2$ and about 100 $mg/m^2$ of the VEGFR2-blocking, human anti-VEGF antibody or immunoconjugate, or therapeutic cocktail containing such, about 1 to 3 times a week, preferably by intravenous or intramuscular administration, and most preferably, intravenously.

In administering the particular doses, one would preferably provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

Naturally, before wide-spread use, clinical trials will be conducted. The various elements of conducting a clinical trial, including patient treatment and monitoring, will be known to those of skill in the art in light of the present disclosure. The following information is being presented as a general guideline for use in establishing such trials.

Patients chosen for the first VEGFR2-blocking, human anti-VEGF antibody treatment studies will have failed to respond to at least one course of conventional therapy, and will have objectively measurable disease as determined by physical examination, laboratory techniques, and/or radiographic procedures. Any chemotherapy should be stopped at least 2 weeks before entry into the study. Where murine monoclonal antibodies or antibody portions are employed, the patients should have no history of allergy to mouse immunoglobulin.

Certain advantages will be found in the use of an indwelling central venous catheter with a triple lumen port. The VEGFR2-blocking, human anti-VEGF antibody should be filtered, for example, using a 0.22µ filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87% to 99%, and adjustments for protein loss can then be accounted for.

The VEGFR2-blocking, human anti-VEGF antibodies or conjugates may be administered over a period of approximately 4-24 hours, with each patient receiving 2-4 infusions at 2-7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses of VEGFR2-blocking, human anti-VEGF antibody should be administered to groups of patients until approximately 60% of patients showed unacceptable Grade III or IV toxicity in any category. Doses that are ⅔ of this value are defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the administered therapeutic, and antibodies against any portions thereof. Immunological analyses of sera, using any standard assay such as, for example, an ELISA or RIA, will allow the pharmacokinetics and clearance of the VEGFR2-blocking, human anti-VEGF antibody to be evaluated.

To evaluate the anti-tumor responses, the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites. In light of results from clinical trials, such as those described above, an even more precise treatment regimen may be formulated. Even so, some variation in dosage may later be necessary depending on the condition of the subject being treated. The physician responsible for administration will, in light of the present disclosure, be able to determine the appropriate dose for the individual subject. Such optimization and adjustment is routinely carried out in the art and by no means reflects an undue amount of experimentation.

G. Combination Therapies

Whether used for treating angiogenic diseases, such as arthritis, psoriasis, atherosclerosis, diabetic retinopathy, age-related macular degeneration, Grave's disease, vascular restenosis, hemangioma and neovascular glaucoma (or other diseases described above), or solid tumors, the present invention can be combined with other therapies.

The VEGFR2-blocking, human anti-VEGF antibody treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the VEGFR2-blocking, human anti-VEGF antibody treatment, its combination with the present invention is contemplated.

In connection solid tumor treatment, the present invention may be used in combination with classical approaches, such as surgery, radiotherapy, chemotherapy, and the like. The invention therefore provides combined therapies in which VEGFR2-blocking, human anti-VEGF antibody constructs are used simultaneously with, before, or after surgery or radiation treatment; or are administered to patients with, before, or after conventional chemotherapeutic, radiotherapeutic or anti-angiogenic agents, or targeted immunotoxins or coaguligands.

The combined use of the invention with radiotherapy, radiotherapeutics, anti-angiogenic agents, apoptosis-inducing agents and anti-tubulin drugs is particularly preferred. Many examples of such agents have been described above in conjunction with the immunoconjugates of the present invention. Any of the agents initially described for use as one part of a therapeutic conjugate may also be used separately, but still in operable combination with the present invention.

When one or more agents are used in combination with the VEGFR2-blocking, human anti-VEGF antibody therapy, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

To practice combined anti-angiogenic therapy, e.g., to treat an ocular or other angiogenic disease or disorder, one would simply administer to an animal a VEGFR2-blocking, human anti-VEGF antibody in combination with another therapeutic agent, including another (second) anti-angiogenic agent, in a manner effective to result in their combined therapeutic or anti-angiogenic actions within the animal. The agents would therefore be provided in amounts effective and for periods of time effective to result in their combined presence within the disease site and their combined actions in the disease environment, such as the eye.

To achieve this goal, the VEGFR2-blocking, human anti-VEGF antibody and other therapeutic or anti-angiogenic agent(s) may be administered to the animal simultaneously, either in a single composition, or as two distinct compositions using different administration routes. Alternatively, the VEGFR2-blocking, human anti-VEGF antibody treatment may precede, or follow, the other therapeutic or anti-angiogenic treatment by, e.g., intervals ranging from minutes to weeks and months. One would perform such treatment so that the VEGFR2-blocking, human anti-VEGF antibody and other therapeutic or anti-angiogenic agent(s) exert an advantageously combined therapeutic effect.

As to tumor therapy, to practice combined anti-tumor therapy, one would likewise administer to an animal a VEGFR2-blocking, human anti-VEGF antibody in combination with another anti-cancer agent in a manner effective to result in their combined anti-tumor actions within the animal. The agents would again be provided in amounts effective and for periods of time effective to result in their combined presence within the tumor vasculature and their combined actions in the tumor environment.

The VEGFR2-blocking, human anti-VEGF antibody and anti-cancer agents may be administered to the animal simultaneously, either in a single composition, or as two distinct compositions using different administration routes. Alternatively, the VEGFR2-blocking, human anti-VEGF antibody may be given before, or after, the anti-cancer agent, e.g., from minutes to weeks and months apart. The anti-cancer agent and VEGFR2-blocking, human anti-VEGF antibody would exert an advantageously combined effect on the tumor. Many anti-cancer agents would be given prior to VEGFR2-blocking, human anti-VEGF antibody anti-angiogenic therapy. However, many other anti-cancer agents would be administered simultaneously with the VEGFR2-blocking, human anti-VEGF antibody or subsequently thereto, particularly when used after VEGFR2-blocking, human anti-VEGF immunoconjugates.

The general use of combinations of substances in cancer treatment is well known. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

In some situations, it may even be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as surgery or chemotherapy, and another treatment was intended to prevent micrometastasis or tumor re-growth, such as anti-angiogenic based therapy. Anti-angiogenics should be administered at a careful time after surgery to allow effective wound healing.

It also is envisioned that more than one administration of either the VEGFR2-blocking, human anti-VEGF antibody or the anti-cancer agent will be utilized. The agents may be administered interchangeably, on alternate days or weeks; or a sequence of VEGFR2-blocking, human anti-VEGF antibody treatment may be given, followed by a sequence of anti-cancer agent therapy. In any event, to achieve tumor regression using a combined therapy, all that is required is to deliver both agents in a combined amount effective to exert an anti-tumor effect, irrespective of the times for administration.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means, and preferably, VEGFR2-blocking, human anti-VEGF antibodies.

Cytokine therapy also has proven to be an effective partner for combined therapeutic regimens. Various cytokines may be employed in such combined approaches. Examples of cytokines include IL-1αIL-1β, IL-2, L-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LiF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

G1. Chemotherapeutics

In certain embodiments, the VEGFR2-blocking, human anti-VEGF antibodies of the present invention may be administered in combination with a chemotherapeutic agent. A variety of chemotherapeutic agents may be used in the combined treatment methods disclosed herein. Chemotherapeutic agents contemplated as exemplary include, e.g., adriamycin, dactinomycin, mitomycin, caminomycin, daunomycin, doxorubicin, tamoxifen, taxol, taxotere, vincristine, vinblastine, vinorelbine, etoposide (VP-16), 5-fluorouracil (5FU), cytosine arabinoside, cyclophohphamide, thiotepa, methotrexate, camptothecin, actinomycin-D, mitomycin C, cisplatin (CDDP), aminopterin, combretastatin(s) and derivatives and prodrugs thereof.

As will be understood by those of ordinary skill in the art, the appropriate doses of chemotherapeutic agents will be generally around those already employed in clinical therapies wherein the chemotherapeutics are administered alone or in combination with other chemotherapeutics. By way of example only, agents such as cisplatin, and other DNA alkylating may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25-75 mg/m$^2$ at 21 day intervals for adriamycin, to 35-50 mg/m$^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents for combined therapy are listed in Table C. Each of the agents listed are exemplary and not limiting. The skilled artisan is directed to "Remington's Pharmaceutical Sciences" 15th Edition, chapter 33, in particular pages 624-652. Variation in dosage will likely occur depending on the condition being treated. The physician administering treatment will be able to determine the appropriate dose for the individual subject.

TABLE C

CHEMOTHERAPEUTIC AGENTS
USEFUL IN NEOPLASTIC DISEASE

| CLASS | TYPE OF AGENT | EXAMPLES | DISEASE |
|---|---|---|---|
| Alkylating Agents | Nitrogen Mustards | Mechlorethamine (chlormethine, mustine, nitrogen mustard, HN$_2$) Mustargen ® | Hodgkin's disease, non-Hodgkin's lymphomas |
| | | Cyclophosphamide (cytophosphane) Cytoxan ®, Neosar ®, Revimmune ® | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Ifosfamide Mitoxana ®, Ifex ® | Non-Hodgkin's lymphomas, soft tissue sarcoma, osteogenic sarcoma, testicular, breast, lung, cervical, ovarian, bone |
| | | Melphalan (L-sarcolysin) Alkeran ® | Multiple myeloma, breast, ovary, melanoma |
| | | Chlorambucil Leukeran ® | Chronic lymphocytic leukemia, primary macroglobulinemia, Hodgkin's disease, non- |

TABLE C-continued

CHEMOTHERAPEUTIC AGENTS USEFUL IN NEOPLASTIC DISEASE

| CLASS | TYPE OF AGENT | EXAMPLES | DISEASE |
|---|---|---|---|
| | Ethylenimenes and Methylmelamines | Hexamethylmelamine (Altretamine, HMM) Hexalen ® | Hodgkin's lymphomas, ovarian Ovary |
| | Alkyl Sulfonates | ThioTEPA Busulfan Mylran ®, Busulfex ® | Bladder, breast, ovary Chronic granulocytic leukemia |
| | Nitrosoureas | Carmustine BiCNU ® | Hodgkin's disease, non-Hodgkin's lymphomas, primary brain tumors, multiple myeloma, malignant melanoma, glioma, glioblastoma multiforme, medulloblastoma, astrocytoma |
| | | Lomustine (CCNU) CeeNU ® | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) Zanosar ® | Malignant pancreatic insulinoma, malignant carcinoid |
| | Triazines | Dacarbazine (dimethyltriazenoimidazolecarboxamide, imidazole carboxamide) DTIC ®, DTIC-Dome ® | Malignant melanoma, Hodgkin's disease, soft-tissue sarcomas, malignant pancreatic insulinoma |
| | | Temozolomide Temodar ®, Temodal ® | Astrocytoma |
| | Methyl Hydrazine Derivative | Procarbazine (N-methylhydrazine, MIH) Matulane ®, Natulan ®, Indicarb ® | Hodgkin's disease, glioblastoma multiforme |
| Antimetabolites | Folic Acid Analogs Folate antimetabolites | Methotrexate (amethopterin) | Acute lymphocytic leukemia, choriocarcinoma, mycosis fungoides, breast, head and neck, lung, osteogenic sarcoma, glioblastoma |
| | | Aminopterin Pemetrexed Alimta ® | Leukemia pleural mesothelioma, non-small cell lung cancer, esophageal |
| | | Raltitrexed Tomudex ® | Colorectal |
| | Pyrimidine Analogs | Fluorouracil (5-fluorouracil, 5-FU, fluouracil, fluorodeoxyuridine) Efudex ®, Carac ®, Fluoroplex ® | Breast, colon, stomach, pancreas, ovary, head and neck, urinary bladder, premalignant skin lesions (topical) |
| | | Floxuridine (prodrug) FUDR ® Cytarabine (cytosine arabinoside, ara C) Cytosar-U ®, Tarabine PFS ®, Depocyt ® Capecitabine (prodrug) Xeloda ® | Acute granulocytic and acute lymphocytic leukemias, non-Hodgkin's lymphoma |
| | Purine Analogs and Related Inhibitors | Gemcitabine Gemzar ® | Pancreatic, bladder, breast, oesophageal and non-small cell lung cancers, lymphomas |
| | | Thioguanine (tioguanine, 6-thioguanine; TG) | Acute granulocytic, acute lymphocytic, chronic granulocytic and chronic myeloid leukemias |
| | | Pentostatin (2-deoxycoformycin) | Hairy cell leukemia, mycosis fungoides, chronic lymphocytic leukemia |
| | | Mercaptopurine (6-mercaptopurine, 6-MP) Purinethol ® | Acute lymphocytic, acute granulocytic and chronic granulocytic leukemias, non-Hodgkin's lymphoma |
| | | Cladribine (2CDA) Leustatin ® | Hairy cell leukemia, Bcell leukemias, lymphomas |
| | | Clofarabine Clolar ®, Evoltra ® | Acute lymphoblastic leukaemia, acute myeloid leukaemia, juvenile myelomonocytic leukaemia |
| | | Fludarabine (fludarabine phosphate) Fludara ® | Hematological malignancies |
| | Vinca Alkaloids | Vinblastine (VLB) | Hodgkin's disease, non-Hodgkin's lymphomas, breast, testis, non-small cell lung cancer |
| | | Vincristine Oncovin ® | Acute lymphocytic leukemia, neuroblastoma, Wilms' tumor (nephroblastoma), rhabdomyosarcoma, Hodgkin's disease, non-Hodgkin's lymphomas, small-cell lung |
| | | Vindescine Eldisine ® | Leukaemia, lymphoma, melanoma, breast, lung |
| | | Vinorelbine Navelbine ® | Breast, non-small cell lung |
| | Podophyllotoxins Epipodophyllotoxins | Etoposide (etoposide phosphate) Eposin ®, Etopophos ®, Vepesid ®, VP-16 ® | Testis, small-cell lung and other lung, breast, Hodgkin's disease, non-Hodgkin's lymphomas, acute granulocytic leukemia, Kaposi's sarcoma, glioblastoma multiforme |
| | | Teniposide Vumon ®, VM-26 ® | Acute lymphocytic leukemia |
| Natural Products | Anthracycline Antibiotics (Anthracyclines) | Daunorubicin (daunomycin, rubidomycin, Cerubidine ® | Acute granulocytic and acute lymphocytic leukemias, neuroblastoma |
| | | Doxorubicin (hydroxydaunorubicin, adriamycin, Rubex ®, Doxil ® | Soft-tissue, osteogenic and other sarcomas; Hodgkin's disease, non-Hodgkin's lymphomas, acute leukemias; breast, genitourinary, thyroid, lung, stomach, ovarian, thyroid, bladder, neuroblastoma, multiple myeloma |
| | | Epirubicin Ellence ®, | Breast, ovarian, gastric, lung; lymphomas |

TABLE C-continued

CHEMOTHERAPEUTIC AGENTS USEFUL IN NEOPLASTIC DISEASE

| CLASS | TYPE OF AGENT | EXAMPLES | DISEASE |
|---|---|---|---|
| | | Pharmorubicin ®, Ebewe ® Idarubicin (4-demethoxy-daunorubicin) Zavedos ® Idamycin ® | Acute myeloid leukemia |
| | | Valrubicin (N-trifluoro-acetyl-adriamycin-14-valerate) Valstar ® | Bladder |
| | Anthracenedione | Mitoxantrone | Acute granulocytic leukemia, breast, non-Hodgkin's lymphoma |
| | | Pixantrone | Breast, non-Hodgkin's lymphoma |
| | Polypeptide and peptide Antibiotics | Bleomycin Blenoxane ® | Testis, head and neck, skin, esophagus, lung and genitourinary tract; Hodgkin's disease, non-Hodgkin's lymphomas, squamous cell carcinomas |
| | | Actinomycin-D Dactinomycin ® | Choriocarcinoma, Wilms' tumor, rhabdomyosarcoma, testis, Kaposi's sarcoma |
| | | Plicamycin (mithramycin) Mithracin ® | Testis, malignant hypercalcemia |
| | | Mitomycin (mitomycin C) | Stomach, cervix, colon, breast, pancreas, bladder, head and neck, esophageal |
| | Enzymes | L-Asparaginase Elspar ® | Acute lymphocytic leukemia, mast cell tumors |
| | Biological Response Modifiers | Interferon alpha (IFNα) Pegylated interferons Multiferon ®, Roferon ®, Pegasys ®, IntronA ®, PegIntron ® | Hairy cell leukemia, Kaposi's sarcoma, melanoma, carcinoid, renal cell, ovary, bladder, non-Hodgkin's lymphomas, mycosis fungoides, multiple myeloma, chronic granulocytic leukemia |
| Cytoskeletal Disruptors | Taxanes | Taxol (paclitaxel) Abraxane ® | Breast, ovarian, lung, head and neck, Kaposi's sarcoma |
| | | Docetaxel Taxotere ® | Breast, ovarian, lung, colorectal, ovarian, gastric, renal, prostate, liver, head and neck, melanoma |
| | Combretastatins | Combretastatin A-4 CA-4-P | Thyroid |
| | Platinum Coordination Complexes | Cisplatin (cis-DDP, cisplatinum) | Testis, ovary, bladder, head and neck, lung, thyroid, cervix, endometrium, neuroblastoma, osteogenic sarcoma, lymphoma |
| | | Carboplatin Paraplatin ® | Ovarian, lung, head and neck |
| | | Oxaliplatin Eloxatin ®, Oxaliplatin Medac ® | Colorectal |
| | Camptothecins | Topotecan Hycamtin ® | Ovarian, lung |
| | | Irinotecan (CPT-11) Camptosar | Colon |
| Other Agents | Substituted Urea | Hydroxyurea (hydroxycarbamide) | Chronic granulocytic leukemia, polycythemia vera, essential thrombocytosis; malignant melanoma |
| | Adrenocortical | Mitotane (o,p'-DDD) Lysodren ® | Adrenal cortex |
| | Steroid Suppressant | Aminoglutethimide Cytadren ® | Breast |
| | Tyrosine Kinase Inhibitors | Axitinib | Breast, renal cell carcinoma, pancreas |
| | | Dasatinib (BMS-354825) Sprycel ® | Chronic myelogenous leukemia, acute lymphoblastic leukemia, metastatic melanoma |
| | | Erlotinib (OSI-774) Tarceva ® | Non-small cell lung cancer, pancreatic |
| | | Gefitinib (ZD1839) Iressa ® | Non-small cell lung cancer |
| | | Imatinib (CGP57148B or STI-571) Gleevec ®, Glivec ® | Chronic myelogenous leukemia, gastrointestinal |
| | | Lapatinib (GW572016) Tykerb ®, Tyverb ® | Breast |
| | | Sorafenib Nexavar ® | Renal cell carcinoma, hepatocellular carcinoma |
| | | Sunitinib (SU11248) Sutent ® | Renal cell carcinoma, gastrointestinal, non-small cell lung cancer, breast |
| | Receptor tyrosine kinases | Cetuximab (anti-EGFR) Erbitux ® | Colorectal, head and neck |
| | | Panitumumab (anti-EGFR) Vectibix ® | Colorectal |
| | | Trastuzumab (anti-HER2/neu, erbB2 receptor) Herceptin ® | Breast, HER2/neu cancers |
| | CD20 | Rituximab Rituxan ®, MabThera ®, Reditux ® | Non-Hodgkin's lymphoma, B-cell leukemias |
| | | Tositumomab (anti-CD20-$^{131}$I) Bexxar ® | Follicular lymphoma, non-Hodgkin's lymphoma |
| | | Alemtuzumab (anti-CD52) Campath ® | Chronic lymphocytic leukemia (CLL), T-cell lymphoma |
| | | Bevacizumab (anti-VEGF) Avastin ® | Colon, non-small cell lung cancer, breast, renal cell carcinoma, glioblastoma multiforme, hormone-refractory prostate cancer, pancreas |
| | | Gemtuzumab (anti-CD33-calicheamicin) Mylotarg ® | Acute myelogenous leukemia |
| Hormones and Antagonists | Adrenocorticosteroids | Prednisone | Acute and chronic lymphocytic leukemias, non-Hodgkin's lymphomas, Hodgkin's disease, breast, multiple myeloma |

TABLE C-continued

CHEMOTHERAPEUTIC AGENTS
USEFUL IN NEOPLASTIC DISEASE

| CLASS | TYPE OF AGENT | EXAMPLES | DISEASE |
|---|---|---|---|
| | Progestins | Hydroxyprogesterone caproate<br>Medroxyprogesterone acetate<br>Megestrol acetate<br>Megace ® | Endometrium, breast |
| | Estrogens | Diethylstilbestrol<br>Ethinyl estradiol<br>Estramustine ®<br>(mechlorethamine derivative) | Breast, prostate |
| | Antiestrogen | Tamoxifen<br>Nolvadex ®,<br>Istubal ®,<br>Valodex ® | Breast |
| | Androgens | Testosterone propionate<br>Fluoxymesterone<br>(Halotestin) | Breast |
| | Antiandrogen | Flutamide<br>(Flutamin)<br>Eulexin ® | Prostate |
| | Gonadotropin-releasing hormone analog | Leuprolide<br>Lupron ®, Lupron Depot ®,<br>Viadur ®,<br>Eligard ®,<br>Prostap ® | Prostate, breast |

G2. Anti-Angiogenics

Under normal physiological conditions, humans or animals undergo angiogenesis only in very specific restricted situations. For example, angiogenesis is normally observed in wound healing, fetal and embryonic development and formation of the corpus luteum, endometrium and placenta. Uncontrolled (persistent and/or unregulated) angiogenesis is related to various disease states, and occurs during tumor metastasis.

Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

The present VEGFR2-blocking, human anti-VEGF antibody may be used in combination with any one or more other anti-angiogenic therapies. Combinations with other agents that inhibit VEGF are included, such as other neutralizing antibodies (Kim et al., 1992; Presta et al., 1997; Sioussat et al., 1993; Kondo et al., 1993; Asano et al., 1995; Hurwitz et al., 2004), soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors (Saleh et al., 1996; Cheng et al., 1996; each incorporated herein by reference). Variants of VEGF with antagonistic properties may also be employed, as described in WO 98/16551, specifically incorporated herein by reference.

The anti-angiogenic therapies may be based upon the provision of an anti-angiogenic agent or the inhibition of an angiogenic agent. Inhibition of angiogenic agents may be achieved by one or more of the methods described for inhibiting VEGF, including neutralizing antibodies, soluble receptor constructs, small molecule inhibitors, antisense, RNA aptamers and ribozymes may all be employed. For example, antibodies to angiogenin may be employed, as described in U.S. Pat. No. 5,520,914, specifically incorporated herein by reference. In that FGF is connected with angiogenesis, FGF inhibitors may also be used. Certain examples are the compounds having N-acetylglucosamine alternating in sequence with 2-O-sulfated uronic acid as their major repeating units, including glycosaminoglycans, such as archaran sulfate. Such compounds are described in U.S. Pat. No. 6,028,061, specifically incorporated herein by reference, and may be used in combination herewith.

Numerous tyrosine kinase inhibitors useful for the treatment of angiogenesis, as manifest in various diseases states, are now known. These include, for example, the 4-aminopyrrolo[2,3-d]pyrimidines of U.S. Pat. No. 5,639,757, specifically incorporated herein by reference, which may also be used in combination with the present invention. Further examples of organic molecules capable of modulating tyrosine kinase signal transduction via the VEGFR2 receptor are the quinazoline compounds and compositions of U.S. Pat. No. 5,792,771, which is specifically incorporated herein by reference for the purpose of describing further combinations for use with the present invention in the treatment of angiogenic diseases.

Compounds of other chemical classes have also been shown to inhibit angiogenesis and may be used in combination with the present invention. For example, steroids such as the angiostatic 4,9(11)-steroids and C21-oxygenated steroids, as described in U.S. Pat. No. 5,972,922, specifically incorporated herein by reference, may be employed in combined therapy. U.S. Pat. Nos. 5,712,291 and 5,593,990, each specifically incorporated herein by reference, describe thalidomide and related compounds, precursors, analogs, metabolites and hydrolysis products, which may also be used in combination with the present invention to inhibit angiogenesis. The compounds in U.S. Pat. Nos. 5,712,291 and 5,593,990 can be administered orally. Further exemplary anti-angiogenic agents that are useful in connection with combined therapy are listed in Table D. Each of the agents listed therein are exemplary and by no means limiting.

TABLE D

INHIBITORS AND NEGATIVE
REGULATORS OF ANGIOGENESIS

| Substances | References |
|---|---|
| Soluble VEGFR1 | Shibuya, 2006 |
| Soluble Neuropilin-1 (NRP-1) | Gagnon et al., 2000 |
| Angiostatin | O'Reilly et al., 1994 |
| Endostatin | O'Reilly et al., 1997 |
| Angiopoietin 2 | Maisonpierre et al., 1997 |
| Calreticulin | Pike et al., 1999 |
| Vasostatin | Pike et al., 1998 |
| Vasculostatin | Kaur et al., 2005 |
| Canstatin | Kamphaus et al., 2000 |
| Maspin | Zou et al., 1994 |
| 16 kDa prolactin fragment | Ferrara et al., 1991; Clapp et al., 1993; D'Angelo et al., 1995; Lee et al., 1998 |
| Laminin peptides | Kleinman et al., 1993; Yamamura et al., 1993; Iwamoto et al., 1996; Tryggvason, 1993 |

TABLE D-continued

INHIBITORS AND NEGATIVE REGULATORS OF ANGIOGENESIS

| Substances | References |
| --- | --- |
| Fibronectin peptides | Grant et al., 1998; Sheu et al., 1997 |
| Tissue metalloproteinase inhibitors (TIMP 1, 2, 3, 4) | Sang, 1998 |
| Plasminogen activator inhibitors (PAI-1, -2) | Soff et al., 1995 |
| Tumor necrosis factor α (high dose, in vitro) | Frater-Schroder et al., 1987 |
| TGF-β1 | RayChadhury and D'Amore, 1991; Tada et al., 1994 |
| Interferons (IFN-α, -β, γ) | Moore et al., 1998; Lingen et al., 1998 |
| ELR-CXC Chemokines: IL-12; IL-4; IL-18; SDF-1; MIG; Platelet factor 4 (PF4); IP-10; CXCL10 | Moore et al., 1998; Hiscox and Jiang, 1997; Coughlin et al., 1998; Tanaka et al., 1997 |
| Thrombospondin (TSP), TSP-1 and TSP-2 | Good et al., 1990; Frazier, 1991; Bornstein, 1992; Tolsma et al., 1993; Sheibani and Frazier, 1995; Volpert et al., 1998 |
| SPARC | Hasselaar and Sage, 1992; Lane et al., 1992; Jendraschak and Sage, 1996 |
| 2-Methoxyoestradiol | Fotsis et al., 1994 |
| Proliferin-related protein | Jackson et al., 1994 |
| Suramin | Gagliardi et al., 1992; Takano et al., 1994; Waltenberger et al., 1996; Gagliardi et al., 1998; Manetti et al., 1998 |
| Thalidomide | D'Amato et al., 1994; Kenyon et al., 1997 Wells, 1998 |
| Carboxyamidotriazole (CAI) | Hussain et al., 2003 |
| Cortisone | Thorpe et al., 1993 Folkman et al., 1983 Sakamoto et al., 1986 |
| Linomide | Vukanovic et al., 1993; Ziche et al., 1998; Nagler et al., 1998 |
| Fumagillin (AGM-1470; TNP-470) | Sipos et al., 1994; Yoshida et al., 1998 |
| Tamoxifen | Gagliardi and Collins, 1993; Lindner and Borden, 1997; Haran et al., 1994 |
| Korean mistletoe extract (Viscum album coloratum) | Yoon et al., 1995 |
| Retinoids | Oikawa et al., 1989; Lingen et al., 1996; Majewski et al., 1996 |
| CM101 | Hellerqvist et al., 1993; Quinn et al., 1995; Wamil et al., 1997; DeVore et al., 1997 |
| Dexamethasone | Hori et al., 1996; Wolff et al., 1997 |
| Leukemia inhibitory factor (LIF) | Pepper et al., 1995 |

Certain preferred components for use in inhibiting angiogenesis are angiostatin, endostatin, vasculostatin, canstatin and maspin. Such agents are described above in conjunction with the immunoconjugates of the present invention, but may be used in combined, but unconjugated form.

Certain anti-angiogenic therapies have already been shown to cause tumor regressions, including the bacterial polysaccharide CM101 and the antibody LM609. CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is a uniquely antipathoangiogenic agent that downregulates the expression VEGF and its receptors. CM101 is currently in clinical trials as an anti-cancer drug, and can be used in combination herewith.

Thrombospondin (TSP-1) and platelet factor 4 (PF4) may also be used in combination with the present invention. These are both angiogenesis inhibitors that associate with heparin and are found in platelet α-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be combined with the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be successfully treated with IFNα.

Tissue inhibitors of metalloproteinases (TIMPs) are a family of naturally occurring inhibitors of matrix metalloproteases (MMPs) that can also inhibit angiogenesis and can be used in combined treatment protocols. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin αvβ3 presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used in combination with the present invention. These include AGM-1470/TNP-470, thalidomide, and carboxyamidotriazole (CAI). Fumagillin was found to be a potent inhibitor of angiogenesis in 1990, and since then the synthetic analogues of fumagillin, AGM-1470 and TNP-470 have been developed. Both of these drugs inhibit endothelial cell proliferation in vitro and angiogenesis in vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiological attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors, including, but not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $\alpha_v\beta_3$ integrin may also be used to inhibit angiogenesis in combination with the present invention. As disclosed in U.S. Pat. No. 5,766,591 (incorporated herein by reference), RGD-containing polypeptides and salts thereof, including cyclic polypeptides, are suitable examples of $\alpha_v\beta_3$ integrin antagonists.

The antibody LM609 against the $\alpha_v\beta_3$ integrin also induces tumors regressions. Integrin $\alpha_v\beta_3$ antagonists, such as LM609, induce apoptosis of angiogenic endothelial cells leaving the quiescent blood vessels unaffected. LM609 or other $\alpha_v\beta_3$ antagonists may also work by inhibiting the interaction of $\alpha_v\beta_3$ and MMP-2, a proteolytic enzyme thought to play an important role in migration of endothelial cells and fibroblasts. U.S. Pat. No. 5,753,230 is specifically incorporated herein by reference to describe antibodies against $\alpha_v\beta_3$ (vitronectin $\alpha_v\beta_3$) for combined with the present invention for inhibiting angiogenesis.

Apoptosis of the angiogenic endothelium in this case may have a cascade effect on the rest of the vascular network. Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Other methods of therapeutic intervention based upon altering signaling through the Tie2 receptor can also be used in combination with the present invention, such as using a soluble Tie2 receptor capable of blocking Tie2 activation (Lin et al., 1998). Delivery of such a construct using recombinant adenoviral gene therapy has been shown to be effective in treating cancer and reducing metastases (Lin et al., 1998).

G3. Apoptosis-Inducing Agents

VEGFR2-blocking, human anti-VEGF antibody therapeutic agents may also be advantageously combined with methods to induce apoptosis. Various apoptosis-inducing agents have been described above in connection with the immunoconjugates of the present invention. Any such apoptosis-inducing agent may be used in combination with the present invention without being linked to an antibody of the invention.

Aside from the apoptosis-inducing agents described above as immunoconjugates, a number of oncogenes have been identified that inhibit apoptosis, or programmed cell death.

Exemplary oncogenes in this category include, but are not limited to, bcr-abl, bcl-2 (distinct from bcl-1, cyclin D1; GenBank accession numbers M14745, X06487; U.S. Pat. Nos. 5,650,491; and 5,539,094; each incorporated herein by reference) and family members including Bcl-xl, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed.

Inhibition of this class of oncogenes, e.g., using antisense nucleotide sequences, is contemplated for use in the present invention to give enhancement of apoptosis (U.S. Pat. Nos. 5,650,491; 5,539,094; and 5,583,034; each incorporated herein by reference).

G4. Immunotoxins and Coaguligands

The treatment methods of the invention may be used in combination with immunotoxins and/or coaguligands in which the targeting portion thereof, e.g., antibody or ligand, is directed to a relatively specific marker of the tumor cells, tumor vasculature or tumor stroma. In common with the chemotherapeutic and anti-angiogenic agents discussed above, the combined use of targeted toxins or coagulants will generally result in additive, markedly greater than additive or even synergistic anti-tumor results.

Generally speaking, antibodies or ligands for use in these additional aspects of the invention will preferably recognize accessible tumor antigens that are preferentially, or specifically, expressed in the tumor site. The antibodies or ligands will also preferably exhibit properties of high affinity; and the antibodies, ligands or conjugates thereof, will not exert significant in vivo side effects against life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The term "significant side effects", as used herein, refers to an antibody, ligand or antibody conjugate, that, when administered in vivo, will produce only negligible or clinically manageable side effects, such as those normally encountered during chemotherapy.

At least one binding region of these second anti-cancer agents employed in combination with the invention will be a component that is capable of delivering a toxin or coagulation factor to the tumor region, i.e., capable of localizing within a tumor site. Such targeting agents may be directed against a component of a tumor cell, tumor vasculature or tumor stroma. The targeting agents will generally bind to a surface-expressed, surface-accessible or surface-localized component of a tumor cell, tumor vasculature or tumor stroma. However, once tumor vasculature and tumor cell destruction begins, internal components will be released, allowing additional targeting of virtually any tumor component.

Many tumor cell antigens have been described, any one which could be employed as a target in connection with the combined aspects of the present invention. Appropriate tumor cell antigens for additional immunotoxin and coaguligand targeting include those recognized by the antibodies B3 (U.S. Pat. No. 5,242,813); incorporated herein by reference; ATCC HB 10573); KSI/4 (U.S. Pat. No. 4,975,369); incorporated herein by reference; obtained from a cell comprising the vectors NRRL B-18356 and/or NRRL B-18357); 260F9 (ATCC HB 8488); and D612 (U.S. Pat. No. 5,183,756); incorporated herein by reference; ATCC HB 9796). One may also consult the ATCC Catalogue of any subsequent year to identify other appropriate cell lines producing anti-tumor cell antibodies.

For tumor vasculature targeting, the targeting antibody or ligand will often bind to a marker expressed by, adsorbed to, induced on or otherwise localized to the intratumoral blood vessels of a vascularized tumor. Appropriate expressed target molecules include, for example, endoglin, E-selectin, P-selectin, VCAM-1, ICAM-1, PSMA (Liu et al., 1997), a TIE, a ligand reactive with LAM-1, a VEGF/VPF receptor, an FGF receptor, $\alpha_v\beta_3$ integrin, pleiotropin and endosialin. Suitable adsorbed targets are those such as VEGF, FGF, TGFβ, HGF, PF4, PDGF, TIMP, a ligand that binds to a TIE and tumor-associated fibronectin isoforms. Antigens naturally and artificially inducible by cytokines and coagulants may also be targeted, such as ELAM-1, VCAM-1, ICAM-1, a ligand reactive with LAM-1, endoglin, and even MHC Class II (cytokine-inducible, e.g., by IL-1, TNF-α, IFN-γ, IL-4 and/or TNF-β); and E-selectin, P-selectin, PDGF and ICAM-1 (coagulant-inducible e.g., by thrombin, Factor IX/IXa, Factor X/Xa and/or plasmin).

The following patents are specifically incorporated herein by reference for the purposes of even further supplementing the present teachings regarding the preparation and use of immunotoxins directed against expressed, adsorbed, induced or localized markers of tumor vasculature: U.S. Pat. Nos. 6,093,399; 5,855,866; 5,965,132; 6,051,230; 6,004,555; 5,877,289; 6,004,554; 5,776,427; 5,863,538; 5,660,827 and 6,036,955.

Further tumor vasculature targeting compositions and methods include those targeting aminophospholipids, such as phosphatidylserine and phosphatidylethanolamine, recently discovered to be accessible, specific markers of tumor blood vessels. Administration of anti-aminophospholipid antibodies alone is sufficient to induce thrombosis and tumor regression. The present invention can thus be effectively combined with unconjugated, anti-phosphatidylserine and/or phosphatidylethanolamine antibodies; or immunoconjugates of such antibodies can be used.

The following patents are specifically incorporated herein by reference for the purposes of even further supplementing the present teachings regarding the preparation and use of anti-aminophospholipid antibodies and immunotoxins: U.S. Pat. Nos. 6,406,693; 6,312,694; 6,783,760; 6,818,213; and 7,067,109. U.S. Pat. Nos. 6,312,694; 6,783,760; 6,818,213; and 7,067,109 are further incorporated herein by reference for the purposes of further supplementing the present teachings regarding the use of aminophospholipid binding protein conjugates, such as annexin conjugates, for use in delivering toxins and coagulants to tumor blood vessels and for inducing thrombosis and tumor regression.

Suitable tumor stromal targets include components of the tumor extracellular matrix or stroma, or components those bound therein; including basement membrane markers, type IV collagen, laminin, heparan sulfate, proteoglycan, fibronectins, activated platelets, LIBS and tenascin. A preferred target for such uses is RIBS.

The following patents are specifically incorporated herein by reference for the purposes of even further supplementing the present teachings regarding the preparation and use of tumor stromal targeting agents: U.S. Pat. Nos. 6,093,399; 6,004,555; 5,877,289; and 6,036,955.

The second anti-cancer therapeutics may be operatively attached to any of the cytotoxic or otherwise anti-cellular agents described herein for use in the VEGFR2-blocking, anti-VEGF antibody or the VEGFR2-blocking, anti-VEGF antibody-based immunotoxins. However, suitable anti-cellular agents also include radioisotopes. Toxin moieties will be preferred, such as ricin A chain and deglycosylated A chain (dgA).

The second, targeted agent for optional use with the invention may comprise a targeted component that is capable of promoting coagulation, i.e., a coaguligand. Here, the targeting antibody or ligand may be directly or indirectly, e.g., via another antibody, linked to any factor that directly or indirectly stimulates coagulation, including any of those described herein for use in the VEGFR2-blocking, anti-VEGF antibody or VEGFR2-blocking, anti-VEGF antibody-based coaguligands. Preferred coagulation factors for such uses are Tissue Factor (TF) and TF derivatives, such as truncated TF (tTF), dimeric and multimeric TF, and mutant TF deficient in the ability to activate Factor VII.

Effective doses of immunotoxins and coaguligands for combined use in the treatment of cancer will be between about 0.1 mg/kg and about 2 mg/kg, and preferably, of between about 0.8 mg/kg and about 1.2 mg/kg, when administered via the IV route at a frequency of about 1 time per week. Some variation in dosage will necessarily occur depending on the condition of the subject being treated. The physician responsible for administration will determine the appropriate dose for the individual subject.

G5. TLR Agonists

It has now been established that signaling via Toll-Like Receptors (TLRs) contributes to the effects of known anti-cancer agents, including attenuated *S. choleraesuis*, BCG and taxol, which each activate TLR4. Indeed, TLR4 signaling contributes to the anti-cancer effects of chemotherapy and radiotherapy (Apetoh et al., 2007). As well as better understanding the mechanisms of action of certain known anti-cancer agents, recognizing the importance of TLR signaling has also prompted the development of new cancer therapeutics that function by activating TLRs.

Therefore, the VEGFR2-blocking, human anti-VEGF antibodies of the present invention may be used in cancer treatment in combination with one or more agents that stimulate signaling via a TLR, i.e., with one or more TLR agonists. At least a first TLR agonist may also be operatively attached to a human antibody of the invention to create a therapeutic conjugate, as described herein in the immunoconjugate section. Any one or more of the following or other TLR agonists may be used in the present combination cancer treatments.

Suitable TLR agonists include agonists of any one or more of TLR1 to TLR11, preferably TLR1, TLR2, TLR4, TLR7, TLR8 or TLR9, and most preferably TLR4, TLR7, TLR8 or TLR9. TLR1/TLR2 agonists include lipoproteins, e.g., OspA, and triacylated lipopeptides, and TLR2 agonists include bacterial lipoproteins, LAM, MALP-2, GPI, glycolipids and porins.

Particular examples of TLR4 agonists include the agonistic anti-TLR4 antibody termed 5D24.D4 (Cohen et al., 2003), LPS, lipid A and derivatives thereof, of which monophosphoryl lipid A (MPL) and MPL analogues are currently preferred. MPL analogues known as AGPs may be used as synthetic TLR4 agonists in combination with the present invention (Alderson et al., 2006). Agonists stimulating signaling via TLR4 and CD14 also include LPS, lipid A, MPL and MPL analogues, as well as taxol, paclitaxel, flavolipin and GIPLs. The TLR4 agonists OK-432 and OK-PSA have been used to treat cervical cancer and non-small-cell lung carcinoma.

TLR7 agonists include imiquimod, resiquimod and isatoribine (Finberg et al., 2005; Horsmans et al., 2005), and imiquimod is approved for use to treat basal cell carcinoma. Other TLR7 agonists include gardiquimod, loxoribine and bropirimine. Resiquimod is also a TLR8 agonist. TLR9 agonists, such as CpG, have been used to treat non-small-cell lung carcinoma, non-Hodgkin's lymphoma, renal cell carcinoma and colorectal cancer.

G6. ADEPT and Prodrug Therapy

The VEGFR2-blocking, human anti-VEGF antibodies of the present invention may be used in conjunction with prodrugs, wherein the VEGFR2-blocking, human anti-VEGF antibody is operatively associated with a prodrug-activating component, such as a prodrug-activating enzyme, which converts a prodrug to the more active form only upon contact with the antibody. This technology is generally termed "ADEPT", and is described in, e.g., WO 95/13095; WO 97/26918, WO 97/24143, and U.S. Pat. Nos. 4,975,278 and 5,658,568, each specifically incorporated herein by reference.

The term "prodrug", as used herein, refers to a precursor or derivative form of a biologically or pharmaceutically active substance that exerts reduced cytotoxic or otherwise anticellular effects on targets cells, including tumor vascular endothelial cells, in comparison to the parent drug upon which it is based. Preferably, the prodrug or precursor form exerts significantly reduced, or more preferably, negligible, cytotoxic or anticellular effects in comparison to the "native" or parent form. "Prodrugs" are capable of being activated or converted to yield the more active, parent form of the drug.

The technical capability to make and use prodrugs exists within the skill of the ordinary artisan. Willman et al. (1988) and Stella and Himmelstein (1985) are each specifically incorporated herein by reference for purposes of further supplementing the description and teaching concerning how to make and use various prodrugs. Exemplary prodrug constructs that may be used in the context of the present invention include, but are not limited to, phosphate-containing prodrugs (U.S. Pat. No. 4,975,278), thiophosphate-containing prodrugs, sulfate-containing prodrugs, peptide-based prodrugs (U.S. Pat. Nos. 5,660,829; 5,587,161; 5,405,990; WO 97/07118), D-amino acid-modified prodrugs, glycosylated prodrugs (U.S. Pat. Nos. 5,561,119; 5,646,298; 4,904,768; 5,041,424), β-lactam-containing prodrugs, optionally substituted phenoxyacetamide-containing prodrugs (U.S. Pat. No. 4,975,278), optionally substituted phenylacetamide-containing prodrugs, and even 5-fluorocytosine (U.S. Pat. No. 4,975,278) and 5-fluorouridine prodrugs and the like, wherein each of the patents are specifically incorporated herein by reference.

The type of therapeutic agent or cytotoxic drug that can be used in prodrug form is virtually limitless. The more cytotoxic agents will be preferred for such a form of delivery, over, e.g., the delivery of coagulants, which are less preferred for use as prodrugs. All that is required in forming the prodrug is to design the construct so that the prodrug is substantially inactive and the "released" or activated drug has substantial, or at least sufficient, activity for the intended purpose.

Various improvements on the original prodrugs are also known and contemplated for use herewith, as disclosed in WO 95/03830; EP 751,144 (anthracyclines); WO 97/07097 (cyclopropylindoles); and WO 96/20169. For example, prodrugs with reduced Km are described in U.S. Pat. No. 5,621,002, specifically incorporated herein by reference, which may be used in the context of the present invention. Prodrug therapy that be conducted intracellularly is also known, as exemplified by WO 96/03151, specifically incorporated herein by reference, and can be practiced herewith.

For use in ADEPT, the agent that activates or converts the prodrug into the more active drug is operatively attached to the VEGFR2-blocking, human anti-VEGF antibody. The VEGFR2-blocking, human anti-VEGF antibody thus localizes the prodrug converting capability within the angiogenic site, preferably, within the tumor vasculature and stroma, so that active drug is only produced in such regions and not in circulation or in healthy tissues.

Enzymes that may be attached to VEGFR2-blocking, human anti-VEGF antibodies to function in prodrug activation include, but are not limited to, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as β-galactosidase and neuraminidase for use in combination with glycosylated prodrugs (U.S. Pat. Nos. 5,561,119; 5,646,298); β-lactamase for use in combination with β-lactam-containing prodrugs; penicillin amidases, such as penicillin V amidase (U.S. Pat. No. 4,975,278) or penicillin G amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), wherein each of the patents are specifically incorporated herein by reference.

Antibodies with enzymatic activity, known as catalytic antibodies or "abzymes", can also be employed to convert prodrugs into active drugs. Abzymes based upon VEGFR2-blocking, human anti-VEGF antibodies thus form another aspect of the present invention. The technical capacity to make abzymes also exists within one of ordinary skill in the art, as exemplified by Massey (1987), specifically incorporated herein by reference for purposes of supplementing the abzyme teaching. Catalytic antibodies capable of catalyzing the breakdown of a prodrug at the carbamate position, such as a nitrogen mustard aryl carbamate, are further contemplated, as described in EP 745,673, specifically incorporated herein by reference.

G7. Ocular Combinations

The VEGFR2-blocking, human anti-VEGF antibodies of the invention may be used in combination with other therapies to treat ocular diseases and angiogenic ocular diseases, including diabetic retinopathy, macular degeneration, age-related macular degeneration, neovascular glaucoma and the other ocular diseases described above. The antibodies may be combined with any other methods generally employed in the treatment of ocular diseases, including surgery.

As to combinations with other therapeutic agents, the VEGFR2-blocking, human anti-VEGF antibodies may be administered before, after or at substantially the same time as the other therapeutic agent. Substantially simultaneous administration may be achieved from a single composition, or from two distinct compositions.

As to choroidal neovascularization, such as that associated with macular degeneration, age-related macular degeneration (AMD) and other ocular indications, certain preferred combinations of the invention are those using a second agent that blocks, inhibits, reduces, down-regulates or antagonizes SPARC (secreted protein, acidic and rich in cysteine) (Nozaki et al., 2006; U.S. 2006/0135423). As the antibodies of the invention already block VEGFR2 activation, but not VEGFR1 activation, their combination with one or more agents that block SPARC would form a particularly effective method to further reduce VEGF-induced angiogenesis in the eye.

SPARC inhibitors or antagonists include, for example, those of the same molecular types as have been successfully developed against VEGF itself. Exemplary SPARC inhibitors thus include inhibitory anti-SPARC antibodies and antigen-binding fragments thereof (e.g., Sweetwyne et al., 2004); antisense strategies, such as RNA aptamers and RNA/DNA aptamers, silencing RNAs (siRNAs or RNAi) that silence or interfere with SPARC expression; ribozymes; and other protein, peptide and small molecule inhibitors. Many such SPARC inhibitors, including polyclonal and monoclonal antibodies and siRNAs, are available commercially, e.g., from Sigma/Aldrich, Santa Cruz Biotechnology, Inc., R&D Systems. Any one or more SPARC inhibitors may thus be used in conjunction with the present invention to additionally block, inhibit, reduce, down-regulate or antagonize SPARC levels or activity, either at the DNA, RNA and/or protein levels.

H. Diagnostics and Imaging

The present invention further provides in vitro and in vivo diagnostic and imaging methods. Such methods are applicable for use in generating diagnostic, prognostic or imaging information for any angiogenic disease, as exemplified by arthritis, psoriasis and solid tumors, but including all the angiogenic diseases disclosed herein. Outside the field of tumor diagnostics and imaging, these aspects of the invention are most preferred for use in in vitro diagnostic tests, preferably either where samples can be obtained non-invasively and tested in high throughput assays and/or where the clinical diagnosis in ambiguous and confirmation is desired.

H1. Immunodetection Methods and Kits

In still further embodiments, the present invention concerns immunodetection methods for binding, purifying, removing, quantifying or otherwise generally detecting VEGF and for diagnosing angiogenic diseases. The VEGFR2-blocking, human anti-VEGF antibodies of the present invention may be employed to detect VEGF in vivo (see below), in isolated issue samples, biopsies or swabs and/or in homogenized tissue samples. Such immunodetection methods have evident diagnostic utility, but also have applications to non-clinical samples, such as in the titering of antigen samples, and the like.

The steps of various useful immunodetection methods have been described in the scientific literature, such as, e.g., Nakamura et al. (1986, incorporated herein by reference). In general, the immunobinding methods include obtaining a sample suspected of containing VEGF and contacting the sample with VEGFR2-blocking, human anti-VEGF antibodies under conditions effective to allow the formation of immunocomplexes. In such methods, the antibody may be linked to a solid support, such as in the form of a column matrix, and the sample suspected of containing VEGF will be applied to the immobilized antibody.

More preferably, the immunobinding methods include methods for detecting or quantifying the amount of VEGF in a sample, which methods require the detection or quantification of any immune complexes formed during the binding process. Here, one would obtain a sample suspected of containing VEGF and contact the sample with an antibody in accordance herewith and then detect or quantify the amount of immune complexes formed under the specific conditions.

The biological sample analyzed may be any sample that is suspected of containing VEGF, generally from an animal or patient suspected of having an angiogenic disease. The samples may be a tissue section or specimen, a biopsy, a swab or smear test sample, a homogenized tissue extract or separated or purified forms of such.

Contacting the chosen biological sample with the antibody under conditions effective and for a period of time sufficient to allow the formation of immune complexes (primary immune complexes) is generally a matter of simply adding an antibody composition to the sample and incubating the mixture for a period of time lone enough for the antibodies to form immune complexes with, i.e., to bind to, any VEGF present. After this time, the sample-antibody composition, such as a tissue section, ELISA plate, dot blot or western blot, will generally be washed to remove any non-specifically bound antibody species, allowing only those antibodies specifically bound within the primary immune complexes to be detected.

The detection of immunocomplex formation is well known in the art and may be achieved through the application of numerous approaches. These methods are generally based upon the detection of a label or marker, such as any radioactive, fluorescent, biological or enzymatic tags or labels known in the art. U.S. Patents concerning the use of such labels include U.S. Pat. Nos. 3,817,837; 3,850,752; 3,939,350; 3,996,345; 4,277,437; 4,275,149 and 4,366,241, each incorporated herein by reference. The use of enzymes that generate a colored product upon contact with a chromogenic substrate are generally preferred. Secondary binding ligand, such as a second antibody or a biotin/avidin ligand binding arrangement, may also be used, as is known in the art.

The VEGFR2-blocking, human anti-VEGF antibodies employed in the detection may themselves be linked to a detectable label, wherein one would then simply detect this label, thereby allowing the amount of the primary immune complexes in the composition to be determined.

Preferably, the primary immune complexes are detected by means of a second binding ligand that has binding affinity for the antibodies of the invention. In such cases, the second binding ligand may be linked to a detectable label. The second binding ligand is itself often an antibody, and may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

In the clinical diagnosis or monitoring of patients with an angiogenic disease, the detection of VEGF, or an increase in the levels of VEGF, in comparison to the levels in a corresponding biological sample from a normal subject is indicative of a patient with an angiogenic disease.

However, as is known to those of skill in the art, such a clinical diagnosis would not likely be made on the basis of this method in isolation. Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

H2. Imaging

These aspects of the invention are preferred for use in tumor imaging methods and combined tumor treatment and imaging methods. VEGFR2-blocking, human anti-VEGF antibodies that are linked to one or more detectable agents are envisioned for use in imaging per se, or for pre-imaging the tumor to form a reliable image prior to treatment. Such compositions and methods can also be applied to the imaging and diagnosis of any other angiogenic disease or condition, particularly non-malignant tumors, atherosclerosis and conditions in which an internal image is desired for diagnostic or prognostic purposes or to design treatment.

VEGFR2-blocking, human anti-VEGF antibody imaging antibodies will generally comprise a VEGFR2-blocking, human anti-VEGF antibody operatively attached, or conjugated to, a detectable label. "Detectable labels" are compounds or elements that can be detected due to their specific functional properties, or chemical characteristics, the use of which allows the component to which they are attached to be detected, and further quantified if desired. In antibody conjugates fQr in vivo diagnostic protocols or "imaging methods" labels are required that can be detected using non-invasive methods.

Many appropriate imaging agents are known in the art, as are methods for their attachment to antibodies and binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II, neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (HII), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technetium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled VEGFR2-blocking, human anti-VEGF antibody antibodies for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetracetic acid (EDTA).

Monoclonal antibodies can also be iodinated by contact with sodium or potassium iodide and a chemical oxidizing agent such as sodium hypochlorite, or an enzymatic oxidizing agent, such as lactoperoxidase. Antibodies according to the invention may be labeled with technetium-$^{99m}$ by ligand exchange process, for example, by reducing pertechnate with stannous solution, chelating the reduced technetium onto a Sephadex column and applying the antibody to this column; or by direct labeling techniques, e.g., by incubating pertechnate, a reducing agent such as SNCl$_2$, a buffer solution such as sodium-potassium phthalate solution, and the antibody.

Any of the foregoing type of detectably labeled VEGFR2-blocking, human anti-VEGF antibodies may be used in the imaging or combined imaging and treatment aspects of the present invention. They are equally suitable for use in in vitro diagnostics. Dosages for in vivo imaging embodiments are generally less than for therapy, but are also dependent upon the age and weight of a patient. One time doses should be sufficient.

The in vivo diagnostic or imaging methods generally comprise administering to a patient a diagnostically effective amount of a VEGFR2-blocking, human anti-VEGF antibody that is conjugated to a marker that is detectable by non-invasive methods. The antibody-marker conjugate is allowed sufficient time to localize and bind to VEGF within the tumor. The patient is then exposed to a detection device to identify the detectable marker, thus forming an image of the tumor.

H3. Diagnostic Kits

In still further embodiments, the present invention provides diagnostic kits, including both immunodetection and imaging kits, for use with the immunodetection and imaging methods described above. Accordingly, the VEGFR2-blocking, human anti-VEGF antibodies are provided in the kit, generally comprised within a suitable container.

For immunodetection, the antibodies may be bound to a solid support, such as a well of a microtitre plate, although antibody solutions or powders for reconstitution are preferred. The immunodetection kits preferably comprise at least a first immunodetection reagent. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present invention. These kits may contain antibody-label conjugates either in fully conjugated form, in the form of intermediates, or as separate moieties to be conjugated by the user of the kit.

The imaging kits will preferably comprise a VEGFR2-blocking, human anti-VEGF antibody that is already attached to an in vivo detectable label. However, the label and attachment means could be separately supplied.

Either kit may further comprise control agents, such as suitably aliquoted compositions of VEGF, whether labeled or unlabeled, as may be used to prepare a standard curve for a detection assay. The components of the kits may be packaged either in aqueous media or in lyophilized form.

The container means of the kits will generally include at least one vial, test tube, flask, bottle, syringe or other container means, into which the antibody or antigen may be placed, and preferably, suitably aliquoted. Where a second or third binding ligand or additional component is provided, the kit will also generally contain a second, third or other additional container into which this ligand or component may be placed. The kits may also include other diagnostic reagents for use in the diagnosis of any one or more angiogenic diseases. Preferably, second diagnostics not based upon VEGF binding will be used.

The kits of the present invention will also typically include a means for containing the antibody, and any other reagent containers in close confinement for commercial sale. Such containers may include injection or blow-molded plastic containers into which the desired vials are retained.

TABLE 1

| SEQ ID NO: | Description | Sequence |
|---|---|---|
| Clone EJ173-112-C11 (r84 scFv) | | |
| 1 | VH domain (nt) | CAGGTGCAGCTGGTGCAATCTGGGGCTGAGGT GAAGAAGCCTGGGGCCTCAGTGAAGGTCTCCT GCAAGGCTTCTGGAGGCACCTTCAGCAGCTAT GCTATCAGCTGGGTGCGACAGGCCCCTGGACA AGGGCTTGAGTGGATGGGAGGTTTTGATCCTG AAGATGGTGAAACAATCTACGCACAGAAGTTC CAGGGCAGAGTCACCATGACCGAGGACACATC TACAGACACAGCCTACATGGAGCTGAGCAGCC TGAGATCTGAGGACACGGCCGTGTATTACTGT GCAACAGGACGTTCTATGGTTCGGGGAGTCAT TATACCTTTTAACGGTATGGACGTCTGGGGCC AAGGGACCACGGTCACCGTCTCCTCA See FIG. 1 |
| 2 | VL domain (nt) | GACATCCGGATGACCCAGTCTCCATCCTCCCTG TCTGCATCTGTAGGAGACAGAGTCACCATCACT TGCCGGGCAAGTCAGAGCATTAGCAGCTATTTA AATTGGTATCAGCAGAAACCAGGGAAAGCCCC TAAGCTCCTGATCTATGCTGCATCCAGTTTGCAA AGTGGGGTCCCATCAAGGTTCAGTGGCAGTGGA TCTGGGACAGATTTCACTCTCACCATCAGCAGTC TGCAACCTGAAGATTTTGCAACTTACTACTGTCA ACAGAGTTACAGTACCCCGCTCACTTTCGGCGG AGGGACCAAGGTGGAGATCAAA See FIG. 1 |
| 3 | VH domain (aa) | QVQLVQSGAEVKKPGASVKVSCKASGGTFSSYAIS WVRQAPGQGLEWMGGFDPEDGETIYAQKFQGRVT MTEDTSTDTAYMELSSLRSEDTAVYYCATGRSMVR GVIIPFNGMDVWGQGTTVTVSS See FIG. 1 |
| 4 | VL domain (aa) | DIRMTQSPSSLSASVGDRVTITCRASQSISSYLNWYQ QKPGKAPKLLIYAASSLQSGVPSRFSGSGSGTDFTLT ISSLQPEDFATYYCQQSYSTPLTFGGGTKVEIK See FIG. 1 |
| 5 | Heavy CDR1 | SYAIS |
| 6 | Heavy CDR2 | GFDPEDGETIYAQKFQG |
| 7 | Heavy CDR3 | GRSMVRGVIIPFNGMDV |
| 8 | Light CDR1 | RASQSISSYLN |
| 9 | Light CDR2 | AASSLQS |
| 10 | Light CDR3 | QQSYSTPLT |
| 11 | Heavy FR1 | QVQLVQSGAEVKKPGASVKVSCKASGGTFS |
| 12 | Heavy FR2 | WVRQAPGQGLEWMG |

TABLE 1-continued

| SEQ ID NO: | Description | Sequence |
|---|---|---|
| 13 | Heavy FR3 | RVTMTEDTSTDTAYMELSSLRSEDTAVYYCAT |
| 14 | Heavy FR4 | WGQGTTVTVSS |
| 15 | Light FR1 | DIRMTQSPSSLSASVGDRVTITC |
| 16 | Light FR2 | WYQQKPGKAPKLLIY |
| 17 | Light FR3 | GVPSRFSGSGSGTDFTLTISSLQPEDFATYYC |
| 18 | Light FR4 | FGGGTKVEIK |
| 19 | Linker | KLSGSASAPKLEEGEFSEARV |
| 20 | Whole scFv clone (nt) | See FIG. 1 |
| 21 | Whole scFv clone (aa) | See FIG. 1 |
| r84 Full length IgG | | |
| 22 | IgG heavy chain (nt) | See Example 6 |
| 23 | IgG light chain (nt) | See Example 6 |
| 24 | IgG heavy chain (aa) | See Example 6 |
| 25 | IgG light chain (aa) | See Example 6 |
| 26 | IgG VH domain (nt) | See Example 6 |
| 27 | IgG VL domain (nt) | See Example 6 |

* * *

The following examples are included to demonstrate preferred embodiments of the invention. It should be appreciated by those of skill in the art that the techniques disclosed in the examples that follow represent techniques discovered by the inventor to function well in the practice of the invention, and thus can be considered to constitute preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Antibody Selection

VEGF is a key regulator of physiological angiogenesis during embryogenesis, skeletal growth, and reproductive functions. VEGF signaling through interaction with the tyrosine kinase receptor VEGFR2 is also important in pathological angiogenesis, including that associated with tumor growth. Given the need for therapeutic specific human antibodies that block angiogenesis, human antibodies have been identified that are reactive against an epitope on VEGF that specifically and substantially blocks its interaction with VEGFR2 (KDR/Flk-1), but does not substantially block its interaction with VEGFR1 (Flt-1).

Figure 9:
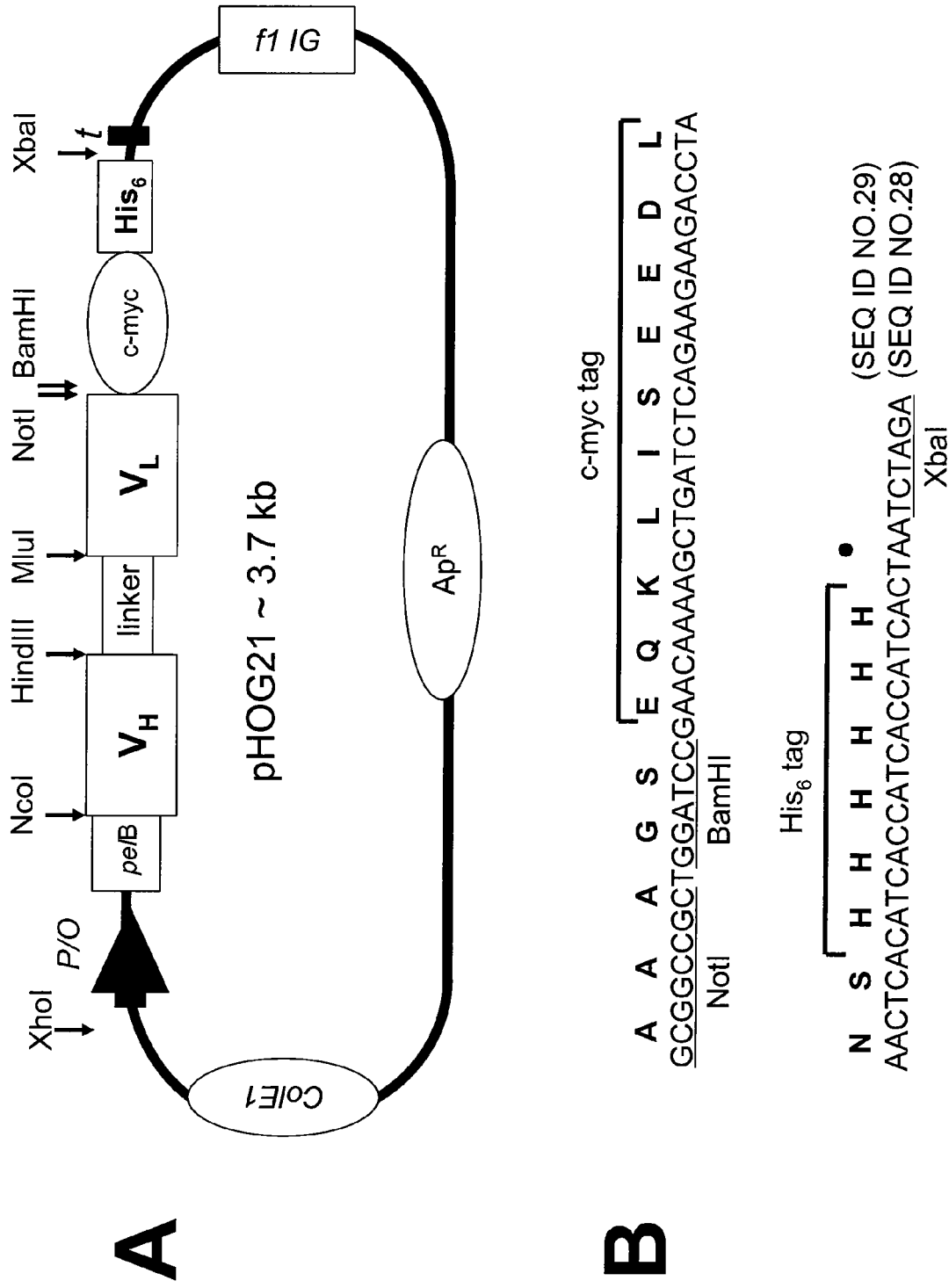
FIG. 9A and FIG. 9B show the scFv expression vector.

Single chain forms of antibodies were cloned in the pHOG2 Iplasmid (Kipriyanov et al., 1996; 1997) (FIG. 9A and FIG. 9B) (at the NcoI and Not I restriction sites), which contains c-myc and 6×His tag epitopes. E. coli cells, XL-1 blue, were transformed, selected on ampicillin plates and the scFv was expressed upon IPTG induction. Purified scFv were tested by ELISA for selective biological activity against VEGF. The selective biological activity was further confirmed by competitive ELISA assays using the murine antibody 2C3, which specifically blocks VEGF and VEGFR2 interaction and not VEGF and VEGFR1 interaction (Brekken et al., 1998; 2000). Also Biacore showed the binding of scFv antibodies to immobilized VEGF-A. Binding to murine VEGF as well as human VEGF was also assessed.

A. Sequencing

The nucleotide sequences of the heavy and light chains of one preferred antibody-producing clone is shown. The antibody is designated as EJ173/112-Cl1 (r84/PGN311) and has been produced in both a scFv form (Example 1 and FIG. 1) and a full length IgG form (Example 6). The nucleotide sequence and amino acid sequence of the light and heavy chains of a single chain form of EJ 173/112-Cl1 (r84/PGN311) are shown in FIG. 1 and Table 1. The nucleotide and amino acid sequence of the light and heavy chains of a full length IgG form of r84/PGN311 are shown in Example 6. The CDR and framework regions of the light and heavy chains of EJ173/112-Cl1 (r84/PGN311) are shown in Table 1.

Example 2

EJ173/112-Cl1 (r84/PGN311) Binds to VEGF with High Affinity

To confirm the specificity of the antibody, binding of the scFv form of EJI 73/112-Cl1 (r84/PGN311) was tested by ELISA against plated human VEGF-A (obtained from Dr. Rolf A. Brekken, U T Southwestern Medical Center, Dallas, Tex.). Briefly, 2 µg/ml VEGF-A was plated on a polystyrene plate. Next, 20 µg/ml purified EJ173/112-Cl1 (r84/PGN311) scFv was added to the first well, and titrated with 3-fold dilutions. Bound scFv was detected with an anti-c-myc tag mouse monoclonal antibody (Invitrogen) and HRP-conjugated secondary rabbit anti-mouse antibody.

ELISA results showed that EJ173/112-Cl1 (r84/PGN311) scFv (FIG. 2) bound to VEGF and, importantly, had an increased binding signal, and hence increased affinity, compared to its mother clone. The murine B9 antibody is used as a positive control and is a murine scFv antibody against human VEGF-A (obtained from Dr. Philip E. Thorpe, U T Southwestern Medical Center, Dallas, Tex.).

EJ 173/112-Cl1 (r84/PGN311) showed further beneficial features over the mother clone. It was shown that EJ173/112-Cl1 (r84/PGN311) has a higher stability in serum and a reduced tendency to form aggregates in scFv format compared to the mother clone (data not shown).

Shuffling the Variable Region Heavy Chain of EJ173/112-Cl1 (R84/PGN311) with Seven Different Heavy Chains from Other Anti-VEGF Antibodies The variable region light chain of EJ173/112-Cl1 (r84/PGN311) was combined with seven different variable region heavy chains derived from other antiVEGF antibody clones distinct from r84/PGN311 to confirm the importance of the light chain variable region of r84/PGN311 in maintaining the VEGF binding property. The resulting clones were expressed and purified via their His tag on NiNTA columns. After purification, concentration was determined, and an ELISA against plated human VEGF-A was run. 20 µg/ml of purified scFv was added and bound scFv was detected with an anti-c-myc tag mouse monoclonal antibody (Invitrogen) and HRP-conjugated secondary rabbit anti-mouse antibody.

It was shown that three out of the seven combinations of variable region light chain of EJ173/112-Cl1 (r84/PGN311) with variable region heavy chains derived from other anti-VEGF antibody clones showed significant binding to VEGF in this ELISA. This is a very reasonable proportion and demonstrates that the light chain variable region of r84/PGN311 is important for maintaining the binding to VEGF and also that other heavy chain variable regions which can be combined with this light chain variable region to give rise to antibodies which bind to VEGF can be readily identified.

Example 3

EJ173/112-Cl1 (r84/PGN311) Competes with Murine 2C3

Figure 3:
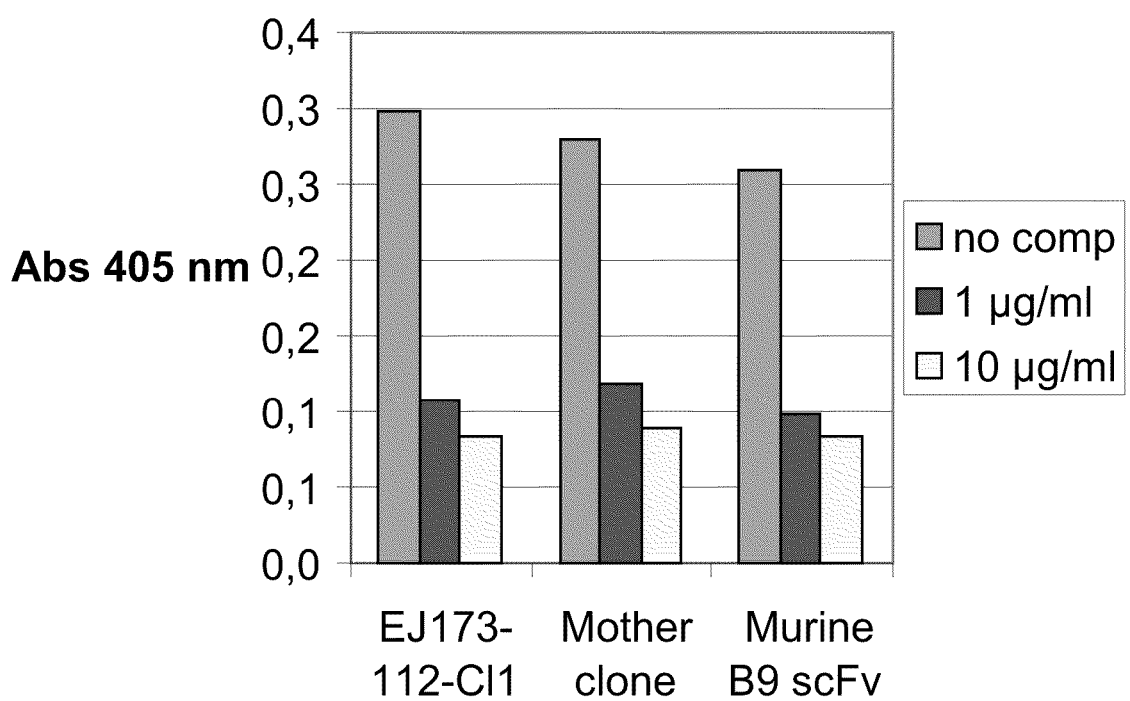
FIG. 3 shows that clone EJ173/112-Cl1 (r84/PGN311) scFv effectively competes with the 2C3 antibody for binding to VEGF, which is shown by the results of a competition ELISA assay. As clone EJ173/112-Cl1 (r84) effectively competes with the 2C3 antibody for binding to VEGF, this shows that clone EJ173/112-Cl1 (r84) binds to substantially the same epitope as the murine 2C3 anti-VEGF antibody.

To further demonstrate the specificity of the antibody, binding of EJ173/112-Cl1 (r84/PGN311) scFv in the presence of two concentrations of 2C3 was tested in an ELISA against plated VEGF-A. Briefly, 2 µg/ml VEGF-A was plated on a polystyrene plate. Next, 1 µg/ml purified EJ173/112-Cl1 (r84/PGN311) scFv, the mother clone or murine B9 scFv (FIG. 3) was added to six parallel wells, of which two contained 0.1 µg and two contained 1 µg murine 2C3 IgG, resulting in a final concentration of 1 and 10 µg/ml, respectively, of 2C3 IgG. Remaining bound scFv was detected with an HRP-conjugated anti-c-myc tag mouse monoclonal antibody (Invitrogen).

The binding of EJ173/112-Cl1 (r84/PGN311) scFv to VEGF was reduced by competition with increasing concentrations of 2C3 IgG. These results therefore show that EJ173/112-Cl1 (r84/PGN311) effectively competes with the 2C3 antibody for binding to VEGF, indicating that EJ173/112-Cl1 (r84/PGN311) binds to substantially the same epitope as 2C3.

Example 4

EJ173/112-Cl1 (r84/PGN311) Binds to Human and Mouse VEGF

The binding of EJ173/112-Cl1 (r84/PGN311) scFv to human and murine VEGF was determined. 1 µg/ml of murine VEGF (R&D Systems 493-MV-005/CF, carrier-free murine VEGF164) and human VEGF was plated on polystyrene immunoplates. 10 µg/ml of purified scFv was added and detected with an anti-c-myc tag mouse monoclonal antibody (Invitrogen) and HRP-conjugated secondary rabbit anti-mouse antibody.

Figure 4:
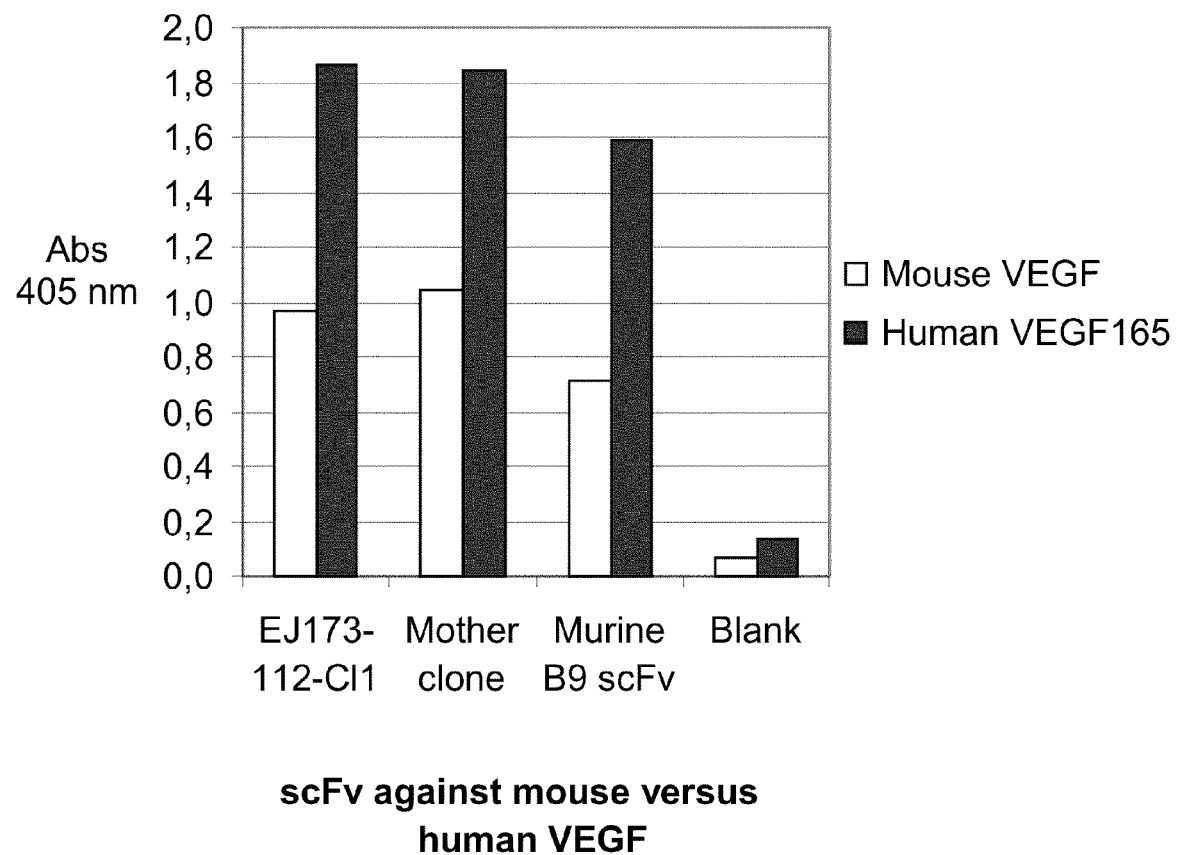
FIG. 4 shows that clone EJ173/112-Cl1 (r84/PGN311) scFv binds to both murine VEGF and human VEGF.

The results showed that EJ173/112-Cl1 (r84/PGN311) scFv (FIG. 4) binds to both murine VEGF and human VEGF.

In addition, a Biacore T100 was used to assess the binding affinity of the scFv forms of r84 and its mother clone to mouse VEGF. To this end 1000 RU of recombinant Mouse VEGF$_{164}$ (493-MV/CF, R&D Systems) was immobilised on a CM5 chip (Biacore), and a dilution series (100 nM and 2-fold dilutions) of monomeric scFv was flown over at a flow rate of 50 μl/min. The binding affinity expressed as the K$_D$ was calculated by the 1:1 Fitting model using software belonging to the Biacore T100 machine. The K$_D$ values were calculated as $1.0 \times 10^{-8}$ M for EJ173/112-Cl1 (r84/PGN311) and $4.0 \times 10^{-8}$ M for the mother clone. r84/PGN311 thus shows a higher binding affinity than the mother clone for murine VEGF.

These results indicate that this selected antibody (r84/PGN311) is suitable for use both in pre-clinical studies in mice and for use in humans.

Figure 19:
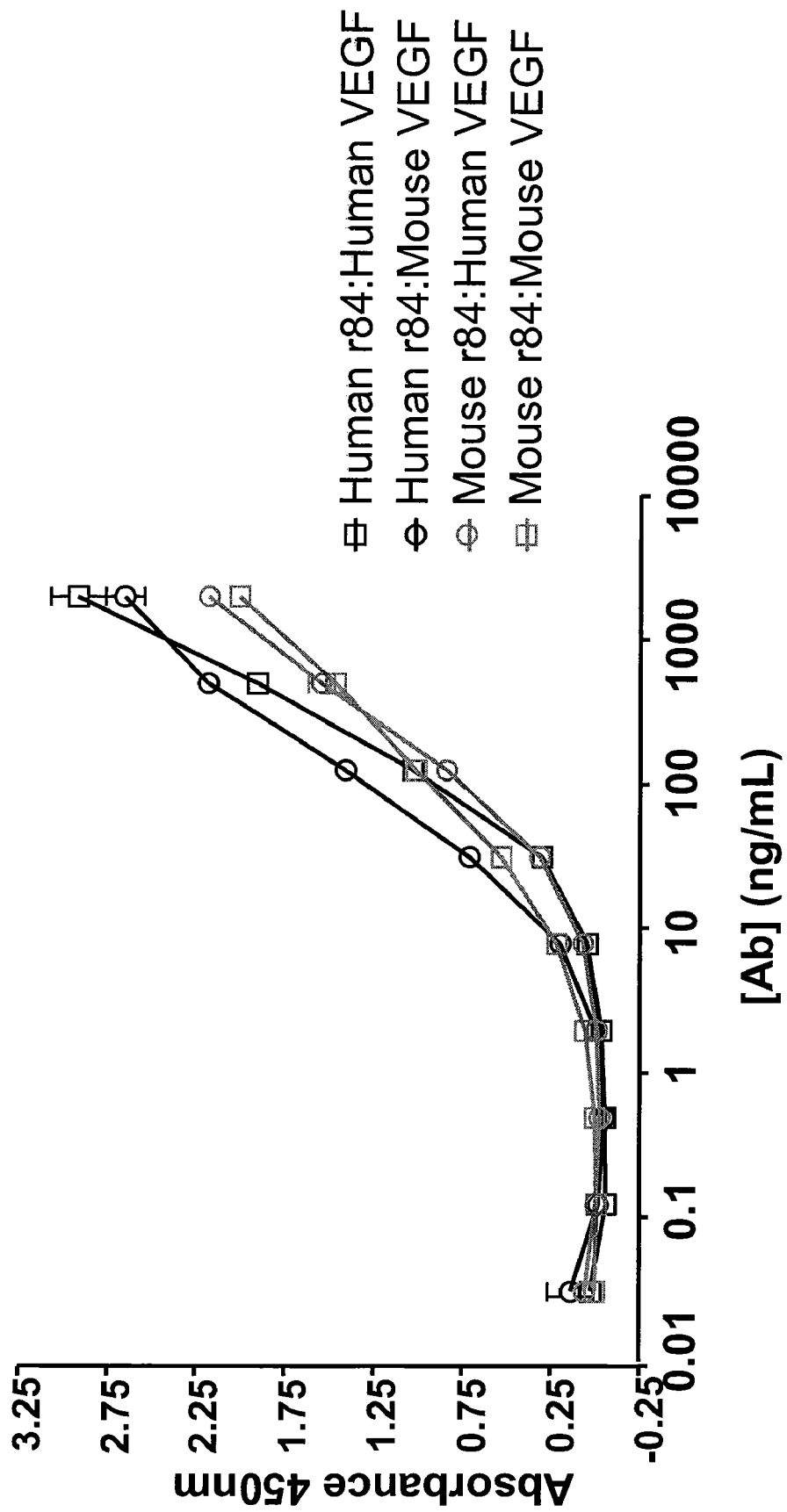
FIG. 19 shows that r84 in fully human and murine chimeric IgG formats binds to both murine VEGF and human VEGF. Human VEGF (0.5 µg/mL, R&D) or mouse VEGF (0.5 µg/mL, Sigma) was coated onto the bottom of 96-well plates. Wells were blocked and then incubated with the indicated concentration of human r84 (blue lines) or mouse chimeric r84 (green lines). Antibody bound to the wells was detected by incubation with anti-human Fc or anti-mouse HRP-conjugated antibody. Average absorbance is displayed.

As detailed below in Example 6, fully human and murine chimeric IgG forms of the r84 antibody have been generated. ELISA binding studies confirmed that each of these IgG format r84 antibodies also binds to both murine VEGF and human VEGF (FIG. 19). These results show another advantage of the selected fully human r84 antibody over the 2C3 antibody, as 2C3 does not exhibit meaningful binding to murine VEGF.

The absence of meaningful binding of 2C3 to murine VEGF has been demonstrated in an indirect ELISA assay. In this assay, the interaction of 2C3 with human and mouse VEGF as well as other VEGF family members was assessed.

The indirect ELISA assays were performed essentially as described in Brekken et al., Cancer Research 1998 and 2000. Briefly, the various growth factors, i.e. human VEGF-A (VEGF), mouse VEGF, PIGF, VEGF-B, VEGF-C and VEGF-D, were purchased from R&D Systems and coated onto the wells of an ELISA plate (50 μl/well at 0.5 g/ml in sensitizing buffer, overnight at 4° C.). The wells were blocked in 5% CAH (casein acid hydrolysate, Sigma, made up in PBS) for 1 hr at 37° C. and incubated in triplicate with the 2C3 anti-VEGF antibody at 1.0 μg/ml for 2 hours at room temperature. Binding was detected with peroxidase-conjugated secondary antibody (either anti-human or anti-mouse IgG, diluted 1:5000). The wells were developed with TMB (a colorimetric substrate for HRP) and absorbance read at 450 nM. The mean absorbance values are as follows: human VEGF-A (3.07), mouse VEGF (0.09) which was the same as the background signal, PIGF (0.1), VEGF-B (0.09), VEGF-C (0.09) and VEGF-D (0.12).

The results demonstrate that 2C3 binds to human VEGF-A but does not react with mouse VEGF-A, PIGF, VEGF-B, VEGF-C, or VEGF-D. This assay has been replicated several times with similar results.

Further evidence that the IgG form of the r84/PGN311 antibody binds to mouse VEGF, whereas 2C3 and Avastin do not bind to mouse VEGF has been obtained in experiments in which mouse VEGF levels in serum have been evaluated in animals treated with r84, 2C3 and Avastin.

Sera from tumor-bearing animals treated with a control IgG (Synagis), avastin, 2C3 or r84 was collected and assayed by ELISA for the level of mouse VEGF using a kit from R&D systems. In addition, some samples of sera from r84 treated mice were immunodepleted of all antibodies by incubation with protein G beads.

Figure 24:
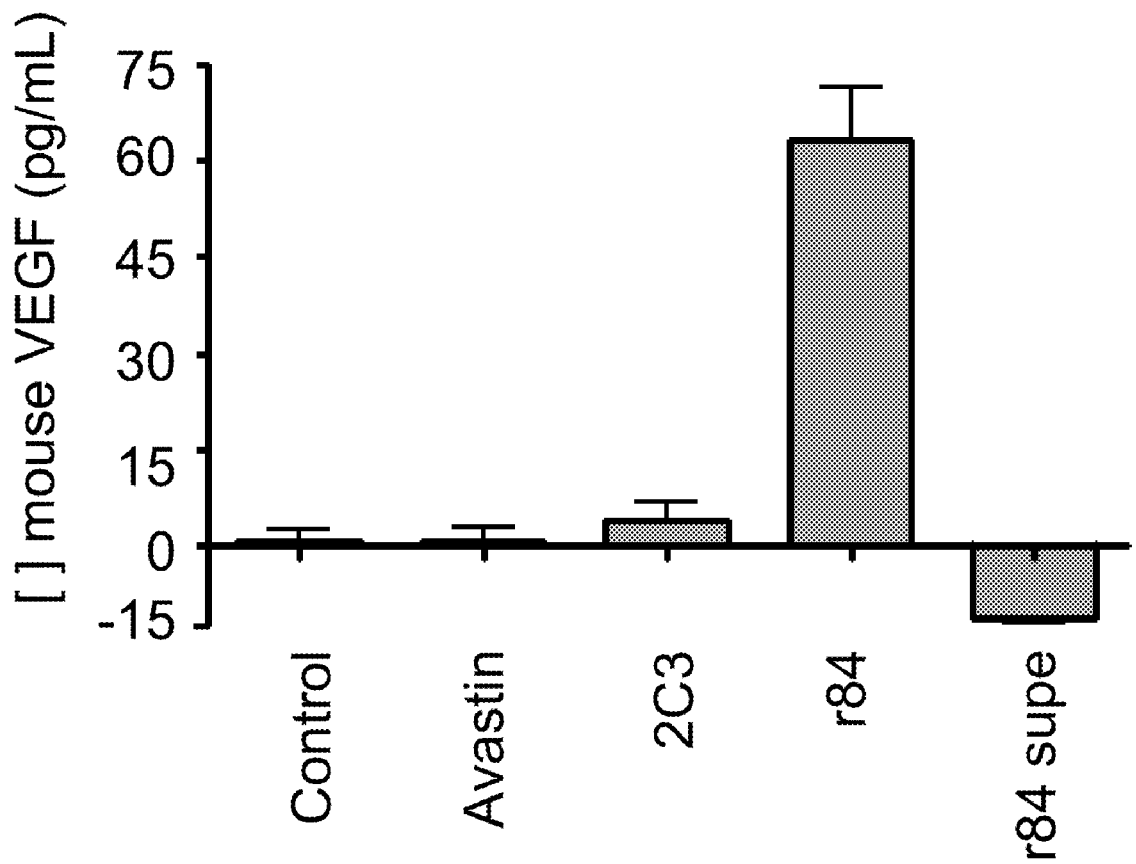
FIG. 24 shows the level of mouse VEGF in sera from tumor-bearing mice that were treated with control IgG, avastin, 2C3 or r84 (as indicated). The sera was collected and assayed by ELISA for the level of mouse VEGF using a kit from R&D systems. In addition, an aliquot of sera from r84 treated mice was pre-cleared with Protein G beads: Supernatant from the Protein G cleared sera (r84 supe) was also tested.

The results are shown in FIG. 24. The serum level of mouse VEGF is very similar between control, avastin and 2C3 treated animals. However, the serum level of mouse VEGF is dramatically higher in animals treated with r84. The difference in level of mouse VEGF between that observed with the control, avastin and 2C3 treated animals and that observed with the r84 treated animals is evidence that the control, avastin and 2C3 antibodies do not bind to mouse VEGF, whereas the r84 IgG antibody does bind to mouse VEGF.

The "r84" column in FIG. 24 shows the total amount of VEGF in the sera (i.e. free (biologically active) VEGF and VEGF complexed with r84). It is believed that the amount of free (biologically active) VEGF is an important parameter to be measured when anti-VEGF antibodies are used therapeutically, in particular to assess the effectiveness of the antibody at binding to VEGF (Loupakis et al., 2007). The "r84 supe" column shows the amount of free VEGF in the sera after the r84 immunoglobulin and r84 bound to murine VEGF were removed by incubation with protein G. FIG. 24 thus shows that free mouse VEGF levels in the serum of r84 treated animals are at baseline levels. Thus, the results in FIG. 24 not only demonstrate that r84 binds well to mouse VEGF but also demonstrate that r84 is very effective at depleting levels of free (biologically active) VEGF in serum, which is an important property for use in therapy.

The results discussed in Example 11E below using a syngeneic mouse mammary tumor model and showing that mouse chimeric r84 significantly improved the survival of tumor bearing mice is further validation that r84 binds and blocks mouse VEGF activity in vivo.

The results described above, show that the fully human r84/PGN311 antibody binds to both murine and human VEGF, whereas the 2C3 and Avastin antibodies do not bind to murine VEGF. This is an important advantage in terms of being able to use r84 to assess for example anti tumor activity both in mouse syngeneic models, i.e. where mouse tumor cells are administered to mice and in xenograft models, i.e. where human tumor cells are administered to mice.

In addition, the ability to bind both mouse and human VEGF as shown by r84/PGN311 but not by antibodies such as 2C3 and Avastin, means that the results shown by r84 in xenograft mouse models are more likely to be representative of the activity of r84 in human subjects, i.e. the results with r84 in pre-clinical mouse models are likely to be a good model for what will be seen when the antibody is put into patients. The reason for this is that antibodies which can only bind to human VEGF (e.g. Avastin and 2C3) will bind to VEGF produced by the human tumor cells but will not be able to bind to endogenous murine VEGF. This is of course unlike the situation in a human patient, in which VEGF produced by the tumor and endogenous VEGF would be present.

The potential disadvantage with such a situation is that an antibody which binds to human VEGF but not mouse VEGF might perform well in a mouse xenograft model but this would not be reflected by a similar performance in a human system where much more VEGF was present. In other words, the anti-tumor effect seen in a mouse xenograft system with an antibody which can only bind to human VEGF might look better than the clinical reality. In contrast, if you are working with an antibody that can bind to both human and mouse VEGF then this will bind to all forms of VEGF present in the mouse model system and is likely to be much more representative of the situation when the antibody is put into humans. This is an important advantage and one which is displayed by the antibodies of the invention.

Example 5

Binding Affinity of EJ173/112-Cl1 (r84/PGN311)

Figure 5:
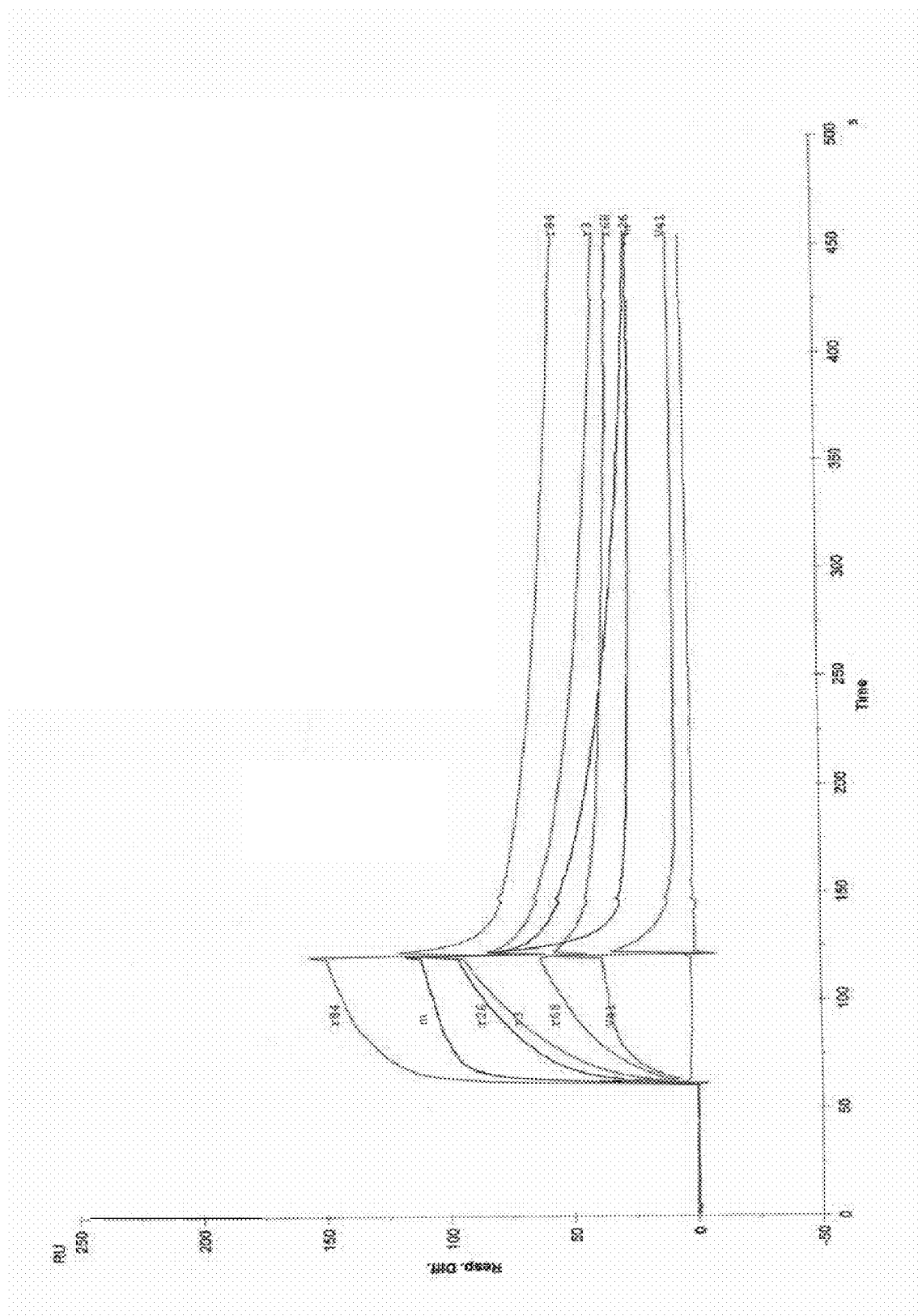
FIG. 5 shows the results of a Biacore assay used to assess the binding affinity of various scFv antibodies to immobilized VEGF-A. The binding curves are shown in FIG. 5 where it can be seen that the scFv form of EJ173/112-Cl1 (r84/PGN311) has a noticeably higher binding affinity than the single chain form of the mother clone (m). Other curves shown are labelled v41, r68, r3 and r26.

Biacore was used to assess the binding affinity of various antibodies. Different scFv antibodies at a concentration of 1 μM (micromolar) were flown over a CM5 chip with immobilized VEGF (amine coupling). The binding curves are shown in FIG. 5, where it can be seen that the scFv form of r84/PGN311 has a noticeably higher binding affinity than the single chain form of the mother clone (m).

In addition, initial studies were carried out to calculate the binding affinity of r84 IgG for VEGF, in which various concentrations of r84 IgG were flown over immobilized VEGF-A. In this regard, the binding affinity, expressed as the $K_d$, was calculated using the 1:1 binding model in the Biacore 3000 Evaluation software. The $K_d$ value obtained for r84 IgG in this initial study was calculated as $6.7 \times 10^{-9}$ M.

Subsequent affinity studies using BiaCore have yielded the affinity data shown in Table 2. For these experiments, the affinity of the IgG formats of EJ173/112-Cl1 (r84/PGN311) and 2C3 were determined by immobilizing 100 RU of human VEGF-A on a CM5 chip (Biacore). A dilution series (100 nM and 2-fold dilutions) of each IgG was flown over the VEGF-coated flow cell at a flow rate of 50 µl/min. The background signal from a flow cell coated with BSA was subtracted from the binding curves. The binding affinity expressed as the $K_D$ was calculated by the 1:1 Fitting model using software belonging to the Biacore T100 machine.

TABLE 2

| KD (M) | Coated VEGF (100 RU), 25° C. | Coated VEGF (100 RU), 37° C. |
|---|---|---|
| 2C3 | $1.24 \times 10^{-8}$ | $3.13 \times 10^{-7}$ |
| r84 | $3.21 \times 10^{-9}$ | $5.22 \times 10^{-9}$ |

The data shows that r84 binds to VEGF with superior affinity than 2C3 at both 25° C. and 37° C. It is reasonable to expect that this difference will lead to superior characteristics of r84 when compared to 2C3 in many clinical settings related to the treatment of angiogenic diseases, including cancer. The results at 37° C. are particularly interesting as this is the temperature the antibodies will be subjected to when used in vivo. It should also be noted, that in this experiment, Avastin showed an about 10 fold loss in affinity when comparing binding at 25° C. and 37° C., while r84 is less sensitive to temperature (reduction of KD not even 2-fold).

Example 6

Conversion of the scFv Form of r84/PGN311 to IgG Forms

A fully human IgG form of r84 was first constructed, as follows. The VH and VL chains of the scFv form of the r84/PGN311 antibody sequence as shown in FIG. 1 were taken and inserted into Lonza pCon IgG1a and kappa expression vectors and then combined to create one vector containing the entire r84 antibody gene. To make the full length IgG antibody, the vector was then transfected into CHO K1SV cells.

Once the growth conditions were optimized, the production rate of the cell line was approximately 5 milligrams of antibody per liter of cell culture. Although this expression method was effective, not all of the purified antibody was stable. After buffer optimization, the aggregation of the antibody was reduced, achieving 89.5% monomer and 10.5% aggregate.

The optimized growth conditions used are Invitrogen CD-CHO with 40 µM MSX, pH 6.8-7.0, 5% $CO_2$, 37° C. The optimized buffer used is 10 mM sodium phosphate, 25 mM sodium acetate, 50 mM Glycine at pH 5.5.

In order to further increase the stability of r84/PGN311, the amino acid sequence was analyzed. Comparing the r84 sequence to typical human antibody sequences indicated that the last amino acid of the VL chain of r84 was missing from the construct being used (i.e., the last Lysine residue, K, was missing). This residue was reintroduced. The DNA sequence was also changed (without changing the translated amino acid sequence) to be more "compatible" with CHO cells. The result was a new DNA sequence, and an amino acid sequence in which the VL chain ended with Lysine. The nucleotide and amino acid sequences of the new complete heavy and light chains of the IgG antibody are shown below:

```
r84/PGN311 IgG Heavy chain (nucleic acid sequence)                    (SEQ ID NO: 22)
CAGGTACAGCTTGTGCAGTCCGGAGCCGAGGTGAAGAAACCCGGAGCATCAGTGAAGGTTAGCT

GCAAGGCATCTGGTGGGACATTTTCCTCCTATGCCATCTCCTGGGTTCGGCAGGCTCCCGGACAG

GGCCTGGAGTGGATGGGGGGGTTCGATCCCGAAGACGGAGAGACCATTTACGCACAGAAGTTTC

AGGGTCGCGTGACCATGACCGAGGATACTTCTACCGACACAGCATATATGGAGCTCAGTAGCTT

GCGCTCCGAGGACACGGCTGTATATTACTGTGCCACTGGACGGAGCATGGTGCGCGGGGTAATC

ATCCCTTTCAACGGGATGGATGTATGGGGCCAAGGGACCACCGTGACAGTCAGCTCTGCCTCCA

CCAAGGGCCCATCGGTCTTCCCCCTGGCACCCTCCTCCAAGAGCACCTCTGGGGCACAGCGGC

CCTGGGCTGCCTGGTCAAGGACTACTTCCCCGAACCGGTGACGGTGTCGTGGAACTCAGGCGCC

CTGACCAGCGGCGTGCACACCTTCCCGGCTGTCCTACAGTCCTCAGGACTCTACTCCCTCAGCAG

CGTGGTGACCGTGCCCTCCAGCAGCTTGGGCACCCAGACCTACATCTGCAACGTGAATCACAAG

CCCAGCAACACCAAGGTGGACAAGAAAGTTGGTGAGAGGCCAGCACAGGGAGGGAGGGTGTCT

GCTGGAAGCCAGGCTCAGCGCTCCTGCCTGGACGCATCCCGGCTATGCAGCCCCATGCCAGGGC

AGCAAGGCAGGCCCCGTCTGCCTCTTCACCCGGAGGCCTCTGCCCGCCCCACTCATGCTCAGGGA

GAGGGTCTTCTGGCTTTTTCCCCAGGCTCTGGGCAGGCACAGGCTAGGTGCCCCTAACCCAGGCC

CTGCACACAAAGGGGCAGGTGCTGGGCTCAGACCTGCCAAGAGCCATATCCGGGAGGACCCTGC

CCCTGACCTAAGCCCACCCCAAAGGCCAAACTCTCCACTCCCTCAGCTCGGACACCTTCTCTCCT
```

```
CCCAGATTCCAGTAACTCCCAATCTTCTCTCTGCAGAGCCCAAATCTTGTGACAAAACTCACACA

TGCCCACCGTGCCCAGGTAAGCCAGCCCAGGCCTCGCCCTCCAGCTCAAGGCGGGACAGGTGCC

CTAGAGTAGCCTGCATCCAGGGACAGGCCCCAGCCGGGTGCTGACACGTCCACCTCCATCTCTTC

CTCAGCACCTGAACTCCTGGGGGGACCGTCAGTCTTCCTCTTCCCCCCAAAACCCAAGGACACCC

TCATGATCTCCCGGACCCCTGAGGTCACATGCGTGGTGGTGGACGTGAGCCACGAAGACCCTGA

GGTCAAGTTCAACTGGTACGTGGACGGCGTGGAGGTGCATAATGCCAAGACAAAGCCGCGGGA

GGAGCAGTACAACAGCACGTACCGTGTGGTCAGCGTCCTCACCGTCCTGCACCAGGACTGGCTG

AATGGCAAGGAGTACAAGTGCAAGGTCTCCAACAAAGCCCTCCCAGCCCCCATCGAGAAAACCA

TCTCCAAAGCCAAAGGTGGGACCCGTGGGGTGCGAGGGCCACATGGACAGAGGCCGGCTCGGC

CCACCCTCTGCCCTGAGAGTGACCGCTGTACCAACCTCTGTCCCTACAGGGCAGCCCCGAGAACC

ACAGGTGTACACCCTGCCCCCATCCGGGATGAGCTGACCAAGAACCAGGTCAGCCTGACCTGC

CTGGTCAAAGGCTTCTATCCCAGCGACATCGCCGTGGAGTGGGAGAGCAATGGGCAGCCGGAGA

ACAACTACAAGACCACGCCTCCCGTGCTGGACTCCGACGGCTCCTTCTTCCTCTACAGCAAGCTC

ACCGTGGACAAGAGCAGGTGGCAGCAGGGGAACGTCTTCTCATGCTCCGTGATGCATGAGGCTC

TGCACAACCACTACACGCAGAAGAGCCTCTCCCTGTCTCCGGGTAAATAG r84/PGN311 IgG Heavy chain (amino acid sequence)
QVQLVQSGAEVKKPGASVKVSCKASGGTFSSYAISWVRQAPGQGLEWMGGFDPEDGETIYAQKFQ          (SEQ ID NO: 24)

GRVTMTEDTSTDTAYMELSSLRSEDTAVYYCATGRSMFRGVIIPFNGMDVWGQGTTVTVSSASTKG

PSVFPLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMISRTPE

VTCVVVDVSHEDPEVKFNWYVDGVEVHNAKTKPREEQYNSTYRVVSVLTVLHQDWLNGKEYKCK

VSNKALPAPIEKTISKAKGQPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQKSLSLSPGK r84/PGN311 IgG Light chain (nucleic acid sequence)
GACATTCGGATGACTCAGTGTCCCTCCTCTTTGAGCGCTTCTGTGGGCGATAGGGTTACTACAC          (SEQ ID NO: 23)

TTGTCGAGCCTCTCAATCCATCAGGTCCTACTTGAACTGGTACCAGCAGAAACCCGGGAAAGCA

CCCAAGCTGCTTATTTACGCCGCCTCCTCCCTGCAATCCGGAGTGCCCTCCCGGTTCAGCGGCTC

CGGCTCTGGAACAGACTTTACCCTGACCATTTCTTCTTTGCAGCCTGAGGATTTTGCTACTTACT

ACTGTCAGCAGAGTTACTCCACCCCTTTGACATTCGGTGGTGGAACGAAAGTAGAAATTAAGCG

TACGGTGGCTGCACCATCTGTCTTCATCTTCCCGCCATCTGATGAGCAGTTGAAATCTGGAACTG

CCTCTGTTGTGTGCCTGCTGAATAACTTCTATCCCAGAGAGGCCAAAGTACAGTGGAAGGTGGA

TAACGCCCTCCAATCGGGTAACTCCCAGGAGAGTGTCACAGAGCAGGACAGCAAGGACAGCACC

TACAGCCTCAGCAGCACCCTGACGCTGAGCAAAGCAGACTACGAGAAACACAAAGTCTACGCCT

GCGAAGTCACCCATCAGGGCCTGAGCTCGCCCGTCACAAAGAGCTTCAACAGGGGAGAGTGTTA

G r84/PGN311 IgG Light chain (amino acid sequence)
DIRMTQSPSSLSASVGDRVTITCRASQSISSYLNWYQQKPGKAPKLLIYAASSLQSGVPSRFSGSGSGT          (SEQ ID NO: 25)

DFTLTISSLQPEDFATYYCQQSYSTPLTFGGGTKVEIKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLSSP

VTKSFNRGLEC
```

The new r84/PGN311 DNA sequences shown above were inserted into Lonza pCon IgG1a and kappa expression vectors and then combined to create one vector containing the entire r84/PGN311 antibody sequence. The vector was then transfected into CHO K1SV cells. Antibody production was increased to over 350 milligrams per liter with little cell culture optimization. Even more importantly, the antibody was much more stable, with monomer over 99%.

The nucleic acid sequences of the variable heavy and variable light chains of the IgG form of r84/PGN311 are also shown below:

```
r84/PGN311 IgG VH chain (nucleic acid sequence)
CAGGTACAGCTTGTGCAGTCCGGAGCCGAGGTGAAGAAACCCGGAGCATCAGTGAAGGTTAGCT    (SEQ ID NO: 26)

GCAAGGCATCTGGTGGGACATTTTCCTCCTATGCCATCTCCTGGGTTCGGCAGGCTCCCGGACAG

GGCCTGGAGTGGATGGGGGGGTTCGATCCCGAAGACGGAGAGACCATTTACGCACAGAAGTTTC

AGGGTCGCGTGACCATGACCGAGGATACTTCTACCGACACAGCATATATGGAGCTCAGTAGCTT

GCGCTCCGAGGACACGGCTGTATATTACTGTGCCACTGGACGGAGCATGGTGCGCGGGGTAATC

ATCCCTTTCAACGGGATGGATGTATGGGCCAAGGGACCACCGTGACAGTCAGCTCT r84/PGN311 IgG VL chain (nucleic acid sequence)
GACATTCGGATGACTCAGTCTCCCTCCTCTTTGAGCGCTTCTGTGGGCGATAGGGTTACTATCAC    (SEQ ID NO: 27)

TTGTCGAGCCTCTCAATCCATCAGCTCCTACTTGAACTGGTACCAGCAGAAACCCGGGAAAGCA

CCCAAGCTGCTTATTTACGCCGCCTCCTCCCTGCAATCCGGAGTGCCCTCCCGGTTCAGCGGCTC

CGGCTCTGGAACAGACTTTACCCTGACCATTTCTTCTTTGCAGCCTGAGGATTTTGCTACTTACT

ACTGTCAGCAGAGTTACTCCACCCCTTTGACATTCGGTGGTGGAACGAAAGTAGAAATTAAG
```

A murine chimeric version of the r84 antibody was also constructed. This was performed to attach the fully human variable region to a mouse constant region, providing a mouse antibody for use in certain preclinical studies in mice. The generation of the murine chimeric antibody was performed as described above for the fully human IgG, but attaching a nucleic acid sequence encoding the fully human variable region to a nucleic acid sequence encoding a mouse constant region.

The nucleotide and amino acid sequences of the new complete heavy and light chains of the murine chimeric IgG antibody are shown below:

```
R84/PGN 311 Chimeric Heavy Chain (nucleic acid sequence)
CAGGTGCAGCTGGTGGAATCTGGGGCTGAGGTGAAGAAGCGTGGGGCCTCAGTGAAGGTCTCCT    (SEQ ID NO: 31)

GCAAGGCTTCTGGAGGCACCTTCAGCAGCTATGCTATCAGCTGGGTGCGACAGGCCCCTGGACA

AGGGCTTGAGTGGATGGGAGGTTTTGATCCTGAAGATGGTGAAACAATCTACGCACAGAAGTTC

CAGGGCAGAGTCACCATGACCGAGGACACATCTACAGACACAGCCTACATGGAGCTGAGCAGCC

TGAGATCTGAGGACACGGCCGTGTATTACTGTGCAACAGGACGTTCTATGGTTCGGGGAGTCAT

TATACCTTTTAACGGTATGGACGTCTGGGGCCAAGGGACCACGGTCACCGTCTCCTCACGCGCCG

ATGCTGCACCGACTGTCTATCCACTGGCCCCTGTGTGTGGAGATACAACTGGCTCCTCGGTGACT

CTAGGATGCCTGGTCAAGGGTTATTTCCCTGAGCCAGTGACCTTGACCTGGAAGTCTGGATGCCT

GTCCAGTGGTGTGCACACCTTCCCAGCTGTCCTGCAGTCTGACCTCTACACCCTCAGCAGCTCAG

TGACTGTAACCTCGAGCACCTGGCCCAGCCAGTCCATCACCTGCAATGTGGCCCACCCGGCAAG

CAGCACCAAGGTGGACAAGAAAGAGCCCAGAGGGCCCACAATCAAGGCCTGTCCTCCATGCAAA

TGCCCAGCACCTAACCTCTTGGGTGGACCATCCGTCTTCATCTTCCCTCCAAAGATCAAGGATGT

ACTCATGATCTCCCTGAGCCCCATAGTCACATGTGTGGTGGTGGATGTGAGCGAGGATGACCCA

GATGTCCAGATCAGCTGGTTTGTGAACAACGTGGAAGTACACACAGCTCAGACACAAACCCATA

GAGAGGATTACAACAGTACTCTCCGGGTGGTCAGTGCCCTCCCCATCCAGCACCAGGACTGGAT
```

-continued

```
GAGTGGCAAGGAGTTCAAATGCAAGGTCAACAACAAAGACCTCCCAGCGCCCATCGAGAGAACC

ATCTCAAAACCCAAAGGGTCAGTAAGAGCTCCACAGGTATATGTCTTGCCTCCACCAGAAGAAG

AGATGACTAAGAAACAGGTCACTCTGACCTGCATGGTCACAGACTTCATGCCTGAAGACATTTA

CGTGGAGTGGACCAACAAGGGGAAAACAGAGCTAACTACAAGAACACTGAACCAGTCCTGGA

CTCTGATGGTTCTTACTTCATGTACAGCAAGCTGAGAGTGGAAAAGAAGAACTGGGTGGAAAGA

AATAGCTACTCCTGTTCAGTGGTCCACGAGGGTCTGCACAATCACCACACGACTAAGAGCTTCTC

CCGGACTCCGGGTAAATGA
```

R84/PGN 311 Chimeric Heavy Chain (amino acid sequence)
QVQLVQSGAEVKKPGASVKVSCKASGGTFSSYAISWVRQAPGQGLEWMGGFDPEDGETIYAQKFQ (SEQ ID NO: 32)

GRVTMTEDTSTDTAYMELSSLRSEDTAVYYCATGRSMVRGVIIPFNGMDVWGQGTTVTVSSRADA

APTVYPLAPVCGDTTGSSVTLGCLVKGYFPEPVTLTWNSGSLSSGVHTFPAVLQSDLYTLSSSVTVTS

STWPSQSITCNVAHPASSTKVDKKEPRGPTIKPCPPCKCPAPNLLGGPSVFIFPPKIKDVLMISLSPIVTC

VVVDVSEDDPDVQISWFVNNVEVHTAQTQTHREDYNSTLRVVSALPIQHQDWMSGKEFKCKVNNK

DLPAPIERTISKPKGSVRAPQVYVLPPPEEEMTKKQVTLTCMVTDFMPEDIYVEWTNNGKTELNYKN

TEPVLDSDGSYFMYSKLRVEKKNWVERNSYSCSVVHEGLHNHHTTKSFSRTPGK

R84/PGN 311 Chimeric Light Chain (nucleic acid sequence)
GATATCAGGATGACGCAGAGTCCAAGCTCTCTGTCTGCCTCTGTGGGGACAGGGTGACTATTA (SEQ ID NO: 33)

CTTGTGGGGCATCACAGAGTATCTCCAGCTACCTTAATTGGTACCAGGAAAAGCCCGGCAAAGC

CCCCAAATTGCTGATTTAGGCAGCCAGCTCCCTTCAGTCTGGCGTCCCTAGCCGCTTCTCCGGGA

GCGGATCAGGCACAGACTTTACGTTGACAATCAGTTCTCTGCAGCCGGAGGATTTTGCCACTTAC

TACTGTCAACAGAGCTACAGTACGCCTCTCACGTTTGGCGGTGGGACAAAGGTGGAAATCAAAC

GGGCTGATGCTGCACCGACTGTGTCCATCTTCCCACCATCCAGTGAGCAGTTAACATCTGGAGGT

GCCTCAGTCGTGTGCTTCTTGAACAACTTCTACCCCAAAGACATGAATGTCAAGTGGAAGATTGA

TGGCAGTGAACGACAAAATGGCGTCCTGAACAGTTGGACTGATCAGGACAGCAAAGACAGCACC

TACAGCATGAGCAGGACCCTCACGTTGACCAAGGACGAGTATGAACGACATAACAGCTATACCT

GTGAGGCCACTCACAAGACATCAACTTCACCCATTGTCAAGAGCTTGAACAGGAATGAGTGT

R84/PGN 311 Chimeric Light Chain (amino acid sequence)
DIRMTQSPSSLSASVGDRVTITCRASQSISSYLNWYQQKPGKAPKLLIYAASSLQSGVPSRFSGSGSGT (SEQ ID NO: 34)

DFTLTISSLQPEDFATYYCQQSYSTPLTFGGGTKVEIKRADAAPTVSIFPPSSEQLTSGGASVVCFLNNF

YPKDINVKWKIDGSERQNGVLNSWTDQDSKDSTYSMSSTLTLTKDEYERHNSYTCEATHKTSTSPIV

KSFNRNEC

Example 7

EJ173/112-Cl1 (r84/PGN311) Inhibits VEGFR2-Mediated Events

A. r84/PGN311 Inhibits Cell Signaling Via VEGFR2

Figure 6:
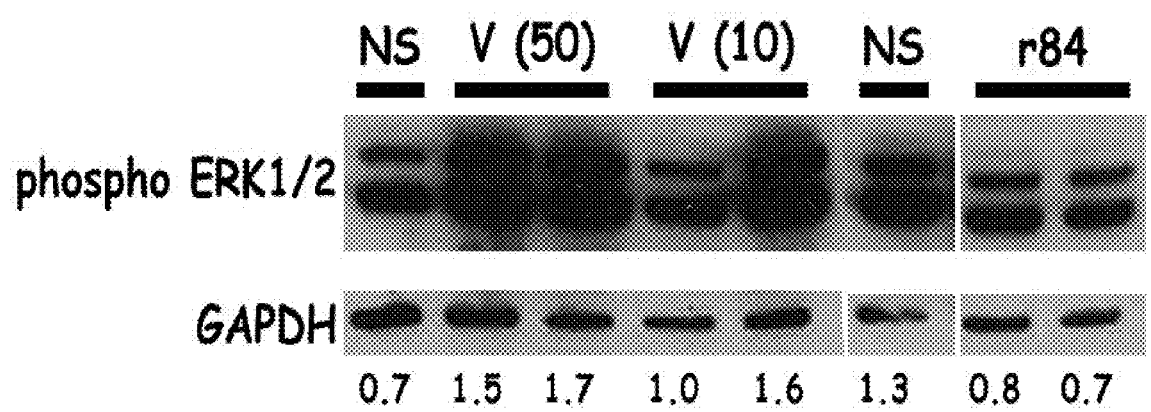
FIG. 6 shows that EJ173/112-Cl1 (r84/PGN311) IgG inhibits VEGF-mediated intracellular cell signalling via VEGFR2, which is shown by the results of an in vivo cell assay wherein it is shown that EJ173/112-Cl1 (r84) IgG inhibits phosphorylation of Erk1/2.

Cell assays were used to confirm the cellular performance of the selected antibody. VEGF stimulates intracellular signaling through the MAPK kinase pathway, which also involves the activation (through phosphorylation) of two proteins called MAPK1 and MAPK2, at 44 and 42 kilo Daltons, respectively. Another name for these proteins is Erk1 and Erk2. Antibodies that inhibit the interaction of VEGF with VEGFR2 can inhibit Erk1/2 activation as well.

bEnd.3 or PAE/KDR cell lines (obtained from Dr. Philip Thorpe at UT-Southwestern Medical Center, Dallas, Tex. and Dr. Johannes Waltenberger, Ulm University Medical Center, Ulm, Germany, respectively) express VEGFR2 on their surface, allowing them to be stimulated with VEGF. The cell lines were starved 48 hours for serum and growth factors, and next stimulated through the addition of 10 (V10) and 50 ng/ml VEGF165 (V50) in the presence or absence of the candidate in IgG format at 4 µg/ml. Non stimulated cells were the negative control (NS). After this stimulation, the cells were washed with ice cold PBS containing different phosphatase inhibitors before they were lysed. The centrifuged cell extract was run on a polyacrylamide gel, and the separated proteins were subsequently blotted to a nitrocellulose membrane. The blot was probed with an anti-phospho Erk1/2 antibody to monitor the inhibition of Erk1/2 phosphorylation (FIG. 6). Total Erk1/2 was also detected as an internal control of cell levels. The r84/PGN311 IgG clone inhibited phosphorylation of Erk1/2.

VEGF also stimulates intracellular signaling through the phospholipase Cγ (PLC-γ) pathway, which involves the activation (through phosphorylation) of protein at 155 kilo Daltons. Antibodies that inhibit the interaction of VEGF with VEGFR2 can inhibit PLC-γ activation as well.

Human dermal microvascular endothelial cell lines (HD-MEC, Lonza, catalog #CC2810) express VEGFR2 on their surface allowing them to be stimulated with VEGF. HDMECs were plated at 250,000 cells per well using 6-well plates. Cells were allowed to adhere overnight in 5% FBS ECM (endothelial cell media). The cells were then serum starved for 24 hours and stimulated through the addition of 50 ng/ml VEGF165 (+VEGF) in the presence of the antibodies, Avastin (bevacizumab, Presta et al., 1997), r84/PGN311, 2C3 (all in IgG format) or a control IgG antibody (Synagis (palivizumab), human anti-RSV, MedImmune). The IgGs were used at 90 µg/ml. Non stimulated cells were the negative control (NT). Avastin and r84/PGN311 were also added to cells in the absence of VEGF.

Figure 16A:
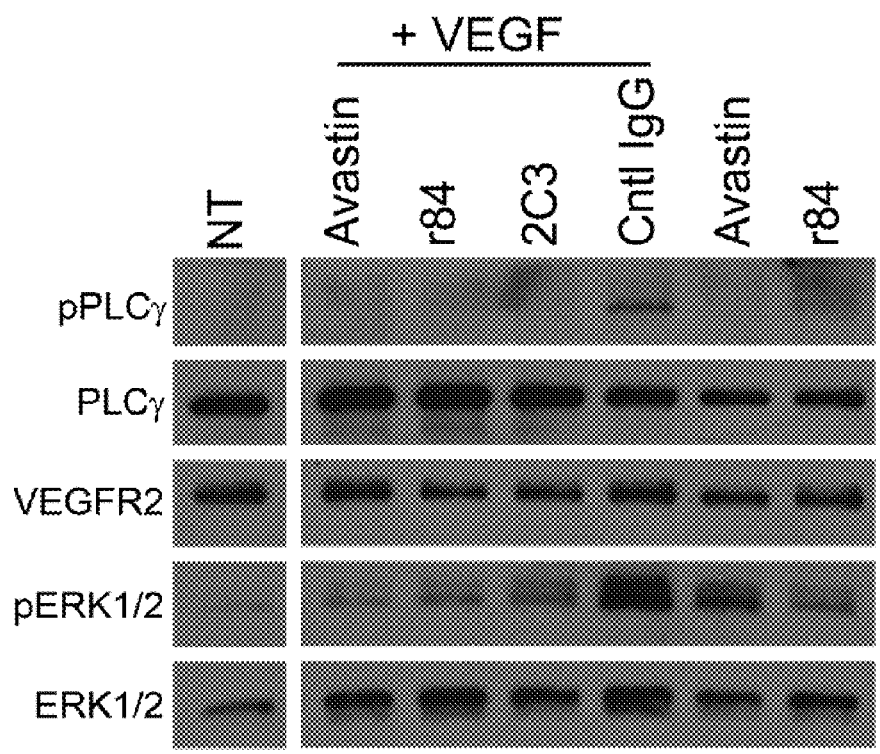
FIG. 16A and FIG. 16B show that r84/PGN311 selectively blocks the VEGFR2 pathway.

After this stimulation, the cells were washed with ice cold PBS containing different phosphatase inhibitors before they were lysed. The centrifuged cell extract was run on a polyacrylamide gel, and the separated proteins were subsequently transferred to a nitrocellulose membrane. The blots were probed with an anti-phospho Erk1/2 antibody (FIG. 16A, pERK1/2) and anti-phospho PLC-γ antibody (FIG. 16A, pPLC-γ) to monitor the inhibition of phosphorylation. Total Erk1/2 (FIG. 16A, ERK1/2) and PLC-γ (FIG. 16A, PLC-γ) were also detected as an internal control of cell levels. The expression of VEGFR2 on the HDMECs was detected with an antibody to VEGFR2 (FIG. 16A). FIG. 16A shows that the r84/PGN311 IgG antibody inhibited phosphorylation of both Erk1/2 and PLC-γ.

Figure 16B:
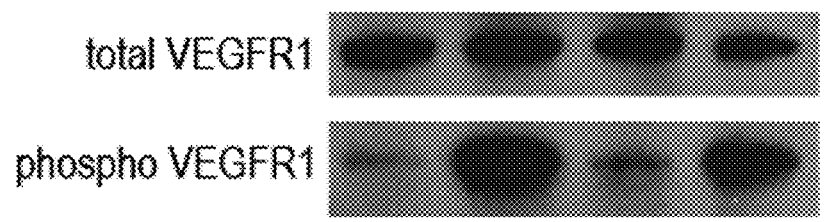

Using the same methodology as described above, PAE Flt1 cells expressing VEGFR1 were treated and starved in the same way before being left untreated or being stimulated through the addition of 50 ng/ml VEGF165 in the presence or absence of the antibodies, Avastin or r84/PGN311 (in IgG format). Blots were prepared and probed with an anti-phospho VEGFR1 antibody (FIG. 16B, phospho VEGFR1). Total VEGFR1 (FIG. 16B, total VEGFR1) was also detected as an internal control of cell levels. The data in FIG. 16B show that r84/PGN311 did not inhibit phosphorylation of VEGFR1, whereas the positive control, Avastin, did inhibit phosphorylation of VEGFR1. Together, FIG. 16A and FIG. 16B confirm that r84/PGN311 selectively blocks the VEGFR2 pathway.

B. r84/PGN311 Blocks VEGF-Induced Migration of VEGFR2-Expressing Cells

Figure 21:
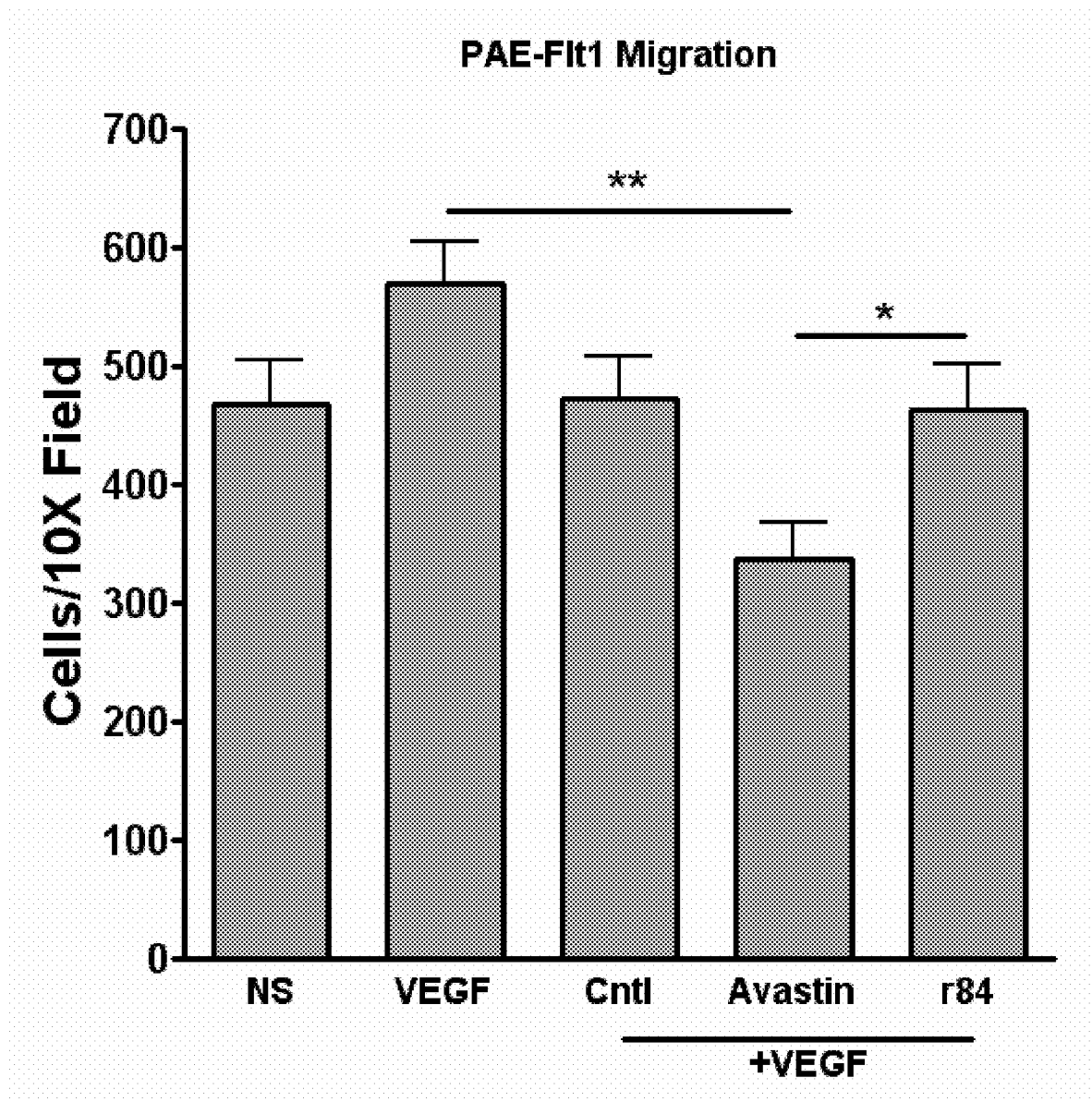
FIG. 21 shows that r84/PGN311 does not inhibit VEGF-induced migration of VEGFR1-expressing endothelial cells. PAE Flt1-expressing cells were either not stimulated (NS), or exposed to VEGF (VEGF) to stimulate migration (VEGF), and the ability of r84, Avastin (Avas) or control (Cntl) antibodies to inhibit VEGF-induced migration was tested. VEGF induces migration in comparison to not stimulated cells. Avastin significantly inhibits VEGF-induced migration, whereas r84 does not. Thus.

As expected, it was also confirmed that r84/PGN311 is able to potently inhibit VEGF-induced migration of VEGFR2-expressing endothelial cells. Examples of this activity are shown in FIG. 20A for HDMEC, and in FIG. 20B for PAE KDR-expressing cells. In each of these assays, it will be noted that r84 significantly inhibits VEGF-induced migration of VEGFR2-expressing cells and performs at least as well as Avastin. Comparative studies using VEGFR1-expressing PAE Flt1 cells showed that r84 does not inhibit VEGF-induced migration of VEGFR1-expressing cells (FIG. 21). In contrast, Avastin significantly inhibits VEGF-induced migration of VEGFR1-expressing cells (FIG. 21).

Example 8

EJ173/112-Cl1 (r84/PGN311) Binds to VEGF121

The binding of EJ173/112-Cl1 (r84/PGN311) scFv to a biologically active isoform of VEGF-A, VEGF121, was determined (R&D Systems HuVEGF121 298-VS-005/CF). 2 µg/ml of carrier free VEGF121 was plated on polystyrene immunoplates. 10 µg/ml of purified scFv was added and detected with an anti-c-myc tag mouse monoclonal antibody (Invitrogen) and HRP-conjugated secondary rabbit anti-mouse antibody.

Figure 7:
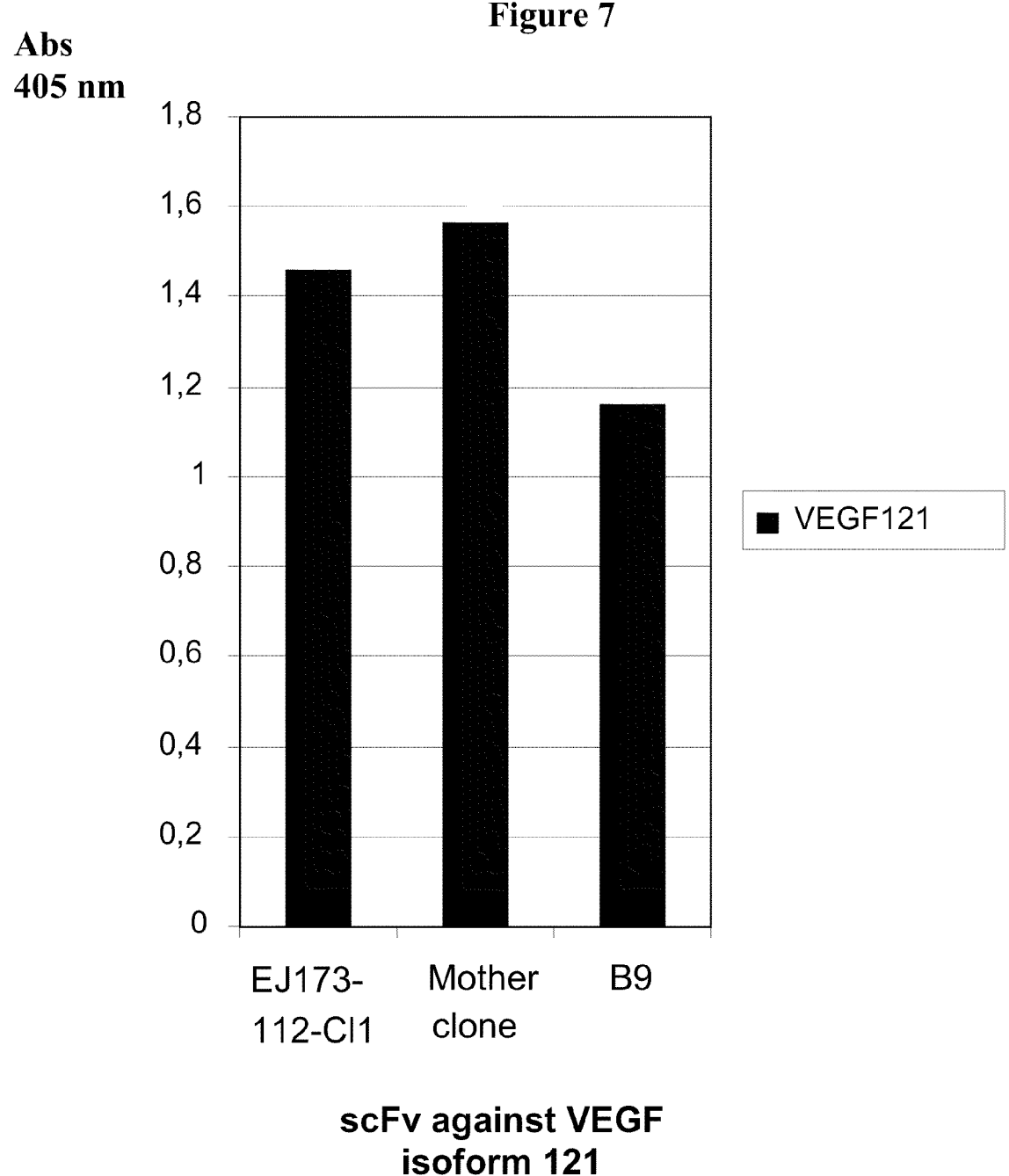
FIG. 7 shows that clone EJ173/112-Cl1 (r84/PGN311) recognizes the truncated 121 isoform of VEGF (VEGF121), which is shown by results from an ELISA assay.

The results showed that EJ173/112-Cl1 (r84/PGN311) (FIG. 7) was positive for VEGF121. The B9 murine scFv control recognized VEGF121, but at a lower level than the human variants.

Example 9

EJ173/112-CI1 (r84/PGN311) Blocks VEGF Binding to VEGFR2 but not VEGFR1

96-well ELISA plates (BD Falcon, cat #353279) were coated overnight at 4° C. with soluble HuVEGFR1/Fc (R&D Systems, cat #321-FL-050, CF) or HuVEGFR2 (R&D Systems 357-KD-050/CF) at a concentration of 1.0 µg/ml in 50 µl of sensitizing buffer/well. The wells were washed in wash buffer (WB) (TBSt (Tris buffer Saline, 0.1% Tween 20)) and blocked for 1 hr at 37° C. in 20% Aquablock (East Coast Biologics, Inc.) in WB. 50 µl of IgG at the appropriate concentration or WB was added to the wells followed immediately by VEGF-biotin at a final concentration of 100 ng/ml. The plate was incubated for 2 hr at RT, washed 3× and incubated for 1 hr at RT with 100 µl/well of peroxidase-conjugated avidin (JacksonImmuno Research) at a 1:7500 dilution in WB. After washing the plates 4×, signal was developed with TMB, stopped with acid and read at 450 nM.

Figure 8B:
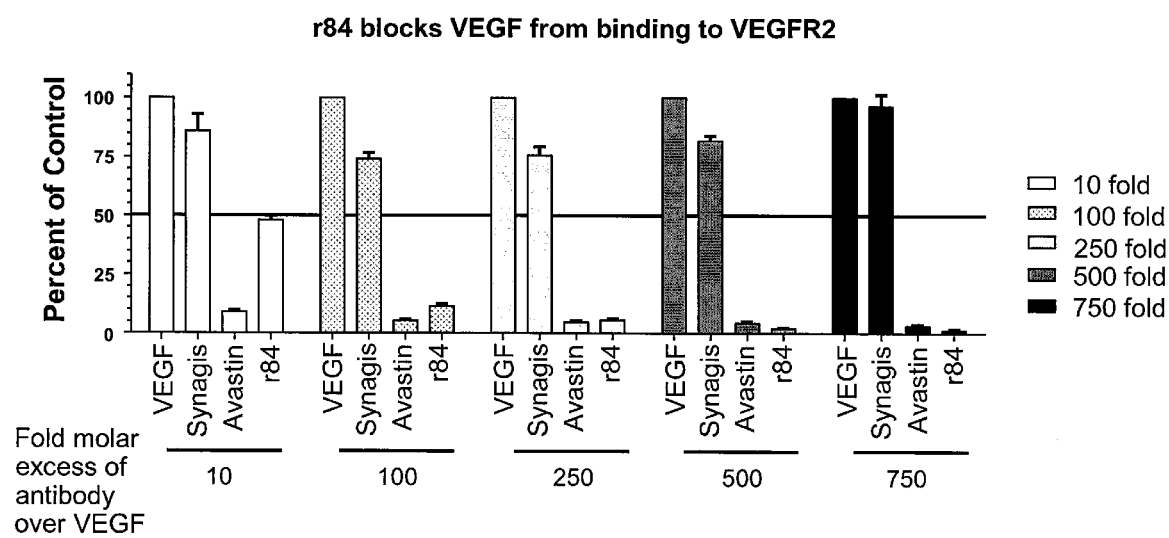

The results of these assays are shown in FIG. 8A and FIG. 8B. The signal of VEGF alone (VEGF) or VEGF in the presence of the indicated antibody was normalized to VEGF alone (100%). The mean+/−SEM is shown. N=12 (4 identical plates with each treatment performed in triplicate). A signal of less than 50% is considered significant inhibition of binding.

As shown in FIG. 8A and FIG. 8B, the results from this controlled study show that r84/PGN311 substantially blocks the interaction of VEGF with VEGFR2, but does not substantially block the interaction of VEGF with VEGFR1. Parallel studies using r84/PGN311 and Avastin (bevacizumab) (Presta et al., 1997) confirmed the known properties of Avastin as substantially blocking the interaction of VEGF with both VEGFR2 and VEGFR1. In addition, parallel studies using r84/PGN311 and the original murine 2C3 antibody showed that the differential in substantially blocking VEGF binding to VEGFR2, but not substantially blocking VEGF binding to VEGFR1, was even greater for r84 than for 2C3. This shows another surprising advantage of r84 over the 2C3 antibody.

Example 10

Tumor Associated Macrophages Express VEGFR2

A. Model

Orthotopic tumors were established in athymic nude mice (7-9 weeks) by injecting 1×10$^6$ MiaPaCa-2 cells into the tail of the pancreas. Tumors were allowed to develop for one week prior to initiating therapy.

B. Treatment

Animals were treated with control antibody (C44), or the murine 2C3 antibody via i.p. injection twice a week for three weeks. At sacrifice, tumors were excised and with the residual pancreas, weighed and were snap frozen or fixed in methyl carnoys for histochemical and immunohistochemical analysis.

C. IHC

Antibodies used for macrophage markers include CD86, CD14 and F4/80. VEGFR2 antibodies T014 and RAFL-2 were used.

D. Peritoneal Macrophage Isolation

Macrophages from tumor-bearing (TB) or non-tumor bearing (NTB) animals were isolated by sterile peritoneal lavage.

E. Results

Surprisingly, it was found that tumor associated macrophages (TAM) expressed VEGFR2. This explains the observation that 2C3 reduced infiltration of VEGFR2-positive TAM in vivo. The results are shown in FIGS. 10A, B and C.

Figure 10:
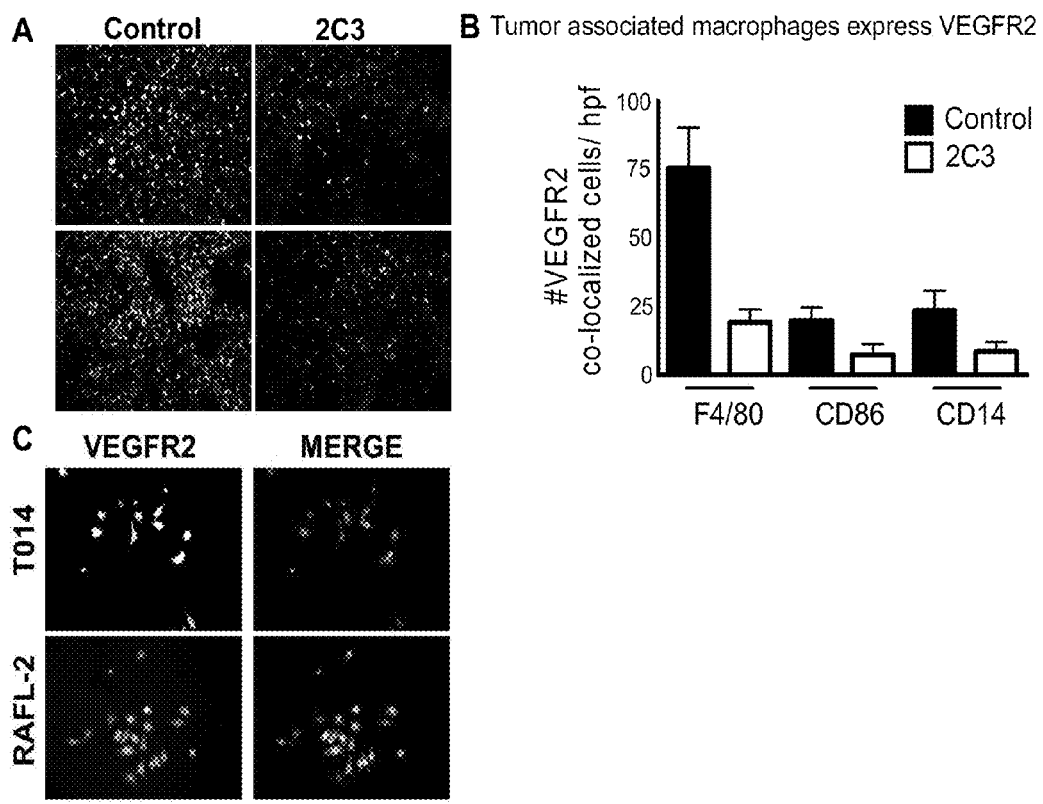
FIG. 10A, FIG. 10B and FIG. 10C show that tumor associated macrophages express VEGFR2.

In this regard, FIG. 10A depicts co-localization of T014 (VEGFR2 antibody) and F4/80 (macrophage marker) staining on tumor sections from control treated or 2C3 treated animals. 2C3 decreases macrophage infiltration. However, both groups demonstrate co-localization of VEGFR2 and macrophage markers. The number of cells double positive for one of three different macrophage markers and VEGFR2 is depicted in FIG. 10B. In FIG. 10C, peritoneal macrophages from tumor bearing animals demonstrate VEGFR2 using two different antibodies.

Example 11 r84/PGN311 Decreases Tumor Volume in Animals

Animal models were used to show that administration of the r84/PGN311 antibody leads to a significant reduction in tumor volumes.

Figure 11:
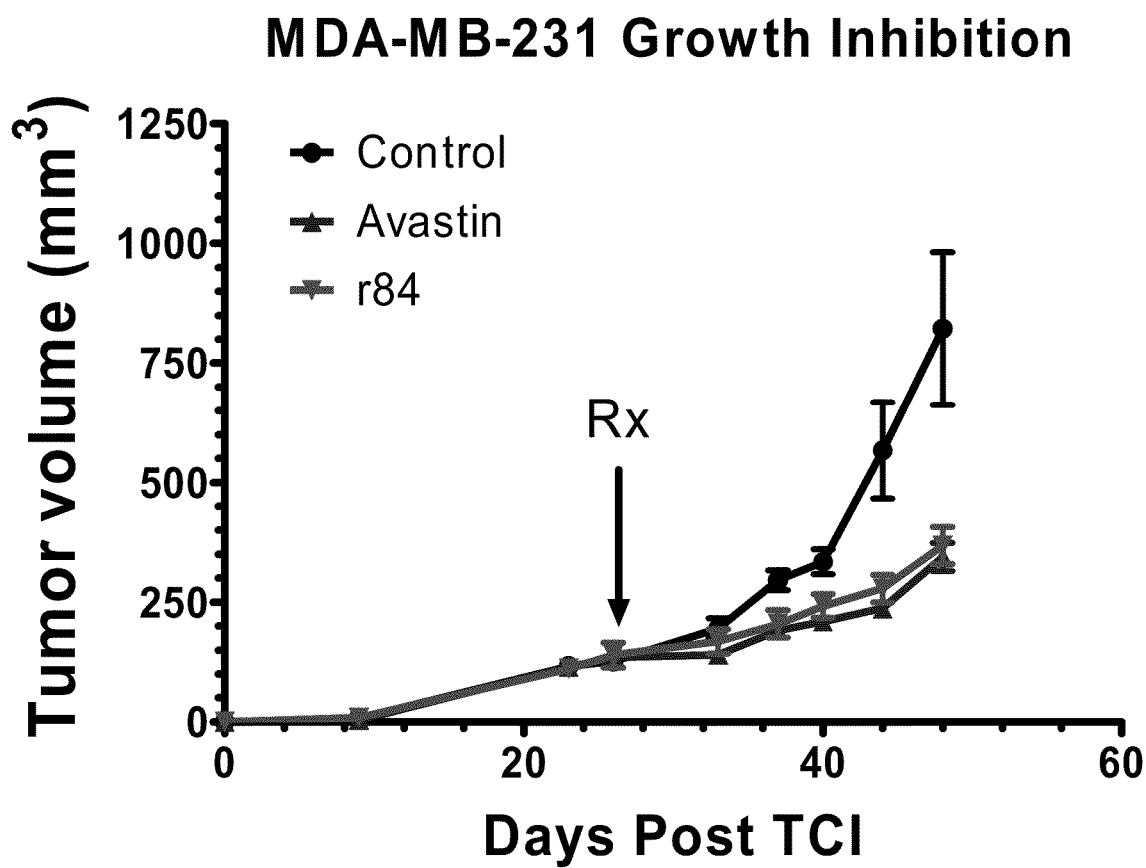
FIG. 11 shows that r84/PGN311 inhibits the growth of MDA-MB-231 tumors.
Figure 12:
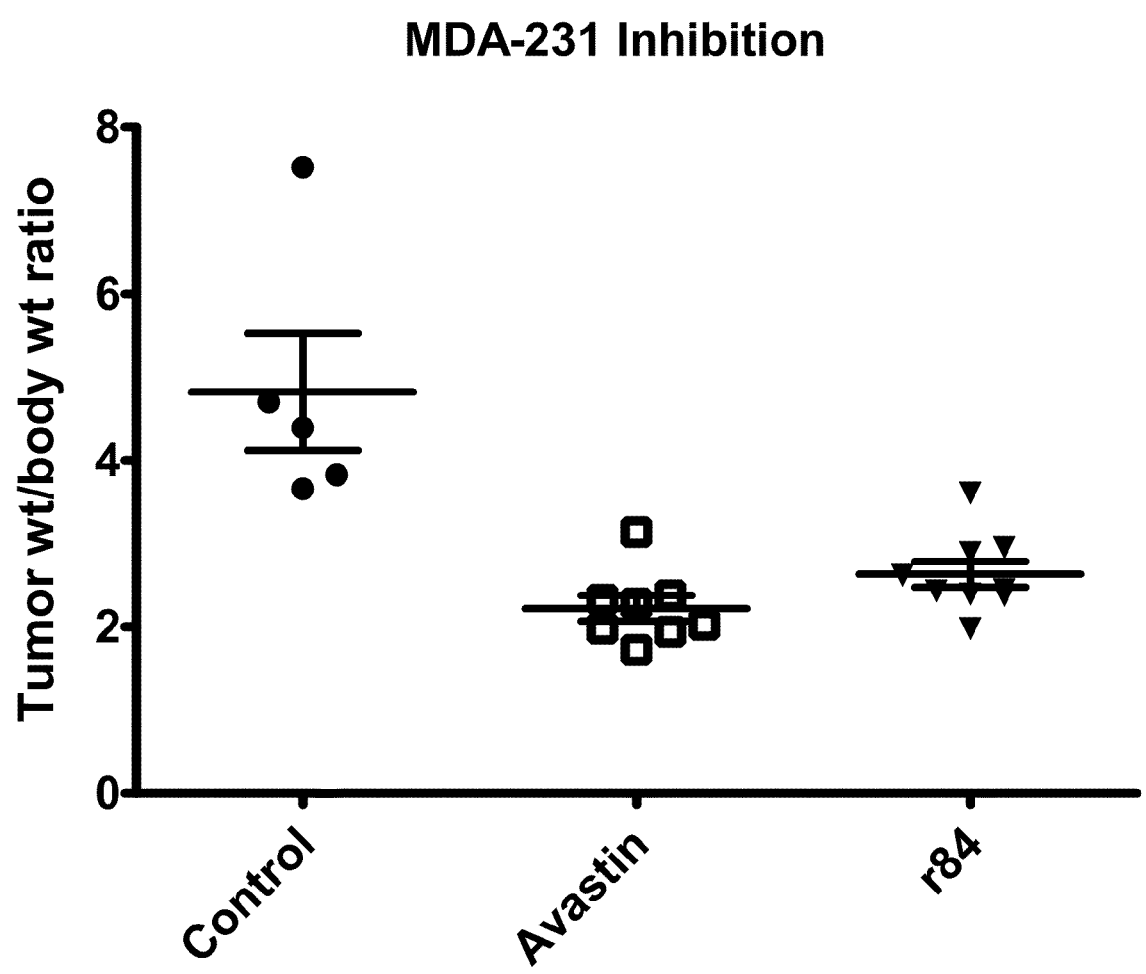
FIG. 12 shows results from the same study as shown in FIG. 11, except that FIG. 12 shows the tumor weight/body weight ratio for individual animals in each group. Avastin and r84/PGN311 treated mice have tumor weight/body weight ratios that are significantly smaller than control treated animals.

A. MDA-MB-231 Breast Cancer Cell Tumor Model 5 million MDA-MB-231 cells were injected into the mammary fat pad of SCID mice. Tumors developed for 26 days prior to the start of therapy. At this time, animals were randomly assigned to treatment groups. 100 µl of saline (control, n=5) or 250 µg in 100 µl of buffer of Avastin IgG (n=8) or r84/PGN311 IgG (n=9) was given by subcutaneous injection 2× per week. The results are shown in FIG. 11, which displays mean tumor volume+/−SEM. Avastin and r84 treated mice have tumor volumes that are significantly smaller than control treated animals. FIG. 12 displays tumor weight/body weight for individual animals in each group. Avastin and r84 treated mice have tumor/body ratios that are significantly smaller than control treated animals. The results in FIG. 11 and FIG. 12 show that r84 performs essentially as effectively as Avastin.

B. A673 Rhabdomyosarcoma Tumor Model $1.0 \times 10^6$ A-673 cells (a human rhabdomyosarcoma cell line-ATCC CRL-1598) were injected subcutaneously into 22 nu/nu (NCI) mice. The mice were divided into 3 groups (n=8/grp for 2C3 and r84/PGN311, n=6/control grp) and therapy was initiated 5 days post tumor cell injection (TCI). Therapy consisted of 50 µg of the indicated IgG injected ip 2×/week. Animal weight and tumor volume was monitored. The control antibody was Synagis (human anti-RSV).

Figure 13:
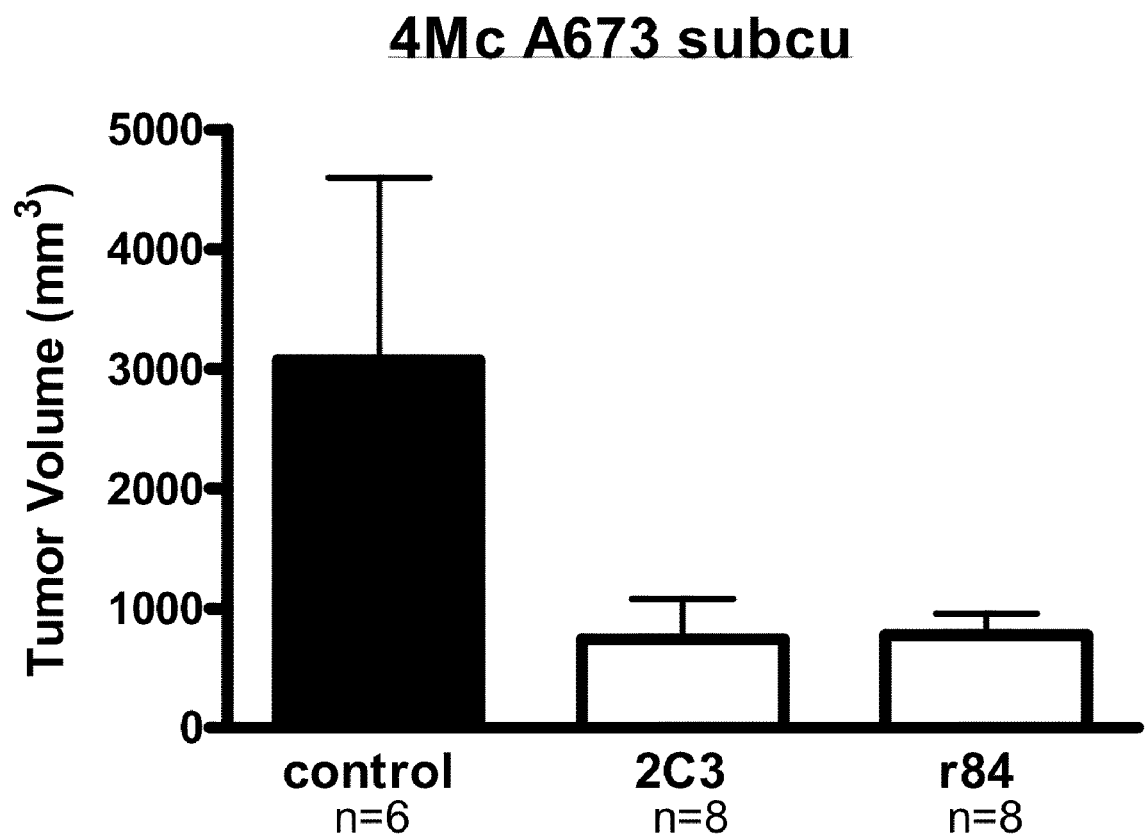
FIG. 13 shows that r84/PGN311 inhibits the growth of A673 tumors.

The mice received 8 injections of therapy between day 5 and day 29 post TCI. FIG. 13 shows the tumor volume of each group on day 30 post TCI. One-way ANOVA indicates that the groups are statistically different; furthermore 2C3 and r84/PGN311 are different from control by "Dunnett's Multiple Comparison Test" (p<0.05). It is clear from these results that 2C3 and r84 reduced tumor growth at the modest dose of 50 µg/injection 2×/week. r84 displayed activity that was essentially the same as 2C3. The overall conclusion from this animal study is that 2C3 and r84 are effective at controlling the growth of A673 tumors.

C. Human Non-Small Cell Lung Cancer (NSCLC) Models

Further in vivo animal models were used to show that administration of the r84/PGN311 antibody leads to significant reductions in tumor growth.

Figure 17C:
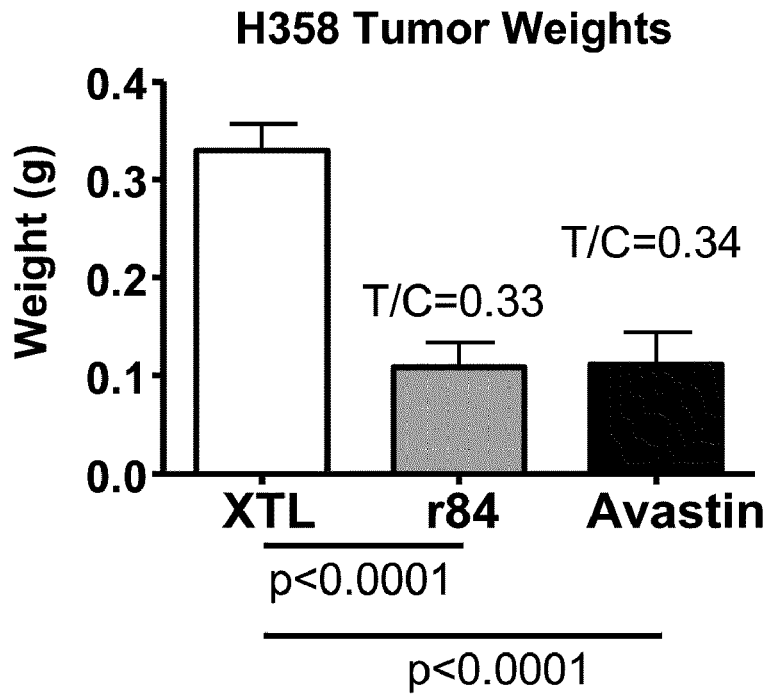
Figure 17D:
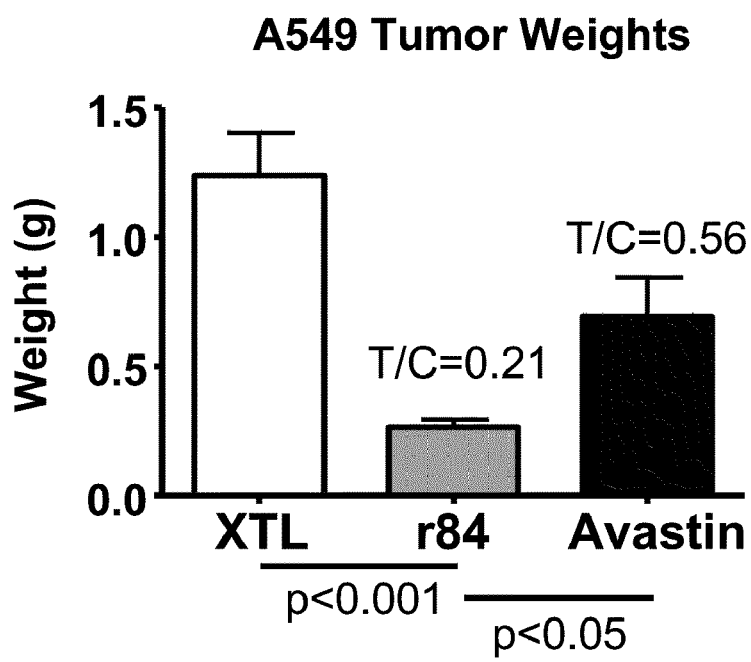

The ability of r84/PGN311 to inhibit tumor growth in vivo was tested in four different human non-small cell lung cancers (NSCLC), H1299 (ATCC CRL-5803), H460 (ATCC HTB-177), H358 (ATCC CRL-5807) and A549 (ATCC CCL-185). SCID mice (n=25 per cell line) were injected subcutaneously with $2.5 \times 10^6$ cells and therapy was initiated 1 day post TCI. Therapy consisted of 250 µg of Synagis or XTL (negative control), Avastin IgG (positive control) or 500 µg of r84/PGN311 IgG delivered intra peritoneally (i.p.) 2 times each week. Therapy was given until the mice were sacrificed. The H460 mice were sacrificed after 40 days, the H1299 mice were sacrificed after 48 days, the A549 mice were sacrificed after 55 days, and the H358 mice were sacrificed after 83 days. The tumor weights were measured, and the results are shown in FIG. 17A (for H460), FIG. 17B (for H1299), FIG. 17C (for H358) and FIG. 17D (for A549) as mean tumor weight+/−SEM. The ratios of the treated tumor weights over the control tumor weights are also shown in FIG. 17A, FIG. 17B, FIG. 17C and FIG. 17D ("T/C").

FIG. 17A, FIG. 17B, FIG. 17C and FIG. 17D show that the Avastin and r84/PGN311 treated animals have tumor weights that are significantly smaller than control treated animals. r84/PGN311 performs better than Avastin in the H460 (FIG. 17A), H1299 (FIG. 17B) and the A549 (FIG. 17D) models. r84/PGN311 performs at least as effectively as Avastin in the H358 assay (FIG. 17C).

D. Panc1 Pancreatic Cancer Cell Tumor Model

Figure 22:
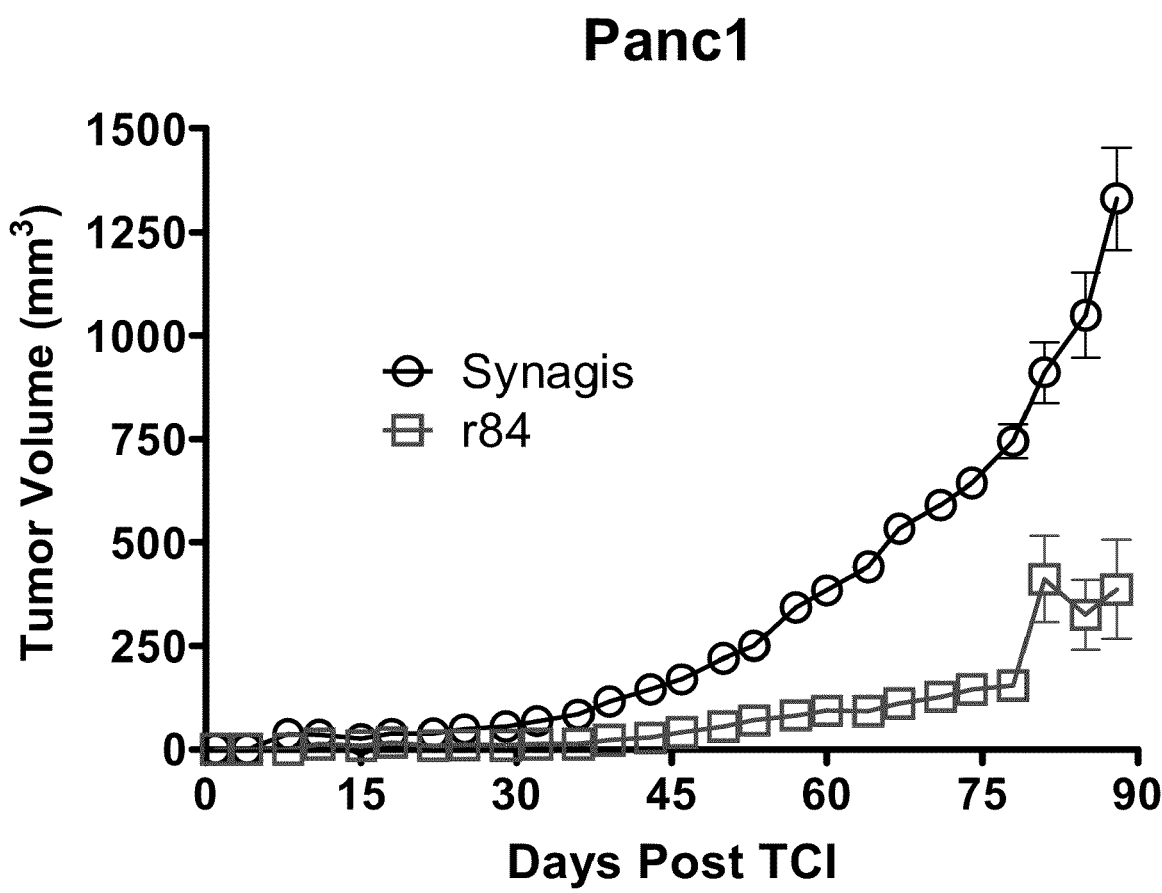
FIG. 22 shows that r84/PGN311 markedly reduces the growth of Panc1 pancreatic tumor cells in mice. Mice bearing Panc1 pancreatic adenocarcinoma cells were given either r84/PGN311 IgG or Synagis (negative control). Tumor volumes are depicted over the time course of treatment. Thus.

Mice bearing pancreatic adenocarcinoma cells, Panc1, were given either r84/PGN311 IgG or Synagis as a negative control. Therapy was given until the mice were sacrificed. The tumor volumes were measured and the results are shown in FIG. 22. It can be seen that r84/PGN311 markedly reduces Panc1 tumor growth in comparison to control (FIG. 22).

E. 4T1 Mammary Tumor Model

Figure 23:
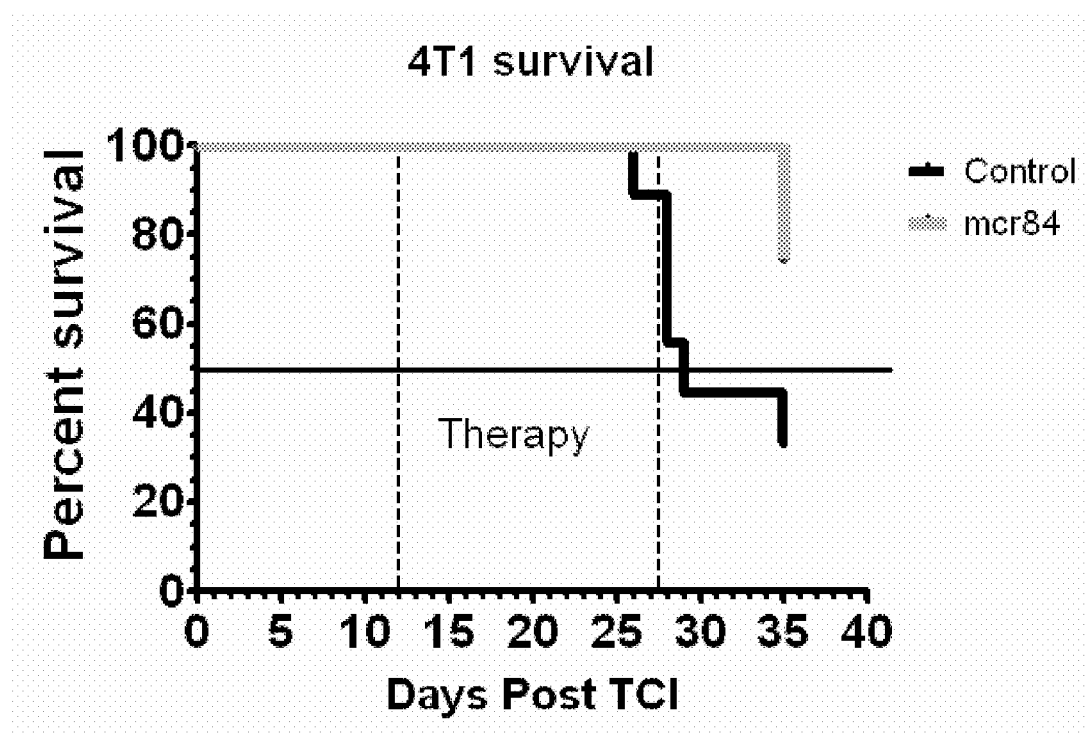
FIG. 23 shows that the mouse chimeric version of r84/PGN311 prolongs survival of mice bearing syngeneic 4T1 mammary tumors. Murine 4T1 tumors were injected orthotopically into Balb/C mice (n=8 mice per group). Either the mouse chimeric version of r84/PGN311 (mcr84, red line) or control (Control, black line) antibody was administered via i.p. injection twice a week starting on day 12 and continuing for 3 weeks. r84/PGN311 prolonged survival in comparison to control.

Controlled studies using the mouse chimeric version of r84/PGN311 showed that the r84 antibody is able to prolong the survival of mice bearing syngeneic 4T1 mammary tumors. As shown in FIG. 23, treatment with mouse chimeric r84/PGN311 resulted in the mice surviving longer than the animals in the control treated group.

Figure 14:
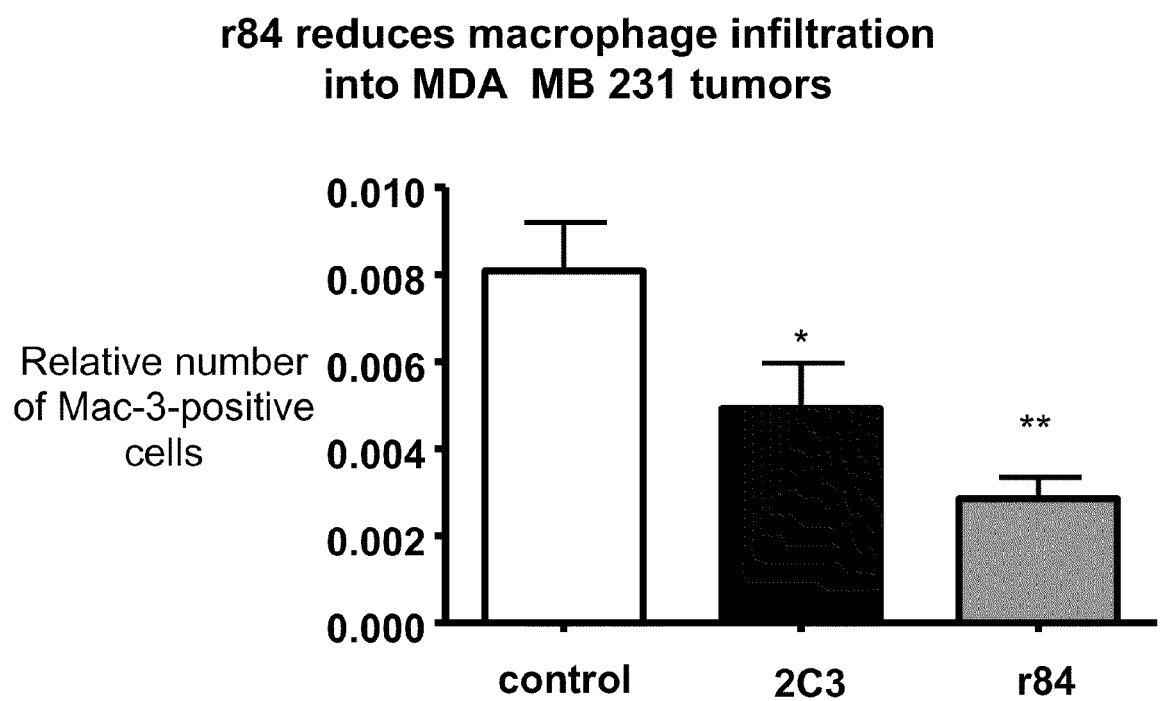
FIG. 14 shows that r84/PGN311 significantly reduces infiltration of tumor associated macrophages. Tumors were taken from mice with MDA-MB-231 tumor cells and sectioned and stained with antibodies to a macrophage marker (Mac-3). Three tumors from control animals and three tumors each from r84 and 2C3 treated animals were analyzed and 5 images from each tumor were studied.
Figure 15:
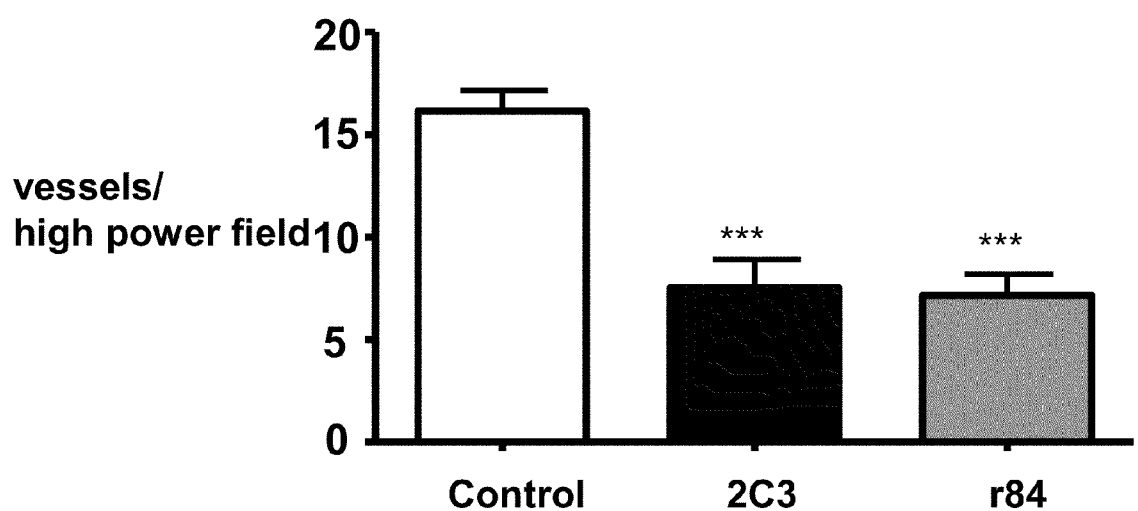
FIG. 15 shows that r84/PGN311 significantly reduces microvessel density in MDA-MB-231 animal model tumors. Tumors were taken from mice with MDA-MB-231 tumor cells and sectioned and stained with antibodies to mouse endothelial cells (MECA-32). Three tumors from control animals and three tumors each from r84 and 2C3 treated animals were analyzed and 5 images from each tumor were studied.

Example 12 r84/PGN311 Reduces Microvessel Density and Infiltration of Tumor Associated Macrophages Tumors were taken from the mice used in the MDA-MB-231 animal model study described in Example 11 and also from mice which had been treated in parallel in accordance with the same regimen with 250 µg in 100 µl of buffer of 2C3 IgG. These tumors were sectioned and stained with antibodies to mouse endothelial cells (MECA-32) and to a macrophage marker (Mac-3). Three tumors from control animals and three tumors each from r84/PGN311 and 2C3 treated animals were analyzed and 5 images from each tumor were studied. The results are shown in FIG. 14 and FIG. 15, which show that tumors from r84 and 2C3 treated animals showed significantly reduced number of blood vessels/high power field (MECA-32, p<0.0001, FIG. 15) and significantly reduced expression of the macrophage marker (Mac-3, p<0.01 for r84, FIG. 14). This is evidence that r84 significantly reduces microvessel density and infiltration of tumor associated macrophages and that r84 has a more pronounced effect than 2C3 on reducing the infiltration of tumor associated macrophages (FIG. 14).

Example 13

Effects of r84/PGN311 on Cells Infiltrating Tumors

A. Polymorphonuclear Leukocytes

Tumors were taken from the mice used in the MDA-MB-231 animal model study described in Example 11 and also from mice which had been treated in parallel in accordance with the same regimen with 250 µg in 100 µl of buffer of 2C3 IgG.

The study has shown that tumors from r84 and 2C3 treated animals have significantly increased polymorphonuclear leukocyte (PMN) infiltration in comparison to control. This effect was statistically significant for the r84 and 2C3 antibodies. Although Avastin (bevacizumab) also increased PMN infiltration into MDA-MB-231 tumors in comparison to control, in contrast to r84 and 2C3, this increase was not statistically significant for Avastin.

B. CD11b+/Gr1+ Cells

Further studies in MDA-MB-231 tumor-bearing mice have shown that significantly less CD11b/Gr1 double positive cells infiltrate the tumors in r84-treated animals as opposed to control. In comparative studies, neither the 2C3 antibody nor Avastin showed a statistically significant decrease in CD11b+/Gr1+ infiltration, although some reduction was measurable in Avastin-treated animals.

Tumors were taken from the mice used in the MDA-MB-231 animal model study described in Example 11 and also from mice which had been treated in parallel in accordance with the same regimen with 250 µg in 100 µl of buffer of 2C3 IgG.

The study has shown that significantly less CD11b+/Gr1+ double positive cells infiltrate the tumors in r84-treated animals as opposed to control (as assessed by ANOVA, p<0.01, shown by ** in FIG. 25). The decrease in the number of double-positive cells was 39%.

In comparative studies, 2C3 did not show a statistically significant decrease in CD11b+/Gr1+ infiltration (FIG. 25).

The reduced infiltration of myeloid derived suppressor cells CD11b+/Gr1+ is of special interest, as cells expressing both markers have recently been associated with mediation of tumor refractoriness to anti-VEGF therapy (Shojaei et al., 2007). Myeloid-derived suppressor cells (CD11b+Gr1+) are also an important contributor to tumor progression. In the tumor microenvironment these cells secrete immunosuppressive mediators and induce T-lymphocyte dysfunction (Gabrilovich et al., 2001; Serafini et al., 2004).

As the tumor infiltration of CD11b+/Gr1+ cells is least pronounced/significantly lower in the r84-treated animals, it suggests that treatment with r84 is less prone to the development of drug resistance or refractoriness to anti-VEGF therapy than treatment with other drugs targeting VEGF.

This ability to reduce infiltration of CD11b+/Gr1+ cells into tumors is thus a further advantageous property shown by the r84/PGN311 antibody and is a property which has a potential importance for therapeutic applications of r84/PGN311. Furthermore, this property is not shown by the 2C3 antibody and only at a more reduced level by Avastin.

Example 14 r84/PGN311 Reduces Lymphatic Density in Tumors

Mice with MDA-MB-231 tumors were treated with r84/PGN311 or control antibody and tumor sections analyzed to show the lymphatic vessels within the tumors. The results are presented in FIG. 18A, FIG. 18B and FIG. 18C, which show that the lymphatic vessel density in r84-treated tumors is significantly lower than in control tumors.

In particular, immunofluorescence staining of frozen MDA-MB-231 tumor sections was first performed to identify lymphatic vessels via the lymphatic markers, podoplanin and Prox1. These results are set forth in FIG. 18A, which shows podoplanin (green), Prox1 (red) and the merged images, thus identifying lymphatic vessels in control (top panels) and r84-treated tumors (bottom panels). LYVE-1 staining was also performed in consecutive MDA-MB-231 tumor sections. As shown in FIG. 18B, these results indicate that the pattern of lymphatic vessels in MDA-MB-231 tumor sections stained for LYVE-1 is similar to that observed for podoplanin and Prox1 (FIG. 18A).

To determine whether the density of lymphatic vessels in control and r84-treated tumors was different, the entire area of each LYVE-1 stained tumor section was examined at low magnification and the percent of LYVE-1 positive area was determined for each field using NIS-Elements imaging software. The ten fields with the highest LYVE-1 positive percent area were averaged together to yield a final score for each tumor and group means were tested for significance by an unpaired student's t-test. As depicted in FIG. 18C, the percent of LYVE-1 positive area of control tumors (7.03±1.013; n=6) was significantly greater than r84 treated tumors (2.23±0.986; n=5), with P=0.0042. These results, showing that treatment with r84/PGN311 significantly lowers tumor lymphatic vessel density, thus support the use of the human antibodies of the invention to inhibit lymphangiogenesis.

Example 15

Chronic Administration of r84/PGN311 Does not Induce Toxicity in Mice

Non-tumor bearing and tumor-bearing mice were used in these studies.

$5 \times 10^6$ Panc-1 cells (human pancreatic cancer cell line, ATCC CRL-1469), were injected into 10 SCID mice. On Day 1 post TCI, 5 tumor-bearing and 5 non-tumor bearing mice were injected i.p. with 500 µg of Synagis or r84/PGN311 IgG. Therapy was given by injection 2 times per week and was continued for 12 weeks, after which the mice were sacrificed. At the time of sacrifice blood was taken and analyzed for standard blood chemistry. The liver, kidney, and thyroid were also harvested for histological evaluation.

These analyses showed that there were no overt changes in histology of any tissue examined by H&E staining (this examination was carried out in a blinded fashion by a pathologist who specializes in mouse tissue histology). Furthermore, blood chemistry was analyzed for 22 different analytes and no significant changes between control, naïve mice, or r84 treated animals were found.

* * *

While the compositions and methods of this invention have been described in terms of preferred embodiments, it will be apparent to those of skill in the art that variations may be applied to the composition, methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams and Oldham, "In: Monoclonal Antibody Therapy of Human Cancer", Foon and Morgan (Eds.), Martinus Nijhoff Publishing, Boston, 103-120, 1985.

Aiello, Pierce, Foley, Takagi, Chen, Riddle, Ferrara, King, Smith, "Suppression of retinal neovascularization in vivo by inhibition of vascular endothelial growth factor (VEGF) using soluble VEGF-receptor chimeric proteins," Proc. Natl. Acad. Sci., USA, 92:10457-10461, 1995.

Alderson, McGowan, Baldridge, Probst, "TLR4Agonists as Immunomodulatory Agents", J. Endoxin Res., 12(5):313-319, 2006 Alon, Hemo, Itin, Pe'er, Stone, Keshet, Vascular endothelial growth factor acts as a survival factor for newly formed retinal vessels and has implications for retinopathy of prematurity," Nature Med., 1: 1024-1028, 1995.

Altschul, Madden, Schaffer, Zhang, Zhang, Miller, Lipman, "Gapped BLAST and PSI-BLAST: a new generation of protein database search programs", Nucleic Acids Res., 25:3389-3402, 1997.

Anthony, Wheeler, Elcock, Pickett, Thomas, "Short report: identification of a specific pattern of vascular endothelial growth factor mRNA expression in human placenta and cultured placental fibroblasts", Placenta, 15:557-61, 1994.

Apetoh, Ghiringhelli, Tesniere, Obeid, Ortiz, Criollo, Mignot, Maiuri, Ullrich, Saulnier, Yang, Amigorena, Ryffel, Barrat, Saftig, Levi, Lidereau, Nogues, Mira, Chompret, Joulin, Clavel-Chapelon, Bourhis, Andre, Delaloge, Tursz, Kroemer, Zitvogel, "Toll-Like Receptor 4-Dependent Contribution of the Immune System to Anticancer Chemotherapy and Radiotherapy", Nat. Med., 13:1050-1059, 2007.

Arbabi-Ghahroudi, Desmyter, Wyns, Hamers, Muyldermans, "Selection and identification of single domain antibody fragments from camel heavy-chain antibodies", FEBS Lett., 414:521-526, 1997;

Asahara, Murohara, Sullivan, Silver, van der Zee, L1, Witzenbichler, Schatteman, Isner, "Isolation of putative progenitor endothelial cells for angiogenesis," Science, 275 (5302):964-967, 1997.

Asano, Yukita, Matsumoto, Kondo, Suzuki, "Inhibition of tumor growth and metastasis by an immunoneutralizing monoclonal antibody to human vascular endothelial growth factor/vascular permeability factor," Cancer Res., 55:5296-5301, 1995.

Asano, Yukita, Matsumoto, Hanatani, Suzuki, "An anti-human VEGF monoclonal antibody, MV833, that exhibits potent anti-tumor activity in vivo," Hybridoma, 17:185-90, 1998.

Baca, Presta, O'Connor, Wells, "Antibody humanization using monovalent phage display," J. Biol. Chem., 272(16): 10678-84, 1997.

Baldari, Murray, Ghiara, Cesareni, Galeotti, "A Novel Leader Peptide Which Allows Efficient Secretion of a Fragment of Human Interleukin 1 Beta in Saccharomyces Cerevisiae", EMBO J., 6:229-234, 1987.

Barbas, Kang, Lerner and Benkovic, "Assembly of combinatorial antibody libraries on phage surfaces: the gene III site," Proc. Natl. Acad. Sci. USA, 88(18):7978-7982, 1991.

Baxter and Jain, "Transport of fluid and macromolecules in tumors," Micro. Res., 41:5-23, 1991.

Beckman, Weiner and Davis, "Antibody Constructs in Cancer Therapy", Cancer, 109(2):170-179, 2006.

Benjamin, Golijanin, Itin, Pode and Keshet, "Selective ablation of immature blood vessels in established human tumors follows vascular endothelial growth factor withdrawal," J. Clin. Invest., 103(2): 159-165, 1999.

Berman, Mellis, Pollock, Smith, Suh, Heinke, Kowal, Surti, Chess, Cantor, et al., "Content and organization of the human Ig VH locus: definition of three new VH families and linkage to the Ig CH locus," EMBO J., 7(3):727-738, 1988.

Borgstrom, Hillan, Sriramarao, Ferrara, "Complete inhibition of angiogenesis and growth of microtumors by anti-vascular endothelial growth factor neutralizing antibody: novel concepts of angiostatic therapy from intravital videomicroscopy," Cancer Res., 56(17):4032-1439, 1996.

Borgstrom Bourdon, Hillan, Sriramarao, Ferrara, "Neutralizing anti-vascular endothelial growth factor antibody completely inhibits angiogenesis and growth of human prostate carcinoma micro tumors in vivo," Prostate, 35(1):1-10, 1998.

Borgstrom, Gold, Hillan, Ferrara, "Importance of VEGF for breast cancer angiogenesis in vivo: implications from intravital microscopy of combination treatments with an anti-VEGF neutralizing monoclonal antibody and doxorubicin," Anticancer Research, 19(5B):4203-11, 1999.

Bornstein, "Thrombospondins: structure and regulation of expression," FASEB J, 6(14):3290-3299, 1992.

Brekken, Huang, King, Thorpe, "Vascular endothelial growth factor as a marker of tumor endothelium," Cancer Res., 58(9):1952-1959, 1998.

Brekken, Overholser, Stasny, Waltenberger, Minna, Thorpe, "Selective inhibition of VEGFR2 activity by a monoclonal anti-VEGF antibody blocks tumor growth in mice", Cancer Res., 60:5117-24, 2000.

Brem, "Angiogenesis antagonists: current clinical trials," Angiogenesis, 2: 9-20, 1998.

Brinster, Chen, Trumbauer, Yagle, Palmiter, "Factors Affecting the Efficiency of Introducing Foreign DNA into Mice by Microinjecting Eggs", Proc. Natl. Acad. Sci. USA, 82(13):4438-4442, 1985.

Burke, Carle, Olson, "Cloning of large segments of exogenous DNA into yeast by means of artificial chromosome vectors", Science, 236, 806-812, 1987.

Burke, Lehmann-Bruinsma, Powell, "Vascular endothelial growth factor causes endothelial proliferation after vascular injury," Biochem. Biophys. Res. Comm., 207:348-354, 1995.

Burrows and Thorpe, "Vascular targeting-a new approach to the therapy of solid tumors," Pharmacol. Ther., 64:155-174, 1994.

Burrows and Thorpe, "Eradication of large solid tumors in mice with an immunotoxin directed against tumor vasculature," Proc. Natl. Acad. Sci. USA, 90:8996-9000, 1993.

Burrows, Watanabe, Thorpe, "A murine model for antibody-directed targeting of vascular endothelial cells in solid tumors," Cancer Res., 52:5954-5962, 1992.

Carmeliet, Ferreira, Breier, Pollefeyt, Kieckens, Gertsenstein, Fahrig, Vandenhoeck, Harpal, Eberhardt, Declercq, Pawling, Moons, Collen, Risau, Nagy, "Abnormal blood vessel development and lethality in embryos lacking a single VEGF allele," Nature, 380(6573):435-439, 1996.

Carillo and Lipton, "The Multiple Sequence Alignment Problem in Biology", SIAM J. Applied Math., 48:1073, 1988.

Cheng, Huang, Nagane, Ji, Wang, Shih, Arap, Huang, Cavenee, "Suppression of glioblastoma angiogenicity and tumorigenicity by inhibition of endogenous expression of vascular endothelial growth factor," *Proc. Natl. Acad. Sci. USA*, 93:8502-8507, 1996.

Claffey, Brown, del Aguila, Tognazzi, Yeo, Manseau, Dvorak, "Expression of vascular permeability factor/vascular endothelial growth factor by melanoma cells increases tumor growth, angiogenesis, and experimental metastasis," *Cancer Res.*, 56:172-181, 1996.

Clapp, Martial, Guzman, Fentier-Delure, Weiner, "The 16-kilodalton N-terminal fragment of human prolactin is a potent inhibitor of angiogenesis," *Endocrinology*, 133(3): 1292-1299, 1993.

Clauss, Weich, Breier, Knies, Rockl, Waltenberger, Risau, "The vascular endothelial cell growth factor receptor Flt-1 mediates biological activities," *J. Biol. Chem.*, 271(30): 17629-17634, 1996.

Cohen, Gaskins, Nasoff, "Generation of a Monoclonal Antibody Agonist to Toll-Like Receptor 4", *Hybridoma*, 24(1): 27-35, 2005.

Condeelis and Pollard, "Macrophages: Obligate Partners for Tumor Cell Migration, Invasion, and Metastasis", *Cell*, 124:263-266, 2006.

Connolly, Heuvelman, Nelson, Olander, Eppley, Delfino, Siegel, Leimgruber, Feder, "Tumor vascular permeability factor stimulates endothelial cell growth and angiogenesis," *J. Clin. Invest.*, 84:1470-1478, 1989.

Coughlin, Salhany, Wysocka, Aruga, Kurzawa, Chang, Hunter, Fox, Trinchieri, Lee, "Interleukin-12 and interleukin-18 synergistically induce murine tumor regression which involves inhibition of angiogenesis," *J. Clin. Invest.*, 101 (6):1441-1452, 1998.

Cullen, Gray, Wilson, Hayenga, Lamsa, Rey, Norton, Berka, "Controlled Expression and Secretion of Bovine-Chymosin in *Aspergillus Nidulans*", *BioTechnology*, 5:369, 1987.

D'Amato, Loughnan, Flynn, Folkman, "Thalidomide is an inhibitor of angiogenesis," *Proc. Natl. Acad. Sci. USA*, 91(9):4082-4085, 1994.

D'Angelo, Struman, Martial, Weiner, "Activation of mitogen-activated protein kinases by vascular endothelial growth factor and basic fibroblast growth factor in capillary endothelial cells is inhibited by the antiangiogenic factor 16-kDa N-terminal fragment of prolactin," *Proc. Natl. Acad. Sci. USA*, 92(14):6374-6378, 1995.

Davies and Cohen, "Interactions of protein antigens with antibodies," *Proc Natl. Acad. Sci. U.S.A.* 93:7-12, 1996

Davies, Padlan, Sheriff, "Antibody-antigen complexes," *Annu. Rev. Biochem.* 59:439-473, 1990.

Davies and Riechmann, "Antibody VH domains as small recognition units", *Biotechnology* (NY), 13:475-479, 1995.

Davis and Yancopoulos, "The angiopoietins: Yin and Yang in angiogenesis", *Curr. Top. Microbiol. Immunol.*, 237:173-85, 1999.

Detmar, Brown, Claffey, Yeo, Kocher, Jackman, Berse, Dvorak, "Overexpression of vascular permeability factor/vascular endothelial growth factor and its receptors in psoriasis," *J. Exp. Med.*, 180:1141-1146, 1994.

Devereux, Haeberli, Smithies, "A Comprehensive Set of Sequence Analysis Programs for the VAX", *Nucleic Acids Res.*, 12:387, 1984.

DeVore, Hellerqvist, Wakefield, Wamil, Thurman, Minton, Sundell, Yan, Carter, Wang, York, Zhang, Johnson, "Phase I Study of the Antineovascularization Drug CM101," *Clin. Cancer Res.*, 3(3):365-372, 1997.

deVries, Escobedo, Ueno, Houck, Ferrara, Williams, "The fms-like tyrosine kinase, a receptor for vascular endothelial growth factor," *Science*, 255(5047):989-991, 1992.

Dvorak, Nagy, Dvorak, "Structure of solid tumors and their vasculature: implications for therapy with monoclonal antibodies," *Cancer Cells*, 3:77-85, 1991a.

Dvorak, Sioussat, Brown, Berse, Nagy, Sotrel, Manseau, Vandewater, Senger, "Distribution of vascular permeability factor (vascular endothelial growth factor) in tumors—concentration in tumor blood vessels," *J. Exp. Med.*, 174: 1275-1278, 1991b.

Ferrara, "The role of vascular endothelial growth factor in pathological angiogenesis," *Breast Cancer Res. Treat.*, 36:127-137, 1995.

Ferrara, Clapp, Weiner, "The 16K fragment of prolactin specifically inhibits basal or fibroblast growth factor stimulated growth of capillary endothelial cells," *Endocrinology*, 129(2):896-900, 1991.

Ferrara, Houck, Jakeman, Winer, Leung, "The vascular endothelial growth factor family of polypeptides," *J. Cell. Biochem.*, 47:211-218, 1991.

Ferrara, Carver-Moore, Chen, Dowd, Lu, O'Shea, Powell-Braxton, Hillan, Moore, "Heterozygous embryonic lethality induced by targeted inactivation of the VEGF gene," *Nature*, 380(6573):439-442, 1996.

Fidler and Ellis, "The implications of angiogenesis for the biology and therapy of cancer metastasis [comment]," *Cell*, 79(2):185-188, 1994.

Fidler, Kumar, Bielenberg, Ellis, "Molecular determinants of angiogenesis in cancer metastasis," *Cancer J. Sci. Am.*, 4 Suppl 1:S58-66, 1998.

Finberg, Knipe, Kurt-Jones, "Herpes Simplex Virus and Toll-Like Receptors", Viral Immunol., 18(3):457-465, 2005.

Folkman and Shing, "Angiogenesis," *J. Biol. Chem.*, 267: 10931-10934, 1992.

Folkman, Langer, Linhardt, Haudenschild, Taylor, "Angiogenesis inhibition and tumor regression caused by heparin or a heparin fragment in the presence of cortisone," *Science*, 221:719-725, 1983.

Fong, Rossant, Gertsenstein, Breitman, "Role of the Flt-1 receptor tyrosine kinase in regulating the assembly of vascular endothelium," *Nature*, 376:66-70, 1995.

Forsythe, Jiang, Iyer, Agani, Leung, Koos, Semenza, "Activation of vascular endothelial growth factor gene transcription by hypoxia-inducible factor 1," *Mol. Cell. Biol.*, 16:4604-4613, 1996.

Fotsis, Zhang, Pepper, Adlercreutz, Montesano, Nawroth, Schweigerer, "The endogenous oestrogen metabolite 2-methoxyoestradiol inhibits angiogenesis and suppresses tumour growth," *Nature*, 368(6468):237-239, 1994.

Frank, Hubner, Breier, Longaker, Greenhalgh, Werner, "Regulation of vascular endothelial growth factor expression in cultured growth factor expression in cultured keratinocytes. Implications for normal and impaired wound healing," *J. Biol. Chem.*, 270:12607-12613, 1995.

Frankel, "Genetically Engineered Toxins", Editor Arthur E. Frankel, Marcel Dekker Inc., New York, N.Y., 1992.

Frater-Schroder, Risau, Hallmann, Gautschi, Bohlen, "Tumor necrosis factor type alpha, a potent inhibitor of endothelial cell growth in vitro, is angiogenic in vivo," *Proc. Natl. Acad. Sci. USA*, 84(15):5277-5281, 1987.

Frazier, "Thrombospondins," *Curr. Opin. Cell Biol.*, 3(5): 792-799, 1991.

Frische, Meldal, Werdelin, Mouritsen, Jensen, Galli-Stampino, Bock, "Multiple Column Synthesis of a Library of T-Cell Stimulating Tn-Antigenic Glycopeptide Analogues for the Molecular Characterization of T-Cell-Glycan Specificity", *J. Pept. Sci.*, 2(4): 212-22, 1996.

Gabrilovich, D. I., Velders, M. P., Sotomayor, E. M. & Kast, W. M. (2001). Mechanism of immune dysfunction in cancer mediated by immature Gr1+ myeloid cells. *J Immunol*, 166, 5398-406.

Gagliardi, Hadd, Collins, "Inhibition of angiogenesis by suramin," *Cancer Res.*, 52(18):5073-5075, 1992.

Gagliardi and Collins, "Inhibition of angiogenesis by antiestrogens," *Cancer Res.*, 53(3):533-535, 1993.

Gagliardi, Kassack, Kreimeyer, Muller, "Antiangiogenic and antiproliferative activity of suramin analogues," *Cancer Chemother. Pharmacol.*, 41(2):117-124, 1998.

Gagnon, Bielenberg, Gechtman, Miao, Takashima, Soker, Klagsbrun, "Identification of a natural soluble neuropilin-1 that binds vascular endothelial growth factor: In vivo expression and antitumor activity", *Proc. Natl. Acad. Sci. USA,* 97(6):2573-2578, 2000.

Gerber, Condorelli, Park, Ferrara, "Differential transcriptional regulation of the two vascular endothelial growth factor receptor genes," *J. Biol. Chem.*, 272:23659-23667, 1997.

Gerber, Vu, Ryan, Kowalski, Werb, Ferrara, "VEGF couples hypertrophic cartilage remodeling, ossification and angiogenesis during endochondral bone formation"; *Nature Medicine,* 5(6):623-8, 1999.

Giovarelli, Cappello, Formi, Salcedo, Moore, LeFleur, Nardelli, Di Carlo, Lollini, Ruben, Ullrich, Garotta, Musiam, "Tumor rejection and immune memory elicited by locally released LEC chemokine are associated with an impressive recruitment of APCs, lymphocytes, and granulocytes", *J. Immunol.*, 164, 3200-3206, 2000.

Glennie, McBride, Worth, Stevenson, "Preparation and performance of bispecific F(ab' gamma)$_2$ antibody containing thioether-linked Fab' gamma fragments," *J. Immunol.,* 139: 2367-2375, 1987.

Goeddel, "Gene Expression Technology: Methods in Enzymology 185, Academic Press, San Diego, Calif., 1990.

Good, Polyerini, Rastinejad, Beau, Lemons, Frazier, Bouck, "A tumor suppressor-dependent inhibitor of angiogenesis is immunologically and functionally indistinguishable from a fragment of thrombospondin," *Proc. Natl. Acad. Sci. USA,* 87(17):6624-6628, 1990.

Goswami, Sahai, Wyckoff, Cammer, Cox, Pizley, Stanley, Segall and Condeelis, "Macrophages Promote the Invasion of Breast Carcinoma Cells via a Colony-Stimulating Factor-1/Epidermal Growth Factor Paracrine Loop", *Cancer Res.*, 65(12):5278-5283, 2005.

Grant, Caballero, Bush, Spoerri, "Fibronectin fragments modulate human retinal capillary cell proliferation and migration," *Diabetes,* 47(8):1335-1340, 1998.

Guo, Jia, Song, Warren, Donner, "Vascular endothelial cell growth factor promotes tyrosine phosphorylation of mediators of signal transduction that contain SH2 domains," *J. Biol. Chem.*, 270:6729-6733, 1995.

Hamers-Casterman and Atarhouch, "Naturally Occurring antibodies Devoid of Light Chains", *Nature,* 363(6428): 446-448, 1993.

Hammer, Pursel, Rexroad, Wall, Bolt, Ebert, Palmiter, Brinster, "Production of Transgenic Rabbits, Sheep and Pigs by Microinjection", *Nature,* 315:680-683, 1985.

Hanahan and Folkman, "Patterns and emerging mechanisms of the angiogenic switch during tumorigenesis," *Cell,* 86(3):353-364, 1996.

Harada, Mitsuyama, Yoshida, Sakisaka, Taniguchi, Kawaguchi, Ariyoshi, Saiki, Sakamoto, Nagata, Sata, Matsuo, Tanikawa, "Vascular endothelial growth factor in patients with rheumatoid arthritis", *Scandinavian J. Rheumatol.,* 27(5):377-80, 1998.

Haran, Maretzek, Goldberg, Horowitz, Degani, "Tamoxifen enhances cell death in implanted MCF7 breast cancer by inhibiting endothelium growth," *Cancer Res.,* 54(21): 5511-5514, 1994.

Hasselaar and Sage, "SPARC antagonizes the effect of basic fibroblast growth factor on the migration of bovine aortic endothelial cells," *J. Cell Biochem.,* 49(3):272-283, 1992.

Harlow and Lane, "Antibodies: a Laboratory Manual", *Cold Spring Harbor Laboratory*, Cold Spring Harbor Laboratory, ISBN 978-087969314-5:1-726, 1988.

Hellerqvist, Thurman, Page, Wang, Russell, Montgomery, Sundell, "Antitumor effects of GBS toxin: a polysaccharide exotoxin from group B beta-hemolytic *streptococcus*," *J. Cancer Res. Clin. Oncol.,* 120(1-2):63-70, 1993.

Henikoff and Henikoff, "Amino acid Substitution Matrices from Protein Blocks", *Proc. Natl. Acad. Sci. USA,* 89:10915-10919, 1992.

Hinnen, Hicks, Fink, "Transformation of Yeast", *Proc. Natl. Acad. Sci. USA,* 75:1929, 1978.

Hiratsuka, Minowa, Kuno, Noda, Shibuya, "Flt-1 lacking the tyrosine kinase domain is sufficient for normal development and angiogenesis in mice," *Proc. Natl. Acad. Sci. USA,* 95(16):9349-9354, 1998.

Hiscox and Jiang, "Interleukin-12, an emerging anti-tumour cytokine," In Vivo, 11 (2): 125-132, 1997.

Holash, Maisonpierre, Compton, Boland, Alexander, Zagzag, Yancopoulos, Wiegand, "Vessel Cooption, Regression, and Growth in Tumors Mediated by Angiopoietins and VEGF", *Science,* 284:1994-1998, 1999.

Holliger and Hudson, "Engineered Antibody Fragments and the Rise of Single Domains", *Nature Biotechnology,* 23(9): 1126-1136, 2005.

Holm, "Dali: a Network Tool for Protein Structure Comparison", *Trends in Biochemical Sciences,* 20:478-480, 1995.

Holm, "Protein Structure Comparison by Alignment of Distance Matrices", *J. Mol. Biol.*, 233:123-38, 1993

Holm, "Touring Protein Fold Space With Dali/FSSP", *Nucleic Acid Res.,* 26:316-9, 1998.

Hood and Granger, "Protein kinase G mediates vascular endothelial growth factor-induced Raf-1 activation and proliferation in human endothelial cells," *J. Biol. Chem.,* 273(36):23504-23508, 1998.

Hood, Meininger, Ziche, Granger, "VEGF upregulates ecNOS message, protein, and NO production in human endothelial cells," *Am. J. Physiol.,* 274(3 Pt 2):H1054-1058, 1998.

Hori, Hu, Yasui, Smither, Gresham, Fan, "Differential effects of angiostatic steroids and dexamethasone on angiogenesis and cytokine levels in rat sponge implants," *Br. J. Pharmacol.,* 118(7):1584-1591, 1996.

Horsmans, Berg, Desager, Mueller, Schott, Fletcher, Steffy, Bauman, Kerr, Averett, "Isatoribine, an agonist of TLR7, reduces plasma virus concentration in chronic hepatitis C infection," Hepatology, 42(3):724-31, 2005 Houben-weyl, *Methods of Organic Chemistry,* ed. E. Wansch, Vol. 15 I and II, Thieme, Stuttgart, 1987.

Houck, Ferrara, Winer, Cachianes, L1, Leung, "The vascular endothelial growth factor family: Identification of a fourth molecular species and characterization of alternative splicing of RNA," *Mol. Endocrinol.,* 5(12):1806-1814, 1991.

Huang, Molema, King, Watkins, Edgington, Thorpe, "Tumor infarction in mice by antibody-directed targeting of tissue factor to tumor vasculature," Science, 275:547-550, 1997.

Hurwitz, Fehrenbacher, Novotny, Cartwright, Hainsworth, Heim, Berlin, Baron, Griffing, Holmgren, Ferrara, Fyfe, Rogers, Ross, Kabbinavar, "Bevacizumab plus Irinotecan, Fluorouracil, and Leucovorin for Metastatic Colorectal Cancer", *N. Engl. J. Med.*, 350:2335-2342, 2004.

Huse, Sastry, Iverson, Kang, Alting-Mees, Burton, Benkovic and Lerner, "Generation of a Large Combinatorial Library of the Immunoglobulin Repertoire in Phage Lambda, *Science,* 246(4935):1275-1281, 1989.

Hussain, Kotz, Minasian, Premkumar, Sarosy, Reed, Zhai, Steinberg, Raggio, Oliver, Figg, Kohn, "Phase II Trial of Carboxyamidotriazole in Patients With Relapsed Epithelial Ovarian Cancer", *J. Clin. Oncol.,* 21(23):4356-4363, 2003.

Ingber, Fujita, Kishimoto, Sudo, Kanamaru, Brem, Folkman, "Angioinhibins: Synthetic analogues of fumagillin which inhibit angiogenesis and suppress tumor growth," *Nature,* 48:555-557, 1990.

Inoue, Itoh, Ueda, Naruko, Kojima, Komatsu, Doi, Ogawa, Tamura, Takaya, Igaki, Yamashita, Chun, Masatsugu, Becker, Nakao, "Vascular endothelial growth factor (VEGF) expression in human coronary atherosclerotic lesions: possible pathophysiological significance of VEGF in progression of atherosclerosis", *Circulation,* 98(20):2108-16, 1998.

Ito, Fukuda, Murata, Kimura, "Transformation of Intact Yeast Cells Treated with Alkali Cations", *J. Bacteriol.,* 153:163-168, 1983.

Iwamoto, Nomizu, Yamada, Ito, Tanaka, Sugioka, "Inhibition of angiogenesis, tumour growth and experimental metastasis of human fibrosarcoma cells HT1080 by a multimeric form of the laminin sequence Tyr-Ile-Gly-Ser-Arg (YIGSR)," *Br. J. Cancer,* 73(5):589-595, 1996.

Jackson, Volpert, Bouck, Linzer, "Stimulation and inhibition of angiogenesis by placental proliferin and proliferin-related protein," *Science,* 266(5190): 1581-1584, 1994.

Jendraschak and Sage, "Regulation of angiogenesis by SPARC and angiostatin: implications for tumor cell biology," *Semin. Cancer Biol.,* 7(3): 139-146, 1996.

Kabat, Wu, Perry, Gottesman, Foeller, "Sequences of Proteins of Immunological Interest", 5th Ed. *Public Health Service, National Institutes of Health*, Bethesda, Md., 647-669, 1991.

Kamphaus, Colorado, Panka, Hopfer, Ramchandran, Torre, Maeshima, Mier, Sukhatme, and Kalluri, "Canstatin, a Novel Matrix-derived Inhibitor of Angiogenesis and Tumor Growth", *J. Biol. Chem.,* 275(2): 1209-1215, 2000.

Kang, Barbas, Janda, Benkovic and Lerner, "Linkage of Recognition and Replication Functions by Assembling Combinatorial Antibody Fab Libraries Along Phage Surfaces", *Proc. Natl. Acad. Sci., U.S.A.,* 88(10):4363-4366, 1991.

Kaufman, Murtha, Davies, "Translational Efficiency of Polycistronic Mrnas and Their Utilization to Express Heterologous Genes in Mammalian Cells", *EMBO J.,* 6:187-195, 1987.

Kaur, Brat, Devi and Van Meir, "Vasculostatin, a proteolytic fragment of Brain Angiogenesis Inhibitor 1, is an antiangiogenic and antitumorigenic factor", *Oncogene,* 24:3632-3642, 2005.

Keck, Hauser, Krivi, Sanzo, Warren, Feder, Connolly, "Vascular permeability factor, an endothelial cell mitogen related to PDGF," *Science,* 246:1309-1312, 1989.

Kendall and Thomas, "Inhibition of vascular endothelial cell growth factor activity by an endogenously encoded soluble receptor," *Proc. Natl. Acad. Sci. USA,* 90:10705-10709, 1993.

Kenyon, Browne, D'Amato, "Effects of thalidomide and related metabolites in a mouse corneal model of neovascularization," *Exp. Eye Res.,* 64(6):971-978, 1997.

Kerbel, Viloria-Petit, Okada, Rak, "Establishing a link between oncogenes and tumor angiogenesis," *Mol. Med.,* 4(5):286-295, 1998.

Keyt, Nguyen, Berleau, Duarte, Park, Chen, Ferrara, "Identification of vascular endothelial growth factor determinants for binding KDR and FLT-1 receptors. Generation of receptor-selective VEGF variants by site-directed mutagenesis," *J. Biol. Chem.,* 271(10):563846, 1996.

Kim, L1, Houck, Winer, Ferrara, "The vascular endothelial growth factor proteins: identification of biologically relevant regions by neutralizing monoclonal antibodies," *Growth Factors,* 7:53-64, 1992.

Kim, L1, Winer, Armanini, Gillett, Phillips, "Inhibition of vascular endothelial growth factor-induced angiogenesis suppresses tumour growth in vivo," *Nature,* 362:841-844, 1993.

Kim, Kwak, Ahn, So, Liu, Koh, Koh, "Molecular cloning and characterization of a novel angiopoietin family protein, angiopoietin-3", *FEBS Lett.,* 443(3):353-6, 1999.

Kipriyanov, Kupriyanova, Little, Moldenhauer, "Rapid detection of recombinant antibody fragments directed against cell-surface antigens by flow cytometry", *J. Immunol. Meth.,* 196:51-62, 1996.

Kipriyanov, Moldenhauer, Little, "High level production of soluble single chain antibodies in small-scale *Escherichia coli* cultures", *J. Immunol. Meth.,* 200:69-77, 1997.

Kiss, Fisher, Pesavento, Dai, Valero, Ovecka, Nolan, Phipps, Velappan, Chasteen, Martinez, Waldo, Pavlik, Bradbury, "Antibody binding loop insertions as diversity elements", *Nucleic Acids Research,* 34(19):e132, 2006.

Kleinman, Weeks, Schnaper, Kibbey, Yamamura, Grant, "The laminins: a family of basement membrane glycoproteins important in cell differentiation and tumor metastases," *Vitam. Horm.,* 47:161-186, 1993.

Kondo, Asano, Suzuki, "Significance of vascular endothelial growth factor/vascular permeability factor for solid tumor growth, and its inhibition by the antibody," *Biochem. Biophys. Res. Commun,* 194(3):1234-1241, 1993.

Korpelainen and Alitalo, "Signaling angiogenesis and lymphangiogenesis," *Curr. Opin. Cell Biol.,* 10(2):159-164, 1998.

Kremer, Breier, Risau, Plate, "Up-regulation of flk-1/vascular endothelial growth factor receptor 2 by its ligand in a cerebral slice culture system," *Cancer Res.,* 57:3852-3859, 1997.

Kroll and Waltenberger, "The vascular endothelial growth factor receptor KDR activates multiple signal transduction pathways in porcine aortic endothelial cells", *J. Biol. Chem.,* 272:32521-7, 1997.

Kroll and Waltenberger, "VEGF-A induces expression of eNOS and iNOS in endothelial cells via VEGF receptor-2 (KDR)," *Biochem. Biophys. Res. Commun.,* 252(3):743-746, 1998.

Kurjan and Herskowitz, "Structure of a Yeast Pheromone Gene (MFa): a Putative α-Factor Precursor Contains Four Tandem Copies of mature α-Factor", *Cell,* 30:933-943, 1982.

Kyte and Doolittle, "A simple method for displaying the hydropathic character of a protein," *J. Mol. Biol.,* 157(1): 105-132, 1982.

Lane, Iruela-Arispe, Sage, "Regulation of gene expression by SPARC during angiogenesis in vitro. Changes in fibronectin, thrombospondin-14, and plasminogen activator inhibitor-1," *J. Biol. Chem.,* 267(23): 16736-16745, 1992.

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection,* 17(4):357-366, 2004.

Lee, Clapp, Martial, Weiner, "Inhibition of urokinase activity by the antiangiogenic factor 16K prolactin: activation of plasminogen activator inhibitor 1 expression," *Endocrinology,* 139(9):3696-3703, 1998.

Lewis and Pollard, "Distinct Role of Macrophages in Different Tumor Microenvironments", *Cancer Res.,* 66(2):605-612, 2006.

Lin, Sankar, Shan, Dewhirst, Polyerini, Quinn, Peters, "Inhibition of tumor growth by targeting tumor endothelium using a soluble vascular endothelial growth factor receptor," *Cell Growth Differ.,* 9:49-58, 1998.

Lin, Buxton, Acheson, Radziejewski, Maisonpierre, Yancopoulos, Channon, Hale, Dewhirst, George, Peters, "Anti-angiogenic gene therapy targeting the endothelium-specific receptor tyrosine kinase Tie2", *Proc. Natl. Acad. Sci., USA,* 95(15):8829-34, 1998.

Lin, Nguyen, Mendoza, Escandon, Fei, Meng, Modi, "Preclinical pharmacokinetics, interspecies scaling, and tissue distribution of a humanized monoclonal antibody against vascular endothelial growth factor", *J. Pharmacol. Exp. Therap.,* 288(1):371-8, 1999.

Lin, Nguyen, Russell and Pollard, "Colony-Stimulating Factor 1 Promotes Progression of Mammary Tumors to Malignancy", *J. Exp. Med.,* 193(6):727-739, 2001.

Lin, L1, Gnatovskiy, Deng, Zhu, Grzesik, Qian, Xue and Pollard, "Macrophages Regulate the Angiogenic Switch in a Mouse Model of Breast Cancer", *Cancer Res.,* 66(23): 11238-11246, 2006.

Lindner and Borden, "Effects of tamoxifen and interferon-beta or the combination on tumor-induced angiogenesis," *Int. J. Cancer,* 71(3):456-461, 1997.

Lingen, Polyerini, Bouck, "Retinoic acid and interferon alpha act synergistically as antiangiogenic and antitumor agents against human head and neck squamous cell carcinoma," *Cancer Res.,* 58(23):5551-5558, 1998.

Lingen, Polyerini, Bouck, "Inhibition of squamous cell carcinoma angiogenesis by direct interaction of retinoic acid with endothelial cells," *Lab. Invest.,* 74(2):476-483, 1996.

Lin-ke, Hong-Qu, Nagy, Eckelhoefer, Masse, Dvorak, Dvorak, "Vascular targeting of solid and ascites tumours with antibodies to vascular endothelial growth factor," *Eur. J. Cancer,* 32A(14):2467-2473, 1996.

Loupakis, Falcone, Masi, Fioravanti, Kerbel, Del Tacca, Bocci "Vascular Endothelial Growth Factor Levels in Immunodepleted plasma of Cancer Patients As a Possible Pharmacodynamic Marker for Bevacizumab Activity," *J. Clin. One,* 1816-1818, 2007.

Luckow and Summers, "High Level Expression of Nonfused Foreign Genes with Autographa Californica Nuclear Polyhedrosis Virus Expression Vectors", *Virology,* 170:31-39, 1989.

Luo, Toyoda, Shibuya, "Differential inhibition of fluid accumulation and tumor growth in two mouse ascites tumors by an antivascular endothelial growth factor/permeability factor neutralizing antibody," *Cancer Res.,* 58(12):2594-2600, 1998a.

Luo, Yamaguchi, Shinkai, Shitara, Shibuya, "Significant expression of vascular endothelial growth factor/vascular permeability factor in mouse ascites tumors," *Cancer Res.,* 58(12):2652-2660, 1998b.

Majewski, Skopinska, Marczak, Szmurlo, Bollag, Jablonska "Vitamin D3 is a potent inhibitor of tumor cell-induced angiogenesis," *J. Investig. Dermatol. Symp. Proc.,* 1(1):97-101, 1996.

Malecaze, Clameris, Simorre-Pinatel, Mathis, Chollet, Favard, Bayard, Plouet, "Detection of vascular endothelial growth factor messenger RNA and vascular endothelial growth factor-like activity in proliferative diabetic retinopathy," *Arch. Opthalmol.,* 112:1476-1482, 1994.

Maisonpierre, Suri, Jones, Bartunkova, Wiegand, Radziejewski, Compton, McClain, Aldrich, Papadopoulos, Daly, Davis, Sato, Yancopoulos, "Angiopoietin-2, a natural antagonist for Tie2 that disrupts in vivo angiogenesis," *Science,* 277(5322):55-60, 1997 Manetti, Cappello, Botta, Corelli, Mongelli, Biasoli, Borgia, Ciomei, "Synthesis and binding mode of heterocyclic analogues of suramin inhibiting the human basic fibroblast growth factor," *Bioorg. Med. Chem.,* 6(7):947-958, 1998.

Massey, "Catalytic Antibodies Catching On", *Nature,* 328: 457-458, 1987.

Mazure, Chen, Yeh, Laderoute, Giaccia, "Oncogenic transformation and hypoxia synergistically act to modulate vascular endothelial growth factor expression," *Cancer Res.,* 56:3436-3440, 1996.

McNamara, Harmey, Walsh, Redmond, Bouchier-Hayes, "Significance of angiogenesis in cancer therapy [published erratum appears in Br J. Surg., October; 85(10):1449, 1998," *Br. J. Surg.,* 85(8):1044-1055. 1998.

Merrifield, "Solid Phase Peptide Synthesis 1. Synthesis of a Tetrapeptide", *J. Am. Chem. Assoc.,* 85:2149-2154, 1964.

Mesiano, Ferrara, Jaffe, "Role of vascular endothelial growth factor in ovarian cancer: inhibition of ascites formation by immunoneutralization," *Am. J. Pathol.,* 153(4):1249-1256, 1998.

Millauer, Longhi, Plate, Shawver, Risau, Ullrich, Strawn, "Dominant-negative inhibition of Flk-1 suppresses the growth of many tumor types in vivo," *Cancer Res.,* 56:1615-1620, 1996.

Mills, Brooker and Camerini-Otero, "Sequences of human immunoglobulin switch regions: implications for recombination and transcription," *Nucl. Acids Res.,* 18:7305-7316, 1990.

Moore, Arenberg, Addison, Keane, Streiter, "Tumor angiogenesis is regulated by CXC chemokines," *J. Lab. Clin. Med.,* 132(2):97-103, 1998.

Mordenti, Thomsen, Licko, Chen, Meng, Ferrara, "Efficacy and concentration-response of murine anti-VEGF monoclonal antibody in tumor-bearing mice and extrapolation to humans", *Toxicologic Pathology,* 27(1): 14-21, 1999.

Morrison, Wims, Kobrin and Oi, "Production of novel immunoglobulin molecules by gene transfection," *Mt. Sinai J. Med.,* 53(3):175, 1986.

Muller, L1, Christinger, Wells, Cunningham, De Vos, "Vascular Endothelial growth factor: Crystal structure and functional mapping of the kinase domain receptor binding site", *Proc. Natl. Acad. Sci. USA.,* 94:7192-7197, 1997.

Muller, Chen, Christinger, L1, Cunningham, Lowman, de Vos, "VEGF and the Fab fragment of a humanized neutralizing antibody: crystal structure of the complex at 2.4 A resolution and mutational analysis of the interface," *Structure,* 6(9): 1153-67, 1998.

Mustonen and Alitalo, "Endothelial receptor tyrosine kinases involved in angiogenesis," *J. Cell Biol.,* 129:895-898, 1995.

Myers and Miller, "Optical Alignments in Linear Space", *CABIOS,* 4:11-17, 1988.

Nagashima, Yoshino, Aono, Takai, Sasano, "Inhibitory effects of anti-rheumatic drugs on vascular endothelial growth factor in cultured rheumatoid synovial cells", *Clin. Exp. Immunol.*, 116(2):360-5, 1999.

Nagler, Feferman, Shoshan, "Reduction in basic fibroblast growth factor mediated angiogenesis in vivo by linomide," *Connect Tissue Res.*, 37(1-2):61-68, 1998.

Nakamura Voller and Bidwell, "Enzyme Immunoassays: Heterogeneous and Homogeneous Systems", *In: Handbook of Experimental Immunology*, Vol. 1: Immunochemistry, D. M. Weir (Ed.), Blackwell Scientific Publications, Oxford 1986, Chapter 27.

Needleman and Wunsch, "A General Method Applicable to the Search For Similarities in the Amino Acid Sequence of Two Proteins", *J. Mol. Biol.*, 48:443, 1970.

Neuberger and Milstein, "Somatic hypermutation," *Curr. Opin. Immunol.*, 7:248-254, 1995.

Neufeld, Cohen, Gengrinovitch, Poltorak, "Vascular endothelial growth factor (VEGF) and its receptors," *FASEB J.*, 13(1):9-22, 1999.

Nicaise, Valerio-Lepiniec, Minard, Desmadril, "Affinity transfer by CDR grafting on a nonimmunoglobulin scaffold", *Protein Sci.*, 13: 1882-1891, 2004.

Niida, Kaku, Amano, Yoshida, Kataoka, Nishikawa, Tanne, Maeda, Nishikawa, Kodama, "Vascular endothelial growth factor can substitute for macrophage colony-stimulating factor in the support of osteoclastic bone resorption", *J. Exp. Med.*, 190(2):293-8, 1999.

Nozaki, Sakurai, Raisler, Baffi, Witta, Ogura, Brekken, Sage, Ambati, Ambati, "Loss of SPARC-mediated VEGFR-1 suppression after injury reveals a novel antiangiogenic activity of VEGF-A", *J. Clin. Invest.*, 116(2):422-9, 2006.

Oikawa, Hirotani, Nakamura, Shudo, Hiragun, Iwaguchi, "A highly potent antiangiogenic activity of retinoids," *Cancer Lett.*, 48(2):157-162, 1989.

Olander, Connolly, DeLarco, "Specific binding of vascular permeability factor to endothelial cells," *Biochem. Biophys. Res. Comm.*, 175:68-76, 1991.

O'Reilly, Holmgren, Shing, Chen, Rosenthal, Moses, Lane, Cao, Sage, Folkman "Angiostatin: a novel angiogenesis inhibitor that mediates the suppression of metastases by a Lewis lung carcinoma," *Cell*, 79:315-328, 1994.

O'Reilly, Boehm, Shing, Fukai, Vasios, Lane, Flynn, Birkhead, Olsen, Folkman "Endostatin: an endogenous inhibitor of angiogenesis and tumor growth," *Cell*, 88(2):277-285, 1997.

Palmiter and Brinster, "Transgenic Mice", Cell, 41:343-345, 1985.

Palmiter, Norstedt, Gelinas, Hammer, Brinster, "Metallothionein-Human GH Fusion Genes Stimulate Growth of Mice", *Science*, 222:809-814, 1983.

Parmley and Smith, "Antibody-selectable filamentous fd phage vectors: affinity purification of target genes," *Gene*, 73(2):305-318, 1988.

Pearson and Lipman, "Improved tools for biological sequence analysis", *Proc. Natl. Acad. Sci. USA*, 85:2444-2448, 1988.

Pearson, "Rapid and sensitive sequence comparison with FASTP and FASTA", *Methods in Enzymology*, 183:63-98, 1990.

Pepper, Ferrara, Orci, Montesano, "Leukemia inhibitory factor (LIF) inhibits angiogenesis in vitro," *J. Cell Sci.*, 108 (1):73-83, 1995.

Petersen, Wang, Yalcin-Chin, Li, Peyton, Minna, Harran, Wang, "Autocrine TNFα Signaling Renders Human Cancer Cells Susceptible to Smac-Mimetic-Induced Apoptosis", *Cancer Cell*, 12(5):445-456, 2007.

Petrova, Nykanen, Norrmen, Ivanov, Andersson, Haglund, Puolakkainen, Wempe, von Melchner, Gradwohl, Vanharanta, Aaltonen, Saharinen, Gentile, Clarke, Taipale, Oliver, Alitalo, "Transcription factor PROX1 induces colon cancer progression by promoting the transition from benign to highly dysplastic phenotype", *Cancer Cell*, 13(5):407-19, 2008.

Pike, Yao, Jones, Cherney, Appella, Sakaguchi, Nakhasi, Teruya-Feldstein, Wirth, Gupta and Tosato, "Vasostatin, a Calreticulin Fragment, Inhibits Angiogenesis and Suppresses Tumor Growth", *J. Exp. Med.*, 188(12):2349-2356, 1998.

Pike, Yao, Setsuda, Jones, Cherney, Appella, Sakaguchi, Nakhasi, Atreya, Teruya-Feldstein, Wirth, Gupta and Tosato, "Calreticulin and Calreticulin Fragments Are Endothelial Cell Inhibitors That Suppress Tumor Growth", *Blood*, 94(7):2461-2468, 1999.

Plate, Breier, Weich, Mennel, Risau, "Vascular endothelial growth factor and glioma angiogenesis: coordinate induction of VEGF receptors, distribution of VEGF protein and possible in vivo regulatory mechanisms," *Int. J. Cancer*, 59:520-529, 1994.

Potgens, Westphal, DeWaal, Ruiter, "The role of vascular permeability factor and basic fibroblast growth factor in tumor angiogenesis," *In: Growth Factors in Tumor Angiogenesis*, Berlin: Walter de Gruyer & Co. pp. 57-70, 1995.

Presta, Chen, O'Connor, Chisholm, Meng, Krummen, Winkler, Ferrara, "Humanization of an anti-vascular endothelial growth factor monoclonal antibody for the therapy of solid tumors and other disorders," *Cancer Res.*, 57:4593-4599, 1997.

Qiu, Wang, Cai, Wang, Yue, "Small antibody mimetics comprising two complementarity-determining regions and a framework region for tumor targeting|, *Nature Biotechnology*, 25(8): 921-929, 2007

Quinn, Thurman, Sundell, Zhang, Hellerqvist, "CM 101, a polysaccharide antitumor agent, does not inhibit wound healing in murine models," *J. Cancer Res. Clin. Oncol.*, 121(4):253-256, 1995. Raychaudhury and D'Amore, "Endothelial cell regulation by transforming growth factor-beta," *J. Cell Biochem.*, 47(3):224-229, 1991.

Reff and Heard, "A Review of Modifications to Recombinant Antibodies: Attempt to Increase Efficacy in Oncology Applications", *Critical Reviews in Oncology Hematology*, 40:25-35, 2001.

Reiter, Ulrich Brinkmann, Lee and Pastan, "Engineering Antibody Fv Fragements for Cancer Detection and Therapy: Disulfide-Stabilized Fv Fragments", *Nature Biotechnology*, 14:1239-1245, 1996.

Richer and Lo, "Introduction of human DNA into mouse eggs by injection of dissected human chromosome fragments", *Science*, 245:175-177, 1989.

Ryan, Eppler, Hagler, Bruner, Thomford, Hall, Shopp, O'Neill, "Preclinical safety evaluation of rhuMAbVEGF, an antiangiogenic humanized monoclonal antibody", *Toxicologic Pathology*, 27(1):78-86, 1999.

Sakamoto, Tanaka, Togho, Ogawa, "Heparin plus cortisone acetate inhibit tumor growth by blocking endothelial cell proliferation," *Canc. J*, 1:55-58, 1986.

Saleh, Stacker, Wilks, "Inhibition of growth of C6 glioma cells in vivo by expression of antisense vascular endothelial growth factor sequence," *Cancer Res.*, 56:393-401, 1996.

Sambrook, Fritsch and Maniatis, *Molecular Cloning: A Laboratory Manual*, 2nd Ed., Cold Spring Harbor Press, Cold Spring Harbor, N.Y., 1989.

Sang, "Complex role of matrix metalloproteinases in angiogenesis," *Cell Res.*, 8(3): 171-177, 1998.

Schultz, Tanner, Hofmann, Emini, Condra, Jones, Kieff, Ellis, "Expression and Secretion in Yeast of a 400-Kda Envelope Glycoprotein Derived from Epstein-Barr Virus", *Gene*, 54:113-123, 1987.

Seed, "an LFA-3 Cdna Encodes a Phospholipid-Linked Membrane Protein Homologous to its Receptor CD2", *Nature*, 329:840, 1987.

Senger, Galli, Dvorak, Perruzzi, Harvey, Dvorak, "Tumor cells secrete a vascular permeability factor that promotes accumulation of ascites fluid," *Science*, 219:983-985, 1983.

Senger, Perruzzi, Feder, Dvorak, "A highly conserved vascular permeability factor secreted by a variety of human and rodent tumor cell lines," *Cancer Res.*, 46:5629-5632, 1986.

Senger, Connolly, Vandewater, Feder, Dvorak, "Purification and NH2-terminal amino acid sequence of guinea pig tumor secreted vascular permeability factor," *Cancer Res.*, 50:1774-1778, 1990.

Serafini, P., De Santo, C., Marigo, I., Cingarlini, S., Dolcetti, L., Gallina, G., Zanovello, P. & Bronte, V. (2004). "Derangement of immune responses by myeloid suppressor cells", *Cancer Immunol Immunother*, 53, 64-72.

Shalaby, Rossant, Yamaguchi, Gertsenstein, Wu, Breitman, Schuh, "Failure of blood-island formation and vasculogenesis in Flk-1-deficient mice," *Nature*, 376:62-66, 1995.

Sheibani and Frazier, "Thrombospondin 1 expression in transformed endothelial cells restores a normal phenotype and suppresses their tumorigenesis," *Proc. Natl. Acad. Sci. USA*, 92(15):6788-6792, 1995.

Sheu, Yen, Kan, "Inhibition of angiogenesis in vitro and in vivo: comparison of the relative activities of triflavin, an Arg-Gly-Asp-containing peptide and anti-alpha(v) beta3 integrin monoclonal antibody," *Biochim. Biophys. Acta*, 1336(3):445-454, 1997.

Shibuya, "Vascular endothelial growth factor receptor-1 (VEGFR-1/Flt-1): a dual regulator for angiogenesis", *Angiogenesis*, 9(4):225-30, 2007.

Shojaei, Wu, Malik, Zhong, Baldwin, Schanz, Fuh, Gerber, Ferrara, "Tumor refractoriness to anti-VEGF treatment is mediated by CD11b+Gr1+ myeloid cells", Nature *Biotechnology*, 25:911-920, 2007.

Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.*, 1(6):631-642, 1989.

Siemeister, Martiny-Baron, Marme, "The pivotal role of VEGF in tumor angiogenesis: molecular facts and therapeutic opportunities," *Cancer Metastasis Rev.*, 17(2):241-248., 1998.

Sinkar, White, Gordon, "Molecular Biology of Ri-Plasmid a Review", *J. Biosci (Bangalore)*, 11:47-58, 1987.

Sioussat, Dvorak, Brock, Senger, "Inhibition of vascular permeability factor (vascular endothelial growth factor) with antipeptide antibodies," *Arch. Biochem. Biophys.*, 301:15-20, 1993.

Sipos, Tamargo, Weingart, Brem, "Inhibition of tumor angiogenesis," *Ann. NY Acad. Sci.*, 732:263-272, 1994.

Smith and Waterman, "Comparison of Biosequences", *Adv. Appl. Math.*, 2:482, 1981.

Smith, Summers, Fraser, "Production of Human Beta Interferon in Insect Cells Infected With Baculovirus Expression Vector", *Mol. Cell. Biol.*, 3:2156-2165, 1983.

Soff, Sanderowitz, Gately, Verrusio, Weiss, Brem, Kwaan, "Expression of plasminogen activator inhibitor type 1 by human prostate carcinoma cells inhibits primary tumor growth, tumor-associated angiogenesis, and metastasis to lung and liver in an athymic mouse model," *J. Clin. Invest.*, 96(6):2593-2600, 1995.

Soker, Takashima, Miao, Neufeld, Klagsbrun., "Neuropilin-1 is expressed by endothelial and tumor cells as an isoform-specific receptor for vascular endothelial growth factor," *Cell*, 92(6):735-745, 1998.

Springer, Chen, Kraft, Bednarski, Blau, "VEGF gene delivery to muscle: potential role for vasculogenesis in adults," *Mol. Cell*, 2(5):549-558, 1998.

Stella and Himmelstein, "Prodrugs: A chemical approach to targeted drug delivery", *Directed Drug Delivery*, Borchardt et al., Eds. Human Press, 1985, pp 247-267.

Sweetwynehttp://www.jhc.org/cgi/content/full/52/6/723-FN2#FN2, Brekkenhtt2://www.jhc.org/cgi/content/full/52/6/723-FN3#FN3, Workman, Bradshaw, Carbon, Siadak, Murri and Sage, "Functional Analysis of the Matricellular Protein SPARC with Novel Monoclonal Antibodies", *J. Histochem. Cytochem.*, 52(6):723-733, 2004.

Tada, Fukunaga, Wakabayashi, Masumi, Sato, Izumi, Kohno, Kuwano, "Inhibition of tubular morphogenesis in human microvascular endothelial cells by co-culture with chondrocytes and involvement of transforming growth factor beta: a model for avascularity in human cartilage," *Biochim. Biophys. Acta*, 1201(2):135-142, 1994.

Takano, Gately, Neville, Herblin, Gross, Engelhard, Perricone, Eidsvoog, Brem, "Suramin, an anticancer and angiosuppressive agent, inhibits endothelial cell binding of basic fibroblast growth factor, migration, proliferation, and induction of urokinase-type plasminogen activator," *Cancer Res.*, 54(10):2654-2660, 1994.

Tanaka, Manome, Wen, Kufe, Fine, "Viral vector-mediated transduction of a modified platelet factor 4 cDNA inhibits angiogenesis and tumor growth," *Nat. Med.*, 3(4):437-442, 1997.

Terman, Dougher-Vermazen, Carrion, Dimitrov, Armellino, Gospodarowicz, Bohlen, "Identification of the KDR tyrosine kinase as a receptor for vascular endothelial cell growth factor," *Biochem. Biophys. Res. Comm.*, 187:1579-1586, 1992.

Terman, Khandke, Dougher-Vermazan, Maglione, Lassam, Gospodarowicz, Persico, Bohlen, Eisinger, "VEGF receptor subtypes KDR and FLT1 show different sensitivities to heparin and placenta growth factor," *Growth Factors*, 11(3):187-195, 1994.

Thomas, "Vascular endothelial growth factor, a potent and selective angiogenic agent," *J. Biol. Chem.*, 271:603-606, 1996.

Thompson, Higgins, Gibson, "CLUSTAL W: Improving the sensitivity of progressive multiple sequence alignment through sequence weighting, position-specific gap penalties and weight matrix choice", *Nucleic Acids Res.*, 22:4673-4680, 1994.

Thorpe, Derbyshire, Andrade, Press, Knowles, King, Watson, Yang, Rao-Bette, "Heparin-Steroid Conjugates New Angiogenesis Inhibitors with Antitumor Activity in Mice," *Cancer Res.*, 53:3000-3007, 1993.

Tischer, Mitchell, Hartman, Silva, Gospodarowicz, Fiddes, Abraham, "The human gene for vascular endothelial growth factor," *J. Biol. Chem.*, 266:11947-11954, 1991.

Tolsma, Volpert, Good, Frazier, Polyerini, Bouck, "Peptides derived from two separate domains of the matrix protein thrombospondin-1 have anti-angiogenic activity," *J. Cell Biol.*, 122(2):497-511, 1993.

Tryggvason, "The laminin family," *Curr. Opin. Cell Biol.*, 5(5):877-882, 1993.

Valenzuela, Griffiths, Rojas, Aldrich, Jones, Zhou, McClain, Copeland, Gilbert, Jenkins, Huang, Papadopoulos, Maisonpierre, Davis, Yancopoulos, "Angiopoietins 3 and 4: diverging gene counterparts in mice and humans", *Proc. Natl. Acad. Sci., USA,* 96(5): 1904-9, 1999.

van den Beucken, Neer, Sablon, Desmet, Celis, Hoogenboom, Hufton, "Building novel binding ligands to B7.1 and B7.2 based on human antibody single variable light chain domains", *J. Mol. Biol.,* 310:591-601, 2001.

van dijk, Warnaar, van Eendenburg, Thienpont, Braakman, Boot, Fleuren and Bolhuis, "Induction of tumor-cell lysis by bi-specific monoclonal antibodies recognizing renal-cell carcinoma and CD3 antigen," *Int. J. Cancer,* 43:344-349, 1989.

Varfolomeev, Blankenship, Wayson, Fedorova, Kayagaki, Garg, Zobel, Dynek, Elliott, Wallweber, Flygare, Fairbrother, Deshayes, Dixit, Vucic, "IAP Antagonists Induce Autoubiquitination of c-IAPs, NF-κB Activation, and TNFα-Dependent Apoptosis", *Cell,* 131(4):669-681, 2007.

Vince, Wong, Khan, Feltham, Chau, Ahmed, Benetatos, Chunduru, Condon, McKinlay, Brink, Leverkus, Tergaonkar, Schneider, Callus, Koentgen, Vaux, Silke, "IAP Antagonists Target cIAP1 to Induce TNFα-Dependent Apoptosis", *Cell,* 131(4):682-693, 2007.

Volpert, Lawler, Bouck, "A human fibrosarcoma inhibits systemic angiogenesis and the growth of experimental metastases via thrombospondin-1," *Proc. Natl. Acad. Sci. USA,* 95(11):6343-6348, 1998.

Vukanovic, Passaniti, Hirata, Traystman, Hartley-Asp, Isaacs, "Antiangiogenic effects of the quinoline-3-carboxamide linomide," *Cancer Res.,* 53(8):1833-1837, 1993.

Wagner, Milstein, Neuberger, "Codon bias targets mutation," *Nature,* 376:732, 1995.

Waltenberger, Claesson-Welsh, Siegbahn, Shibuya, Heldin, "Different signal transduction properties of KDR and Flt1, two receptors for vascular endothelial growth factor," *J. Biol. Chem.,* 269(43):26988-26995, 1994;

Waltenberger, Mayr, Pentz, Hombach, "Functional-upregulation of the vascular endothelial growth factor receptor KDR by hypoxia," *Circulation,* 94:1647-1654, 1996.

Waltenberger, Mayr, Frank, Hombach, "Suramin is a potent inhibitor of vascular endothelial growth factor. A contribution to the molecular basis of its antiangiogenic action," *J. Mol. Cell. Cardiol.,* 28(7):1523-1529, 1996.

Wamil, Thurman, Sundell, DeVore, Wakefield, Johnson, Wang, Hellerqvist, "Soluble E-selectin in cancer patients as a marker of the therapeutic efficacy of CM101, a tumor-inhibiting anti-neovascularization agent, evaluated in phase I clinical trail," *J. Cancer Res. Clin. Oncol.,* 123(3): 173-179, 1997.

Ward, Güssow, Griffiths, Jones, Winter, "Binding Activities of a Repertoire of Single Immunoglobulin Variable Domains Secreted from *Escherichia Coli*", *Nature,* 341 (6242):544-546, 1989.

Wells, "Starving cancer into submission", *Chem. Biol.,* 5(4): R87-88, 1998.

Whitehurst, Flister, Bagaitkar, Volk, Bivens, Pickett, Castro-Rivera, Brekken, Gerard, Ran, "Anti-VEGF-A therapy reduces lymphatic vessel density and expression of VEGFR-3 in an orthotopic breast tumor model", *Int. J. Cancer,* 121(10):2181-91, 2007.

Wiesmann, Fuh, Christinger, Eigenbrot, Wells, de Vos, "Crystal structure at 1.7 A resolution of VEGF in complex with domain 2 of the Flt-1 receptor," *Cell,* 91(5):695-704, 1997.

Willman et al., "Prodrugs in cancer therapy", *Biochem. Soc. Trans.,* 14:375-382, 1988.

Winter and Milstein, "Man-made antibodies," *Nature,* 349: 293-299, 1991.

Wolff, Guerin, Laterra, Bressler, Indurti, Brem, Goldstein, "Dexamethasone inhibits glioma-induced formation of capillary like structures in vitro and angiogenesis in vivo," *Klin. Padiatr.,* 209(4):275-277, 1997.

Wyckoff, Wang, Lin, Wang, Pixley, Stanley, Graf, Pollard, Segall and Condeelis, "A Paracrine Loop Between Tumor Cells and Macrophages is Required for Tumor Cell Migration in Mammary Tumors", *Cancer Res.,* 64:7022-7029, 2004.

Xie, Chen, Fu, Harter, Young, Sunkara, Novak, Villanueva-Siles, Ratech, "Podoplanin (d2-40): a new immunohistochemical marker for reactive follicular dendritic cells and follicular dendritic cell sarcomas", *Int. J. Clin. Exp. Pathol.,* 1(3):276-84, 2008.

Yoon, Yoo, Choi, Do, Kang, Lee, Azuma, Kim, "Inhibitory effect of Korean mistletoe (*Viscum album* coloratum) extract on tumour angiogenesis and metastasis of haematogenous and non-haematogenous tumour cells in mice," *Cancer Lett,* 97(1):83-91, 1995.

Yoshida, Kaneko, Tsukamoto, Han, Ichinose, Kimura, "Suppression of hepatoma growth and angiogenesis by a fumagillin derivative TNP470: possible involvement of nitric oxide synthase," *Cancer Res.,* 58(16):3751-3756, 1998.

Young, MacKenzie, Narang, Oomen and Baenziger, "Thermal Stabilization of a Single-Chain Fv Antibody Fragment by Introduction of a Disulphide Bond", *FEBS Letters,* 16396(377):135-139, 1995.

Yamamura, Kibbey, Jun, Kleinman, "Effect of Matrigel and laminin peptide YIGSR on tumor growth and metastasis," *Semin. Cancer Biol.,* 4(4):259-265, 1993.

Zachary, "Vascular endothelial growth factor: how it transmits its signal," *Exp. Nephrol.,* 6(6):480-487, 1998.

Zambryski, Herrera-Estreila, DeBlock, Van Montagu, Schell "Genetic Engineering, Principles and Methods", *Hollaender and Setlow (eds.),* Vol. VI, pp. 253-278, Plenum Press, New York, 1984.

Zapata, Ridgway, Mordenti, Osaka, Wong, Bennett, Carter, "Engineering Linear F(Ab')$_2$ Fragments For Efficient Production in *Escherichia Coli* and Enhanced Antiproliferative Activity", *Protein Eng.,* 8(10):1057-1062, 1995.

Zhang, Gildersleeve, Yang, Xu, Loo, Uryu, Wong, Schultz, "A New Strategy for the Synthesis of Glycoproteins", *Science,* 303(5656): 371-373, 2004.

Ziche, Donnini, Morbidelli, Parenti, Gasparini, Ledda, "Linomide blocks angiogenesis by breast carcinoma vascular endothelial growth factor transfectants," *Br. J. Cancer,* 77(7):1123-1129, 1998.

Zou, Anisowicz, Hendrix, Thor, Neveu, Sheng, Rafidi, Seftor, Sager, "Maspin, a serpin with tumor-suppressing activity in human mammary epithelial cells", *Science,* 28:263(5146):526-9, 1994.

What is claimed is:

1. An isolated antibody that binds to VEGF and that comprises at least one heavy chain variable region that comprises three CDRs and at least one light chain variable region that comprises three CDRs, wherein said antibody comprises:
   (a) a variable light (VL) CDR1 having the amino acid sequence of SEQ ID NO:8, a VL CDR2 having the amino acid sequence of SEQ ID NO:9, a VL CDR3 having the amino acid sequence of SEQ ID NO:10, a variable heavy (VH) CDR1 having the amino acid sequence of SEQ ID NO:5, a VH CDR2 having the amino acid sequence of SEQ ID NO:6, and a VH CDR3 having the amino acid sequence of SEQ ID NO:7; or
   (b) a light chain variable region that has the amino acid sequence of SEQ ID NO:4, or a heavy chain variable region that has the amino acid sequence of SEQ ID NO:3.

2. The antibody of claim 1, wherein said antibody comprises said VL CDR1 having the amino acid sequence of SEQ ID NO:8, said VL CDR2 having the amino acid sequence of SEQ ID NO:9, said VL CDR3 having the amino acid sequence of SEQ ID NO:10, said VH CDR1 having the amino acid sequence of SEQ ID NO:5, said VH CDR2 having the amino acid sequence of SEQ ID NO:6, and said VH CDR3 having the amino acid sequence of SEQ ID NO:7.

3. The antibody of claim 1, wherein said antibody comprises said light chain variable region having the amino acid sequence of SEQ ID NO:4, or said heavy chain variable region having the amino acid sequence of SEQ ID NO:3.

4. The antibody of claim 3, wherein said antibody comprises said light chain variable region having the amino acid sequence of SEQ ID NO:4.

5. The antibody of claim 3, wherein said antibody comprises said heavy chain variable region having the amino acid sequence of SEQ ID NO:3.

6. The antibody of claim 3, wherein said antibody comprises said light chain variable region having the amino acid sequence of SEQ ID NO:4 and said heavy chain variable region having the amino acid sequence of SEQ ID NO:3.

7. The antibody of claim 1, wherein said antibody comprises the amino acid sequence of SEQ ID NO:21.

8. The antibody of claim 1, wherein said antibody is a fully human antibody.

9. The antibody of claim 1, wherein said antibody is a whole antibody comprising an antibody constant region.

10. The antibody of claim 9, wherein said antibody comprises a heavy chain that has the amino acid sequence of SEQ ID NO:24 and a light chain that has the amino acid sequence of SEQ ID NO:25.

11. The antibody of claim 1, wherein said antibody is an antigen binding fragment of an antibody.

12. The antibody of claim 1, wherein said antibody binds VEGF with a Kd of less than 10 nM when said antibody is an IgG antibody.

13. The antibody of claim 1, wherein said antibody is attached to at least a first diagnostic or therapeutic agent.

14. The antibody of claim 13, wherein said antibody is attached to at least a first radiotherapeutic agent, chemotherapeutic agent, anti-angiogenic agent, apoptosis-inducing agent, anti-tubulin drug, anti-cellular or cytotoxic agent, cytokine, chemokine or coagulant.

15. The antibody of claim 1, wherein said antibody is comprised within a pharmaceutically acceptable composition.

16. The antibody of claim 15, wherein said pharmaceutically acceptable composition is formulated for intravenous administration or for ocular administration.

17. The antibody of claim 15, wherein said pharmaceutically acceptable composition further comprises at least a second therapeutic agent.

18. An isolated antibody that binds to VEGF and significantly inhibits VEGF binding to the VEGF receptor VEGFR2 (KDR/Flk-1) without significantly inhibiting VEGF binding to the VEGF receptor VEGFR1 (Flt-1); wherein said antibody comprises:
   (a) a variable light (VL) CDR1 having the amino acid sequence of SEQ ID NO:8, a VL CDR2 having the amino acid sequence of SEQ ID NO:9, a VL CDR3 having the amino acid sequence of SEQ ID NO:10, a variable heavy (VH) CDR1 having the amino acid sequence of SEQ ID NO:5, a VH CDR2 having the amino acid sequence of SEQ ID NO:6, and a VH CDR3 having the amino acid sequence of SEQ ID NO:7; or
   (b) a light chain variable region that has the amino acid sequence of SEQ ID NO:4, or a heavy chain variable region that has the amino acid sequence of SEQ ID NO:3.

19. An isolated antibody that binds to VEGF with a Kd of less than 10 nM when said antibody is an IgG antibody; wherein said antibody comprises:
   (a) a variable light (VL) CDR1 having the amino acid sequence of SEQ ID NO:8, a VL CDR2 having the amino acid sequence of SEQ ID NO:9, a VL CDR3 having the amino acid sequence of SEQ ID NO:10, a variable heavy (VH) CDR1 having the amino acid sequence of SEQ ID NO:5, a VH CDR2 having the amino acid sequence of SEQ ID NO:6, and a VH CDR3 having the amino acid sequence of SEQ ID NO:7; or
   (b) a light chain variable region that has the amino acid sequence of SEQ ID NO:4, or a heavy chain variable region that has the amino acid sequence of SEQ ID NO:3.

* * * * *